US012152007B2

(12) United States Patent
Schiltz et al.

(10) Patent No.: US 12,152,007 B2
(45) Date of Patent: Nov. 26, 2024

(54) SUBSTITUTED HETEROCYCLES AS c-MYC TARGETING AGENTS

(71) Applicant: Northwestern University, Evanston, IL (US)

(72) Inventors: Gary E. Schiltz, Naperville, IL (US); Rama K. Mishra, Chicago, IL (US); Huiying Han, Chicago, IL (US); Sarki A. Abdulkadir, Lombard, IL (US); Javier Izquierdo-Ferrer, Chicago, IL (US); Atul D. Jain, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/272,346

(22) PCT Filed: Aug. 31, 2018

(86) PCT No.: PCT/US2018/049175
§ 371 (c)(1),
(2) Date: Feb. 28, 2021

(87) PCT Pub. No.: WO2020/046382
PCT Pub. Date: Mar. 5, 2020

(65) Prior Publication Data
US 2021/0395206 A1 Dec. 23, 2021

(51) Int. Cl.
| | | |
|---|---|---|
| C07D 231/20 | (2006.01) |
| A61P 35/00 | (2006.01) |
| C07D 231/06 | (2006.01) |
| C07D 231/12 | (2006.01) |
| C07D 239/26 | (2006.01) |
| C07D 239/42 | (2006.01) |
| C07D 249/06 | (2006.01) |
| C07D 261/08 | (2006.01) |
| C07D 401/04 | (2006.01) |
| C07D 401/12 | (2006.01) |
| C07D 401/14 | (2006.01) |
| C07D 403/04 | (2006.01) |
| C07D 403/12 | (2006.01) |
| C07D 405/04 | (2006.01) |
| C07D 405/10 | (2006.01) |
| C07D 405/12 | (2006.01) |
| C07D 409/10 | (2006.01) |
| C07D 498/04 | (2006.01) |

(52) U.S. Cl.
CPC ............ *C07D 231/20* (2013.01); *A61P 35/00* (2018.01); *C07D 231/06* (2013.01); *C07D 231/12* (2013.01); *C07D 239/26* (2013.01); *C07D 239/42* (2013.01); *C07D 249/06* (2013.01); *C07D 261/08* (2013.01); *C07D 401/04* (2013.01); *C07D 401/12* (2013.01); *C07D 401/14* (2013.01); *C07D 403/04* (2013.01); *C07D 403/12* (2013.01); *C07D 405/04* (2013.01); *C07D 405/10* (2013.01); *C07D 405/12* (2013.01); *C07D 409/10* (2013.01); *C07D 498/04* (2013.01)

(58) Field of Classification Search
None
See application file for complete search history.

(56) References Cited

U.S. PATENT DOCUMENTS

| | | | | |
|---|---|---|---|---|
| 2008/0090880 A1* | 4/2008 | Eggenweiler | ........... | A61P 21/00 548/366.1 |
| 2012/0316182 A1 | 12/2012 | Whitten | | |
| 2013/0005666 A1 | 1/2013 | Ratan et al. | | |
| 2017/0253581 A1 | 9/2017 | Schiltz | | |

FOREIGN PATENT DOCUMENTS

| | | | | |
|---|---|---|---|---|
| CN | 107739337 A | 2/2018 | | |
| EP | 0280654 A1 | 8/1988 | | |
| FR | 1396684 A | 4/1965 | | |
| JP | 2005225787 A | 8/2005 | | |
| JP | 2008509175 A | 3/2008 | | |
| JP | 2008515823 A | 5/2008 | | |
| JP | WO 2014/051161 | * 9/2013 | ........... | C07D 257/04 |
| JP | 2018514547 A | 6/2018 | | |
| WO | 2006018082 A1 | 2/2006 | | |
| WO | 2007081966 A2 | 7/2007 | | |
| WO | 2007136703 A1 | 11/2007 | | |
| WO | 2017155942 A2 | 9/2017 | | |

OTHER PUBLICATIONS

Database Registry Chemical Abstracts Service, Columbus, Ohio, Accession No. RN 178880-76-7, Entered STN: Jul. 25, 1996.*
Fletcher, S. et al. Small-molecule inhibitors of the MYC oncoprotein, Biochimica et Biophysica Acta (BBA) 1849.5 (2015).
Gabay, M. et al. "MYC activation is a hallmark of cancer initiation and maintenance." Cold Spring Harbor perspectives in medicine 4.6 (2014): a014241.
Huang, M. et al. "Neuroblastoma and MYCN." Cold Spring Harbor perspectives in medicine 3.10 (2013): a014415.
International Searching Authority. International Search Report and Written Opinion for application PCT/US2018/049175. Mailed on May 30, 2019. 10 pages.
McKeown, MR et al. "Therapeutic strategies to inhibit MYC." Cold Spring Harbor perspectives in medicine 4.10 (2014): a014266.
Roussel MF, et al. 2013. Role of MYC in medulloblastoma. Cold Spring Harb Perspect Med 3: a014308.
Schlosser, I., et al. "Dissection of transcriptional programmes in response to serum and c-Myc in a human B-cell line." Oncogene 24.3 (2005): 520-524.
Schmitz R, et. al. 2014. Oncogenic mechanisms in Burkitt lymphoma. Cold Spring Harb Perspect Med 4: a014282.

(Continued)

*Primary Examiner* — Samantha L Shterengarts
(74) *Attorney, Agent, or Firm* — Quarles & Brady LLP

(57) ABSTRACT

Disclosed are substituted heterocycle compounds including substituted pyrazoles, substituted pyrimidines, and substitute triazoles. The substituted heterocycles disclosed herein are shown to be useful in inhibiting c-MYC and may be utilized as therapeutics for treating cancer and cell proliferative disorders.

19 Claims, 20 Drawing Sheets

(56) References Cited

OTHER PUBLICATIONS

Schuhmacher, M., et al. "The transcriptional program of a human B cell line in response to Myc." Nucleic acids research 29.2 (2001): 397-406.

Soucek L, et. al. 2013. Inhibition of MYC family proteins eradicates KRas-driven lung cancer in mice. Genes Dev 27: 504-513.

Zeller, K. I., et al. "An integrated database of genes responsive to the Myc oncogenic transcription factor: identification of direct genomic targets." Genome biology 4.10 (2003): 1-10.

Kim, Y. H., et al. "Combined microarray analysis of small cell lung cancer reveals altered apoptotic balance and distinct expression signatures of MYC family gene amplification." Oncogene 25.1 (2006): 130-138.

Park, H et al. A novel class of Hsp90 inhibitors isolated by structure-based virtual screening. 17.22 (2007): 6345-6349.

Sapegin, AV et al. New tetracyclic 1,4-oxazepines constructed via practically simple tandem condensation strategy from readily available synthons. 70.5. (2014): 1077-1083.

Vishnu Nayak, B., et al. Monoamine oxidase inhibitory activity of 3,5-biaryl-4,5-dihydro-1Hpyrazole-1-carboxylate derivatives. 69 (2013): 762-767.

* cited by examiner

SUBSTITUTED HETEROCYCLES AS c-MYC TARGETING AGENTS

STATEMENT REGARDING FEDERALLY SPONSORED RESEARCH OR DEVELOPMENT

This invention was made with government support under grant number R01 CA123484 awarded by the National Institutes of Health. The government has certain rights in the invention.

CROSS-REFERENCE TO RELATED APPLICATIONS

This is a national stage application, filed under 35 U.S.C. § 371, which claims priority to International Patent Application PCT/US2018/049175, filed Aug. 31, 2018, which is incorporated herein by reference in its entirety for all purposes.

BACKGROUND

The field of the invention relates to substituted heterocycles as c-MYC targeting agents. In particular, the field of the invention relates to substituted pyrazoles, pyrimidines, or trizoles as c-MYC targeting agents for the treatment of cell proliferation diseases and disorders such as cancer.

The c-MYC oncogene is de-regulated and plays a causal role in a majority of human cancer and c-MYC inhibition profoundly affects tumor growth or survival in multiple models. MYC is the most common oncogene involved in human cancers and is overexpressed in up to half of all cancers. Therefore, developing c-MYC inhibitors is among the most attractive potential anti-cancer strategies. Unfortunately, due to the difficulty in targeting transcription factors with small molecules, c-MYC is currently regarded as "undruggable." Here, we disclose a new approach to targeting c-MYC and have developed a series of new small molecule inhibitors. These compounds selectively target c-MYC-driven cell proliferation and interfere with binding of c-MYC to DNA.

SUMMARY

Disclosed are substituted heterocycles which may be utilized as c-MYC targeting agents. The substituted heterocycles may include substituted pyrazoles, substituted pyrimidines, and substituted triazoles. The disclosed heterocycles may be used in pharmaceutical compositions and methods for treating cell proliferative disorders such as cancer.

The disclosed substituted heterocycles may include substituted pyrazoles having a formula I:

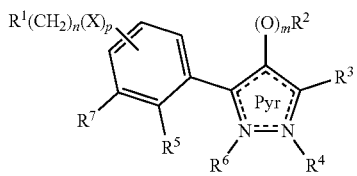

I wherein
$R^1$ is hydrogen, or $R^1$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally $R^1$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, and alkoxycarbonyl;

n is 0, 1, or 2;
p is 0 or 1;
X is O or NH, or $R^1(CH_2)_n(X)_p$— is N-piperazinyl optionally N-substituted with alkyl;
m is 0 or 1;
$R^2$ is hydrogen or halo, or $R^2$ is an alkyl group, an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally $R^2$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl;
$R^3$ is hydrogen, alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), benzyl, hydroxyl, halo, amido, hydrazonyl, carbonyl, carboxyl, or alkoxycarbonyl;
$R^4$ is hydrogen, amino, alkyl, or $R^4$ is aryl (e.g., phenyl), or benzyl; $R^4$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, alkoxycarbonyl, aryloxy (e.g., phenoxy), and alkylaryloxy (e.g., benzyloxy);
$R^5$ is alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, or halo;
$R^6$ is hydrogen, amino, alkyl, or $R^6$ is aryl (e.g., phenyl) or benzyl; $R^6$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, alkoxycarbonyl, aryloxy (e.g., phenoxy), and alkylaryloxy (e.g., benzyloxy), or $R^6$ and $R^5$ together form a ring structure having a formula

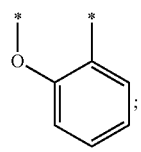 [SMILES: *Oc1ccccc1*]

$R^7$ is hydrogen or halo, or $R^2$ is an alkyl group, an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally $R^7$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl;

optionally with the proviso that at least one of $R^4$ and $R^6$ is hydrogen;

optionally with the proviso that if $R^5$ is hydrogen, then p is 1 and m is 1; and and optionally with the proviso that if $R^1(CH_2)_n(X)_p$— is hydrogen, hydroxyl, or alkyl, and $R^5$ is hydroxyl, then m is 1, or at least one of $R^2$ and $R^3$ is not hydrogen.

In the disclosed formula I, Pyr is a pyrazole ring having two non-adjacent double bonds, for example, where the substituted pyrazoles have a formula I(i) or I(ii):

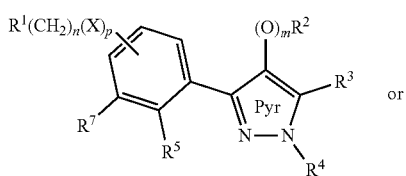

I(i)

or

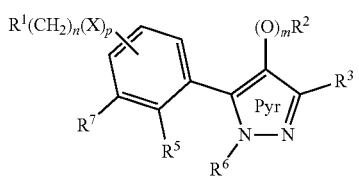

I(ii)

Specifically, the substituted pyrazoles may have a formula Ia(i), Ib(ii), Ib(i), Ib(ii), Ic(i), or Ic(ii):

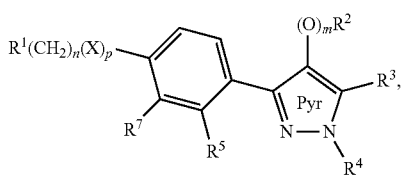

Ia(i)

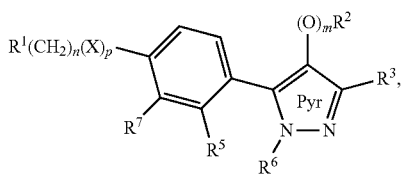

Ia(ii)

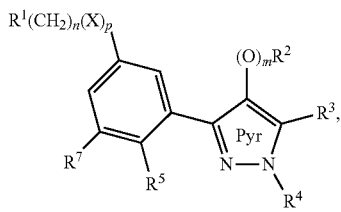

Ib(i)

-continued

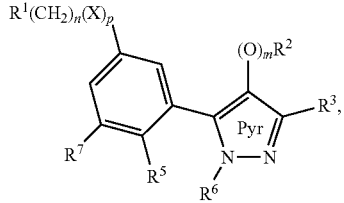

Ib(ii)

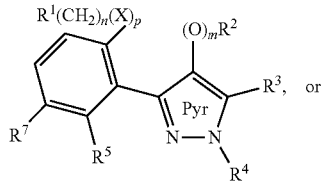

Ic(i)

or

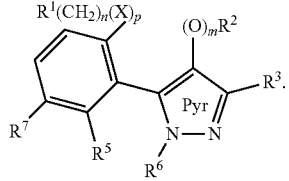

Ic(ii)

The disclosed compounds may exhibit one or more biological activities. The disclosed compounds may inhibit binding of the MYC/Max complex to DNA (e.g., in a DNA gel shifting assay). The disclosed compounds may not produce significant DNA damage (e.g., in an rH2AX staining assay at a concentration greater than about 0.001 μM, 0.005 μM, 0.01 μM, 0.1 μM, 1.0 μM, 10 μM, 100 μM, or higher). The disclosed compounds may inhibit the growth of cells that express c-MYC (preferably by at a concentration of less than about 100 μM, 50 μM, 10 μM, 1 μM, 0.1 μM, 0.05 μM, 0.01 μM, 0.005 μM, 0.001 μM, or less). The disclosed compounds may not inhibit the growth of cells that do not express c-MYC (preferably at a concentration of greater than about 0.001 μM, 0.005 μM, 0.01 μM, 0.5 μM, 0.1 μM, 1.0 μM, 10 μM, and 100 μM or higher).

Also disclosed are pharmaceutical compositions comprising the disclosed compounds and a suitable pharmaceutical carrier, excipient, or diluent. The disclosed pharmaceutical compositions may comprise an effective amount of the compound for inhibiting the growth of cancer cells when administered to a subject in need thereof.

Also disclosed are methods for treating cell proliferation diseases and disorders such as cancer. The methods may include administering the disclosed compounds or pharmaceutical compositions comprising the disclosed compounds to a subject in need thereof, for example, to a subject having cancer. The disclosed compounds or pharmaceutical compositions comprising the disclosed compounds may be administered with additional therapeutic agents, optionally in combination, in order to treat cell proliferative diseases and disorders. Cell proliferative diseases and disorders treated by the disclosed methods may include, but are not limited to, cancers selected from the group consisting of multiple myeloma, leukemia, non-small cell lung cancer, colon cancer, cancer of the central nervous system, melanoma, ovarian cancer, renal cancer, prostate cancer, and breast cancer.

DETAILED DESCRIPTION

Figure 1:
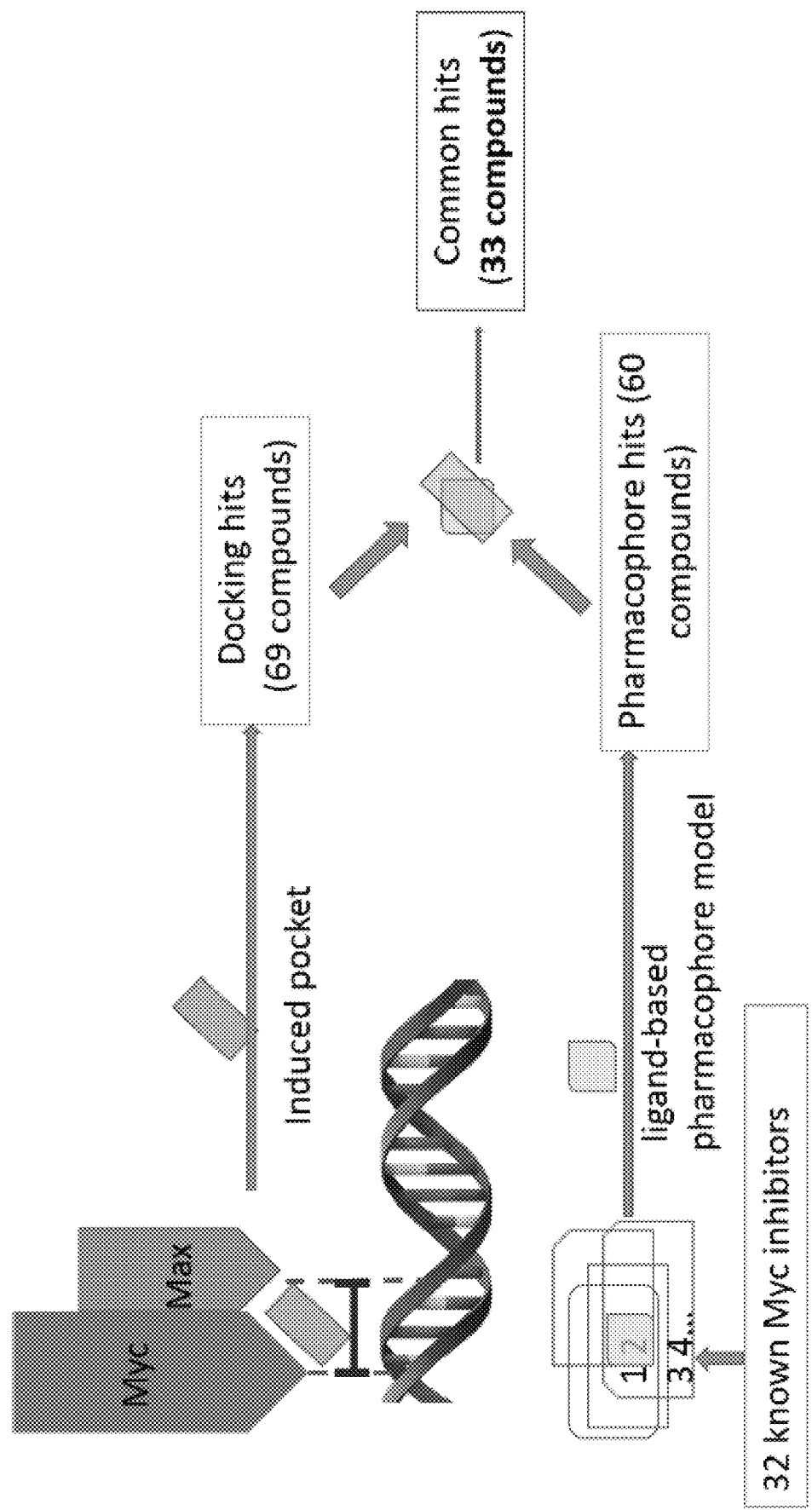
FIG. 1. Scheme for in silico screen to identify c-MYC inhibitors.

The present invention is described herein using several definitions, as set forth below and throughout the application.

Unless otherwise specified or indicated by context, the terms "a", "an", and "the" mean "one or more." For example, "a compound" should be interpreted to mean "one or more compounds."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment.

A "subject in need of treatment" may include a subject having a disease, disorder, or condition that is responsive to therapy with a substituted heterocycle such as the presently disclosed substituted pyrazoles, substituted pyrimidines, and substituted triazoles. For example, a "subject in need of treatment" may include a subject having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, and breast cancer). A "subject in need of treatment" may include a subject having a cell proliferative disease, disorder, or condition such as cancer that is associated with c-MYC activity and/or that may be treated by administering an effective amount of an agent that modulates c-MYC activity.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

As used herein, the term "modulate" means decreasing or inhibiting activity and/or increasing or augmenting activity. For example, modulating c-MYC activity may mean increasing or augmenting c-MYC activity and/or decreasing or inhibiting c-MYC activity. The compounds disclosed herein may be administered to modulate c-MYC activity.

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group (e.g., —(CH$_2$)$_n$— where n is an integer such as an integer between 1 and 20). An exemplary alkylene group is —CH$_2$CH$_2$—.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —$R^1C(O)N(R^2)$—, —$R^1C(O)N(R^2)R^3$—, —$C(O)NR^2R^3$, or —$C(O)NH_2$, wherein $R^1$, $R^2$ and $R^3$, for example, are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Substituted Heterocycles and Uses Thereof for Inhibiting the Biological Activity of C-MYC Disclosed herein are substituted heterocycles. The disclosed heterocycles have been shown to inhibit the biological activity of c-MYC. The disclosed substituted heterocycles may include substituted pyrazoles, substituted pyrimidines, and substituted triazoles.

In some embodiments, the disclosed substituted heterocycles may include substituted pyrazoles having a formula I:

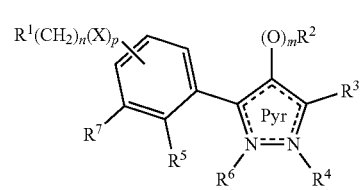

wherein $R^1$ is hydrogen, or $R^1$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally $R^1$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, and alkoxycarbonyl;

n is 0, 1, or 2;

p is 0 or 1;

X is O or NH, or $R^1(CH_2)_n(X)_p$— is N-piperazinyl optionally N-substituted with alkyl;

m is 0 or 1;

$R^2$ is hydrogen or halo, or $R^2$ is an alkyl group, an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), $R^2$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl;

$R^3$ is hydrogen, alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), benzyl, hydroxyl, halo, amido, hydrazonyl, carbonyl, carboxyl, or alkoxycarbonyl;

$R^4$ is hydrogen, amino, alkyl, or $R^4$ is aryl (e.g., phenyl) or benzyl; $R^4$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, alkoxycarbonyl, aryloxy (e.g., phenoxy), and alkylaryloxy (e.g., benzyloxy);

$R^5$ is alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, or halo;

$R^6$ is hydrogen, amino, alkyl, or $R^6$ is aryl (e.g., phenyl), or benzyl; $R^6$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, alkoxycarbonyl, aryloxy (e.g., phenoxy), and alkylaryloxy (e.g., benzyloxy), or $R^6$ and $R^5$ together form a ring structure having a formula

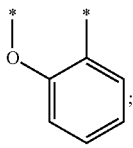

$R^7$ is hydrogen or halo, or $R^7$ is an alkyl group, an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), $R^7$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl;

optionally with the proviso that at least one of $R^4$ and $R^6$ is hydrogen;

optionally with the proviso that if $R^5$ is hydrogen, then p is 1 and m is 1; and optionally with the proviso that if $R^1(CH_2)_n(X)_p$— is hydrogen, hydroxyl, or alkyl, and $R^5$ is hydroxyl, then m is 1, or at least one of $R^2$ and $R^3$ is not hydrogen.

In some embodiments of these disclosed substituted pyrazoles, at least one of $R^2$ and $R^7$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and $R^2$ and $R^7$ optionally are substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl. In some embodiments of the disclosed compounds, m is 0 and $R^2$ is hydrogen, or $R^7$ is hydrogen.

In some embodiments of these disclosed substituted pyrazoles, $R^2$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and $R^2$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl; and $R^7$ is hydrogen.

In some embodiments of these disclosed substituted pyrazoles, m is 0 and $R^2$ is hydrogen; and $R^7$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and $R^7$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl.

In the disclosed formula I, Pyr is a pyrazole ring having two non-adjacent double bonds, for example, where the substituted pyrazoles have a formula I(i) or I(ii):

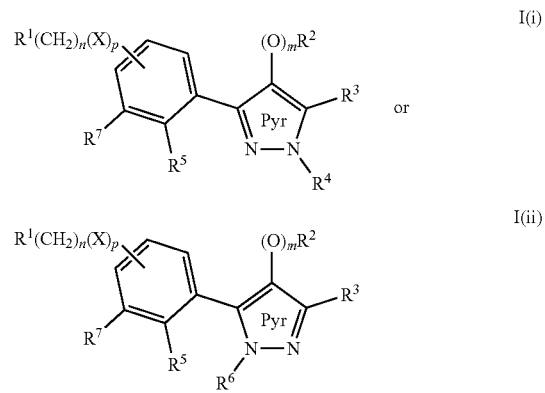

Specifically, the substituted pyrazoles may have a formula Ia(i), Ib(ii), Ib(i), Ib(ii), Ic(i), or Ic(ii):

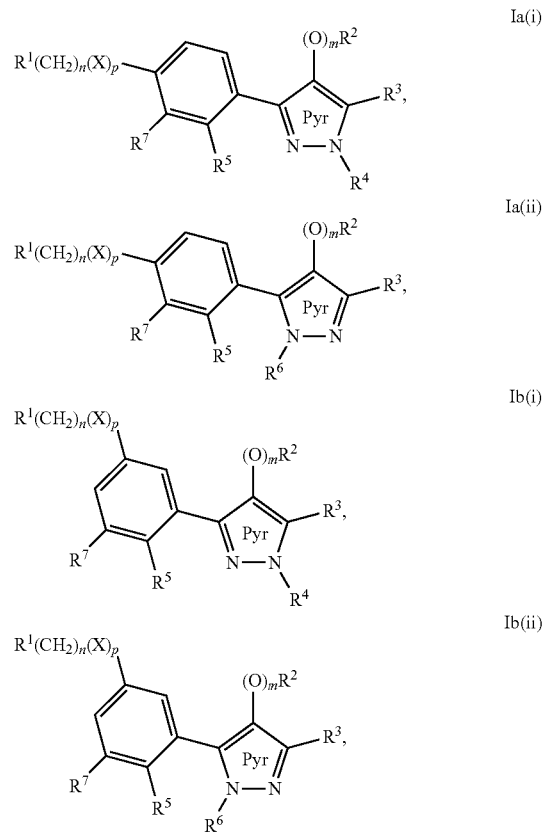

-continued

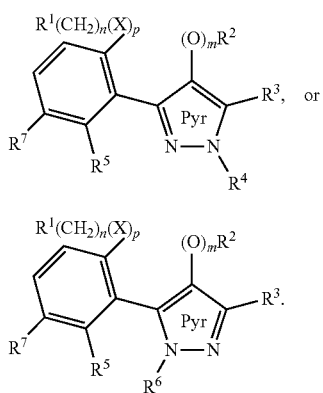

In some embodiments, the disclosed substituted heterocycles may include substituted pyrazoles having a formula II:

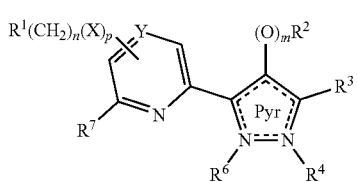

wherein

Y is C or N;

R$^1$ is hydrogen, or R$^1$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally R$^1$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, and alkoxycarbonyl;

n is 0, 1, or 2;

p is 0 or 1;

X is O or NH, or R$^1$(CH$_2$)$_n$(X)$_p$— is N-piperazinyl optionally N-substituted with alkyl;

m is 0 or 1;

R$^2$ is hydrogen or halo, or R$^2$ is an alkyl group, an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally R$^2$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl;

R$^3$ is hydrogen, alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), benzyl, hydroxyl, halo, amido, hydrazonyl, carbonyl, carboxyl, or alkoxycarbonyl;

R$^4$ is hydrogen, amino, alkyl, or R$^4$ is aryl (e.g., phenyl) or benzyl; R$^4$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, alkoxycarbonyl, aryloxy (e.g., phenoxy), and alkylaryloxy (e.g., benzyloxy);

R$^6$ is hydrogen, amino, alkyl, or R$^6$ is aryl (e.g., phenyl), or benzyl; R$^6$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, alkoxycarbonyl, aryloxy (e.g., phenoxy), and alkylaryloxy (e.g., benzyloxy); and R$^7$ is hydrogen or halo, or R$^7$ is an alkyl group, an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), R$^7$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl;

optionally with the proviso that at least one of R$^4$ and R$^6$ is hydrogen;

optionally with the proviso that if R$^5$ is hydrogen, then p is 1 and m is 1; and optionally with the proviso that if R$^1$(CH$_2$)$_n$(X)$_p$— is hydrogen, hydroxyl, or alkyl, and R$^5$ is hydroxyl, then m is 1, or at least one of R$^2$ and R$^3$ is not hydrogen.

In some embodiments of these disclosed substituted pyrazoles, at least one of R$^2$ and R$^7$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and R$^2$ and R$^7$ optionally are substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl. In some embodiments of the disclosed compounds, m is 0 and R$^2$ is hydrogen, or R$^7$ is hydrogen.

In some embodiments of these disclosed substituted pyrazoles, R$^2$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and R$^2$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl; and R$^7$ is hydrogen.

In some embodiments of these disclosed substituted pyrazoles, m is 0 and R² is hydrogen; and R⁷ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and R⁷ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl.

Specifically, the substituted pyrazoles may have a formula IIa:

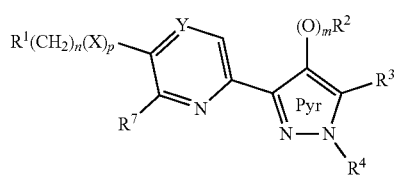

In some embodiments, the disclosed substituted heterocycles may include substituted pyrimidines having a formula III:

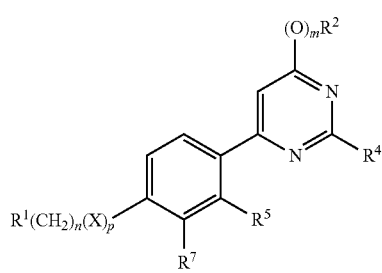

wherein:
R¹ is hydrogen, or R¹ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally R¹ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, and alkoxycarbonyl;
n is 0, 1, or 2;
p is 0 or 1;
X is O, NH, or R¹(CH₂)ₙ(X)ₚ— is N-piperazinyl optionally N-substituted with alkyl;
m is 0 or 1;
R² is hydrogen or halo, or R² is an alkyl group, an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally R² is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl;
R⁴ is hydrogen, amino, alkyl, or R⁴ is aryl (e.g., phenyl) or benzyl; R⁴ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, alkoxycarbonyl, aryloxy (e.g., phenoxy), and alkylaryloxy (e.g., benzyloxy);
R⁵ is alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, or halo; and
R⁷ is hydrogen or halo, or R⁷ is an alkyl group, an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), R⁷ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl.

In some embodiments of these disclosed substituted pyrimidines, at least one of R² and R⁷ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and R² and R⁷ optionally are substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl. In some embodiments of the disclosed compounds, m is 0 and R² is hydrogen, or R⁷ is hydrogen.

In some embodiments of these disclosed substituted pyrimidines, R² is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and R² optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl; and R⁷ is hydrogen.

In some embodiments of these disclosed substituted pyrimidines, m is 0 and R² is hydrogen; and R⁷ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and $R^7$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl.

Specifically, the substituted pyrimidines may have a formula IIIa or IIIb:

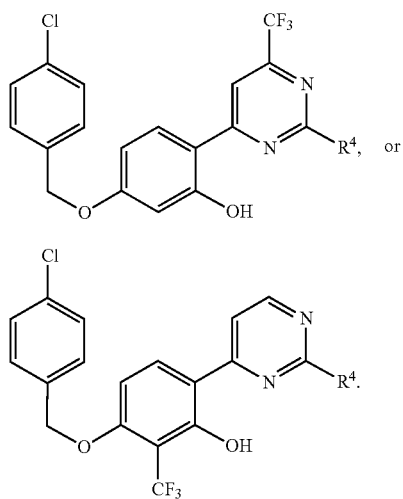

In some embodiments, the disclosed substituted heterocycles may include substitute pyrazoles having a formula IV:

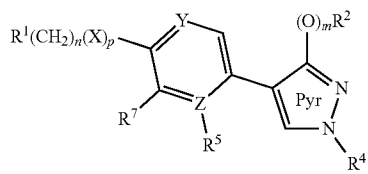

wherein:
$R^1$ is hydrogen, or $R^1$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally $R^1$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, and alkoxycarbonyl;
n is 0, 1, or 2;
p is 0 or 1;
X is O, NH, or $R^1(CH_2)_n(X)_p$— is N-piperazinyl optionally N-substituted with alkyl;
Y is N or C;
Z is N or C;
m is 0 or 1;
$R^2$ is hydrogen or halo, or $R^2$ is and alkyl group, an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally $R^2$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl;
$R^4$ is hydrogen, amino, alkyl, or $R^4$ is aryl (e.g., phenyl) or benzyl; $R^4$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, alkoxycarbonyl, aryloxy (e.g., phenoxy), and alkylaryloxy (e.g., benzyloxy);
$R^5$ is alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, or halo; and
$R^7$ is hydrogen or halo, or $R^7$ is and alkyl group, an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally $R^7$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl.

In some embodiments of these disclosed substituted pyrazoles, at least one of $R^2$ and $R^7$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and $R^2$ and $R^7$ optionally are substituted at one or more positions with one or more of alkyl (e.g., $C_1$-$C_6$alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl. In some embodiments of the disclosed compounds, m is 0 and $R^2$ is hydrogen, or $R^7$ is hydrogen.

In some embodiments of these disclosed substituted pyrazoles, $R^2$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and $R^2$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl; and $R^7$ is hydrogen.

In some embodiments of these disclosed substituted pyrazoles, m is 0 and $R^2$ is hydrogen; and $R^7$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and $R^7$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl.

In some embodiments, the disclosed substituted heterocycles may include substitute triazoles having a formula V:

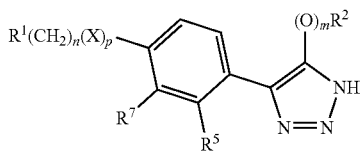

wherein:
$R^1$ is hydrogen, or $R^1$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally $R^1$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, amido, hydrazonyl, carbonyl, carboxyl, and alkoxycarbonyl;
n is 0, 1, or 2;
p is 0 or 1;
X is O or NH, or $R^1(CH_2)_n(X)_p$— is N-piperazinyl optionally N-substituted with alkyl;
m is 0 or 1;
$R^2$ is hydrogen or halo, or $R^2$ is an alkyl group, an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally $R^2$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl;
$R^5$ is alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, or halo; and
$R^7$ is hydrogen or halo, or $R^7$ is and alkyl group, an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), optionally $R^7$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl.

In some embodiments of these disclosed substituted triazoles, at least one of $R^2$ and $R^7$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and $R^2$ and $R^7$ optionally are substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl. In some embodiments of the disclosed compounds, m is 0 and $R^2$ is hydrogen, or $R^7$ is hydrogen.

In some embodiments of these disclosed substituted triazoles, $R^2$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and $R^2$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl; and $R^7$ is hydrogen.

In some embodiments of these disclosed substituted triazoles, m is 0 and $R^2$ is hydrogen; and $R^7$ is an aryl group (e.g., phenyl), a benzyl group, a heteroaryl group (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), a cycloalkyl group (e.g., cyclohexyl), a cycloheteroalkyl group (e.g., piperidinyl, morpholinyl), and $R^7$ optionally is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), hydroxyl, halo, cyano, amido, hydrazonyl, carbonyl, carboxyl, and alkoxycarbonyl.

The formulae of the compounds disclosed herein should be interpreted as encompassing all possible stereoisomers, enantiomers, or epimers of the compounds unless the formulae indicates a specific stereoisomer, enantiomer, or epimer. The formulae of the compounds disclosed herein should be interpreted as encompassing salts, esters, amides, or solvates thereof of the compounds.

Use of the Disclosed Compounds for Inhibiting C-MYC Activity

The disclosed compounds may exhibit one or more biological activities. The disclosed compounds may inhibit binding of the MYC/Max complex to DNA (e.g., in a DNA gel shifting assay). In some embodiments, the disclosed compounds inhibit binding of the MYC/Max complex to DNA by at least 50%, 60%, 70%, 80%, 90%, 95%, 96%, 97%, 98%, or 99% at a concentration of less than about 100 μM, 50 μM, 10 μM, 1 μM, 0.1 μM, 0.05 μM, 0.01 μM, 0.005 μM, 0.001 μM, or less. The disclosed compounds may not produce significant DNA damage (e.g., in an rH2AX staining assay at a concentration greater than about 0.001 μM, 0.005 μM, 0.01 μM, 0.1 μM, 1.0 μM, 10 μM, 100 μM, or higher). The disclosed compounds may inhibit the growth of cells that express c-MYC (preferably by at least 50%, 60%, 70%, 80%, 90%, 95%, 96%, 97%, 98%, or 99% at a concentration of less than about 100 µM, 50 µM, 10 µM, 1 µM, 0.1 µM, 0.05 µM, 0.01 µM, 0.005 µM, 0.001 µM, or less). The disclosed compounds may not inhibit the growth of cells that do not express c-MYC (preferably by not more than 50%, 40%, 30%, 20%, 10%, 5%, 4%, 3%, 2% or less at a concentration of greater than about 0.001 µM, 0.005 µM, 0.01 µM, 0.5 µM, 0.1 µM, 1.0 µM, 10 µM, and 100 µM or higher). Concentration ranges also are contemplated herein, for example, a concentration range bounded by end-point concentrations selected from 0.001 µM, 0.005 µM, 0.01 µM, 0.5 µM, 0.1 µM, 1.0 µM, 10 µM, and 100 µM.

The disclosed compounds may be effective in inhibiting cell proliferation of cancer cells, including cancer cells that express c-MYC and whose proliferation is inhibiting by inhibiting the biological activity of c-MYC. The disclosed compounds may be effective in inhibiting cell proliferation of one or more types of cancer cells including: multiple myeloma cells, such as MM.1S cells; leukemia cells, such as CCRF-CEM, HL-60(TB), MOLT-4, RPMI-8226 and SR; non-small lung cancer cells, such as A549/ATCC, EKVX, HOP-62, HOP-92, NCI-H226, NCI-H23, NCI-H322M, NCI-H460 and NCI-H522; colon cancer cells, such as COLO 205, HCC-2998, HCT-116, HCT-15, HT29, KM12 and SW-620; CNS: SF-268, SF-295, SF-539, SNB-19, SNB-75 and U251; melanoma cancer cells, such as LOX IMVI, MALME-3M, M14, MDA-MB-435, SK-MEL-2, SK-MEL-28, SK-MEL-5, UACC-257 and UACC-62; ovarian cancer cells, such as IGR-OV1, OVCAR-3, OVCAR-4, OVCAR-5, OVCAR-8, NCI/ADR-RES and SK-OV-3; renal cancer cells, such as 786-0, A498, ACHN, CAKI-1, RXF 393, SN12C, TK-10 and UO-31; prostate cancer cells, such as DU-145 and PC-3; and breast cancer cells, such as MCF7, MDA-MB-231/ATCC, MDA-MB-468, HS 578T, BT-549 and T-47D.

Cell proliferation and inhibition thereof by the presently disclosed compounds may be assessed by cell viability methods disclosed in the art including colorimetric assays that utilize dyes such as MTT, XTT, and MTS to assess cell viability. Preferably, the disclosed compounds have an $IC_{50}$ of less than about 10 µM, 5 µM, 1 µM, 0.5 µM, 0.01 µM, 0.005 µM, 0.001 µM or lower in the selected assay.

The disclosed compounds may be formulated as anti-cancer therapeutics, including hematologic malignancies, breast, lung, pancreas and prostate malignancies. The disclosed compounds also may be formulated as anti-inflammation therapeutics.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 µM, 0.005 µM, 0.01 µM, 0.5 µM, 0.1 µM, 1.0 µM, 10 µM, and 100 µM (e.g., 0.1 µM-1.0 µM).

The disclosed compounds and pharmaceutical compositions comprising the disclosed compounds may be administered in methods of treating a subject in need thereof. For example, in the methods of treatment a subject in need thereof may include a subject having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, and breast cancer).

In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds may include doses falling within dose ranges having as end-points any of these disclosed doses (e.g., 2.5 mg-200 mg).

In some embodiments, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds for achieving therapy in the disclosed methods of treatment may include dose levels falling within ranges having as end-points any of these disclosed dose levels (e.g., 500-2000 ng/kg body weight of the subject).

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (Pro-Solv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules. In some embodiments, the compounds are formulated as a composition for administration orally (e.g., in a solvent such as 5% DMSO in oil such as vegetable oil).

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Combination Therapies and Pharmaceutical Compositions

The disclosed compounds or pharmaceutical compositions comprising the disclosed compounds may be administered in methods of treatment. For example, the disclosed compounds or pharmaceutical compositions comprising the disclosed compounds may be administered in methods of treating cell proliferative diseases and disorders. Cell proliferative diseases and disorders treated by the disclosed methods may include, but are not limited to, cancers selected from the group consisting of multiple myeloma, leukemia, non-small cell lung cancer, colon cancer, cancer of the central nervous system, melanoma, ovarian cancer, renal cancer, prostate cancer, and breast cancer.

Optionally, the disclosed compounds or pharmaceutical compositions comprising the disclosed compounds may be administered with additional therapeutic agents, optionally in combination, in order to treat cell proliferative diseases and disorders. In some embodiments of the disclosed methods, one or more additional therapeutic agents are administered with the disclosed compounds or with pharmaceutical compositions comprising the disclosed compounds, where the additional therapeutic agent is administered prior to, concurrently with, or after administering the disclosed compounds or the pharmaceutical compositions comprising the disclosed compounds. In some embodiments, the disclosed pharmaceutical composition are formulated to comprise the disclosed compounds and further to comprise one or more additional therapeutic agents, for example, one or more additional therapeutic agents for treating cell proliferative diseases and disorders.

In some embodiments, additional therapeutic agents may include, but are not limited to, therapeutic agents for treating leukemias and lymphomas, such as acute myeloid leukemia (AML), acute lymphocytic leukemia (ALL), chronic myelogenous leukemia (CML), and non-Hodgkin's lymphoma.

In some embodiments, additional therapeutic agents may include, but are not limited to, antimetabolite antineoplastic agents that inhibit the synthesis of DNA. Suitable antimetabolite antineoplastic agents that inhibit the synthesis of DNA may include, but are not limited to, nucleoside and/or nucleotide derivatives. Suitable nucleoside and/or nucleotide derivatives may include, but are not limited to cytosine arabinoside (ara-C), otherwise called cytarabine.

EXAMPLES

The following Examples are illustrative and are not intended to limit the scope of the claimed subject matter.

Example 1—Identification of Small Molecule Inhibitors of C-MYC DNA Binding Activity Introduction MYC is the most frequently amplified oncogene in human cancers. It has been extensively validated as essential for tumor initiation and maintenance in numerous tumor histologies. Numerous studies have provided solid evidence that pharmacologic targeting of MYC would directly affect tumor progression. One example is OmoMYC, a dominant-negative peptide of MYC that competitively binds MYC in a manner that prevents MYC-Max heterodimerization. OmoMYC expression prompts rapid growth arrest and down-regulation of MYC target genes in cancer cells both in vitro and in vivo. Small molecule inhibitors of MYC will be the optimal form for drug development. However, disruption of MYC-Max interactions through small molecules has been difficult because there are no obvious binding regions in the interface. Thus far, over 30 small molecules have been documented with MYC inhibition activity in vitro, but the evidence for their in vivo activities is lacking, likely due to their poor drug-like properties. Among these compounds, 10058-f4 and 10075-G5 are well-known for their specificities and relatively clear mechanisms in interrupting MYC-Max binding. However, the in vivo studies were quite disappointing because of their rapid metabolism. Thus, developing new MYC inhibitors with high potency and specificity as well as favorable drug-like properties will be critical to effectively target MYC.

To this end, we carried out an in silico screen to identify compounds that might inhibit the binding of c-MYC to DNA. These compounds were tested in several cell-based assays to identify the most active hits. The best hit, Min-9 (NUCC-176234) and its related analogs were shown to prevent c-MYC/DNA binding. We then synthesized a series of novel structural analogs and these were tested in the same c-MYC-relevant assays. Our new compounds display excellent potency at inhibiting c-MYC/DNA binding. The compounds we have developed using a novel approach possess greatly improved drug-like properties over existing small molecules such as 10058-f4 and therefore represent excellent starting points for developing MYC-targeting therapeutics.

Results

In the absence of a regular small-molecule ligand-binding pocket in the c-MYC/Max/DNA ternary complex, we applied multiple independent in silico approaches to increase our likelihood of successfully identifying new small molecule inhibitors. (See FIG. 1). We carried out in-silico screening of a 10 million compound drug-like library. We applied two different approaches to screen the ZINC compound database after removing promiscuous and non drug-like compounds using PAINS filters. The first approach is based on a 3-tier docking protocol using a published crystal structure of MYC/Max bound to DNA. After defining a putative ligand-binding site as reported in the literature, the compound library was screened using the docking tool. The second approach was based on building a pharmacophore model considering of 32 compounds reported to inhibit MYC and screening the Zinc database against this pharmacophore. We obtained 69 hits from the structure-based screen and 60 hits from the ligand-based pharmacophore screen, with 32 compounds in common between the two approaches.

Figure 2:
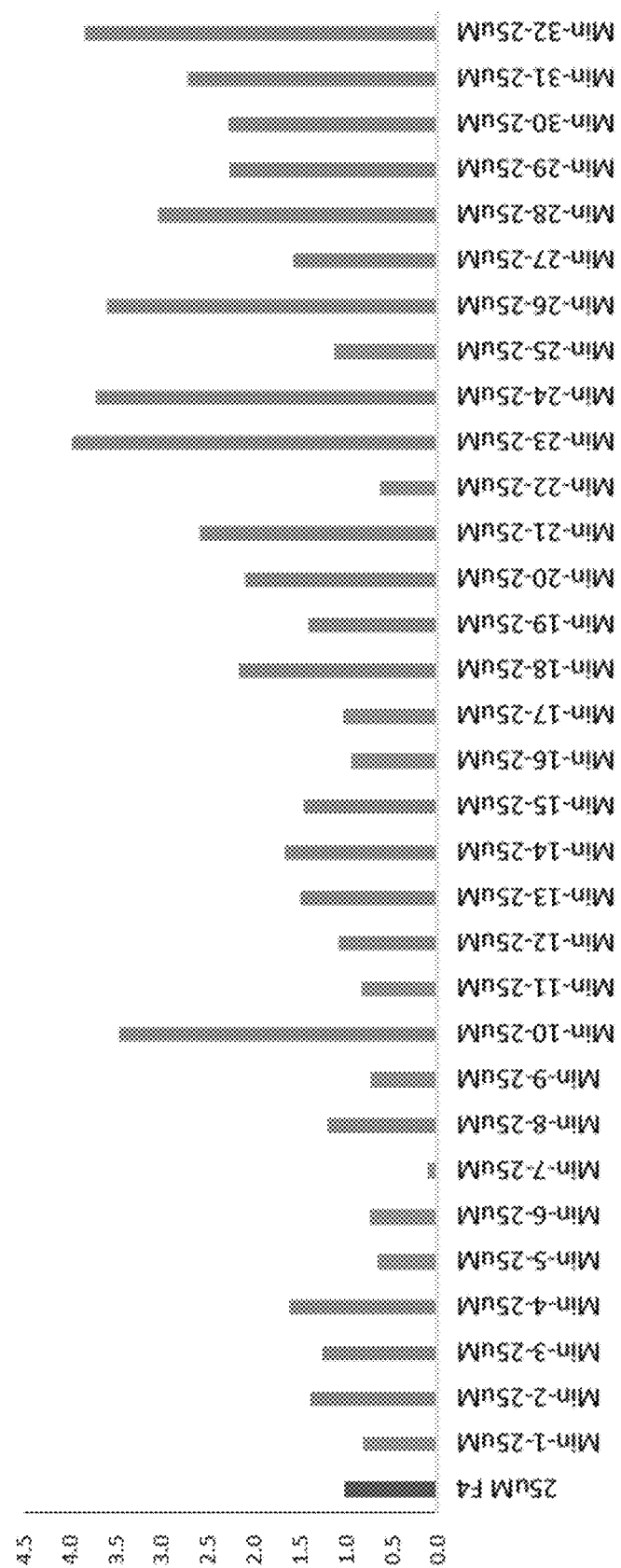
FIG. 2. Relative MYC E-box luciferase inhibitory activity of 32 compounds.

To test the compounds, we evaluated the in silico hits in a MYC E-Box luciferase reporter assay to measure the effects of these compounds (referred to as Min-1 to Min-32) on MYC transcriptional activity. As shown in FIG. 2, about 10 compounds have similar or better activity compared to positive control 10058-F4 at 25 µM. (See FIG. 2).

Figure 3:
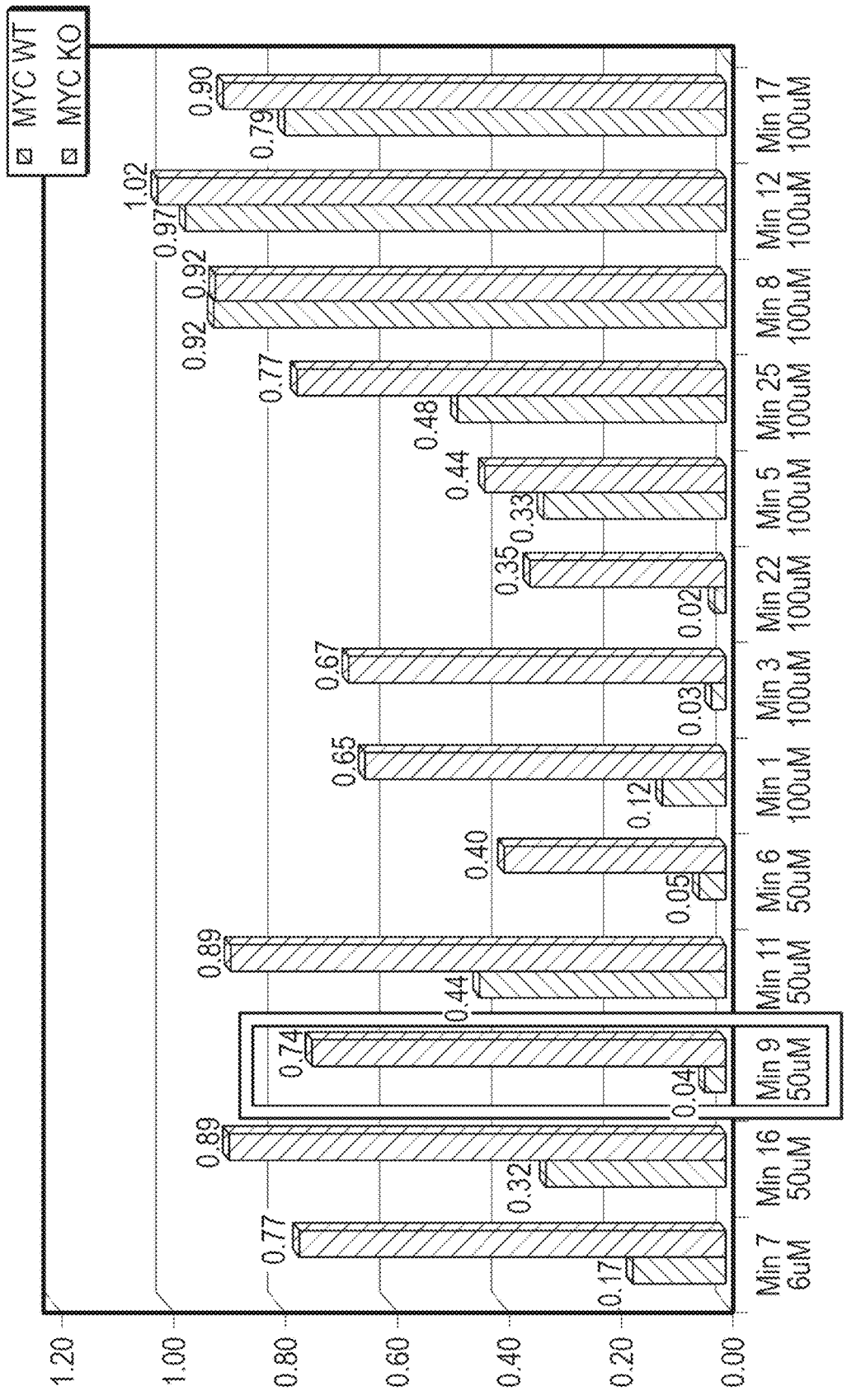
FIG. 3. Growth inhibition by selected hit compound on MYC WT and KO fibroblasts.

We next examined the ability of the compounds to selectively inhibit the proliferation of wild type cells expressing MYC relative to cells with MYC knockout. We tested the top 13 active compounds in the first screen assay. FIG. 3 shows a graph of growth inhibition by each compound on the wild type and MYC knockout rat fibroblasts at the dose with the greatest selectivity. More than half of the tested compounds show better growth inhibitory effect on MYC WT compared to MYC KO cells. Min9-S7 (NUCC-0176248) is very promising because of its low effective concentration (6 µM) and high specificity. Min9-S9 (NUCC-0176250) also shows a great selectivity at an acceptable dosage (50 µM).

Figure 4:
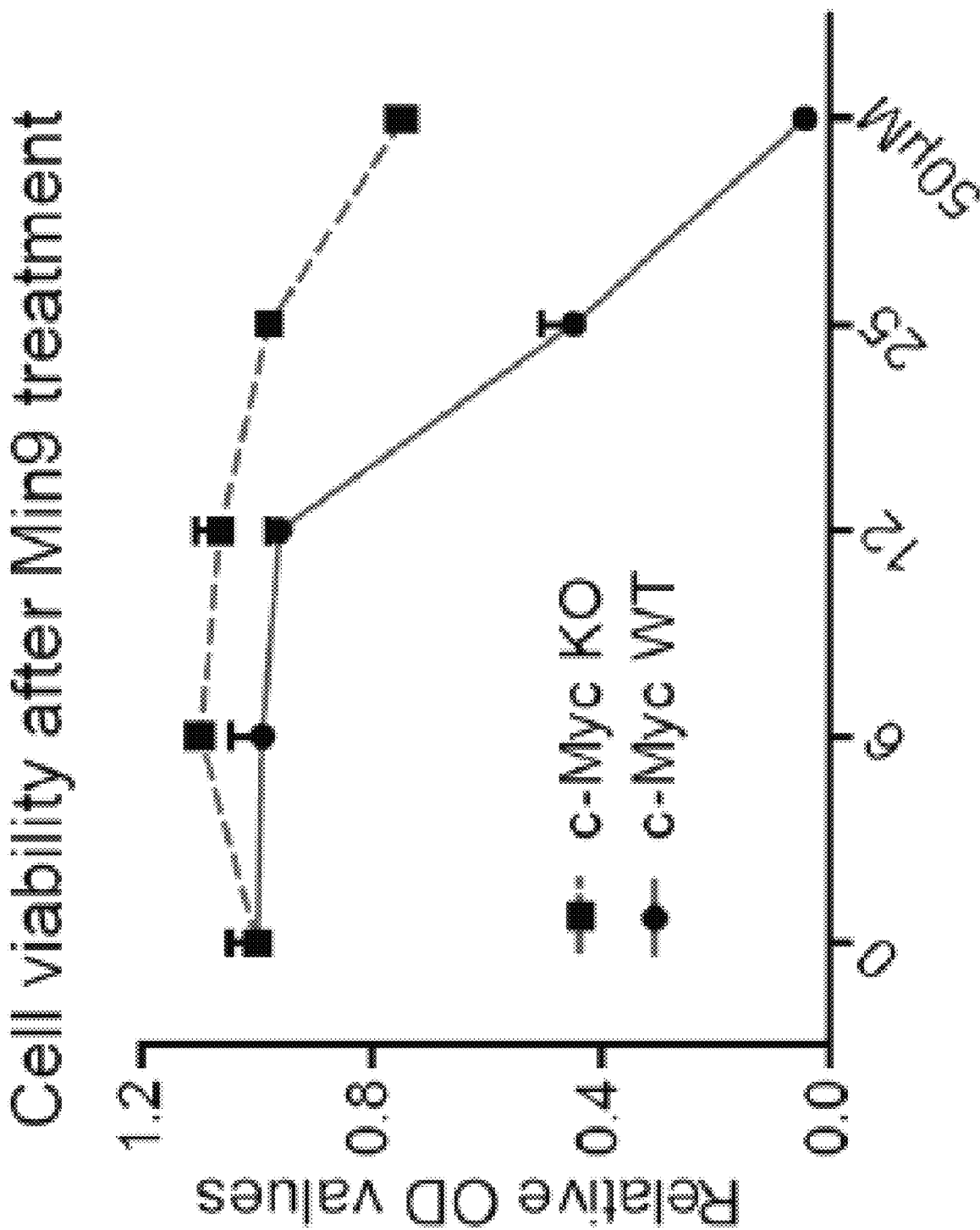
FIG. 4. Cell viability after treatment with Min9 (NUCC-0176234).

Min9 (NUCC-0176234) was also tested in a cell viability assay against a cMYC wild-type (WT) and a cMYC KO line. As shown in FIG. 4, this compound reduces cell viability much more in the WT line than the KO cells, indicating a mechanism directly related to cMYC.

Figure 5:
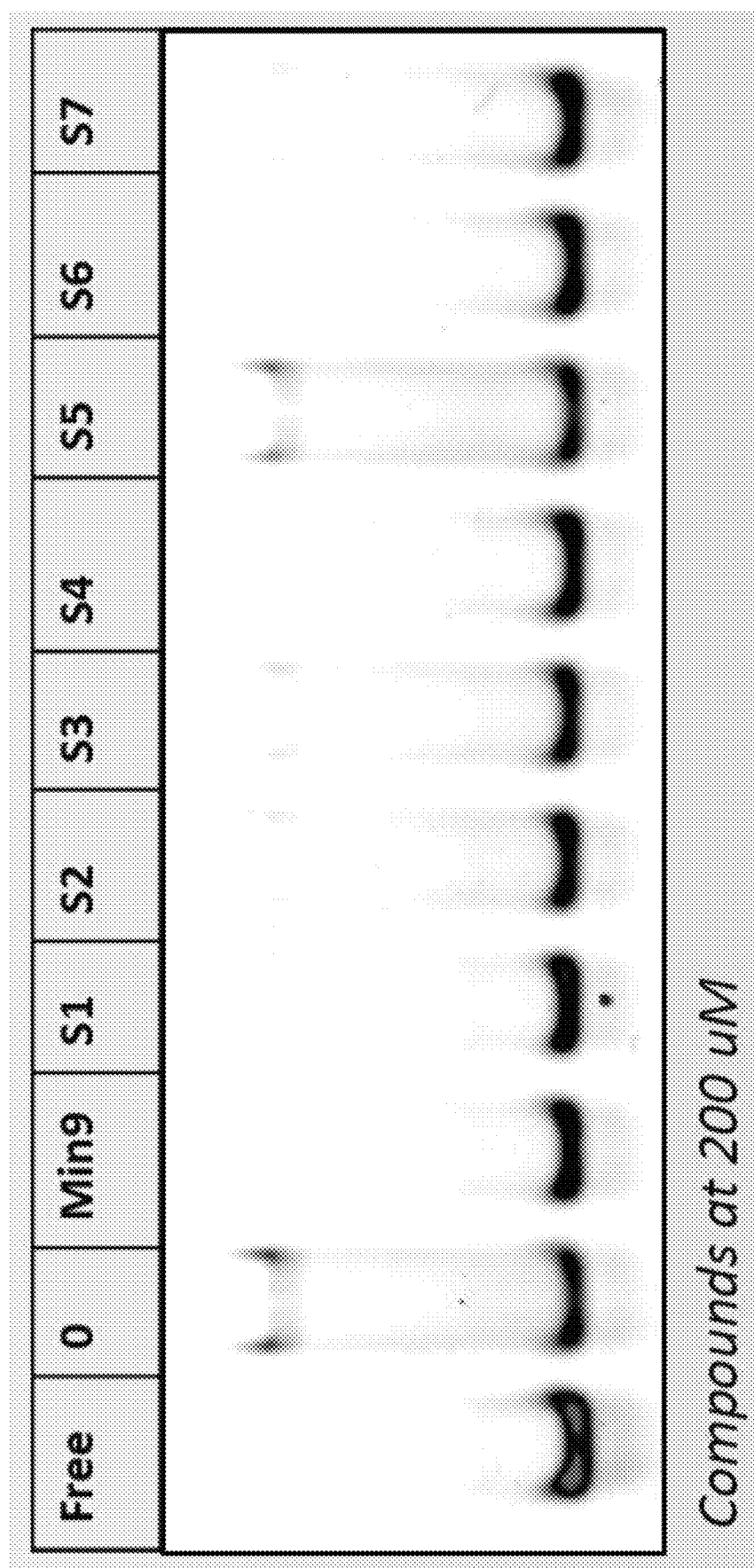
FIG. 5. Electrophoretic mobility shift assay (EMSA) in the presence of 200 μM test compounds.

We also tested our best hit compound Min9 (NUCC-0176234) and newly synthesized analogs for effects of these compounds on MYC/Max binding to DNA in electrophoretic mobility shift assays (EMSAs). (See FIG. 5a and FIG. 5b). We expected the active compounds to impair MYC/Max binding to DNA. Several strucutural analogs of Min9 were tested over multiple doses for inhibiting MYC-DNA binding and we observed a dose-dependent inhibition. (See FIG. 5c).

Figure 6:
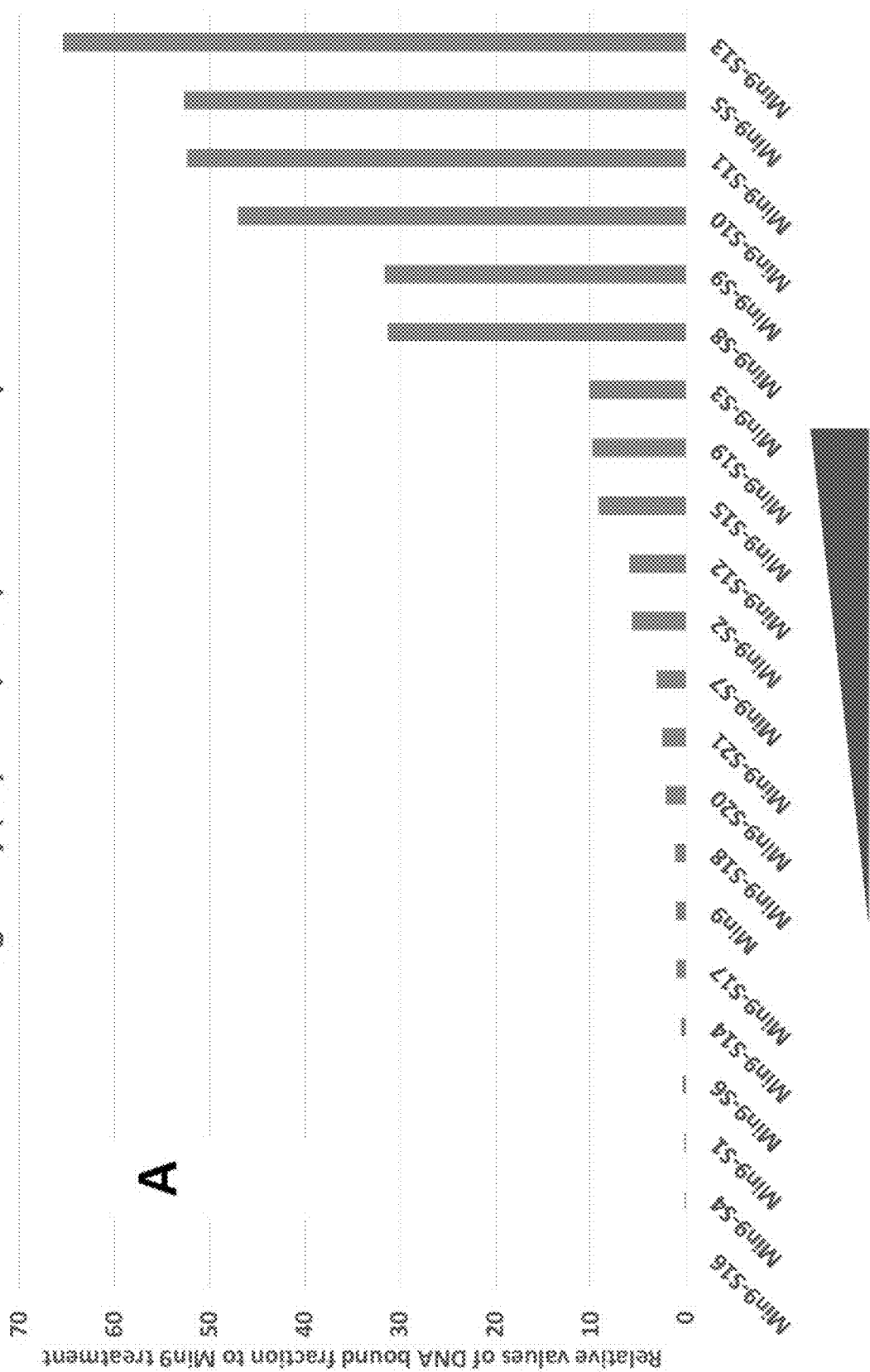
FIG. 6. (B) Relative values of DNA bound for test compounds at 200 μM.
Figure 7:
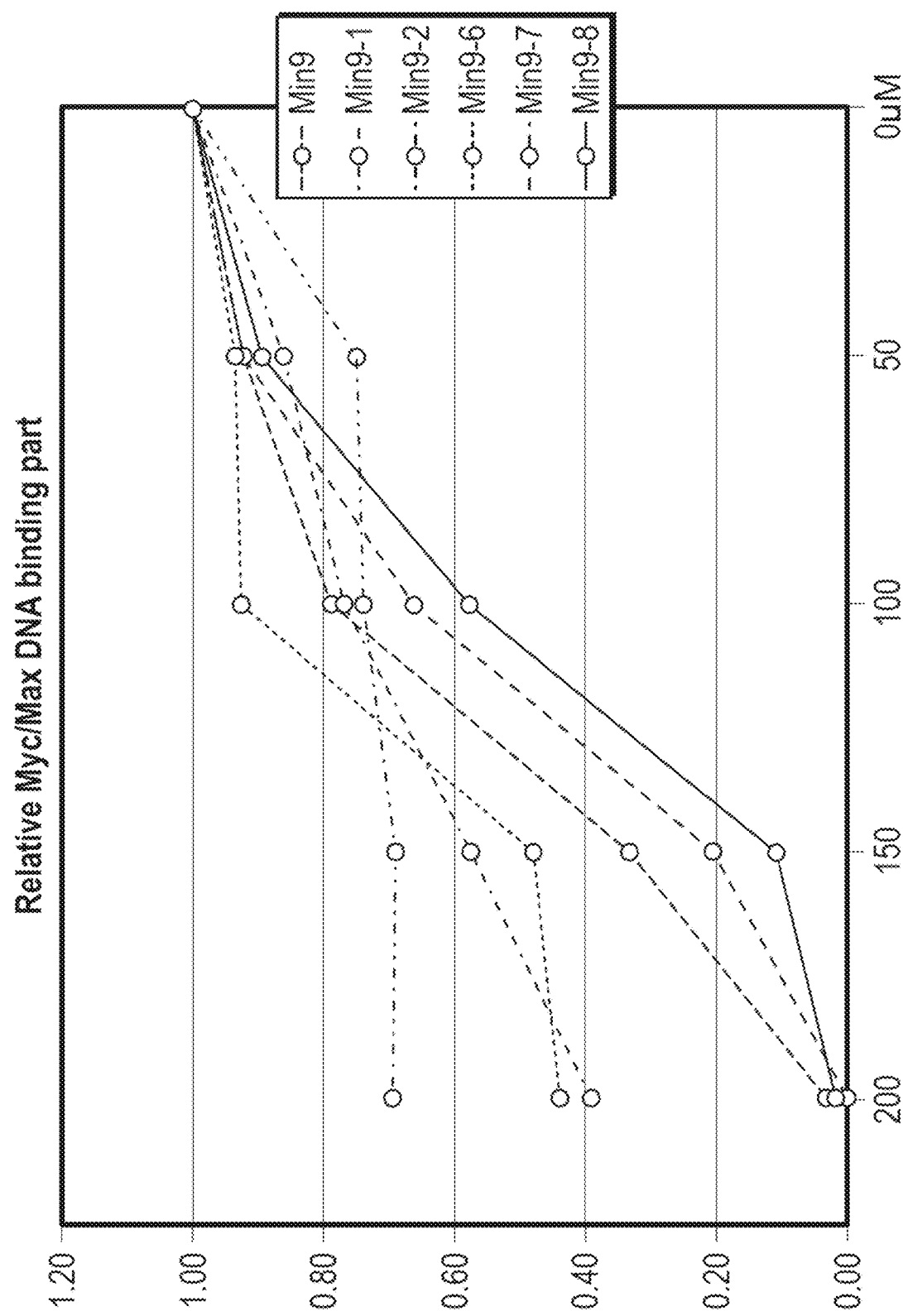
FIG. 7. (C) Relative MYC/Max DNA binding versus concentration of compound.
Figure 8:
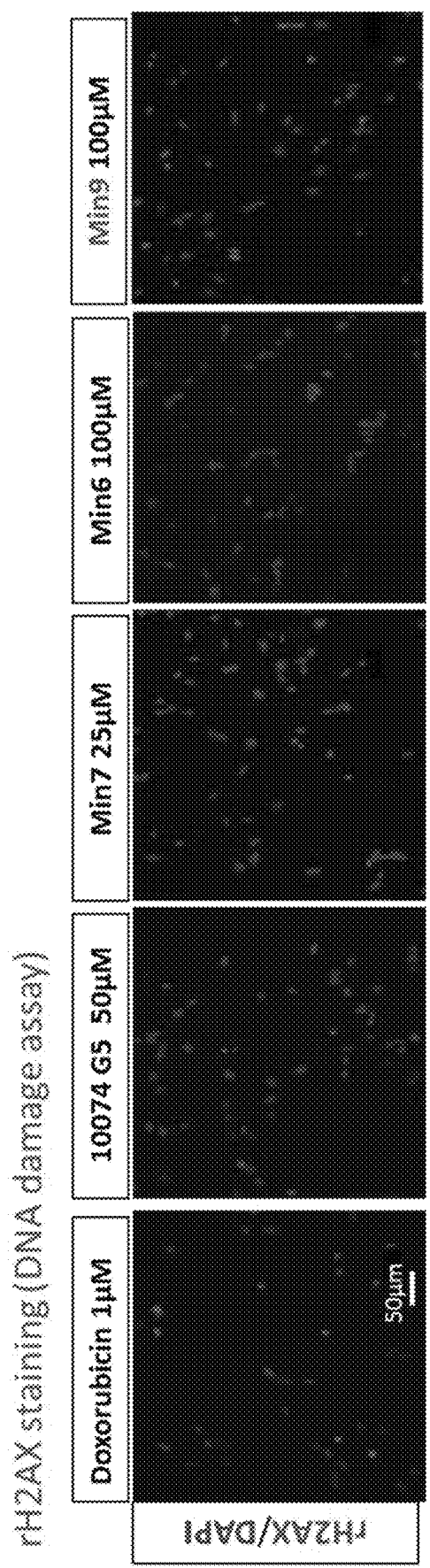
FIG. 8. rH2AX assay for DNA damage.

Min9 (NUCC-0176234) was also tested for its ability to cause DNA damage in an rH2AX staining assay. We would not expect cMYC-targeting agents to produce significant DNA damage. Compounds that act directly against DNA such as doxorubicin do however. We observed essentially no DNA damage caused by Min9 (NUCC-0176234). (See FIG. 6).

Figure 9:
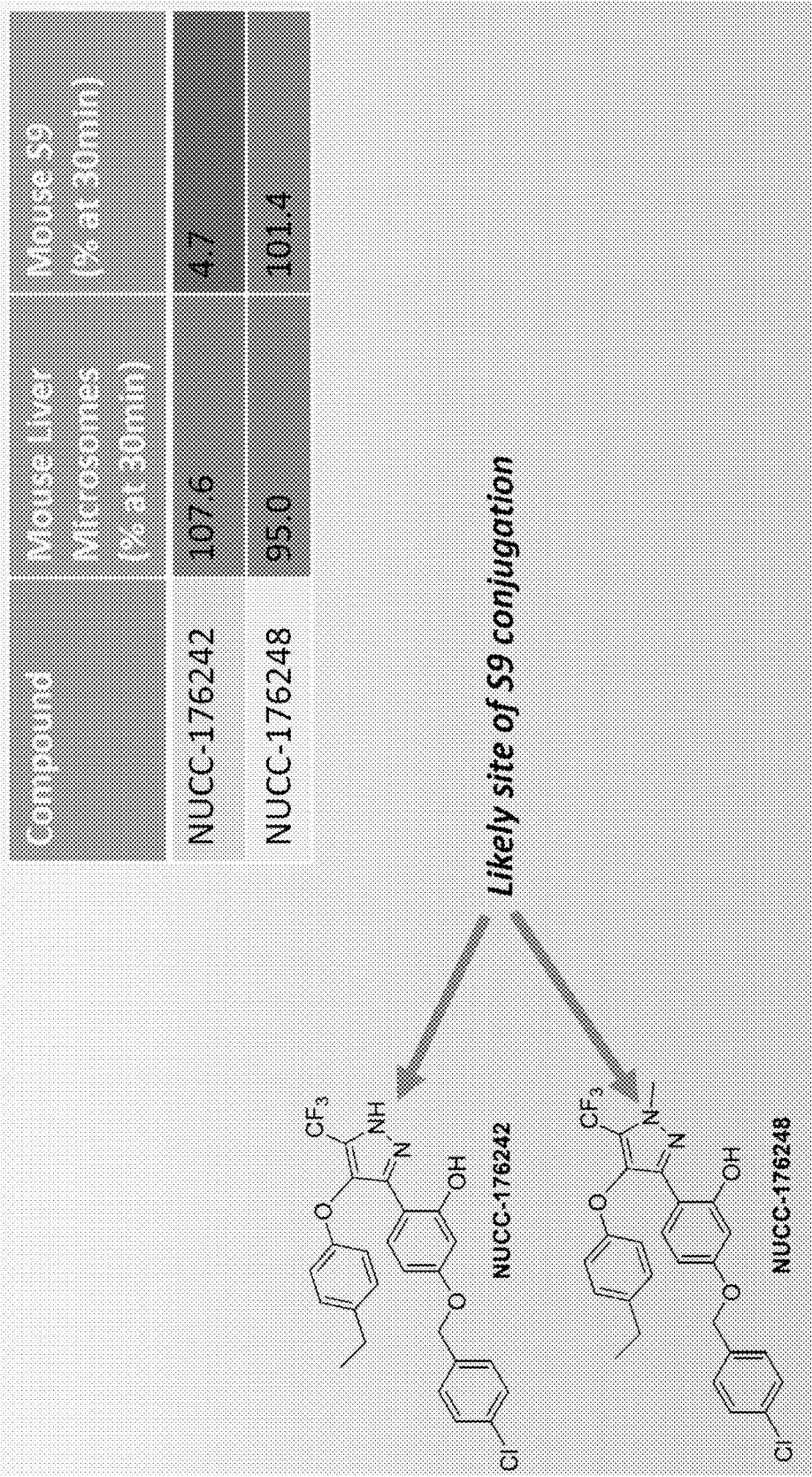
FIG. 9. In vitro metabolism of NUCC-176242 versus NUCC-176248.

In vitro metabolism of NUCC-176242 and NUCC-176248 were tested using mouse liver microsomes and a mouse S9 fraction. (See FIG. 9). NUCC-176242 was significantly metabolism by the mouse S9 fraction versus NUCC-176248 likely due to S9 conjugation at the N-1 nitrogen atom of the pyrazole ring.

Figure 10:
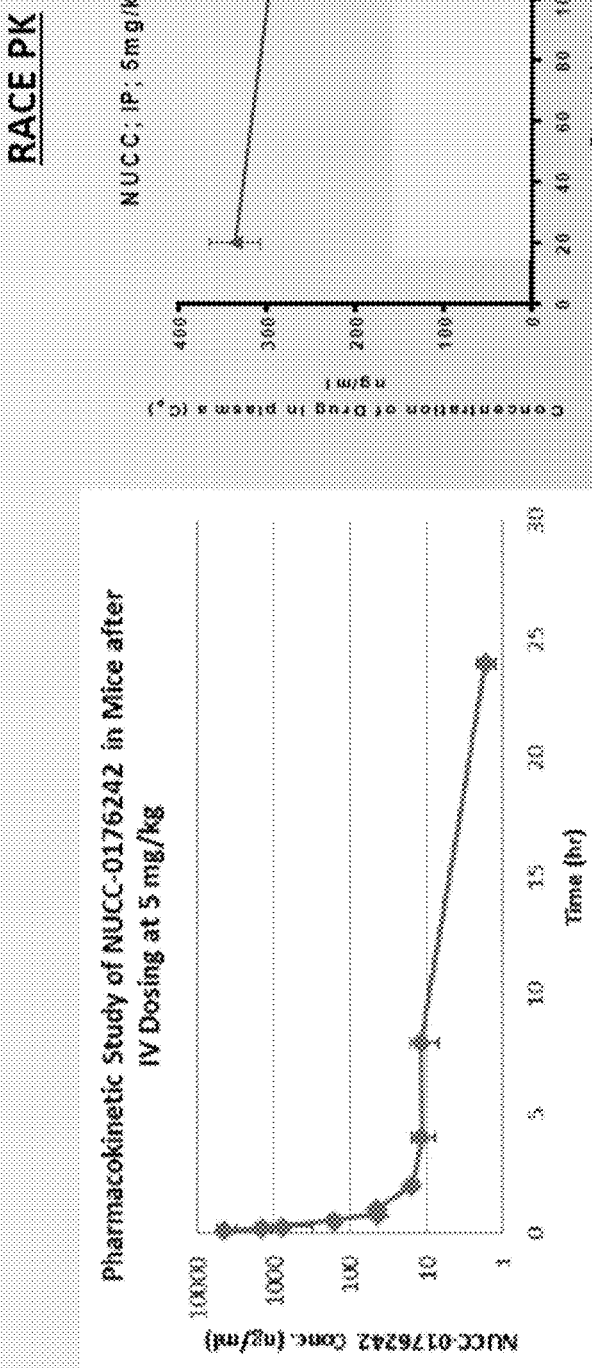
FIG. 10. Pharmacokinetic study of NUCC-176242 in mice after IV dosing at 5 mg/kg.

The pharmacokinetics of NUCC-176242 and NUCC-176248 were studied in mice by administering a dose of 5 mg/kg intravenously and measuring the plasma concentration versus time. (See FIG. 10). The observed in vivo metabolism of NUCC-176242 and NUCC-176248 correlated well with the observed in vitro metabolism tested above for of NUCC-176242 and NUCC-176248.

Chemistry

General Experimental

All chemical reagents were obtained from commercial suppliers and used without further purification unless otherwise stated. Anhydrous solvents were purchased from Sigma-Aldrich, and dried over 3 Å molecular sieves when necessary. DCM and THF were purified by passage through a bed of activated alumina. Normal-phase flash column chromatography was performed using Biotage KP-Sil 50 µm silica gel columns and ACS grade solvents on a Biotage Isolera flash purification system. Analytical thin layer chromatography (TLC) was performed on EM Reagent 0.25 mm silica gel 60 $F_{254}$ plates and visualized by UV light or iodine vapor. Liquid chromatography/mass spectrometry (LCMS) was performed on a Waters Acquity-H UPLC system with a 2.1 mm×50 mm, 1.7 µm, reversed phase BEH C18 column and LCMS grade solvents. A gradient elution from 95% water+0.1% formic acid/5% acetonitrile+0.1% formic acid to 95% acetonitrile+0.1% formic acid/5% water+0.1% formic acid over 2 min plus a further minute continuing this mixture at a flow rate of 0.85 mL/min was used as the eluent. Total ion current traces were obtained for electrospray positive and negative ionization (ESI+/ESI−). Proton ($^1$H) and carbon ($^{13}$C) NMR spectra were recorded on a Bruker Avance III w/direct cryoprobe spectrometer. Chemical shifts were reported in ppm (δ) and were referenced using residual non-deuterated solvent as an internal standard. The chemical shifts for $^1$H NMR and $^{13}$C NMR are reported to the second decimal place. Proton coupling constants are expressed in hertz (Hz). The following abbreviations were used to denote spin multiplicity for proton NMR: s=singlet, d=doublet, t=triplet, q=quartet, m=multiplet, brs=broad singlet, dd=doublet of doublets, dt=doublet of triplets, quin=quintet, tt=triplet of triplets. In some cases, overlapping signals occurred in the $^{13}$C NMR spectra.

Representative Examples for General Synthetic Method

A. Synthetic Method A

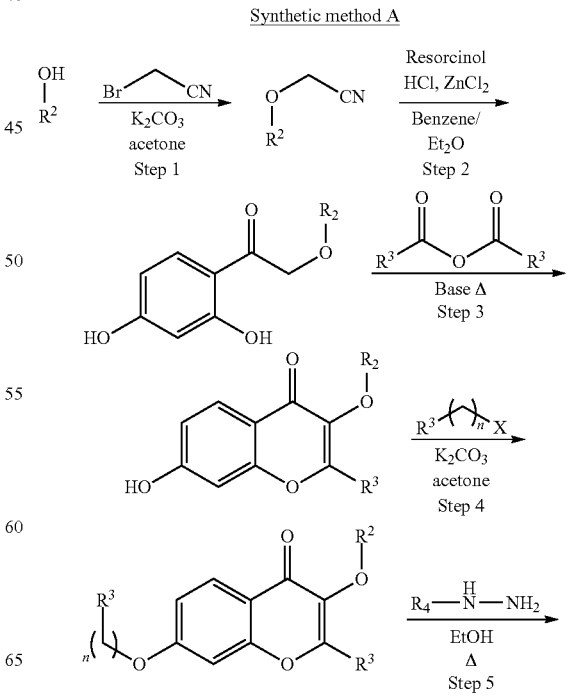

-continued

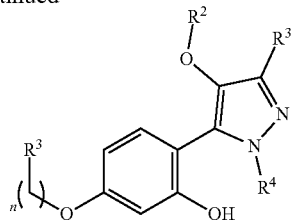

Step 1.

Over a solution of the phenol (1 equiv.), in 100 mL of acetone, bromoacetonitrile (1 equiv.) were added followed by potassium carbonate (1.5 equiv.) were added. Then, the solution stirred at 60° C. for 4.5 h. The reaction was quenched by adding 30 mL of NaHCO$_3$ aqueous solution and water, extracted with of EtOAc (3×30 mL). The combined organic layers were washed with brine and dried over anhydrous Na$_2$SO$_4$. Solvent was then removed under reduced pressure and the residue was purified by silica gel chromatography.

Step 2.

Over a cold ice-bath solution of the acetonitrile-phenoxy intermediate (1 equiv.) in 6.5 mL of benzene (1M solution), a HCL solution in dioxane (10 equiv.) was added dropwise. The resulting solution stirred for 1h before a resorcinol (1 equiv.) and ZnCl$_2$ (1 equiv.) in 10 mL of diethyl ether was added slowly. The resulting solution stirred from 0° C. to RT for 16 h. The resulting suspension was centrifuged and the solid was separated. The solid was washed with water and dried under vacuum.

Step 3.

A suspension of the 0-phenoxy-acetophenone (1 mmol) with TFFA (5 equiv) and pyridine (5 equiv.) was heated at 120° C. for 4h. Then, it was cool down to r.t. In some cases, product was precipitated, in others water was added and then extracted with EtOAc (3×10 mL). The combined organic layers were washed with brine, dried over Na$_2$SO$_4$, filtrated and concentrated. The residue was purified by silica gel chromatography.

Step 4.

A suspension of the phenoxy-chromenone, (1 equiv.), K$_2$CO$_3$ (2 equiv.) and the halo alkane (1.1 equiv.) in 5 mL of acetone (0.8 M) was heated at 60° C. for 16 h. The reaction was filtered through a funnel and the solvent removed under reduced pressure. The crude residue was triturated with water and dried under reduced pressure until dryness.

Step 5.

A solution of the previous phenoxy-chromenone (1 equiv.) with the desired hydrazine (3 equiv.) in 2 mL of EtOH (0.1M) was heated at 70° C. for 45 minutes. The solution was cooled down to room temperature and concentrated. The solid residue was directly purified by silica gel chromatography (n-hexanes/ethyl acetate=5:1 to 1:1) providing the desired pyrazole.

EXAMPLES

NUCC-200683: $^1$H NMR (500 MHz, CDCl$_3$) δ 7.81 (dd, J=7.9, 1.6 Hz, 1H), 7.18 (td, J=7.7, 1.6 Hz, 1H), 7.10-7.02 (m, 2H), 6.92-6.86 (m, 2H), 6.86-6.79 (m, 2H), 2.56 (q, J=7.6 Hz, 2H), 1.17 (t, J=7.6 Hz, 3H) ppm.

NUCC-198411: $^1$H NMR (500 MHz, CDCl$_3$) δ 7.00-6.92 (m, 3H), 6.80-6.68 (m, 2H), 6.44-6.38 (m, 1H), 6.32 (d, J=8.4 Hz, 1H), 2.52 (q, J=7.8 Hz, 2H), 1.13 (t, J=7.4 Hz, 3H) ppm.

NUCC-198406: $^1$H NMR (500 MHz, CDCl$_3$) δ 7.64 (d, J=8.6 Hz, 1H), 7.06 (d, J=8.6 Hz, 2H), 6.82 (d, J=8.6 Hz, 2H), 6.41 (d, J=2.4 Hz, 1H), 6.33 (dd, J=8.6, 2.4 Hz, 1H), 2.56 (q, J=7.5 Hz, 2H), 1.17 (t, J=7.7 Hz, 3H) ppm.

NUCC-196355: $^1$H NMR (500 MHz, CDCl$_3$) δ 7.69 (d, J=8.7 Hz, 1H), 7.47 (d, J=2.0 Hz, 1H), 7.42 (d, J=8.3 Hz, 1H), 7.19 (dd, J=8.3, 2.0 Hz, 1H), 7.07 (d, J=8.7 Hz, 2H), 6.86-6.76 (m, 2H), 6.48 (d, J=13.3 Hz, 2H), 4.95 (s, 2H), 2.57 (q, J=7.6 Hz, 2H), 1.18 (t, J=7.6 Hz, 3H) ppm.

NUCC-196342: $^1$H NMR (500 MHz, CDCl$_3$) δ 7.69 (d, J=8.8 Hz, 1H), 7.43 (dd, J=7.7, 1.5 Hz, 1H), 7.35-7.27 (m, 4H), 7.06 (ddd, J=8.3, 7.7, 1.6 Hz, 1H), 6.96 (td, J=7.6, 1.4 Hz, 1H), 6.65 (dd, J=8.3, 1.5 Hz, 1H), 6.50 (d, J=14.5 Hz, 2H), 4.97 (s, 2H) ppm.

NUCC-196295: $^1$H NMR (400 MHz, CDCl$_3$) δ 7.70 (d, J=8.7 Hz, 1H), 7.37 (s, 1H), 7.28 (dd, J=5.4, 1.2 Hz, 2H), 7.07 (d, J=8.7 Hz, 2H), 6.86-6.79 (m, 2H), 6.50 (s, 2H), 4.98 (s, 2H), 2.57 (q, J=7.6 Hz, 1H), 1.18 (t, J=7.6 Hz, 2H) ppm.

B. Synthetic Method B

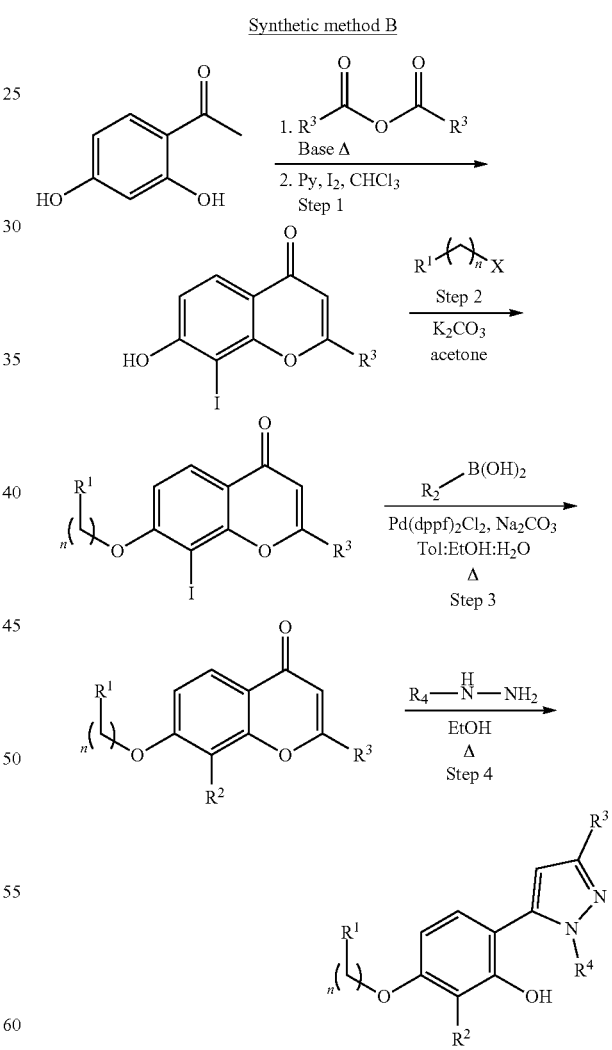

Synthetic method B

Step 1.

Over a suspension of 1-(2,4-dihydroxyphenyl)ethan-1-one (5.00 g, 32.89 mmol, 1 equiv.) in trifluoroacetic anhydride (18.50 mL, 131.56 mmol, 4 equiv.) placed in a high-pressure tube, sodium 2,2,2-trifluoroacetate (9.84 g, 72.36 mmol, 2.2 equiv.) was added and the system was capped and stirred at 110° C. for 24 h. The reaction was allowed to cool down to approximately 70° C. and then was diluted with 200 mL of EtOAc. The mixture was neutralized by adding saturated aqueous $K_2CO_3$ solution until no more bubbling was observed. Layers were separated and the aqueous phase was extracted with more EtOAc (3×150 mL). The combined organic layers were washed with brine and dried over anhydrous $Na_2SO_4$. The solution was then concentrated to 100-150 mL of EtOAc. Then the flask was capped and kept at room temperature for 1-2 days, obtaining a solid which was filtrated and dried under vacuum to obtain 4.09 g of pure 1 as a white solid in 54% yield.

Then, over a solution of the solid obtained (4 g, 17.31 mmol, 1 equiv.) and iodine (17.57 g, 69.24 mmol, 4 equiv.) in 110 mL of $CHCl_3$, pyridine (5.59 mL, 69.24 mmol, 4 equiv.) were added. The resulting solution was stirred at room temperature for 16 h. Then, 120 mL of saturated aqueous $Na_2S_2O_3$ were added and the resulting mixture stirred for one hour. The organic layer was separated and the aqueous phase was extracted with $CH_2Cl_2$ (3×100 mL). The combined organic layers were washed with brine and dried over anhydrous $Na_2SO_4$. Solvent was then removed under reduced pressure and the residue was triturated with diethyl ether several times to obtain a pale white solid in 90% yield (5.55 g, 15.60 mmol): mp 205-206° C. $^1$H NMR (500 MHz, $CDCl_3$) δ 8.11 (dd, J=8.9, 1.0 Hz, 1H), 7.15 (dd, J=8.9, 1.0 Hz, 1H), 6.77-6.69 (m, 1H), 6.36 (s, 1H) ppm. $^{13}$C NMR (126 MHz, $CDCl_3$) δ 175.8, 161.5, 156.0, 152.5 (q, $^2J$=39.1 Hz), 128.1, 119.0, 118.6 (q, $^1J$=272.2 Hz), 117.5, 114.7, 110.9 ppm. LRMS (EI): mass calc for $C_{10}H_5F_3IO_3^+$ [M+H]$^+$=356.9, found=357.1.

Step 2.

A suspension of 7-hydroxy-3-iodo-2-(trifluoromethyl)-4H-chromen-4-one, (1 g, 2.8 mmol, 1 equiv.), the haloalkane (3.4 mmol, 1.2 equiv.) and $K_2CO_3$ (0.77 g, 5.6 mmol, 2 equiv.) in 5 mL of acetone was heated at 60° C. for 16 h. The reaction was filtered through a funnel and the solvent removed under reduced pressure. The crude residue was triturated with water and dried under reduced pressure until dryness.

Step 3.

A suspension of the previous alkylated chromenone (0.34 mmol, 1 equiv.), with the corresponding boronic acid (0.37 mmol, 1.1 equiv.), $Na_2CO_3$ (0.68 mmol, 2 equiv.) and Pd(dppf)$Cl_2$ (0.026 mmol, 0.08 equiv.) in 3.5 mL of a mixture 1:2:6 of EtOH:water:toluene was bubbled with nitrogen gas for 10 minutes. Then, the flask was capped, and the mixture was heated at 90° C. for 2 h. The dark solution was cool down to room temperature and diluted with EtOAc. The organic layer was separated and the aqueous phase was extracted with EtOAc (3×3 mL). The combined organic layers were washed with brine and dried over anhydrous $Na_2SO_4$. Solvent was then removed under reduced pressure and the residue was purified by silica gel chromatography.

Step 4.

A solution of the previous chromenone (0.2 mmol, 1 equiv.) with the desired hydrazine (0.6 mmol, 3 equiv.) in 2 mL of EtOH was heated at 70° C. for 45 minutes. The solution was cooled down to room temperature and concentrated. The solid residue was directly purified by silica gel chromatography (n-hexanes/ethyl acetate=5:1 to 1:1) providing the desired pyrazole.

EXAMPLES

NUCC-201634: $^1$H NMR (500 MHz, $CDCl_3$) δ 7.75 (d, J=2.2 Hz, 1H), 7.58 (dd, J=15.0, 8.5 Hz, 2H), 7.52 (dd, J=8.5, 2.2 Hz, 1H), 6.87 (s, 1H), 6.65 (d, J=8.8 Hz, 1H), 3.97 (t, J=6.5 Hz, 2H), 1.63-1.47 (m, 5H), 0.84 (d, J=6.5 Hz, 6H) ppm.

NUCC-201632: $^1$H NMR (500 MHz, MeOH-d$_4$) δ 8.82 (d, J=2.1 Hz, 1H), 8.77 (d, J=2.1 Hz, 1H), 8.13 (t, J=2.1 Hz, 1H), 7.33-7.25 (m, 2H), 7.23 (d, J=8.6 Hz, 1H), 7.20-7.14 (m, 2H), 6.77 (d, J=8.6 Hz, 1H), 6.56 (s, 1H), 5.08 (s, 2H), 3.80 (s, 3H) ppm.

NUCC-201227: $^1$H NMR (500 MHz, $CDCl_3$) δ 10.59 (s, 1H), 7.80 (d, J=2.1 Hz, 1H), 7.57 (dd, J=8.2, 2.1 Hz, 1H), 7.51 (d, J=8.2 Hz, 1H), 7.47 (d, J=8.7 Hz, 1H), 6.90 (s, 1H), 6.58 (d, J=8.7 Hz, 1H), 3.97 (s, 3H), 3.94 (t, J=6.3 Hz, 2H), 1.61 (dq, J=7.9, 6.4 Hz, 2H), 1.33 (h, J=7.5 Hz, 2H), 0.87 (t, J=7.4 Hz, 3H) ppm.

NUCC-201226: $^1$H NMR (500 MHz, $CDCl_3$) δ 7.75 (d, J=2.1 Hz, 1H), 7.59 (d, J=8.3 Hz, 1H), 7.50 (dd, J=8.3, 2.1 Hz, 1H), 7.18 (d, J=8.5 Hz, 1H), 6.66 (d, J=8.5 Hz, 1H), 6.54 (s, 1H), 3.96 (t, J=6.3 Hz, 2H), 3.82 (s, 3H), 1.68-1.58 (m, 2H), 1.36-1.29 (m, 2H), 0.87 (t, J=7.4 Hz, 3H) ppm.

NUCC-0201213: $^1$H NMR (500 MHz, $CDCl_3$) δ 8.81 (dd, J=20.5, 2.0 Hz, 2H), 8.03 (d, J=1.9 Hz, 1H), 7.29-7.15 (m, 3H), 6.70 (d, J=8.6 Hz, 1H), 6.59 (s, 1H), 5.50 (s, 1H), 4.13-3.71 (m, 5H), 1.78-1.31 (m, 5H), 0.87 (d, J=6.3 Hz, 7H) ppm.

NUCC-201208: $^1$H NMR (500 MHz, $CDCl_3$) δ 8.83 (d, J=2.1 Hz, 1H), 8.79 (d, J=2.1 Hz, 1H), 8.04 (t, J=2.1 Hz, 1H), 7.21 (d, J=8.7 Hz, 1H), 6.70 (d, J=8.7 Hz, 1H), 6.59 (s, 1H), 4.01 (t, J=6.4 Hz, 2H), 3.83 (s, 3H), 1.71-1.43 (m, 3H), 0.87 (d, J=6.4 Hz, 6H) ppm.

NUCC-0201207: $^1$H NMR (500 MHz, $CDCl_3$) δ 8.93-8.66 (m, 2H), 8.04 (d, J=2.1 Hz, 1H), 7.34-7.12 (m, 2H), 6.82-6.45 (m, 3H), 5.85 (s, 1H), 4.10-3.71 (m, 7H), 1.65 (q, J=6.8 Hz, 3H), 1.40-1.01 (m, 9H), 1.01-0.58 (m, 4H) ppm.

NUCC-201206: $^1$H NMR (500 MHz, $CDCl_3$) δ 8.82 (s, 2H), 8.01 (d, J=2.3 Hz, 1H), 7.21 (d, J=8.6 Hz, 1H), 6.70 (d, J=8.6 Hz, 1H), 6.58 (s, 1H), 4.00 (t, J=6.3 Hz, 2H), 3.84 (s, 3H), 1.65-1.53 (m, 3H), 0.84 (dd, J=6.5, 2.6 Hz, 6H) ppm.

NUCC-0201205: $^1$H NMR (500 MHz, $CDCl_3$) δ 8.74 (d, J=43.1 Hz, 2H), 8.04 (s, 1H), 7.30-7.14 (m, 2H), 6.74-6.48 (m, 2H), 3.96 (t, J=6.1 Hz, 3H), 3.83 (d, J=3.6 Hz, 2H), 1.62 (q, J=6.7 Hz, 3H), 1.38-1.06 (m, 8H), 0.82 (t, J=6.8 Hz, 4H) ppm.

NUCC-0201204: $^1$H NMR (500 MHz, $CDCl_3$) δ 8.84-8.61 (m, 2H), 8.04 (s, 1H), 7.31-7.14 (m, 1H), 6.67 (d, J=8.6 Hz, 1H), 6.56 (s, 1H), 3.97 (t, J=6.2 Hz, 2H), 3.83 (s, 2H), 1.69-1.54 (m, 2H), 1.30 (q, J=7.5 Hz, 2H), 0.85 (t, J=7.5 Hz, 3H) ppm.

NUCC-0201201: 1H NMR (500 MHz, $CDCl_3$) δ 8.05-7.74 (m, 5H), 7.57 (d, J=8.8 Hz, 1H), 7.09-6.85 (m, 4H), 6.75 (d, J=8.7 Hz, 1H), 6.59 (d, J=8.1 Hz, 3H), 4.95 (s, 2H), 2.90 (d, J=37.0 Hz, 2H) ppm.

NUCC-0201198: $^1$H NMR (500 MHz, $CDCl_3$) δ 10.79 (s, 1H), 7.89 (d, J=40.7 Hz, 3H), 7.57 (d, J=8.7 Hz, 1H), 6.92 (s, 1H), 6.64 (d, J=8.8 Hz, 1H), 3.95 (t, J=6.2 Hz, 2H), 1.77-1.49 (m, 2H), 1.46-1.06 (m, 7H), 0.81 (t, J=6.8 Hz, 3H) ppm.

NUCC-0201197: $^1$H NMR (500 MHz, $CDCl_3$) δ 8.08-7.75 (m, 1H), 3.92 (t, J=6.3 Hz, 1H), 1.65 (q, J=6.8 Hz, 1H), 0.87 (t, J=7.4 Hz, 1H) ppm.

NUCC-0201196: $^1$H NMR (500 MHz, Chloroform-d) δ 10.76 (s, 1H), 7.88 (d, J=35.4 Hz, 3H), 7.57 (d, J=8.7 Hz, 1H), 6.91 (s, 1H), 6.65 (d, J=8.7 Hz, 1H), 3.98 (t, J=6.3 Hz, 2H), 1.54 (dq, J=37.9, 6.7 Hz, 3H), 0.83 (d, J=6.5 Hz, 7H) ppm.

NUCC-0201195: $^1$H NMR (500 MHz, $CDCl_3$) δ 11.63 (s, 1H), 8.96 (s, 1H), 8.77 (s, 1H), 8.12 (s, 1H), 7.57 (d, J=8.7

Hz, 1H), 6.95 (s, 1H), 6.63 (d, J=8.7 Hz, 1H), 4.00 (t, J=6.5 Hz, 2H), 1.59 (ddt, J=32.4, 13.3, 6.6 Hz, 6H), 0.87 (d, J=6.4 Hz, 7H) ppm.

NUCC-0201193: $^1$H NMR (500 MHz, CDCl$_3$) δ 11.25 (s, 1H), 8.93 (d, J=2.1 Hz, 1H), 8.78 (d, J=2.0 Hz, 1H), 8.11 (d, J=2.1 Hz, 1H), 7.57 (d, J=8.8 Hz, 1H), 6.96 (s, 1H), 6.63 (d, J=8.7 Hz, 1H), 3.98 (t, J=6.4 Hz, 2H), 1.81-1.45 (m, 7H), 1.32 (p, J=7.4 Hz, 2H), 0.89 (t, J=7.4 Hz, 4H) ppm.

NUCC-0201192: $^1$H NMR (500 MHz, CDCl$_3$) δ 11.64 (s, 2H), 8.87 (d, J=77.5 Hz, 2H), 8.10 (s, 1H), 7.57 (d, J=8.7 Hz, 1H), 6.94 (s, 1H), 6.63 (d, J=8.7 Hz, 1H), 3.96 (t, J=6.3 Hz, 1H), 1.82-1.40 (m, 10H), 1.40-1.07 (m, 7H), 0.83 (t, J=6.7 Hz, 3H) ppm.

NUCC-0201039: $^1$H NMR (500 MHz, MeOH-d$_4$) δ 8.50 (s, 1H), 7.83 (d, J=2.6 Hz, 1H), 7.67 (d, J=8.5 Hz, 1H), 7.38-7.24 (m, 2H), 7.19 (d, J=8.1 Hz, 2H), 7.04-6.91 (m, 1H), 6.79 (d, J=8.7 Hz, 1H), 5.22-4.99 (m, 2H), 4.41 (dd, J=11.3, 6.9 Hz, 2H), 2.05 (s, 2H), 1.26 (t, J=7.0 Hz, 3H) ppm; $^{13}$C NMR (126 MHz, MeOD) δ 157.2, 135.8, 133.1, 128.6, 128.1, 127.9, 125.3, 101.3, 101.3, 69.1, 62.4, 13.3 ppm.

NUCC-0201037: $^1$H NMR (500 MHz, CDCl$_3$) δ 8.70 (d, J=48.4 Hz, 2H), 8.01 (s, 1H), 7.56-7.38 (m, 1H), 7.17 (td, J=5.1, 2.3 Hz, 2H), 7.04 (dd, J=8.1, 3.8 Hz, 2H), 6.80 (s, 1H), 6.67-6.55 (m, 1H), 4.94 (d, J=4.0 Hz, 2H) ppm.

NUCC-0201036: $^1$H NMR (500 MHz, MeOH-d$_4$) δ 6.49 (d, J=1.8 Hz, 1H), 6.42 (d, J=7.7 Hz, 1H), 6.29-6.09 (m, 3H), 5.83-5.65 (m, 4H), 5.47 (s, 1H), 5.32 (d, J=8.7 Hz, 1H), 3.52 (s, 2H), 3.35 (s, 7H), 1.81 (s, 1H), 1.54 (s, 3H); $^{13}$C NMR (126 MHz, Methanol-d$_4$) δ 161.71, 155.20, 134.93, 134.06, 131.66, 128.50, 126.96, 126.72, 126.63, 99.87, 67.78, 41.46 ppm.

NUCC-0201031: $^1$H NMR (500 MHz, CDCl$_3$) δ 7.89 (d, J=5.8 Hz, 2H), 7.76 (d, J=5.6 Hz, 1H), 7.64-7.36 (m, 1H), 6.82 (d, J=5.9 Hz, 1H), 6.56 (dd, J=10.6, 4.7 Hz, 1H), 3.85 (q, J=6.1, 4.7 Hz, 2H), 3.24 (s, 2H), 1.59 (p, J=6.8 Hz, 2H), 0.99-0.65 (m, 3H); $^{13}$C NMR (126 MHz, CDCl$_3$) δ 157.1, 135.8, 131.7, 127.9, 124.6, 122.5, 120.5, 109.9, 103.9, 100.9, 70.04, 49.6, 49.4, 49.2, 49.1, 48.9, 48.7, 48.57, 22.3, 10.2 ppm.

NUCC-0201027: $^1$H NMR (500 MHz, CDCl$_3$) δ 7.88 (d, J=5.1 Hz, 3H), 7.55 (d, J=8.6 Hz, 1H), 7.35-7.16 (m, 1H), 7.03-6.80 (m, 3H), 6.80-6.66 (m, 2H), 6.61 (d, J=8.7 Hz, 1H), 4.11 (t, J=6.5 Hz, 2H), 3.74 (d, J=1.5 Hz, 3H), 2.84 (t, J=6.6 Hz, 2H) ppm; $^{13}$C NMR (126 MHz, CDCl$_3$) δ 158.2, 157.1, 131.6, 129.8, 129.7, 128.2, 124.5, 122.4, 115.6, 113.7, 109.3, 101.5, 69.7, 55.2, 34.6 ppm.

NUCC-0201025: $^1$H NMR (500 MHz, CDCl$_3$) δ 8.00 (d, J=39.3 Hz, 3H), 7.43-7.29 (m, 1H), 7.29-7.14 (m, 2H), 7.04-6.93 (m, 2H), 6.86-6.75 (m, 1H), 6.70 (s, 1H), 5.28 (s, 1H), 4.28 (t, J=6.6 Hz, 2H), 3.94 (s, 2H), 3.01 (q, J=6.6 Hz, 2H) ppm; $^{13}$C NMR (126 MHz, CDCl$_3$) δ 157.8, 156.9, 151.4, 142.1, 141.8, 139.5, 136.3, 136.2, 134.7, 132.4, 132.3, 132.04, 131.7, 131.5, 131.4, 131.2, 130.1, 130.05, 128.4, 128.4, 128.1, 126.6, 124.4, 122.3, 122.2, 121.5, 121.5, 121.5, 120.05, 115.7, 115.4, 109.5, 109.3, 105.4, 104.7, 104.2, 101.6, 69.3, 69.1, 37.7, 34.9, 34.8 ppm.

NUCC-200736: $^1$H NMR (500 MHz, CDCl$_3$) δ 7.82 (d, J=1.8 Hz, 1H), 7.63 (dd, J=8.0, 1.8 Hz, 1H), 7.47 (d, J=8.0 Hz, 1H), 7.28-7.20 (m, 3H), 7.11 (dd, J=8.5, 3.5 Hz, 2H), 6.68 (d, J=8.5 Hz, 1H), 6.55 (s, 1H), 5.04 (d, J=2.6 Hz, 2H), 3.81 (s, 3H) ppm.

NUCC-200723: $^1$H NMR (500 MHz, CDCl$_3$) δ 13.15 (s, 1H), 7.96-7.81 (m, 1H), 7.72 (d, J=8.9 Hz, 1H), 7.13 (d, J=8.5 Hz, 1H), 6.66 (d, J=8.5 Hz, 1H), 6.59 (d, J=8.7 Hz, 1H), 6.52 (d, J=8.9 Hz, 1H), 3.84 (s, 3H) ppm.

NUCC-200576: $^1$H NMR (500 MHz, MeOH-d$_4$) δ 7.49-7.44 (m, 2H), 7.42-7.37 (m, 2H), 7.34-7.30 (m, 1H), 7.30-7.24 (m, 1H), 7.13 (d, J=8.4 Hz, 1H), 7.05 (s, 1H), 6.91 (d, J=2.3 Hz, 2H), 5.07 (s, 2H), 4.95 (s, 1H) ppm.

NUCC-200495: $^1$H NMR (500 MHz, CDCl$_3$) δ 7.96 (d, J=1.7 Hz, 2H), 7.90 (s, 1H), 7.50 (d, J=8.6 Hz, 1H), 6.97-6.90 (m, 2H), 6.60 (d, J=8.6 Hz, 1H) ppm.

NUCC-198407: $^1$H NMR (500 MHz, CDCl$_3$) δ 7.45-7.33 (m, 4H), 7.13 (d, J=8.5 Hz, 1H), 6.59 (d, J=8.6 Hz, 1H), 6.48 (s, 1H), 5.15 (s, 2H), 3.79 (s, 3H) ppm.

NUCC-198399: $^1$H NMR (500 MHz, CDCl$_3$) δ 7.79-7.72 (m, 2H), 7.68 (dt, J=7.8, 1.4 Hz, 1H), 7.66-7.59 (m, 1H), 7.35-7.32 (m, 2H), 7.24 (d, J=8.6 Hz, 1H), 7.17 (t, J=6.9 Hz, 2H), 6.74 (t, J=5.7 Hz, 1H), 6.59 (s, 1H), 5.07 (s, 2H), 3.87 (s, 3H) ppm.

NUCC-198398: $^1$H NMR (500 MHz, CDCl$_3$) δ 7.78 (s, 1H), 7.75-7.66 (m, 2H), 7.61 (t, J=8.5 Hz, 2H), 7.32 (d, J=8.5 Hz, 2H), 7.13 (t, J=12.8 Hz, 2H), 6.93 (s, 1H), 6.72 (d, J=8.8 Hz, 2H), 5.06 (s, 2H) ppm.

NUCC-198394: $^1$H NMR (500 MHz, CDCl$_3$) δ 8.00 (d, J=8.3 Hz, 1H), 7.62 (d, J=8.6 Hz, 1H), 7.55 (d, J=8.3 Hz, 1H), 7.38 (s, 1H), 7.14 (d, J=8.3 Hz, 1H), 6.88 (s, 1H), 6.74 (d, J=8.9 Hz, 1H), 5.07 (s, 2H) ppm.

NUCC-198391: $^1$H NMR (500 MHz, CDCl$_3$) δ 7.79 (t, J=8.4 Hz, 2H), 7.59 (d, J=8.4 Hz, 2H), 7.31 (d, J=8.4 Hz, 1H), 7.12 (t, J=10.8 Hz, 2H), 6.93 (s, 1H), 6.76 6.65 (m, 1H), 5.06 (s, 2H) ppm.

NUCC-198363: $^1$H NMR (500 MHz, CDCl$_3$) δ 7.64 (d, J=8.7 Hz, 2H), 7.50-7.43 (m, 2H), 7.41-7.35 (m, 1H), 7.31-7.26 (m, 4H), 7.15 (d, J=8.5 Hz, 1H), 6.86 (s, 1H), 5.07 (s, 2H) ppm.

NUCC-196362: $^1$H NMR (500 MHz, CDCl$_3$) δ 7.94 (s, 2H), 7.85 (s, 1H), 7.58 (d, J=8.7 Hz, 2H), 7.27 (d, J=2.0 Hz, 1H), 7.13 (d, J=8.3 Hz, 2H), 6.95 (s, 1H), 6.70 (d, J=8.7 Hz, 1H), 5.03 (s, 2H) ppm.

NUCC-196361: $^1$H NMR (500 MHz, CDCl$_3$) δ 7.88 (s, 2H), 7.84 (s, 1H), 7.28-7.16 (m, 3H), 7.11 (d, J=8.1 Hz, 2H), 6.73 (d, J=8.5 Hz, 1H), 6.56 (s, 1H), 5.01 (s, 2H), 3.80 (s, 3H) ppm; $^{13}$C NMR (126 MHz, CDCl$_3$) δ 157.51, 151.53, 142.21, 141.91, 139.42, 134.56, 134.27, 134.05, 131.82, 131.74, 131.47, 131.41, 131.21, 131.08, 129.16, 128.92, 128.82, 128.33, 128.21, 124.42, 122.26, 122.19, 121.62, 120.05, 115.89, 115.77, 109.80, 107.55, 105.51, 105.30, 69.88 ppm.

NUCC-196344: $^1$H NMR (500 MHz, CDCl$_3$) δ 7.53 (d, J=8.7 Hz, 1H), 7.45 (d, J=8.3 Hz, 1H), 7.35 (d, J=7.7 Hz, 2H), 7.26 (t, J=6.9 Hz, 3H), 7.21 (d, J=7.7 Hz, 1H), 7.11 (d, J=8.3 Hz, 2H), 6.78 (s, 1H), 6.66 (d, J=8.8 Hz, 1H), 5.02 (s, 2H), 2.43 (s, 3H) ppm.

C. Synthetic Method C

Synthetic method C

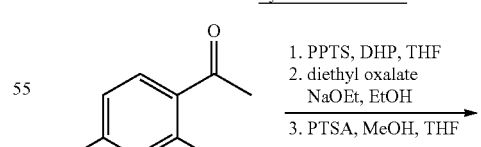

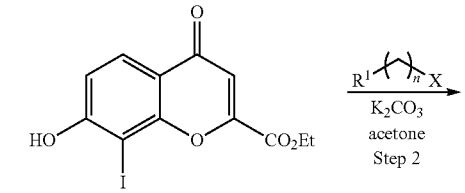

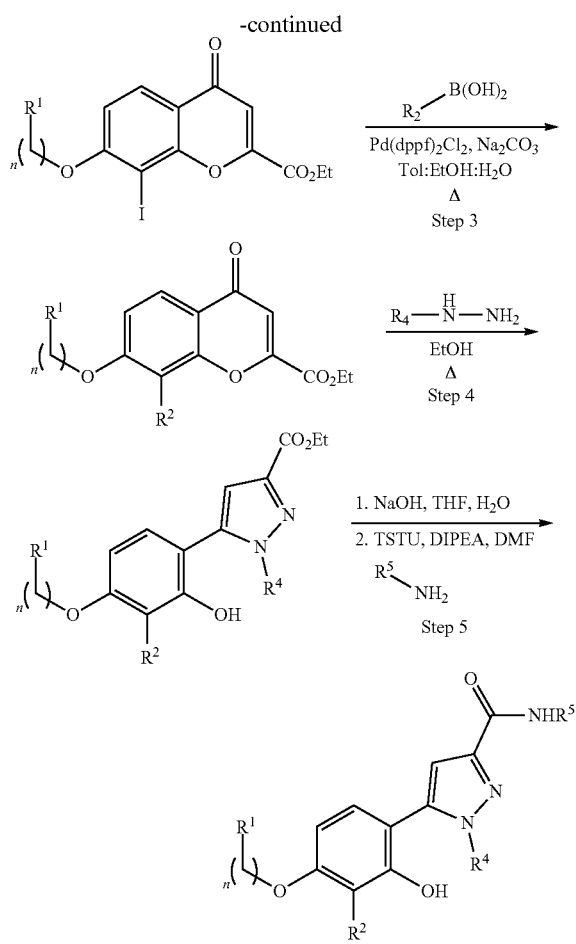

Step 1.

Over a solution of 1-(2,4-dihydroxyphenyl)ethanone (0.92 g, 6.05 mmol) and pyridinium p-toluenesulfonate (0.061 g, 0.242 mmol) were introduced in 9 mL of dichloromethane, 3,6-dihydro-2H-pyran (1.655 ml, 18.14 mmol, 1 equiv.) was added. Then, the resulting solution stirred at rt for 3h. Reaction was quenched by adding 9 mL of an aqueous saturated solution of NaHCO$_3$. Layers were separated and aqueous layer was extracted with dichloromethane (2×10) mL. Combined organic layers were dried over Na$_2$SO$_4$, filtrated and concentrated. After that, the resulting solid was solved in 50 mL of EtOH and ethyl oxalate was added(18.15 mmol, 3 equiv.). The resulting solution was added dropwise over a suspension of sodium ethoxide (30.3 equiv.) in 10 mL of ethanol. After the addition, the reaction was heated at 90 C for 30 minutes. The reaction was cooled down and 50 mL of DCM and 20 mL of HCl 3M were added. Layers were separated, and aqueous layer was extracted with dichloromethane (2×50 mL). Combined organic layers were dried over Na$_2$SO$_4$, filtrated and concentrated. The yellow solid obtained was then solved in 50 mL of a mixture 1:1 of dichloromethane:THF and pTsOH (0.6 mmol, 1 equiv.) were added and it stirred at RT for 1.5 hours. The reaction was directly concentrated under reduced pressure. Finally, over a solution of the solid obtained, iodine (24 mmol) in 75 mL of CHCl$_3$, pyridine (24 mmol, 4 equiv.) were added. The resulting solution was stirred at room temperature for 16 h. Then, 75 mL of saturated aqueous Na$_2$S$_2$O$_3$ were added and the resulting mixture stirred for one hour. The organic layer was separated and the aqueous phase was extracted with CH$_2$Cl$_2$ (3×60 mL). The combined organic layers were washed with brine and dried over anhydrous Na$_2$SO$_4$. Solvent was then removed under reduced pressure and the residue was triturated with diethyl ether several times.

Step 2.

A suspension of 2-carbonyl-chromenone, (3 mmol), the halo-alkane (3.6 mmol, 1.2 equiv.) and K$_2$CO$_3$ (6 mmol) in 30 mL of acetone was heated at 60° C. for 16 h. The reaction was filtered through a funnel and the solvent removed under reduced pressure. The crude residue was triturated with water and dried under reduced pressure until dryness.

Step 3.

A suspension of the previous alkylated chromenone (0.34 mmol, 1 equiv.), with the corresponding boronic acid (0.37 mmol, 1.1 equiv.), Na$_2$CO$_3$ (0.68 mmol, 2 equiv.) and Pd(dppf)Cl$_2$ (0.026 mmol, 0.08 equiv.) in 3.5 mL of a mixture 1:2:6 of EtOH:water:toluene was bubbled with nitrogen gas for 10 minutes. Then, the flask was capped, and the mixture was heated at 90° C. for 2 h. The dark solution was cool down to room temperature and diluted with EtOAc. The organic layer was separated and the aqueous phase was extracted with EtOAc (3×3 mL). The combined organic layers were washed with brine and dried over anhydrous Na$_2$SO$_4$. Solvent was then removed under reduced pressure and the residue was purified by silica gel chromatography.

Step 4.

A solution of the previous chromenone (0.2 mmol, 1 equiv.) with the desired hydrazine (0.6 mmol, 3 equiv.) in 2 mL of EtOH was heated at 70° C. for 45 minutes. The solution was cooled down to room temperature and concentrated. The solid residue was directly purified by silica gel chromatography (n-hexanes/ethyl acetate=5:1 to 1:1) providing the desired pyrazole.

Step 5.

Over a solution of the ethyl-esterpyrazole (0.1 mmol, 1 equiv.) in 0.5 mL of a mixture THF:water 1:1, a drop of 10% NaOH aqueous solution was added stirred at RT for 24 h. The reaction was concentrated to dryness. Then, the resulting solid was solved in 1 mL of DMF and TSTU (0.1 mmol, 1 equiv.) and DIPEA (0.2 mmol) were added and the solution stirred for 20 minutes at RT. After that, the amine (0.2 mmol) were added and stirred at RT for 30 minutes. The reaction was directly purified by preparative reverse phase HPLC.

EXAMPLES

NUCC-201224: $^1$H NMR (500 MHz, CDCl$_3$) δ 11.00 (s, 1H), 7.96 (d, J=1.6 Hz, 2H), 7.79 (s, 1H), 7.46 (d, J=8.7 Hz, 1H), 7.32-7.18 (m, 2H), 7.13 (d, J=8.4 Hz, 2H), 6.74 (s, 1H), 6.62 (d, J=8.7 Hz, 1H), 6.09 (q, J=4.9 Hz, 1H), 4.99 (s, 2H), 4.14 (s, 3H), 2.99 (d, J=4.9 Hz, 3H) ppm.

NUCC-200973: $^1$H NMR (500 MHz, CDCl$_3$) δ 7.90 (s, 2H), 7.72 (s, 1H), 7.52 (d, J=8.6 Hz, 1H), 7.27 (s, 1H), 7.18 (d, J=8.0 Hz, 2H), 7.07 (d, J=8.5 Hz, 2H), 7.03 (s, 1H), 6.60 (d, J=8.6 Hz, 1H), 4.95 (s, 2H) ppm.

NUCC-200558: $^1$H NMR (500 MHz, CDCl$_3$) δ 10.90 (s, 1H), 7.77 (t, J=1.6 Hz, 1H), 7.70 (dt, J=7.8, 1.6 Hz, 1H), 7.60 (dt, J=7.8, 1.6 Hz, 1H), 7.53-7.43 (m, 2H), 7.27 (d, J=8.3 Hz, 2H), 7.12 (d, J=8.3 Hz, 2H), 6.81 (s, 1H), 6.60 (d, J=8.7 Hz, 1H), 5.01 (s, 2H), 4.15 (s, 3H) ppm.

D. Synthetic Method D

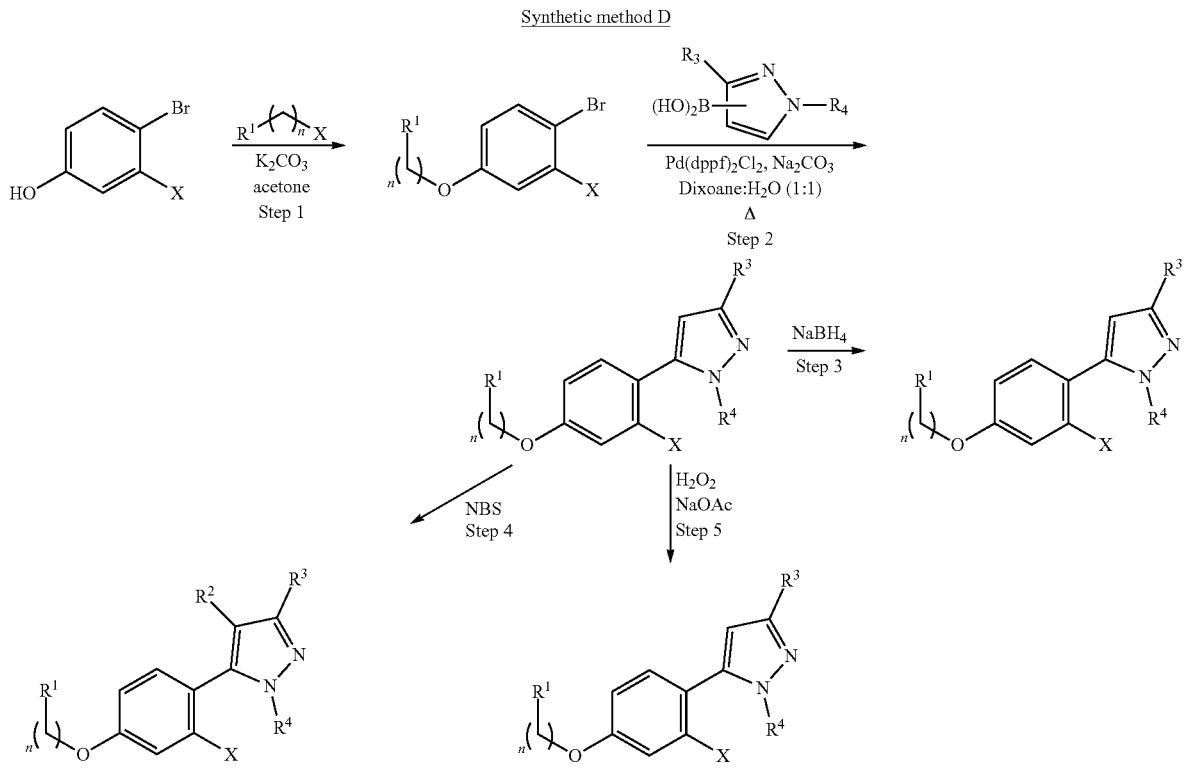

Synthetic method D

Step 1.

In an appropriate sized vial, substituted phenol (1 equiv.), aryl/alkyl chloride (1.1 equiv.), K$_2$CO$_3$ (3 equiv.) in dry acetone were added and stirred at 60° C. overnight. On completion, the solvent was evaporated and the residue was suspended in EtOAc (10 mL). The organic portion is washed with H$_2$O (2×10 mL). The combined aqeuous portion was further extracted with EtOAc (10 mL). The combined organic portion was washed with brine, dried over Na$_2$SO$_4$ and evaporated to yield a crude residue. The residue was used for the next step with further purification.

Step 2.

In an appropriate sized vial, (1-methyl-3-(trifluoromethyl)-1H-pyrazol-5-yl)boronic acid (1 equiv.), step 1 product (1 equiv.), Pd(dppf)$_2$Cl$_2$ (0.05 equiv.), Na$_2$CO$_3$ (3 equiv.) in a mixture of dioxane:H$_2$O (1:1). The vial were flushed with N$_2$ for 1 min and stirred at 100° C. for 1 h. On completion the reaction mixture was cooled to room temp and passed through a silica plug using DCM:MeOH (10:1). The solvent was evaporated to yield the crude residue. The crude was purified by prep HPLC. To obtain the desired product. eg NUCC-0200813: $^1$H NMR (500 MHz, CDCl$_3$) δ 7.32 (s, 1H), 7.28-7.19 (m, 4H), 7.12 (s, 1H), 7.05 (d, J=8.4 Hz, 1H), 7.01 (d, J=2.8 Hz, 1H), 6.77 (dd, J=8.5, 2.8 Hz, 1H), 4.94 (s, 2H), 4.34 (s, 2H), 3.86 (s, 3H); $^{13}$C NMR (126 MHz, CDCl$_3$) δ 158.7, 140.9, 135.3, 133.9, 132.5, 131.9, 128.8, 121.7, 118.9, 114.3, 113.7, 69.3, 63.3, 39.6.

Step 3.

In an appropriate sized vial, add step 2 product (1 equiv.) and NaBH$_4$ (1.2 equiv.) in methanol and stirred at room temp for 7 h. On completion, the reaction was concentrated and suspended in H$_2$O. The suspension was extracted with EtOAc (3×3 mL) and the combined organic portion was evaporated to yield crude residue which was purified by prep HPLC Example NUCC-0200813: prep HPLC condition (40-80%, 5 min, 50×30 mm, Rt=3.74 min). $^1$H NMR (500 MHz, CDCl$_3$) δ 7.32 (s, 1H), 7.30-7.18 (m, 4H), 7.10-6.95 (m, 2H), 6.77 (dd, J=8.5, 2.8 Hz, 1H), 4.94 (s, 2H), 4.34 (s, 2H), 3.86 (s, 3H) ppm; $^{13}$C NMR (126 MHz, CDCl$_3$) δ 158.7, 140.9, 135.3, 133.8, 132.5, 131.9, 128.8, 121.73, 118.9, 114.3, 113.7, 69.3, 63.3, 39.6 ppm.

Step 4.

In an appropriate sized vial, add product of step 2 (1 equiv.), NBS (5 equiv.) in anh. DMF and stir the reagents at room temp for 3 days. On completion, the reaction was quenched with water (4 mL) and extracted with EtOAc (3×3 mL). The combined organic portion was dried and the residue was purified via Biotage (5:1 Hex/EtOAc; 10 g column). Collected fractions: 11-14. eg NUCC-0200979: $^1$H NMR (500 MHz, CDCl$_3$) δ 7.42-7.34 (m, 6H), 7.31 (dd, J=8.7, 2.6 Hz, 1H), 5.11 (s, 2H), 3.82 (s, 3H); $^{13}$C NMR (126 MHz, CDCl$_3$) δ 159.7, 140.2, 140.1, 139.8, 134.6, 133.6, 133.3, 129.1, 128.8, 123.1, 120.1, 119.4, 119.3, 116.3, 115.1, 93.7, 70.0, 38.8.

Step 5.

In an appropriate sized vial, add product of step 2 (1 equiv.), H$_2$O$_2$ (30% aqueous solution, 1 equiv.), Na$_2$CO$_3$ (3 equiv.) in MeOH was stirred at room temp overnight. On completion the solvent was evaporated and the residue was suspended in water (1 mL) and extracted with EtOAc (3×1 mL). The combined organic portion was evaporated to yield the crude which was purified by prep HPLC. eg NUCC-0200816: $^1$H NMR (500 MHz, CDCl$_3$) δ 7.33 (d, J=2.7 Hz, 1H), 7.24 (s, 4H), 7.19-7.04 (m, 2H), 6.99 (dd, J=8.5, 2.7 Hz, 1H), 6.40 (s, 1H), 5.47 (s, 1H), 5.23 (s, 1H), 4.98 (s, 2H), 3.58 (s, 3H); $^{13}$C NMR (126 MHz, CDCl$_3$) δ 168.6, 159.7, 142.6, 136.6, 134.4, 134.2, 132.8, 128.9, 128.8, 119.3, 117.8, 115.1, 104.9, 69.6, 37.5.

E. Synthetic Method E

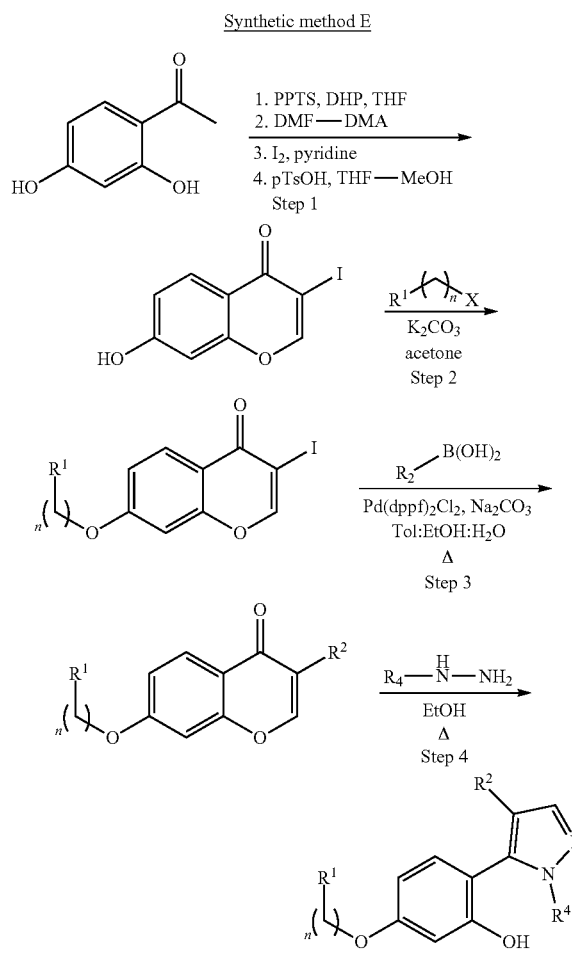

Step 1.

Over a solution of 1-(2,4-dihydroxyphenyl)ethanone (0.92 g, 6.05 mmol, 1 equiv.) and PYRIDINIUM P-TOLUENESULFONATE (0.061 g, 0.242 mmol, 0.04 equiv.) were introduced in 9 mL of dichloromethane, 3,6-dihydro-2H-pyran (1.655 ml, 18.14 mmol, 3 equiv.) was added. Then, the resulting solution stirred at rt for 3h. Reaction was quenched by adding 9 mL of an aqueous saturated solution of NaHCO$_3$. Layers were separated and aqueous layer was extracted with dichloromethane (2×10) mL. Combined organic layers were dried over The redish oil-solid was then solved in DMF-DMA (9.1 mmol) and was heated at 95° C. for 3 h. Then, it was cool down and concentrated under reduced pressure. The solid obtained was then solved in 50 mL of a mixture 1:1 of dichloromethane:THF and pTsOH (0.6 mmol, 1 equiv.) were added and it stirred at RT for 1.5 hours. The reaction was directly concentrated under reduced pressure. Finally, over a solution of the solid obtained, iodine (24 mmol, 4 equiv.) in 75 mL of CHCl$_3$, pyridine (24 mmol, 4 equiv.) were added. The resulting solution was stirred at room temperature for 16 h. Then, 75 mL of saturated aqueous Na$_2$S$_2$O$_3$ were added and the resulting mixture stirred for one hour. The organic layer was separated and the aqueous phase was extracted with CH$_2$Cl$_2$ (3×60 mL). The combined organic layers were washed with brine and dried over anhydrous Na$_2$SO$_4$. Solvent was then removed under reduced pressure and the residue was triturated with diethyl ether several times.

Step 2.

A suspension of the chromenone, (3 mmol,v), the haloalkane (3.6 mmol, 1.2 equiv.) and K$_2$CO$_3$ (6 mmol) in 30 mL of acetone was heated at 60° C. for 16 h. The reaction was filtered through a funnel and the solvent removed under reduced pressure. The crude residue was triturated with water and dried under reduced pressure until dryness.

Step 3.

A suspension of the previous alkylated chromenone (0.34 mmol, 1 equiv.), with the corresponding boronic acid (0.37 mmol, 1.1 equiv.), Na$_2$CO$_3$ (0.68 mmol, 2 equiv.) and Pd(dppf)Cl$_2$ (0.026 mmol, 0.08 equiv.) in 3.5 mL of a mixture 1:2:6 of EtOH:water:toluene was bubbled with nitrogen gas for 10 minutes. Then, the flask was capped, and the mixture was heated at 90° C. for 2 h. The dark solution was cool down to room temperature and diluted with EtOAc. The organic layer was separated and the aqueous phase was extracted with EtOAc (3×3 mL). The combined organic layers were washed with brine and dried over anhydrous Na$_2$SO$_4$. Solvent was then removed under reduced pressure and the residue was purified by silica gel chromatography.

Step 4.

A solution of the previous chromenone (0.2 mmol, 1 equiv.) with the desired hydrazine (0.6 mmol, 3 equiv.) in 2 mL of EtOH was heated at 70° C. for 45 minutes. The solution was cooled down to room temperature and concentrated. The solid residue was directly purified by silica gel chromatography (n-hexanes/ethyl acetate=5:1 to 1:1) providing the desired pyrazole.

EXAMPLES

NUCC-198359: $^1$H NMR (500 MHz, CDCl$_3$) δ 7.45 (s, 1H), 7.35 (s, 3H), 7.00 (s, 2H), 6.82 (d, J=8.8 Hz, 1H), 6.62 (d, J=2.6 Hz, 1H), 6.22 (dd, J=8.8, 2.6 Hz, 1H), 4.99 (s, 3H), 2.38 (s, 3H), 2.03 (d, J=6.1 Hz, 6H) ppm.

NUCC-198322: $^1$H NMR (500 MHz, CDCl$_3$) δ 7.80 (s, 1H), 7.51 (dt, J=9.0, 4.5 Hz, 1H), 7.40-7.37 (m, 4H), 7.32 (d, J=7.3 Hz, 1H), 6.66 (d, J=2.6 Hz, 1H), 6.52-6.41 (m, 3H), 5.05 (s, 2H) ppm.

NUCC-198318: $^1$H NMR (500 MHz, CDCl$_3$) δ 7.87 (s, 1H), 7.85 (s, 2H), 7.77 (s, 1H), 7.38 (s, 4H), 6.95 (d, J=8.7 Hz, 1H), 6.69 (d, J=2.6 Hz, 1H), 6.34 (dd, J=8.7, 2.6 Hz, 1H), 5.04 (s, 2H).

NUCC-196350: $^1$H NMR (500 MHz, CDCl$_3$) δ 7.61 (s, 1H), 7.45 (s, 1H), 7.36 (s, 1H), 7.33 (s, 3H), 7.31-7.28 (m, 2H), 7.08-7.01 (m, 2H), 6.62 (d, J=2.6 Hz, 1H), 6.29 (dd, J=8.7, 2.6 Hz, 1H), 4.99 (s, 2H) ppm.

NUCC-196348: $^1$H NMR (500 MHz, CDCl$_3$) δ 7.41-7.33 (m, 2H), 7.31-7.06 (m, 7H), 6.66 (d, J=8.6 Hz, 1H), 6.51 (s, 1H), 5.02 (s, 2H), 3.82 (s, 3H) ppm.

F. Synthetic Method F

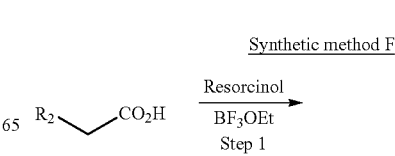

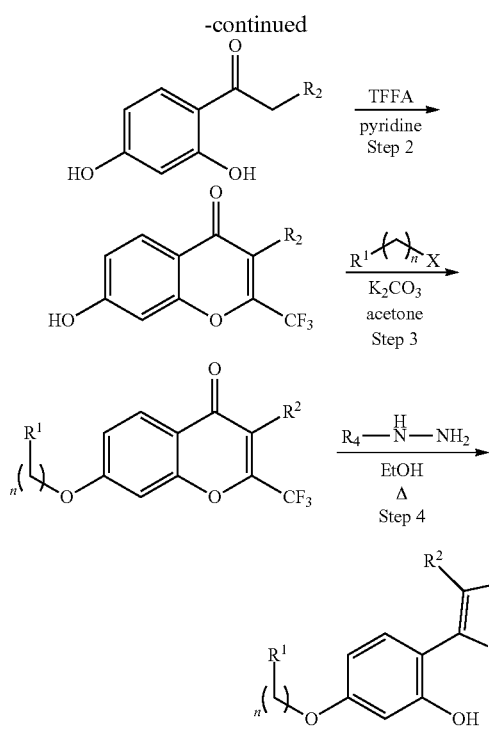

Step 1.

Over a mixture of the 2-phenylacetic acid derivative (10.58 mmol, 1 equiv.) and resorcinol (1.165 g, 10.58 mmol, 1 equiv.), Boron trifluoride etherate ORON (4.02 ml, 31.7 mmol, 3 equiv.) was added. The vial was sealed and it stirred at 90° C. for 1.5 h. The reaction was cool down to RT. The solid obtained was partitioned between 20 mL of water and 20 mL of dichloromethane. Layers were separated and the aqueous one was extracted with dichloromethane 3×10 mL). The combined organic layers were dried over $Na_2SO_4$ filtrated and concentrated under reduced pressure. The residue was purified by silica gel chromatography.

Step 2.

A suspension of the 0-phenoxy-acetophenone (1 mmol) with TFFA (5 equiv) and pyridine (5 equiv.) was heated at 120° C. for 4h. Then, it was cool down to r.t. In some cases product was precipitated, in others water was added and then extracted with EtOAc (3×10 mL). The combined organic layers were washed with brine, dried over Na2SO4, filtrated and concentrated. The residue was purified by silica gel chromatography.

Step 3.

A suspension of the the chromenone, (0.5 mmol, 1 equiv.), $K_2CO_3$ (1 mmol) and the halo alkane (0.6 mmol) in 5 mL of acetone was heated at 60° C. for 16 h. The reaction was filtered through a funnel and the solvent removed under reduced pressure. The crude residue was triturated with water and dried under reduced pressure until dryness.

Step 4.

A solution of the previous O-alkylated-chromenone (0.2 mmol) with the desired hydrazine (0.6 mmol, 3 equiv.) in 2 mL of EtOH was heated at 70° C. for 45 minutes. The solution was cooled down to room temperature and concentrated. The solid residue was directly purified by silica gel chromatography (n-hexanes/ethyl acetate=5:1 to 1:1) providing the desired pyrazole.

EXAMPLES

NUCC-198309: $^1$H NMR (500 MHz, $CDCl_3$) δ 7.38-7.33 (m, 5H), 7.00-6.84 (m, 4H), 6.55 (s, 1H), 6.35 (s, 1H), 5.00 (s, 2H), 3.81 (s, 3H) ppm.

NUCC-198295: $^1$H NMR (500 MHz, $CDCl_3$) δ 7.44 (d, J=2.2 Hz, 3H), 7.38-7.31 (m, 6H), 6.89 (s, 1H), 6.55 (s, 1H), 6.32 (s, 1H), 5.00 (s, 2H) ppm.

NUCC-196340: $^1$H NMR (500 MHz, $CDCl_3$) δ 7.97 (s, 1H), 7.45 (d, J=9.0 Hz, 1H), 7.37-7.28 (m, 2H), 7.18 (d, J=8.7 Hz, 2H), 6.86 (d, J=8.7 Hz, 2H), 6.45 (d, J=2.6 Hz, 1H), 6.37 (dd, J=9.0, 2.6 Hz, 1H), 5.92 (s, 1H), 5.01 (s, 2H), 3.78 (s, 3H) ppm.

NUCC-196282: $^1$H NMR (500 MHz, $CDCl_3$) δ 7.34-7.28 (m, 4H), 6.94 (s, 1H), 6.92-6.84 (m, 2H), 6.79 (d, J=1.8 Hz, 1H), 6.52 (s, 1H), 6.31 (s, 1H), 4.97 (s, 2H), 3.92 (s, 3H), 3.78 (s, 3H) p.

G. Synthetic Method G

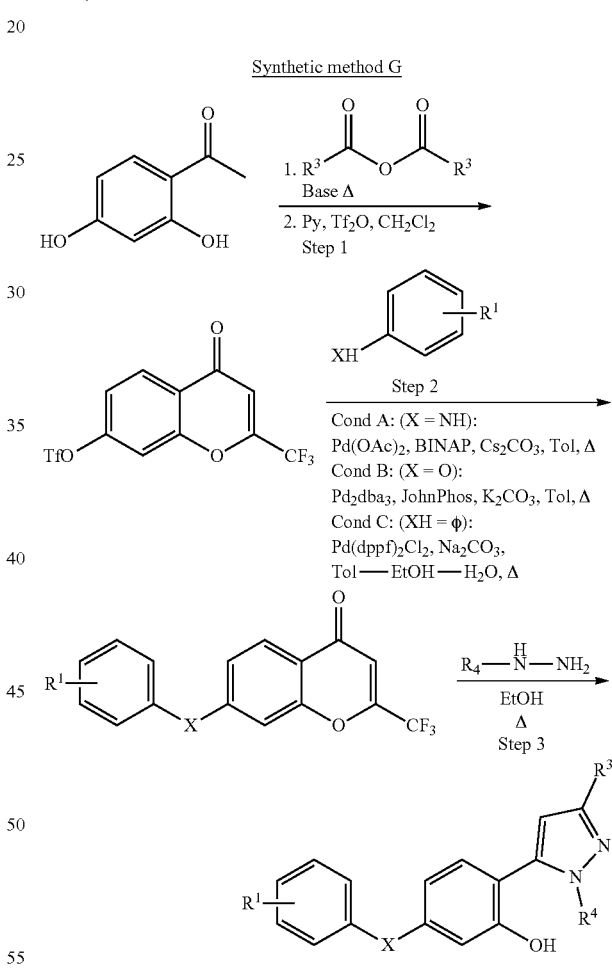

Step 1.

Over a suspension of 1-(2,4-dihydroxyphenyl)ethan-1-one (5.00 g, 32.89 mmol, 1 equiv.) in trifluoroacetic anhydride (18.50 mL, 131.56 mmol, 4 equiv.) placed in a high-pressure tube, sodium 2,2,2-trifluoroacetate (9.84 g, 72.36 mmol, 2.2 equiv.) was added and the system was capped and stirred at 110° C. for 24 h. The reaction was allowed to cool down to approximately 70° C. and then was diluted with 200 mL of EtOAc. The mixture was neutralized by adding saturated aqueous $K_2CO_3$ solution until no more bubbling was observed. Layers were separated and the aqueous phase was extracted with more EtOAc (3×150 mL). The combined organic layers were washed with brine and dried over anhydrous $Na_2SO_4$. The solution was then concentrated to 100-150 mL of EtOAc. Then the flask was capped and kept at room temperature for 1-2 days, obtaining a solid which was filtrated and dried under vacuum to obtain 4.09 g of pure 1 as a white solid in 54% yield.

Then, over an ice-bath solution of the solid obtained (2 g, 8.70 mmol, 1 equiv.) and pyridine (2.81 mL, 34.8 mmol, 4 equiv.) in 18 mL of DCM under nitrogen atmosphere, $Tf_2O$ (2.20 mL, 13.06 mmol, 1.5 equiv.) was added dropwise for 15 min. Then, the mixture stirred from 0° C. to room temperature for 16 h. The reaction was quenched by adding 15 mL of water. The organic layer was separated and the aqueous one was extracted with EtOAc (3×15 mL). The combined organic layers were washed with brine and dried over anhydrous $Na_2SO_4$. Solvent was then removed under reduced pressure and the residue was purified by silica gel chromatography (n-hexanes/ethyl acetate=10:1 to 4:1) providing compound 2 as a yellow solid in 95% yield (3.0 g): mp 46-48° C. $^1$H NMR (500 MHz, DMSO-$d_6$) δ 8.32-8.20 (m, 2H), 7.74 (dd, J=8.8, 2.4 Hz, 1H), 7.17 (s, 1H) ppm. $^{13}$C NMR (126 MHz, DMSO-$d_6$) δ 175.4, 155.6, 152.4, 151.4 (q, $^2$J (C,F)=38.8 Hz), 128.2, 123.7, 120.1, 118.5 (q, $^1$J (C,F)=274.7 Hz), 112.9, 111.5, 111.4 ppm. HRMS (ESI): mass calc for $C_{11}H_5F_6O_5S^+$ [M+H]$^+$=362.9756, found=362.9758.

Step 2.

In order to obtain different Pd-catalyzed coupling products in the position 7 of the 2-CF3-chromenone, different conditions were followed:

Conditions A: Aniline Coupling:

Over a suspension of the chromenone-triflate (150 mg, 0.41 mmol, 1 equiv.), with $Cs_2CO_3$ (202 mg, 0.62 mmol, 1 equiv.), BINAP (25 mg, 0.04 mmol, 0.1 equiv.) and $PdOAc_2$ (4.5 mg, 0.02 mmol, 0.05 equiv.) in 4 mL of toluene was bubbled with nitrogen gas for 10 minutes. Then, the flask was capped, and the mixture was heated at 90° C. for 16 h. The dark solution was cool down to room temperature and diluted with 5 mL of EtOAc and 5 mL of water. The organic layer was separated and the aqueous phase was extracted with $EtOAc_2$ (3×5 mL). The combined organic layers were washed with brine and dried over anhydrous $Na_2SO_4$. Solvent was then removed under reduced pressure and the residue was purified by silica gel chromatography.

Conditions B: Phenol Coupling:

Over a suspension of the chromenone-triflate (150 mg, 0.41 mmol, 1 equiv.), with $K_2CO_3$ (113 mg, 0.82 mmol, 2 equiv.), JohnPhos (12 mg, 0.04 mmol, 0.1 equiv.) and $Pd_2dba_3$ (19 mg, 0.02 mmol, 0.05 equiv.) in 4 mL of toluene, nitrogen gas was bubbled for 10 minutes. Then, the flask was capped, and the mixture was heated at 90° C. for 16 h. The dark solution was cool down to room temperature and diluted with 5 mL of EtOAc and 5 mL of water. The organic layer was separated and the aqueous phase was extracted with $EtOAc_2$ (3×5 mL). The combined organic layers were washed with brine and dried over anhydrous $Na_2SO_4$. Solvent was then removed under reduced pressure and the residue was purified by silica gel chromatography.

Conditions C: Boronic Acid Coupling to Biaryl Chromenones:

A suspension of the chromenone-triflate (150 mg, 0.41 mmol, 1 equiv.), with the corresponding boronic acid (0.46 mmol, 1.1 equiv.), $Na_2CO_3$ (87 mg, 0.82 mmol, 2 equiv.) and $Pd(dppf)Cl_2$ (23 mg, 0.03 mmol, 0.08 equiv.) in 4 mL of a mixture 1:2:6 of EtOH:water:toluene was bubbled with nitrogen gas for 10 minutes. Then, the flask was capped, and the mixture was heated at 90° C. for 20 min. The dark solution was cool down to room temperature and diluted with EtOAc. The organic layer was separated and the aqueous one was extracted with $EtOAc_2$ (3×3 mL). The combined organic layers were washed with brine and dried over anhydrous $Na_2SO_4$. Solvent was then removed under reduced pressure and the residue was purified by silica gel chromatography.

Step 3.

A solution of the previous 7-functionalized chromenone (0.2 mmol, 1 equiv.) with the desired hydrazine (0.6 mmol, 3 equiv.) in 2 mL of EtOH was heated at 70° C. for 45 minutes. The solution was cooled down to room temperature and concentrated. The solid residue was directly purified by silica gel chromatography (n-hexanes/ethyl acetate=5:1 to 1:1) providing the desired pyrazole.

EXAMPLES

NUCC-201223: $^1$H NMR (500 MHz, CDCl$_3$) δ 10.62 (s, 1H), 7.92 (d, J=1.7 Hz, 2H), 7.81 (s, 1H), 7.56 (d, J=8.7 Hz, 1H), 7.23-7.19 (m, 2H), 6.98 (s, 1H), 6.86-6.77 (m, 2H), 6.61 (d, J=8.7 Hz, 1H) ppm.

NUCC-200721: $^1$H NMR (500 MHz, CDCl$_3$) δ 7.46 (d, J=8.4 Hz, 1H), 7.31 (d, J=8.7 Hz, 1H), 7.20 (d, J=2.7 Hz, 1H), 6.92 (dd, J=8.7, 2.7 Hz, 1H), 6.84 (s, 1H), 6.62 (d, J=7.7 Hz, 2H), 5.78 (s, 1H) ppm.

NUCC-200681: $^1$H NMR (500 MHz, CDCl$_3$) δ 7.72 (d, J=8.8 Hz, 1H), 7.28 (d, J=8.8 Hz, 2H), 7.07 (d, J=8.5 Hz, 2H), 6.94 (d, J=8.8 Hz, 2H), 6.81 (d, J=8.7 Hz, 1H), 6.52 (d, J=2.4 Hz, 1H), 6.45 (d, J=8.8 Hz, 1H), 2.57 (q, J=7.6 Hz, 2H), 1.18 (t, J=7.6 Hz, 3H) ppm.

NUCC-200679: $^1$H NMR (500 MHz, CDCl$_3$) δ 7.51 (d, J=8.6 Hz, 1H), 7.33-7.28 (m, 2H), 7.01-6.97 (m, 2H), 6.88 (s, 1H), 6.60 (dd, J=8.5, 2.4 Hz, 1H), 6.56 (d, J=2.4 Hz, 1H) ppm.

NUCC-200559: $^1$H NMR (500 MHz, CDCl$_3$) δ 7.58 (d, J=8.7 Hz, 1H), 7.41 (d, J=8.4 Hz, 1H), 7.05 (q, J=9.1 Hz, 1H), 6.96-6.90 (m, 2H), 6.87 (dd, J=8.7, 2.4 Hz, 1H), 6.77 (d, J=8.2 Hz, 2H), 6.56 (dd, J=8.5, 2.2 Hz, 1H), 6.52 (d, J=2.2 Hz, 1H), 5.72 (s, 1H) ppm.

NUCC-200492: $^1$H NMR (500 MHz, CDCl$_3$) δ 7.28-7.25 (m, 2H), 7.09-7.06 (m, 2H), 7.06-7.02 (m, 1H), 6.61 (d, J=7.7 Hz, 2H), 6.53 (s, 1H), 3.81 (s, 3H) ppm.

NUCC-200491: $^1$H NMR (500 MHz, CDCl$_3$) δ 7.46 (d, J=9.0 Hz, 1H), 7.25 (d, J=8.7 Hz, 2H), 7.10-6.97 (m, 2H), 6.81 (s, 1H), 6.62 (dq, J=5.3, 2.2 Hz, 2H), 5.80 (s, 1H) ppm.

H. Synthetic Method H

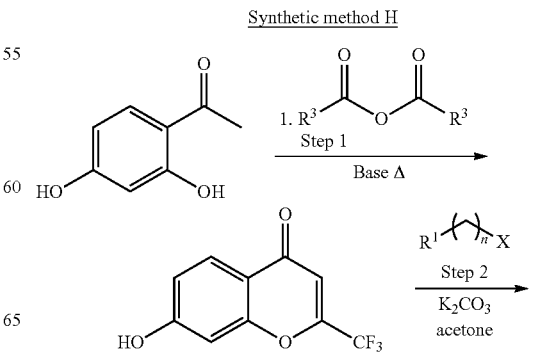

Synthetic method H

-continued

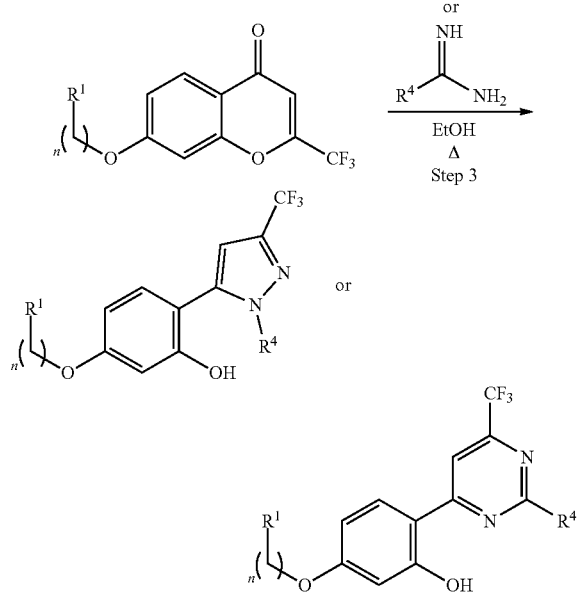

Step 1.

Over a suspension of 1-(2,4-dihydroxyphenyl)ethan-1-one (5.00 g, 32.89 mmol, 1 equiv.) in trifluoroacetic anhydride (18.50 mL, 131.56 mmol, 4 equiv.) placed in a high-pressure tube, sodium 2,2,2-trifluoroacetate (9.84 g, 72.36 mmol, 2.2 equiv.) was added and the system was capped and stirred at 110° C. for 24 h. The reaction was allowed to cool down to approximately 70° C. and then was diluted with 200 mL of EtOAc. The mixture was neutralized by adding saturated aqueous $K_2CO_3$ solution until no more bubbling was observed. Layers were separated and the aqueous phase was extracted with more EtOAc (3×150 mL). The combined organic layers were washed with brine and dried over anhydrous $Na_2SO_4$. The solution was then concentrated to 100-150 mL of EtOAc. Then the flask was capped and kept at room temperature for 1-2 days, obtaining a solid which was filtrated and dried under vacuum to obtain 4.09 g of pure 1 as a white solid in 54% yield.

Step 2.

A suspension of 7-hydroxy-2-(trifluoromethyl)-4H-chromen-4-one, (1 g, 2.8 mmol, 1 equiv.), the halo-alkane (3.4 mmol, 1.2 equiv.) and $K_2CO_3$ (0.77 g, 5.6 mmol, 2 equiv.) in 5 mL of acetone was heated at 60° C. for 16 h. The reaction was filtered through a funnel and the solvent removed under reduced pressure. The crude residue was triturated with water and dried under reduced pressure until dryness.

Step 3.

Synthesis of Pyrazoles.

A solution of the previous chromenone (0.2 mmol, 1 equiv.) with the desired hydrazine (0.6 mmol, 3 equiv.) in 2 mL of EtOH was heated at 70° C. for 45 minutes. The solution was cooled down to room temperature and concentrated. The solid residue was directly purified by silica gel chromatography (n-hexanes/ethyl acetate=5:1 to 1:1) providing the desired pyrazole.

Example

NUCC-198314: $^1$H NMR (500 MHz, CDCl$_3$) δ 7.12 (s, 1H), 6.97 (d, J=8.5 Hz, 1H), 6.51 (dd, J=8.5, 2.4 Hz, 1H), 6.46 (d, J=2.4 Hz, 1H), 6.41 (s, 1H), 4.92 (s, 2H), 3.67 (s, 3H) ppm.

Synthesis of Pyrimidines.

A solution of the previous chromenone (0.2 mmol, 1 equiv.) with the desired benzimidamide (0.26 mmol, 1.3 equiv.) and potassium hydroxide (0.6 mmol, 3 equiv.) in 10 mL of EtOH was heated at 80° C. for 14 hours. The solution was diluted in 5 mL of water, extracted 3×15 mL of EtOAc. Combined organic layers were dried over $Na_2SO_4$, filtrated and concentrated under reduced pressure. The solid residue was directly purified by silica gel chromatography (n-hexanes/ethyl acetate=5:1 to 1:1) providing the desired pyrimidine.

Example

NUCC-0200500: $^1$H NMR (500 MHz, CDCl$_3$) δ 8.80-8.73 (m, 2H), 8.07 (s, 1H), 7.95 (s, 1H), 7.81 (d, J=8.9 Hz, 1H), 7.37 (s, 4H), 6.69-6.59 (m, 2H), 5.10 (s, 2H) ppm.

I. Synthetic Method I

Synthetic method I (PAL)

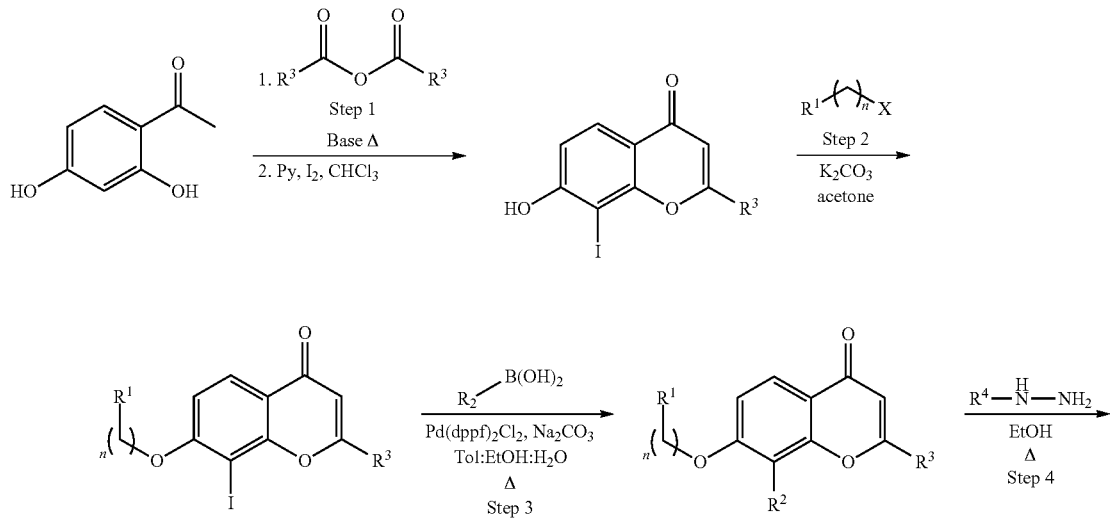

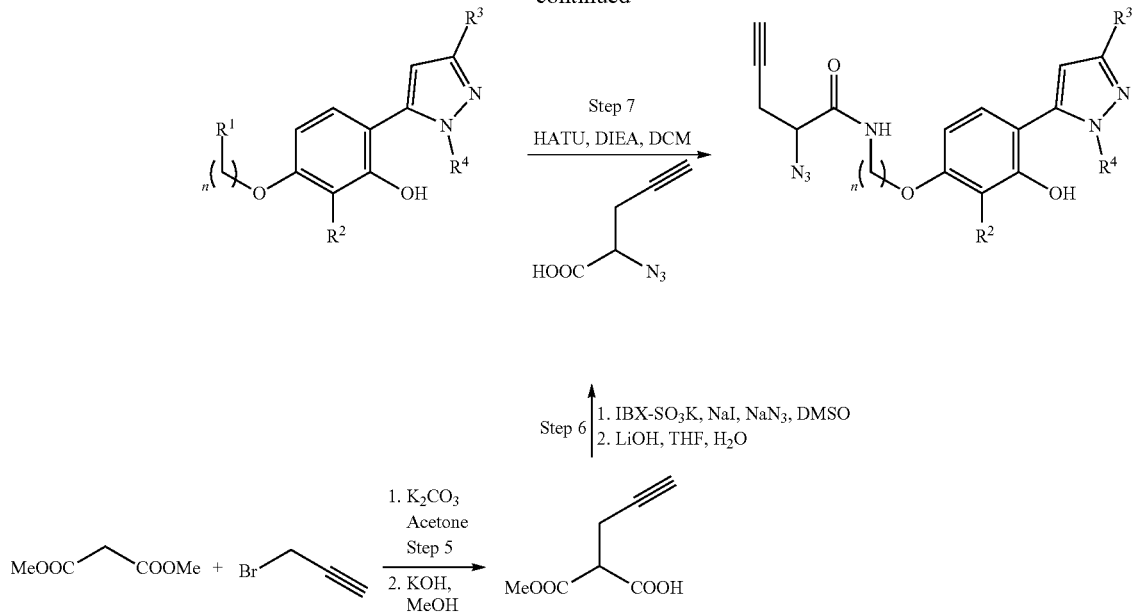

Steps 1-4.
Same as described in Synthetic method B above.

Step 5.
In a 100 mL round bottom flask, dimethyl malonate (1.1 equiv.), propargyl bromide (1 equiv.), $K_2CO_3$ (3 equiv.) in dry acetone was stirred at room temp for 36 h. The reaction mixture was quenched by addition of sat. $NH_4Cl$ solution and extracted with DCM (3 times). The combined organic layers were washed with $H_2O$ (2 times), dried over $Na_2SO_4$ and the solvent was evaporated under reduced pressure to yield a yellow-colored oil which converted into a solid on standing. (Note: Conversion could be monitored by TLC: H:EtOAc:: 5:1, rf=0.42). The crude was stirred with KOH (1 equiv.) in MeOH at room temp for 4. On completion, the solvent was evaporated and the residue was suspended in $H_2O$ and washed with $Et_2O$ (2 times). The aqueous portion was acidified with HCl (2N, to pH 3) and extracted with EtOAc (2 times). The organic portion was dried over Na2SO4 and evaporated to yield the crude yellow-colored oil. (Note: LCMS: shows m/z=157 and 174 (+18)).

Step 6.
In a appropriate sized vial, product from step 5 (1 equiv.), IBX-$SO_3K$ (1.5 equiv.), NaI (0.2 equiv.), $NaN_3$ (3.3 equiv.) in anhydrous DMSO were stirred in an ice-cold water bath for 5 min and further heated at 60° C. for 2 h. On completion, the reaction mixture was quenched with sat. $Na_2S_2O_3$ (25 mL) and extracted with $Et_2O$ (2×25 mL). The combined organic portion was washed with sat. $NaHCO_3$ (2×25 mL) and dried over $Na_2SO_4$. The organic portion was evaporated to yield a yellow-colored residue. The crude along with LiOH (2 equiv.) in THF:$H_2O$ (1:1) was stirred at room temp for 2 h. (Note: LCMS shows a dimer signal for the SM and product indicating that reaction is complete). The solvent was evaporated and the crude was taken for the next step without any further purification.

Step 7.
In an appropriate sized vial, product from step 4 (1 equiv.), product from step 5 (1.5 equiv.), HATU (1.5 equiv.), DIEA (4 equiv.) in anhydrous DCM was stirred at 30° C. for 6 h. On completion, the solvent was evaporated to yield a crude residue. The crude was purified by prep HPLC.

EXAMPLES

NUCC_0201698: Prep HPLC: (25-90%, 50×30, C18, 50 mL/min, Rt=4.3 min). UVmax=222 nm $^1$H NMR (500 MHz, $CDCl_3$) δ 8.84 (dd, J=10.0, 1.9 Hz, 3H), 8.16 (s, 1H), 8.02 (s, 2H), 7.50 (d, J=8.5 Hz, 2H), 7.24 (s, 17H), 6.76 (d, J=8.6 Hz, 1H), 6.59 (s, 2H), 5.22 (s, 1H), 5.06 (s, 2H), 4.28 (dd, J=7.6, 4.1 Hz, 1H), 3.83 (s, 3H), 3.09-2.75 (m, 3H), 2.23-2.06 (m, 1H) ppm.

NUCC-0201694: Prep HPLC: (25-90%, 50×30, C18, 50 mL/min, Rt=3.5 min). UVmax=222 nm $^1$H NMR (500 MHz, $CDCl_3$) δ 10.63 (s, 1H), 7.80 (d, J=2.0 Hz, 1H), 7.70-7.37 (m, 3H), 6.91 (s, 1H), 6.58 (d, J=8.7 Hz, 1H), 6.41 (s, 1H), 4.13-3.85 (m, 4H), 3.27 (dq, J=34.6, 6.8 Hz, 1H), 2.99-2.57 (m, 2H), 1.94-1.77 (m, 1H), 1.23 (s, 1H), 0.81 (s, 1H) ppm.

NUCC-0201695: Prep HPLC: (25-90%, 50×30, C18, 50 mL/min, Rt=4.5-5 min). UVmax=222 nm $^1$H NMR (500 MHz, $CDCl_3$) δ 7.76 (d, J=2.0 Hz, 1H), 7.68-7.48 (m, 2H), 7.19 (d, J=8.6 Hz, 1H), 6.65 (d, J=8.7 Hz, 1H), 6.55 (s, 1H), 6.43 (s, 1H), 5.09 (s, 1H), 4.04 (dt, J=30.2, 6.5 Hz, 3H), 3.82 (s, 3H), 3.27 (dt, J=36.6, 6.8 Hz, 2H), 2.96-2.82 (m, 1H), 2.77-2.62 (m, 1H), 2.05 (t, J=2.7 Hz, 1H), 1.98-1.81 (m, 2H) ppm.

NUCC-0201696: Prep HPLC: (25-90%, 50×30, C18, 50 mL/min, Rt=4.6 min). UVmax=222 nm $^1$H NMR (500 MHz, $CDCl_3$) δ 8.85 (dd, J=9.8, 2.1 Hz, 3H), 8.06 (d, J=2.2 Hz, 1H), 7.24 (s, 13H), 6.69 (d, J=8.6 Hz, 1H), 6.59 (s, 1H), 6.45 (s, 1H), 5.27 (s, 1H), 4.19-3.93 (m, 3H), 3.84 (s, 3H), 3.28 (ddd, J=47.0, 13.7, 6.8 Hz, 2H), 2.88 (ddd, J=17.2, 4.3, 2.6 Hz, 1H), 2.69 (ddd, J=17.1, 7.2, 2.7 Hz, 1H), 1.90 (dt, J=7.7, 3.9 Hz, 2H) ppm.

NUCC-0210697: Prep HPLC: (25-90%, 50×30, C18, 50 mL/min, Rt=3.8-4.1 min). UVmax=222 nm $^1$H NMR (500 MHz, $CDCl_3$) δ 9.03-8.72 (m, 2H), 8.13 (d, J=11.1 Hz, 1H), 7.69-7.40 (m, 4H), 6.95 (d, J=5.2 Hz, 1H), 6.69-6.43 (m, 2H), 4.07 (ddd, J=11.4, 8.8, 5.1 Hz, 3H), 3.71-3.41 (m, 2H), 2.95-2.59 (m, 3H), 2.45 (dq, J=4.9, 2.4 Hz, 1H), 2.04-1.88 (m, 1H) ppm.

J. Synthetic Method J

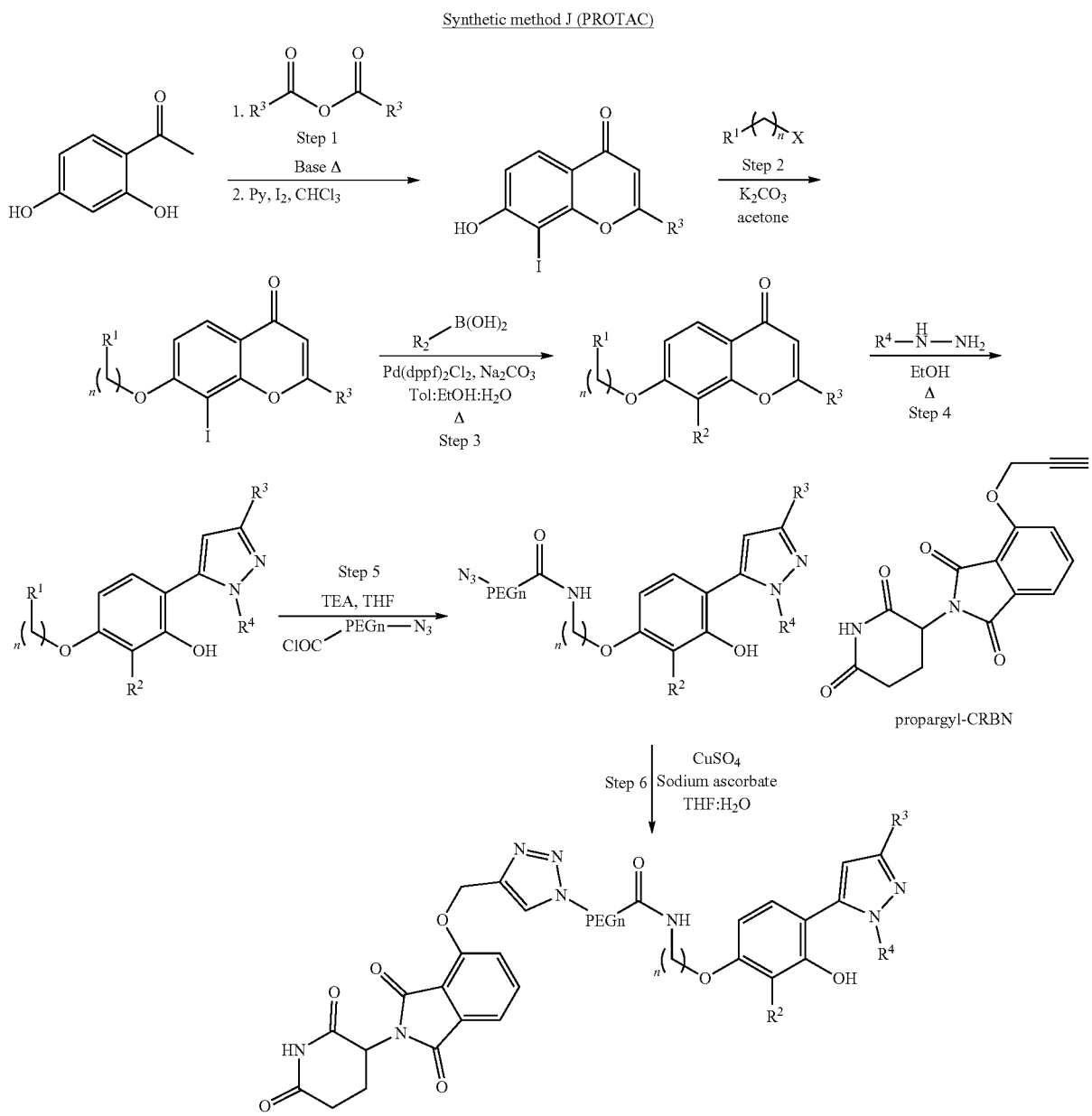

Synthetic method J (PROTAC)

Steps 1-4. Same as described in Synthetic method B above.

Step 5.

In an appropriate sized vial, the azido-PEG carboxylic acid (1 equiv.) was stirred with thionyl chloride (39 equiv.) at room temp for 3 h. On completion, (LCMS shows the methyl ester in indicating reaction completion) the excess thionyl chloride was evaporated to yield the crude acid chloride. A solution of product from step 4 (1 equiv.) was added in anhydrous THF was added to the acid chloride and TEA (5 equiv.) and the reaction mixture was stirred at 60° C. for 3 h. On completion the mixture was filtered through a cotton plug and purified by prep HPLC (50×30, C18, 50 mL/min, Rt. 3.3-3.6 min) which was taken up for the coupling step without further purification (assuming quantitative yield).

Step 6.

In an appropriate sized vial, product from step 5 (1 equiv.), CuSO$_4$ (5 equiv.), sodium ascorbate (5 equiv.), propargyl-CRBN (1 equiv.) in THF:H$_2$O (1:1) was stirred at room temp overnight. On completion, the reaction mixture was diluted with ACN (1 mL) and purified by prep HPLC.

EXAMPLES

NUCC-0201202: Prep HPLC (45-95% 50×30, C18, 50 mL/min, Rt=3.2-3.7 min). UVmax=222 nm. $^1$H NMR (500 MHz, CDCl$_3$) δ 8.80 (s, 1H), 8.26 (s, 1H), 7.90 (s, 2H), 7.79 (s, 1H), 7.71 (s, 1H), 7.65-7.43 (m, 5H), 7.37 (t, J=7.9 Hz, 2H), 7.13 (d, J=8.1 Hz, 2H), 6.86 (s, 1H), 6.68 (d, J=8.7 Hz, 1H), 5.26 (s, 2H), 5.04-4.79 (m, 3H), 4.32 (s, 2H), 4.08 (s, 2H), 3.84-3.45 (m, 13H), 3.04-2.51 (m, 5H), 2.23-1.95 (m, 4H), 1.57 (s, 4H) ppm.

NUCC-0201203: Prep HPLC (45-95% 50×30, C18, 50 mL/min, Rt=3.25-4 min). UVmax=222 nm. $^1$H NMR (500 MHz, CDCl$_3$) δ 8.80 (s, 1H), 8.29 (s, 1H), 7.91 (s, 3H), 7.78 (d, J=11.5 Hz, 3H), 7.61 (t, J=7.9 Hz, 2H), 7.52 (d, J=8.3 Hz, 4H), 7.42 (dd, J=14.9, 7.9 Hz, 3H), 7.14 (d, J=8.1 Hz, 2H), 6.87 (s, 1H), 6.68 (d, J=8.7 Hz, 1H), 5.31 (s, 2H), 5.07-4.79 (m, 4H), 4.37 (t, J=5.1 Hz, 2H), 4.07 (s, 3H), 3.85-3.32 (m, 20H), 3.01-2.53 (m, 5H), 2.26-1.93 (m, 4H), 1.58 (s, 4H) ppm.

NUCC_0201660: Prep HPLC (45-95% 50×30, C18, 50 mL/min, Rt=4.25 min). UVmax=222 nm.

NUCC-0201702: $^1$H NMR (500 MHz, CDCl$_3$) δ 8.35 (s, 1H), 7.86 (s, 1H), 7.75 (d, J=2.0 Hz, 1H), 7.67 (dd, J=8.5, 7.3 Hz, 1H), 7.61-7.37 (m, 4H), 7.17 (d, J=8.6 Hz, 1H), 6.96 (t, J=6.2 Hz, 1H), 6.64 (d, J=8.6 Hz, 1H), 6.53 (s, 1H), 5.39 (d, J=2.8 Hz, 3H), 4.89 (dd, J=12.3, 5.4 Hz, 1H), 4.60-4.40 (m, 2H), 4.08-3.90 (m, 3H), 3.81 (d, J=5.3 Hz, 4H), 3.69-3.48 (m, 7H), 3.27 (q, J=6.8 Hz, 2H), 2.26-2.03 (m, 4H), 1.85 (q, J=6.4 Hz, 2H), 1.23 (d, J=2.2 Hz, 3H) ppm.

NUCC-0201703: Prep HPLC (20-80% 50×30, C18, 50 mL/min, Rt=4.15 min). Uvmax=222 nm. Unable to open NMR-fid NUCC-0201704: Prep HPLC (20-80% 50×30, C18, 50 mL/min, Rt=4 min). Uvmax=222 nm. $^1$H NMR (500 MHz, CDCl$_3$) δ 8.82 (d, J=33.9 Hz, 2H), 8.07 (s, 1H), 7.97 (s, 1H), 7.77 (s, 1H), 7.63 (t, J=7.9 Hz, 1H), 7.53 (d, J=8.8 Hz, 1H), 7.48-7.37 (m, 1H), 7.02 (d, J=4.2 Hz, 1H), 6.88 (s, 1H), 6.61 (d, J=8.8 Hz, 1H), 5.28 (d, J=3.0 Hz, 1H), 4.92 (dd, J=11.9, 5.5 Hz, 1H), 4.40 (t, J=5.1 Hz, 1H), 4.07 (t, J=5.1 Hz, 1H), 3.94 (s, 1H), 3.75 (t, J=5.1 Hz, 1H), 3.68-3.41 (m, 4H), 3.02-2.64 (m, 2H), 2.15 (s, 1H), 1.24 (s, 2H), 0.84 (d, J=22.7 Hz, 1H) ppm.

In vitro metabolism of NUCC-176242 and NUCC-176248 were tested using mouse liver microsomes and a mouse S9 fraction. NUCC-176242 was significantly metabolism by the mouse S9 fraction versus NUCC-176248 likely due to S9 conjugation at the N-1 nitrogen atom of the pyrazole ring.

The pharmacokinetics of NUCC-176242 and NUCC-176248 were studied in mice by administering a dose of 5 mg/kg intravenously and measuring the plasma concentration versus time. The observed in vivo metabolism of NUCC-176242 and NUCC-176248 correlated well with the observed in vitro metabolism tested above for of NUCC-176242 and NUCC-176248.

Tables

TABLE 1

Representative Compounds

| Molecule Name | Molecular weight (g/mol) | Structure | Synthesis Method |
|---|---|---|---|
| NUCC-0176234 | 452.5 | 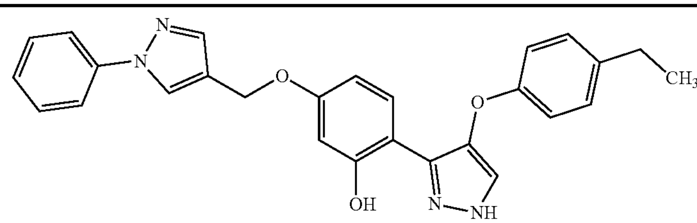 | — |
| NUCC-0176242 | 488.9 | 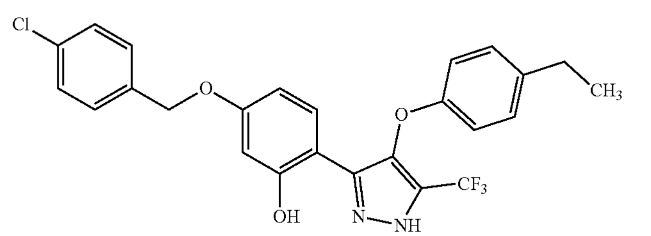 [SMILES: CCc1ccc(Oc2c(-c3ccc(OCc4ccc(Cl)cc4)cc3O)n[nH]c2C(F)(F)F)cc1] | A |
| NUCC-0176243 | 420.9 | 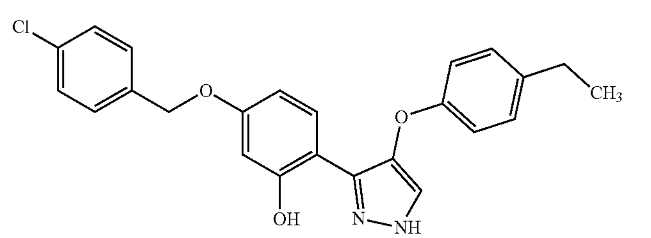 [SMILES: CCc1ccc(Oc2c[nH]nc2-c2ccc(OCc3ccc(Cl)cc3)cc2O)cc1] | A |
| NUCC-0176244 | 454.4 | 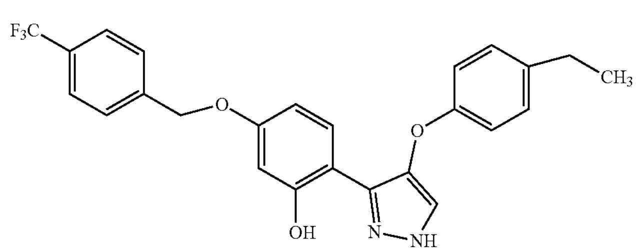 [SMILES: CCc1ccc(Oc2c[nH]nc2-c2ccc(OCc3ccc(C(F)(F)F)cc3)cc2O)cc1] | A |

TABLE 1-continued

Representative Compounds

| Molecule Name | Molecular weight (g/mol) | Structure | Synthesis Method |
|---|---|---|---|
| NUCC-0176245 | 536.5 | 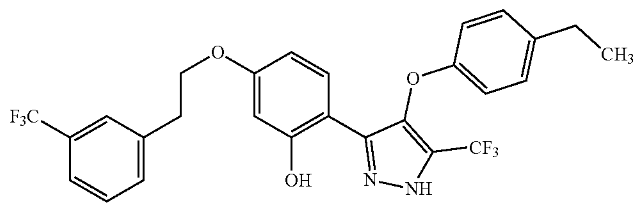 [SMILES: CCc1ccc(Oc2c(-c3ccc(OCCc4cccc(C(F)(F)F)c4)cc3O)n[nH]c2C(F)(F)F)cc1] | A |
| NUCC-0176246 | 390.4 | 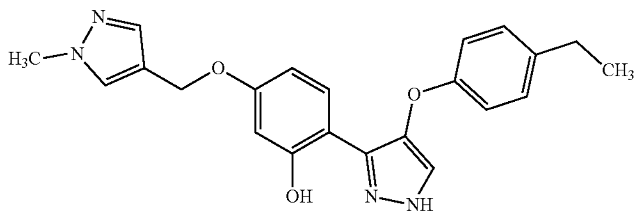 [SMILES: CCc1ccc(Oc2c[nH]nc2-c2ccc(OCc3cnn(C)c3)cc2O)cc1] | A |
| NUCC-0176247 | 392.8 | 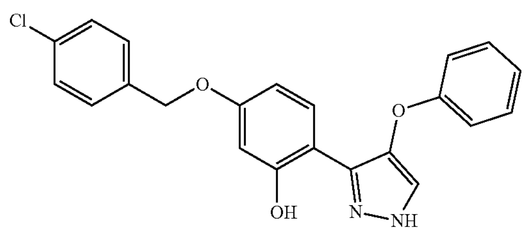 [SMILES: Oc1cc(OCc2ccc(Cl)cc2)ccc1-c1n[nH]cc1Oc1ccccc1] | A |
| NUCC-0176248 | 502.9 | 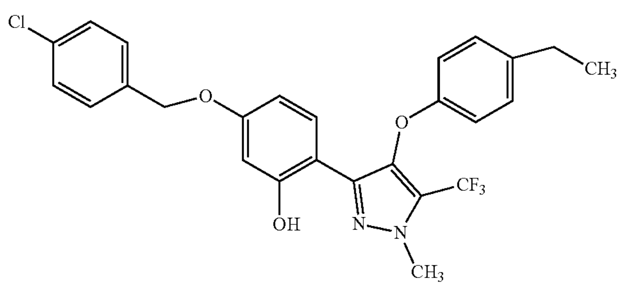 [SMILES: CCc1ccc(Oc2c(-c3ccc(OCc4ccc(Cl)cc4)cc3O)nn(C)c2C(F)(F)F)cc1] | A |
| NUCC-0176249 | 376.4 | 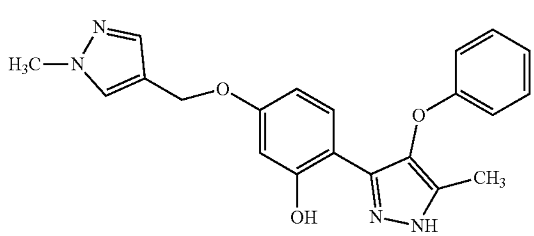 [SMILES: Cc1[nH]nc(-c2ccc(OCc3cnn(C)c3)cc2O)c1Oc1ccccc1] | A |
| NUCC-0176250 | 455.4 | 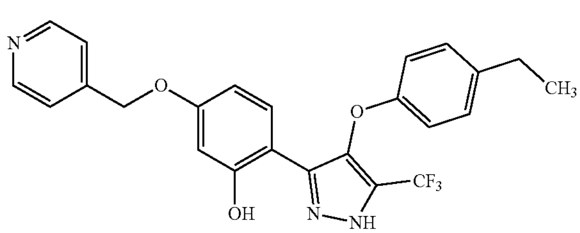 [SMILES: CCc1ccc(Oc2c(-c3ccc(OCc4ccncc4)cc3O)n[nH]c2C(F)(F)F)cc1] | A |

TABLE 1-continued
Representative Compounds
| Molecule Name | Molecular weight (g/mol) | Structure | Synthesis Method |
|---|---|---|---|
| NUCC-0176251 | 359.4 | 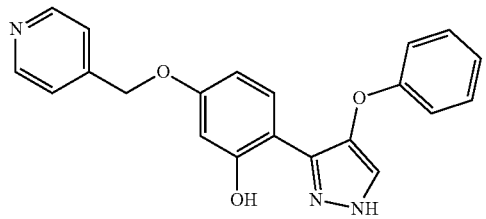 [SMILES: Oc1cc(OCc2ccncc2)ccc1-c1n[nH]cc1Oc1ccccc1] | A |
| NUCC-0176252 | 373.4 | 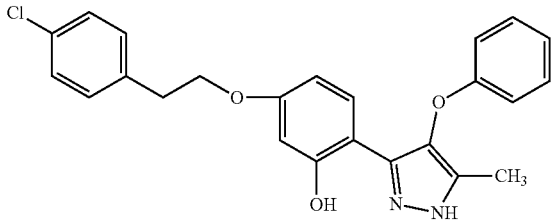 [SMILES: Cc1[nH]nc(-c2ccc(OCCc3ccc(Cl)cc3)cc2O)c1Oc1ccccc1] | A |
| NUCC-0176253 | 406.9 | 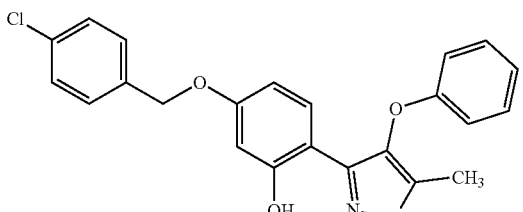 | A |
| NUCC-0176254 | 387.4 | 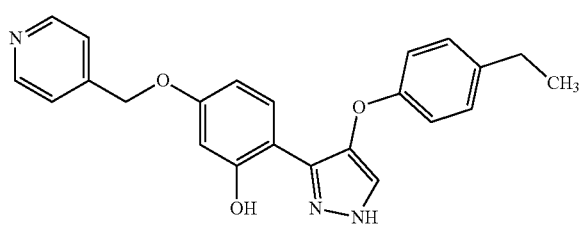 [SMILES: CCc1ccc(Oc2c[nH]nc2-c2ccc(OCc3ccncc3)cc2O)cc1] | A |
| NUCC-0176255 | 358.4 | 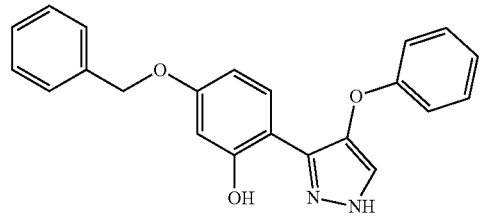 [SMILES: Oc1cc(OCc2ccccc2)ccc1-c1n[nH]cc1Oc1ccccc1] | A |
| NUCC-0176256 | 392.5 | 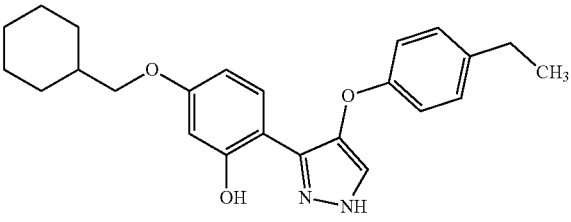 [SMILES: CCc1ccc(Oc2c[nH]nc2-c2ccc(OCC3CCCCC3)cc2O)cc1] | A |

TABLE 1-continued

Representative Compounds

| Molecule Name | Molecular weight (g/mol) | Structure | Synthesis Method |
|---|---|---|---|
| NUCC-0176257 | 404.4 | 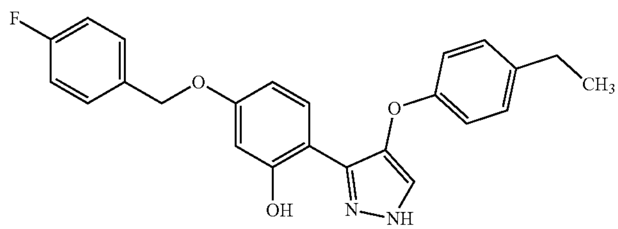 [SMILES: CCc1ccc(Oc2c[nH]nc2-c2ccc(OCc3ccc(F)cc3)cc2O)cc1] | A |
| NUCC-0176258 | 418.5 | 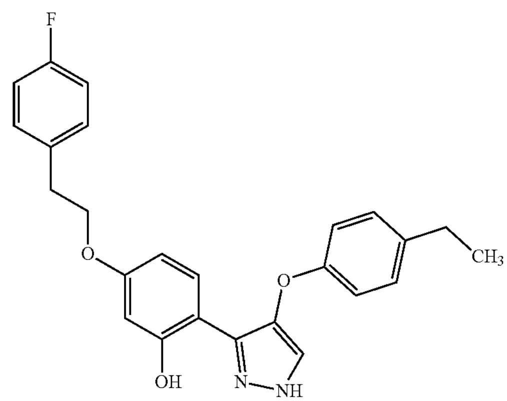 [SMILES: CCc1ccc(Oc2c[nH]nc2-c2ccc(OCCc3ccc(F)cc3)cc2O)cc1] | A |
| NUCC-0176259 | 390.4 | 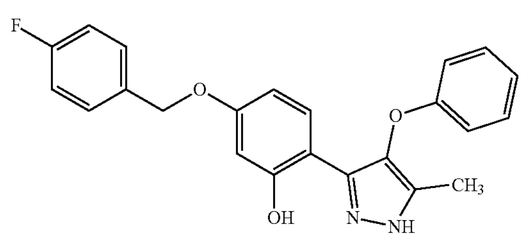 [SMILES: Cc1[nH]nc(-c2ccc(OCc3ccc(F)cc3)cc2O)c1Oc1ccccc1] | A |
| NUCC-0176260 | 434.9 | 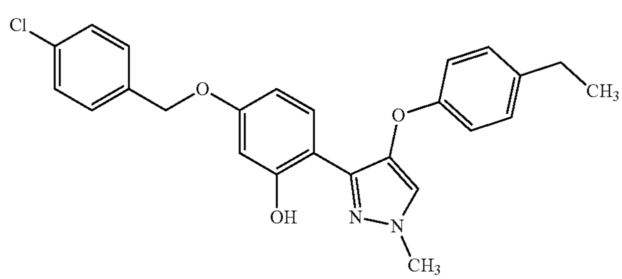 [SMILES: CCc1ccc(Oc2cn(C)nc2-c2ccc(OCc3ccc(Cl)cc3)cc2O)cc1] | A |
| NUCC-0176261 | 434.9 | 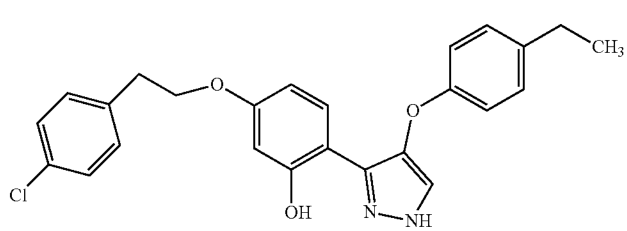 [SMILES: CCc1ccc(Oc2c[nH]nc2-c2ccc(OCCc3ccc(Cl)cc3)cc2O)cc1] | A |

TABLE 1-continued
Representative Compounds
| Molecule Name | Molecular weight (g/mol) | Structure | Synthesis Method |
|---|---|---|---|
| NUCC-0176262 | 420.9 | 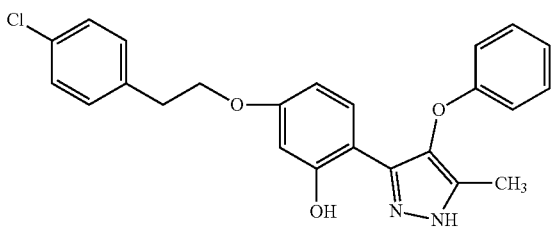 [SMILES: Cc1[nH]nc(-c2ccc(OCCc3ccc(Cl)cc3)cc2O)c1Oc1ccccc1] | A |
| NUCC-0196282 | 449.0 | 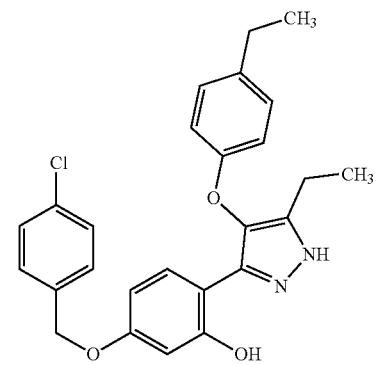 [SMILES: CCc1ccc(Oc2c(-c3ccc(OCc4ccc(Cl)cc4)cc3O)n[nH]c2CC)cc1] | A |
| NUCC-0196283 | 504.9 | 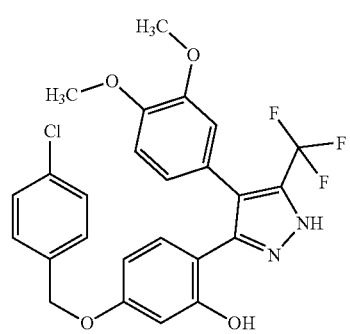 [SMILES: COc1ccc(-c2c(-c3ccc(OCc4ccc(Cl)cc4)cc3O)n[nH]c2C(F)(F)F)cc1OC] | F |
| NUCC-0196284 | 420.9 | 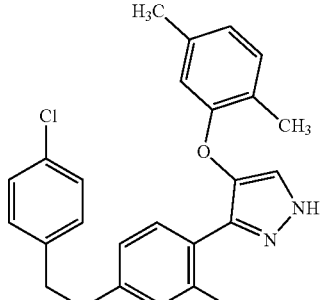 | A |

TABLE 1-continued

Representative Compounds

| Molecule Name | Molecular weight (g/mol) | Structure | Synthesis Method |
|---|---|---|---|
| NUCC-0196285 | 434.9 | 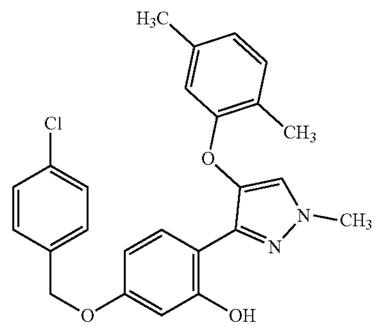 [SMILES: Cc1ccc(C)c(Oc2cn(C)nc2-c2ccc(OCc3ccc(Cl)cc3)cc2O)c1] | A |
| NUCC-0196286 | 420.9 | 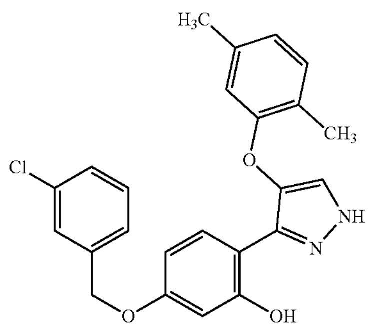 [SMILES: Cc1ccc(C)c(Oc2c[nH]nc2-c2ccc(OCc3cccc(Cl)c3)cc2O)c1] | A |
| NUCC-0196287 | 434.9 | 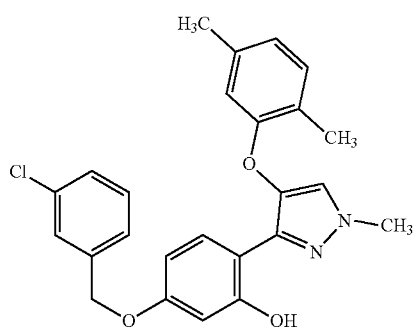 [SMILES: Cc1ccc(C)c(Oc2cn(C)nc2-c2ccc(OCc3cccc(Cl)c3)cc2O)c1] | A |
| NUCC-0196288 | 416.5 | 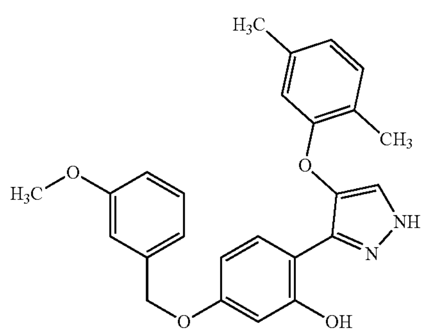 [SMILES: COc1cccc(COc2ccc(-c3n[nH]cc3Oc3cc(C)ccc3C)c(O)c2)c1] | A |

TABLE 1-continued

Representative Compounds

| Molecule Name | Molecular weight (g/mol) | Structure | Synthesis Method |
|---|---|---|---|
| NUCC-0196289 | 430.5 | 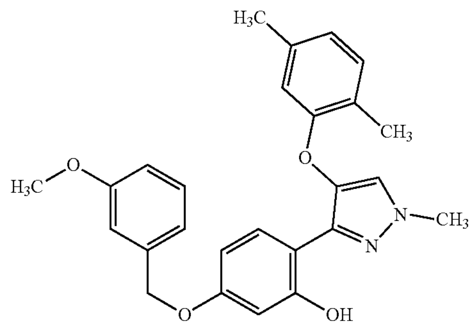 | A |
| NUCC-0196290 | 436.5 | 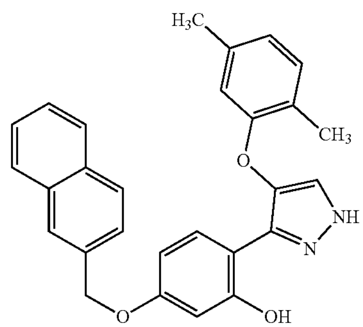 [SMILES: Cc1ccc(C)c(Oc2c[nH]nc2-c2ccc(OCc3ccc4ccccc4c3)cc2O)c1] | A |
| NUCC-0196291 | 450.5 | 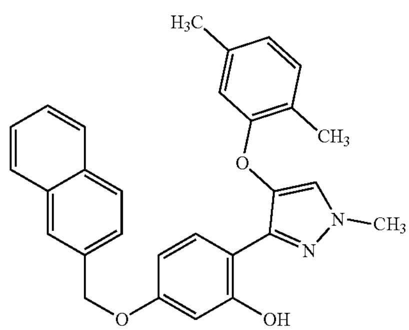 [SMILES: Cc1ccc(C)c(Oc2cn(C)nc2-c2ccc(OCc3ccc4ccccc4c3)cc2O)c1] | A |
| NUCC-0196294 | 463.0 | 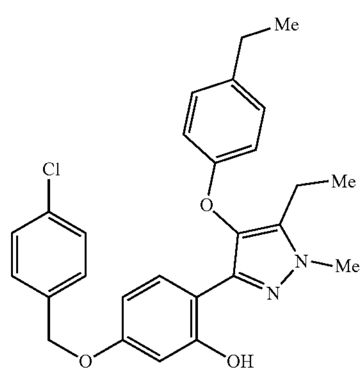 [SMILES: CCc1ccc(Oc2c(-c3ccc(OCc4ccc(Cl)cc4)cc3O)nn(C)c2CC)cc1] | A |

TABLE 1-continued

Representative Compounds

| Molecule Name | Molecular weight (g/mol) | Structure | Synthesis Method |
|---|---|---|---|
| NUCC-0196295 | 488.9 | 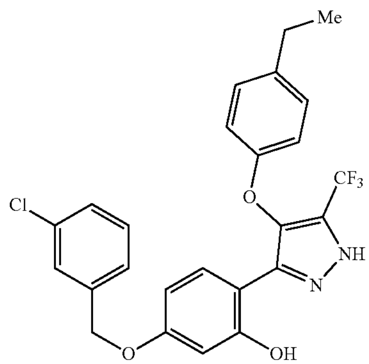 [SMILES: CCc1ccc(Oc2c(-c3ccc(OCc4cccc(Cl)c4)cc3O)n[nH]c2C(F)(F)F)cc1] | A |
| NUCC-0196296 | 502.9 | 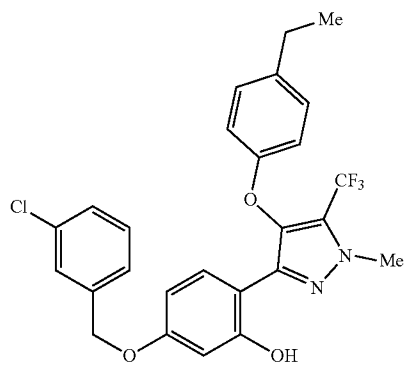 [SMILES: CCc1ccc(Oc2c(-c3ccc(OCc4cccc(Cl)c4)cc3O)nn(C)c2C(F)(F)F)cc1] | A |
| NUCC-0196297 | 484.5 | 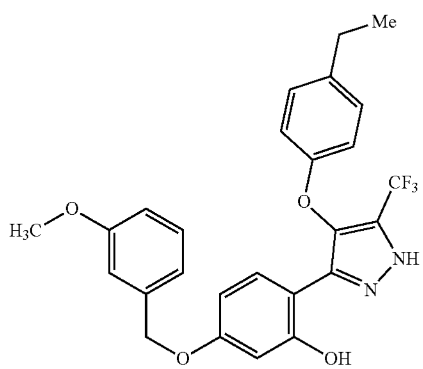 [SMILES: CCc1ccc(Oc2c(-c3ccc(OCc4cccc(OC)c4)cc3O)n[nH]c2C(F)(F)F)cc1] | A |
| NUCC-0196298 | 498.5 | 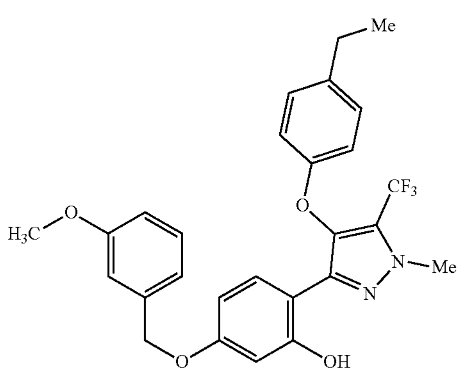 [SMILES: CCc1ccc(Oc2c(-c3ccc(OCc4cccc(OC)c4)cc3O)nn(C)c2C(F)(F)F)cc1] | A |

TABLE 1-continued

Representative Compounds

| Molecule Name | Molecular weight (g/mol) | Structure | Synthesis Method |
| --- | --- | --- | --- |
| NUCC-0196299 | 421.5 | 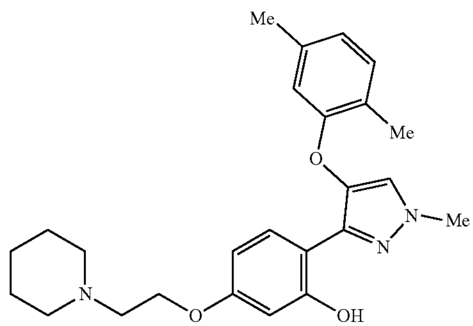 [SMILES: Cc1ccc(C)c(Oc2cn(C)nc2-c2ccc(OCCN3CCCCC3)cc2O)c1] | A |
| NUCC-0196301 | 478.8 | 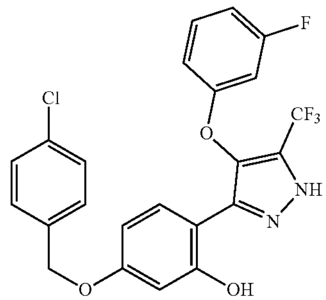 [SMILES: Oc1cc(OCc2ccc(Cl)cc2)ccc1-c1n[nH]c(C(F)(F)F)c1Oc1cccc(F)c1] | A |
| NUCC-0196302 | 492.9 | 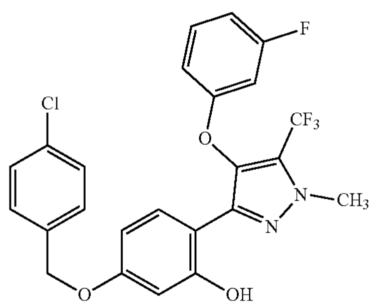 [SMILES: Cn1nc(-c2ccc(OCc3ccc(Cl)cc3)cc2O)c(Oc2cccc(F)c2)c1C(F)(F)F] | A |
| NUCC-0196303 | 427.3 | 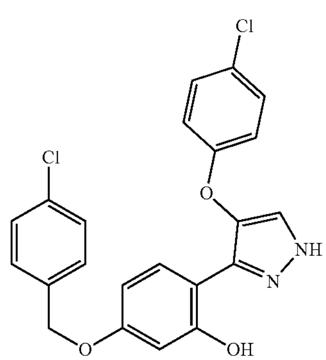 [SMILES: Oc1cc(OCc2ccc(Cl)cc2)ccc1-c1n[nH]cc1Oc1ccc(Cl)cc1] | A |

TABLE 1-continued

Representative Compounds

| Molecule Name | Molecular weight (g/mol) | Structure | Synthesis Method |
|---|---|---|---|
| NUCC-0196304 | 509.3 | 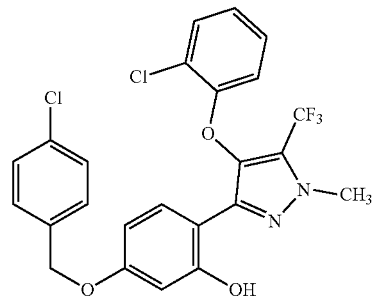 [SMILES: Cn1nc(-c2ccc(OCc3ccc(Cl)cc3)cc2O)c(Oc2ccccc2Cl)c1C(F)(F)F] | A |
| NUCC-0196305 | 441.3 | 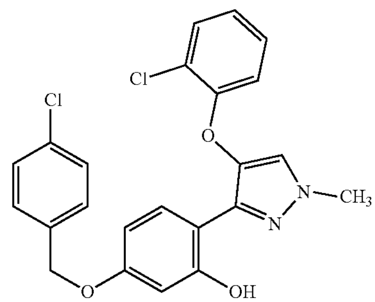 [SMILES: Cn1cc(Oc2ccccc2Cl)c(-c2ccc(OCc3ccc(Cl)cc3)cc2O)n1] | F |
| NUCC-0196306 | 505.9 | 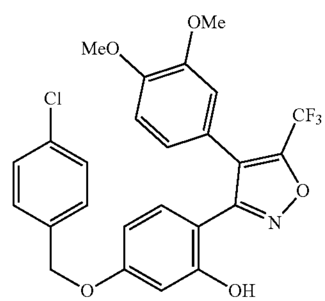 [SMILES: COc1ccc(-c2c(-c3ccc(OCc4ccc(Cl)cc4)cc3O)noc2C(F)(F)F)cc1OC] | A |
| NUCC-0196311 | 518.9 | 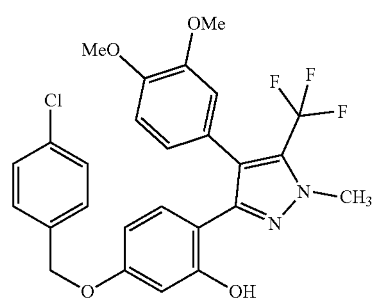 [SMILES: COc1ccc(-c2c(-c3ccc(OCc4ccc(Cl)cc4)cc3O)nn(C)c2C(F)(F)F)cc1OC] | F |
| NUCC-0196312 | 474.9 | 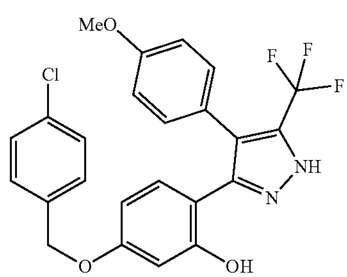 [SMILES: COc1ccc(-c2c(-c3ccc(OCc4ccc(Cl)cc4)cc3O)n[nH]c2C(F)(F)F)cc1] | F |

TABLE 1-continued

Representative Compounds

| Molecule Name | Molecular weight (g/mol) | Structure | Synthesis Method |
|---|---|---|---|
| NUCC-0196313 | 368.7 | 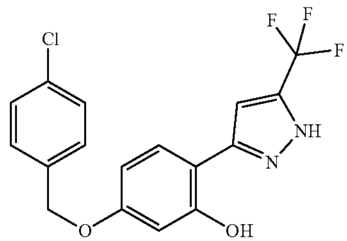 [SMILES: Oc1cc(OCc2ccc(Cl)cc2)ccc1-c1cc(C(F)(F)F)[nH]n1] | H |
| NUCC-0196314 | 382.8 | 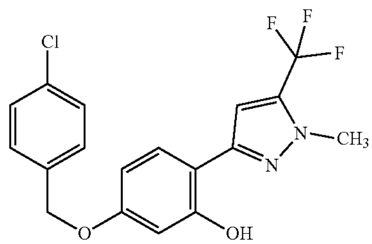 [SMILES: Cn1nc(-c2ccc(OCc3ccc(Cl)cc3)cc2O)cc1C(F)(F)F] | H |
| NUCC-0196340 | 488.9 | 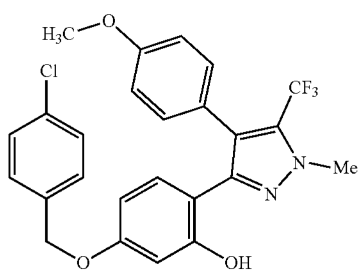 [SMILES: COc1ccc(-c2c(-c3ccc(OCc4ccc(Cl)cc4)cc3O)nn(C)c2C(F)(F)F)cc1] | F |
| NUCC-0196341 | 497.9 | 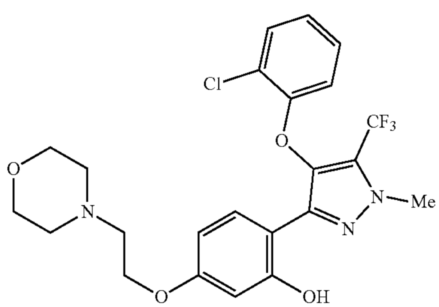 [SMILES: Cn1nc(-c2ccc(OCCN3CCOCC3)cc2O)c(Oc2ccccc2Cl)c1C(F)(F)F] | A |
| NUCC-0196342 | 495.3 | 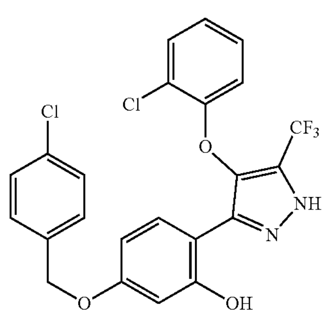 [SMILES: Oc1cc(OCc2ccc(Cl)cc2)ccc1-c1n[nH]c(C(F)(F)F)c1Oc1ccccc1Cl] | A |

TABLE 1-continued

Representative Compounds

| Molecule Name | Molecular weight (g/mol) | Structure | Synthesis Method |
|---|---|---|---|
| NUCC-0196343 | 427.3 | 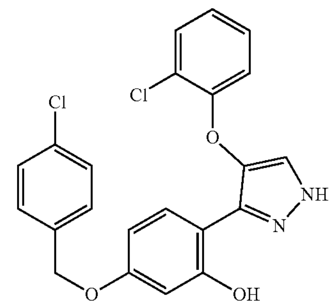 [SMILES: Oc1cc(OCc2ccc(Cl)cc2)ccc1-c1n[nH]cc1Oc1ccccc1Cl] | A |
| NUCC-0196344 | 458.9 | 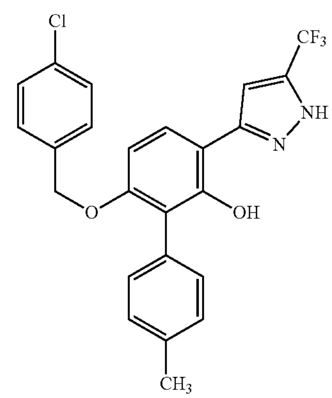 [SMILES: Cc1ccc(-c2c(OCc3ccc(Cl)cc3)ccc(-c3cc(C(F)(F)F)[nH]n3)c2O)cc1] | B |
| NUCC-0196345 | 390.9 | 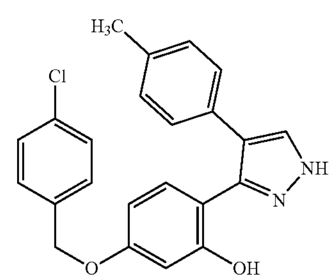 [SMILES: Cc1ccc(-c2c[nH]nc2-c2ccc(OCc3ccc(Cl)cc3)cc2O)cc1] | E |
| NUCC-0196346 | 404.9 | 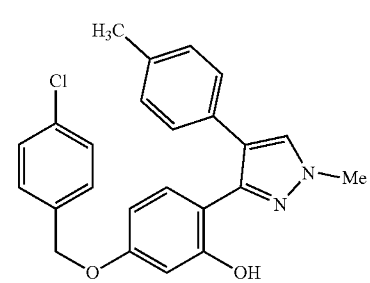 [SMILES: Cc1ccc(-c2cn(C)nc2-c2ccc(OCc3ccc(Cl)cc3)cc2O)cc1] | E |

TABLE 1-continued
Representative Compounds
| Molecule Name | Molecular weight (g/mol) | Structure | Synthesis Method |
|---|---|---|---|
| NUCC-0196347 | 462.8 | 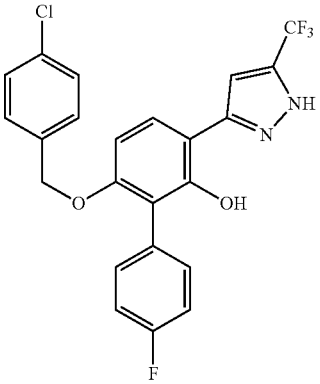 [SMILES: Oc1c(-c2cc(C(F)(F)F)[nH]n2)ccc(OCc2ccc(Cl)cc2)c1-c1ccc(F)cc1] | B |
| NUCC-0196348 | 476.9 | 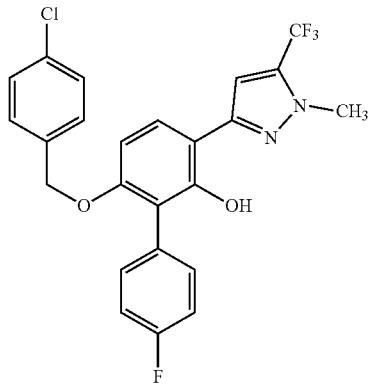 [SMILES: Cn1nc(-c2ccc(OCc3ccc(Cl)cc3)c(-c3ccc(F)cc3)c2O)cc1C(F)(F)F] | B |
| NUCC-0196349 | 408.9 | 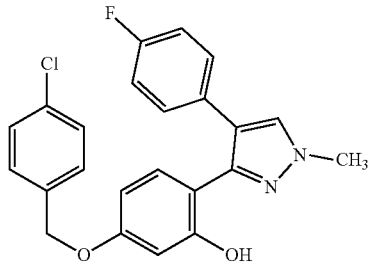 [SMILES: Cn1cc(-c2ccc(F)cc2)c(-c2ccc(OCc3ccc(Cl)cc3)cc2O)n1] | E |
| NUCC-0196350 | 411.3 | 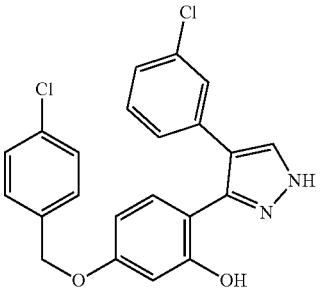 [SMILES: Oc1cc(OCc2ccc(Cl)cc2)ccc1-c1n[nH]cc1-c1cccc(Cl)c1] | E |

TABLE 1-continued

Representative Compounds

| Molecule Name | Molecular weight (g/mol) | Structure | Synthesis Method |
|---|---|---|---|
| NUCC-0196351 | 425.3 | 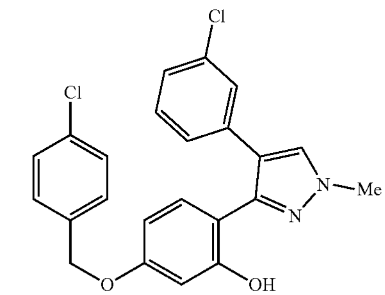 [SMILES: Cn1cc(-c2cccc(Cl)c2)c(-c2ccc(OCc3ccc(Cl)cc3)cc2O)n1] | E |
| NUCC-0196352 | 517.0 | 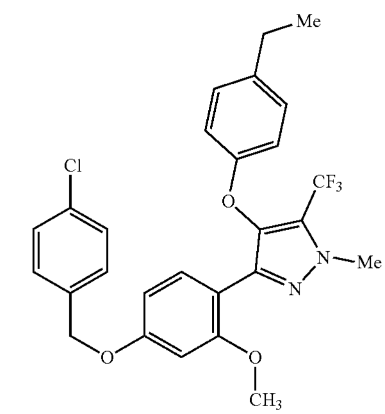 [SMILES: CCc1ccc(Oc2c(-c3ccc(OCc4ccc(Cl)cc4)cc3OC)nn(C)c2C(F)(F)F)cc1] | A |
| NUCC-0196353 | 486.9 | 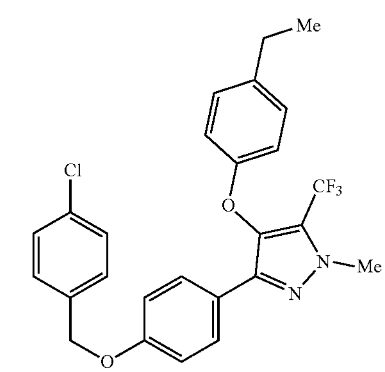 [SMILES: CCc1ccc(Oc2c(-c3ccc(OCc4ccc(Cl)cc4)cc3)nn(C)c2C(F)(F)F)cc1] | A |
| NUCC-0196354 | 537.4 | 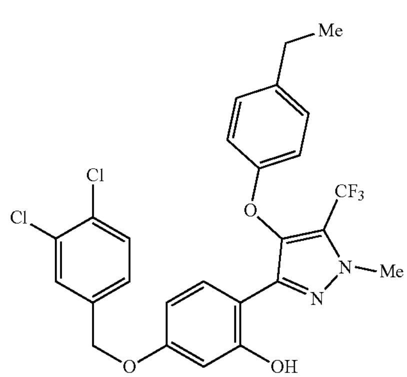 [SMILES: CCc1ccc(Oc2c(-c3ccc(OCc4ccc(Cl)c(Cl)c4)cc3O)nn(C)c2C(F)(F)F)cc1] | A |

TABLE 1-continued

Representative Compounds

| Molecule Name | Molecular weight (g/mol) | Structure | Synthesis Method |
|---|---|---|---|
| NUCC-0196355 | 523.3 | 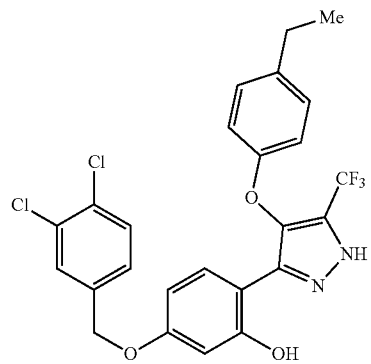 [SMILES: CCc1ccc(Oc2c(-c3ccc(OCc4ccc(Cl)c(Cl)c4)cc3O)n[nH]c2C(F)(F)F)cc1] | A |
| NUCC-0196356 | 517.0 | 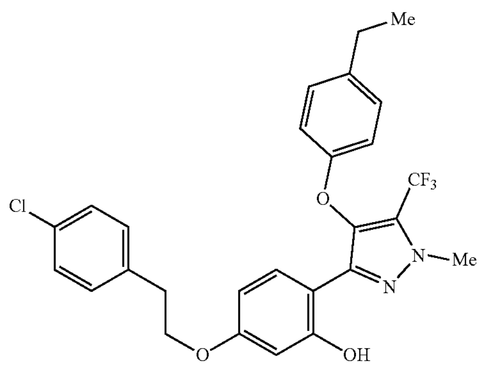 [SMILES: CCc1ccc(Oc2c(-c3ccc(OCCc4ccc(Cl)cc4)cc3O)nn(C)c2C(F)(F)F)cc1] | A |
| NUCC-0196357 | 502.9 | 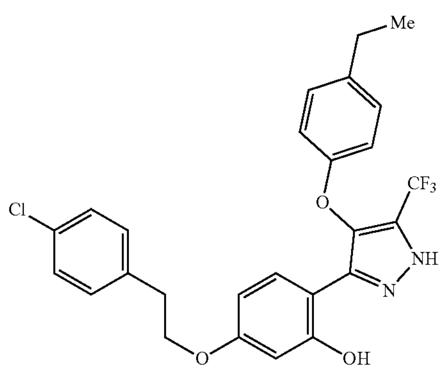 [SMILES: CCc1ccc(Oc2c(-c3ccc(OCCc4ccc(Cl)cc4)cc3O)n[nH]c2C(F)(F)F)cc1] | A |
| NUCC-0196358 | 498.5 | 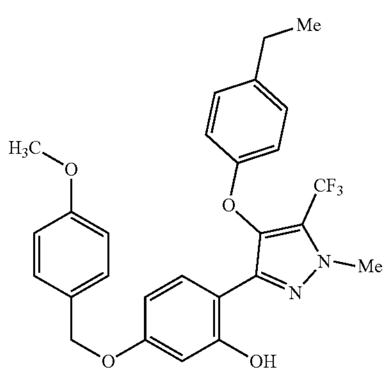 [SMILES: CCc1ccc(Oc2c(-c3ccc(OCc4ccc(OC)cc4)cc3O)nn(C)c2C(F)(F)F)cc1] | A |

TABLE 1-continued

Representative Compounds

| Molecule Name | Molecular weight (g/mol) | Structure | Synthesis Method |
|---|---|---|---|
| NUCC-0196359 | 484.5 | 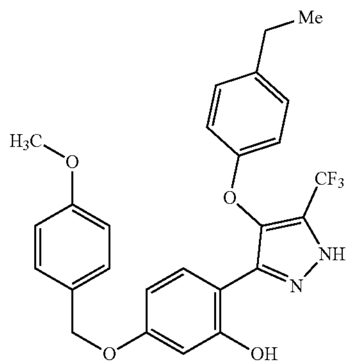 [SMILES: CCc1ccc(Oc2c(-c3ccc(OCc4ccc(OC)cc4)cc3O)n[nH]c2C(F)(F)F)cc1] | A |
| NUCC-0196360 | 594.9 | 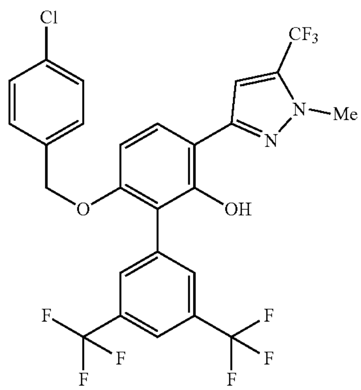 [SMILES: Cn1nc(-c2ccc(OCc3ccc(Cl)cc3)c(-c3cc(C(F)(F)F)cc(C(F)(F)F)c3)c2O)cc1C(F)(F)F] | B |
| NUCC-0196361 | 594.9 | 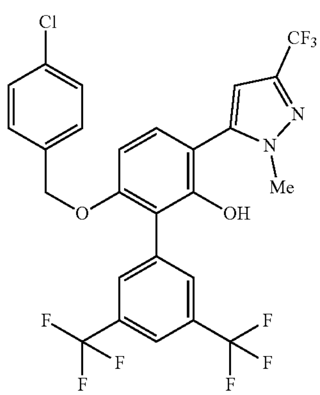 [SMILES: Cn1nc(C(F)(F)F)cc1-c1ccc(OCc2ccc(Cl)cc2)c(-c2cc(C(F)(F)F)cc(C(F)(F)F)c2)c1O] | B |
| NUCC-0196362 | 580.8 | 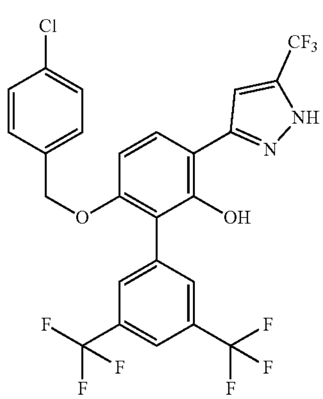 [SMILES: Oc1c(-c2cc(C(F)(F)F)[nH]n2)ccc(OCc2ccc(Cl)cc2)c1-c1cc(C(F)(F)F)cc(C(F)(F)F)c1] | B |

TABLE 1-continued
Representative Compounds
| Molecule Name | Molecular weight (g/mol) | Structure | Synthesis Method |
|---|---|---|---|
| NUCC-0196363 | 479.3 | 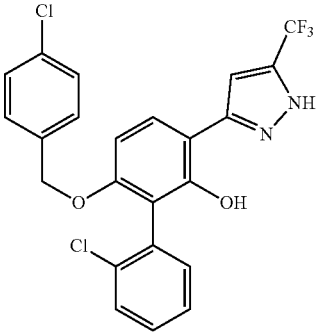 [SMILES: Oc1c(-c2cc(C(F)(F)F)[nH]n2)ccc(OCc2ccc(Cl)cc2)c1-c1ccccc1Cl] | B |
| NUCC-0196364 | 459.9 | 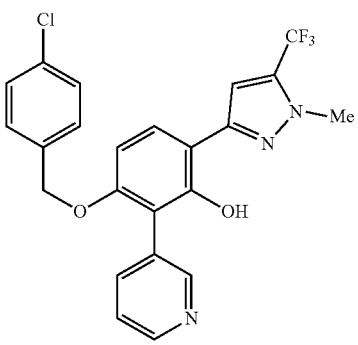 [SMILES: Cn1nc(-c2ccc(OCc3ccc(Cl)cc3)c(-c3cccnc3)c2O)cc1C(F)(F)F] | B |
| NUCC-0196365 | 459.9 | 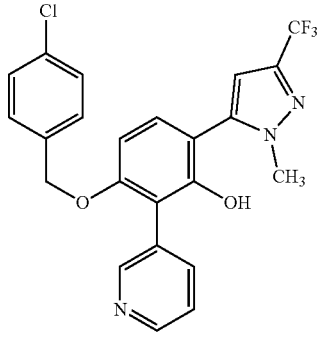 [SMILES: Cn1nc(C(F)(F)F)cc1-c1ccc(OCc2ccc(Cl)cc2)c(-c2cccnc2)c1O] | B |
| NUCC-0196366 | 445.8 | 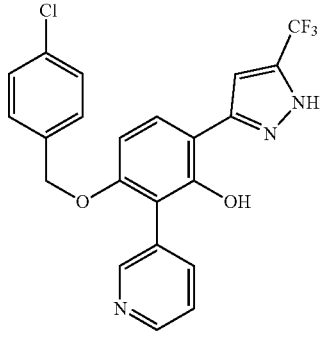 [SMILES: Oc1c(-c2cc(C(F)(F)F)[nH]n2)ccc(OCc2ccc(Cl)cc2)c1-c1cccnc1] | B |

TABLE 1-continued

Representative Compounds

| Molecule Name | Molecular weight (g/mol) | Structure | Synthesis Method |
|---|---|---|---|
| NUCC-0198293 | 376.8 | 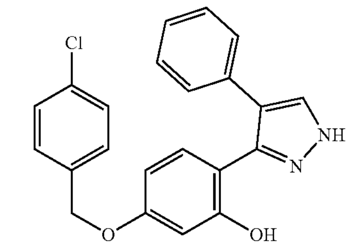 [SMILES: Oc1cc(OCc2ccc(Cl)cc2)ccc1-c1n[nH]cc1-c1ccccc1] | F |
| NUCC-0198294 | 390.9 | 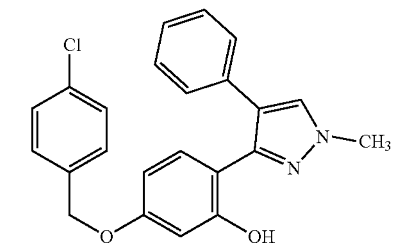 [SMILES: Cn1cc(-c2ccccc2)c(-c2ccc(OCc3ccc(Cl)cc3)cc2O)n1] | F |
| NUCC-0198295 | 444.8 | 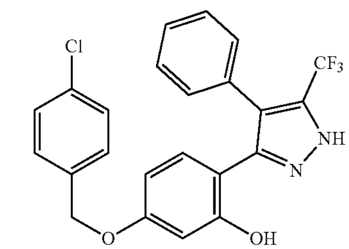 [SMILES: Oc1cc(OCc2ccc(Cl)cc2)ccc1-c1n[nH]c(C(F)(F)F)c1-c1ccccc1] | F |
| NUCC-0198296 | 458.9 | 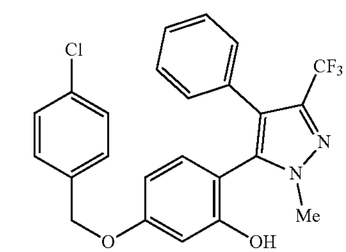 [SMILES: Cn1nc(C(F)(F)F)c(-c2ccccc2)c1-c1ccc(OCc2ccc(Cl)cc2)cc1O] | F |
| NUCC-00198297 | 458.9 | 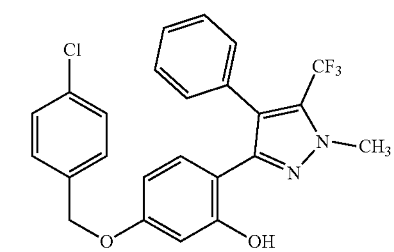 [SMILES: Cn1nc(-c2ccc(OCc3ccc(Cl)cc3)cc2O)c(-c2ccccc2)c1C(F)(F)F] | F |
| NUCC-0198298 | 390.9 | 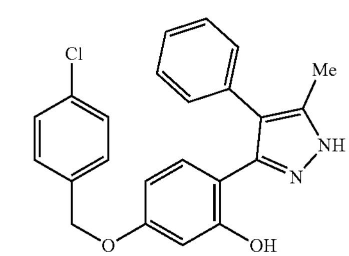 [SMILES: Cc1[nH]nc(-c2ccc(OCc3ccc(Cl)cc3)cc2O)c1-c1ccccc1] | F |

TABLE 1-continued

Representative Compounds

| Molecule Name | Molecular weight (g/mol) | Structure | Synthesis Method |
|---|---|---|---|
| NUCC-0198299 | 404.9 | 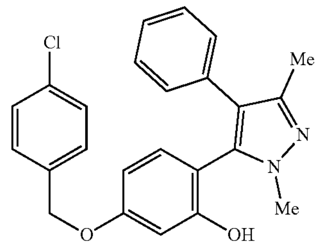 [SMILES: Cc1nn(C)c(-c2ccc(OCc3ccc(Cl)cc3)cc2O)c1-c1ccccc1] | F |
| NUCC-0198300 | 404.9 | 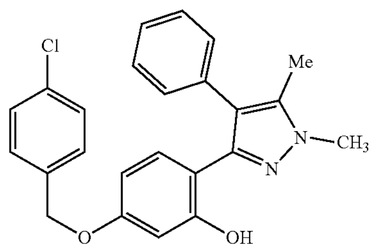 [SMILES: Cc1c(-c2ccccc2)c(-c2ccc(OCc3ccc(Cl)cc3)cc2O)nn1C] | F |
| NUCC-0198301 | 404.9 | 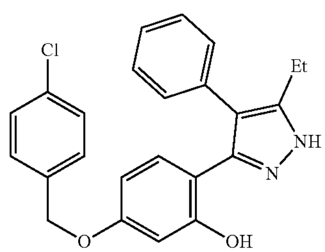 [SMILES: CCc1[nH]nc(-c2ccc(OCc3ccc(Cl)cc3)cc2O)c1-c1ccccc1] | F |
| NUCC-0198302 | 418.9 | 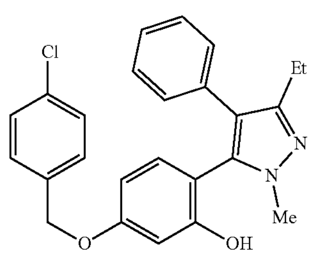 [SMILES: CCc1nn(C)c(-c2ccc(OCc3ccc(Cl)cc3)cc2O)c1-c1ccccc1] | F |
| NUCC-0198303 | 418.9 | 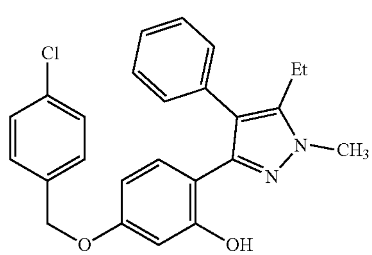 [SMILES: CCc1c(-c2ccccc2)c(-c2ccc(OCc3ccc(Cl)cc3)cc2O)nn1C] | F |

TABLE 1-continued

Representative Compounds

| Molecule Name | Molecular weight (g/mol) | Structure | Synthesis Method |
|---|---|---|---|
| NUCC-0198304 | 406.9 | 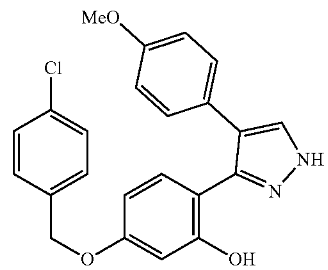 [SMILES: COc1ccc(-c2c[nH]nc2-c2ccc(OCc3ccc(Cl)cc3)cc2O)cc1] | F |
| NUCC-0198305 | 420.9 | 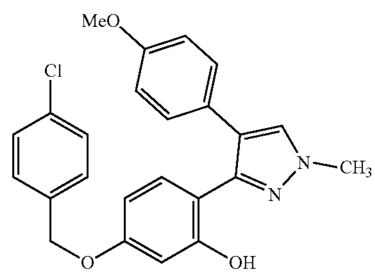 [SMILES: COc1ccc(-c2cn(C)nc2-c2ccc(OCc3ccc(Cl)cc3)cc2O)cc1] | F |
| NUCC-0198306 | 434.9 | 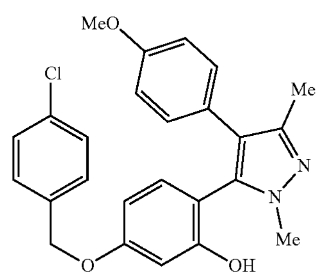 [SMILES: COc1ccc(-c2c(C)nn(C)c2-c2ccc(OCc3ccc(Cl)cc3)cc2O)cc1] | F |
| NUCC-0198307 | 434.9 | 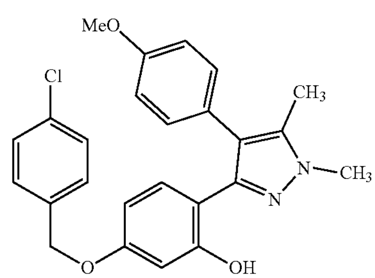 [SMILES: COc1ccc(-c2c(-c3ccc(OCc4ccc(Cl)cc4)cc3O)nn(C)c2C)cc1] | F |
| NUCC-0198308 | 406.9 | 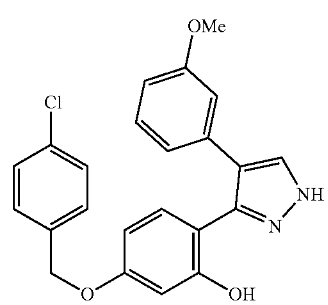 [SMILES: COc1cccc(-c2c[nH]nc2-c2ccc(OCc3ccc(Cl)cc3)cc2O)c1] | F |

TABLE 1-continued

Representative Compounds

| Molecule Name | Molecular weight (g/mol) | Structure | Synthesis Method |
|---|---|---|---|
| NUCC-0198309 | 474.9 | 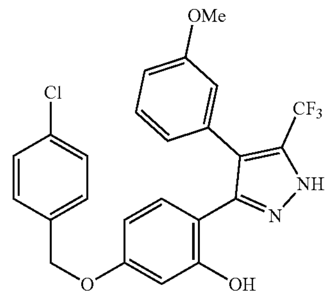 [SMILES: COc1cccc(-c2c(-c3ccc(OCc4ccc(Cl)cc4)cc3O)n[nH]c2C(F)(F)F)c1] | F |
| NUCC-0198310 | 488.9 | 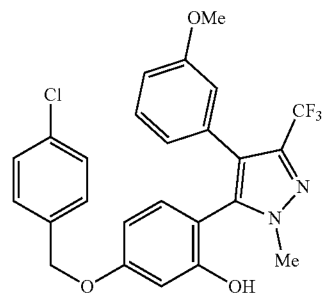 [SMILES: COc1cccc(-c2c(C(F)(F)F)nn(C)c2-c2ccc(OCc3ccc(Cl)cc3)cc2O)c1] | F |
| NUCC-0198311 | 488.9 | 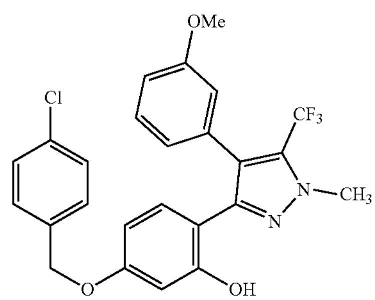 [SMILES: COc1cccc(-c2c(-c3ccc(OCc4ccc(Cl)cc4)cc3O)nn(C)c2C(F)(F)F)c1] | F |
| NUCC-0198312 | 420.9 | 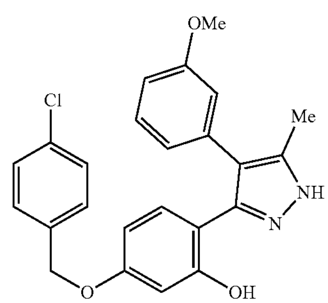 | F |
| NUCC-0198313 | 434.9 | 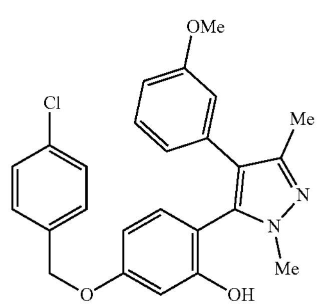 [SMILES: COc1cccc(-c2c(C)nn(C)c2-c2ccc(OCc3ccc(Cl)cc3)cc2O)c1] | F |

TABLE 1-continued

Representative Compounds

| Molecule Name | Molecular weight (g/mol) | Structure | Synthesis Method |
|---|---|---|---|
| NUCC-0198314 | 434.9 | 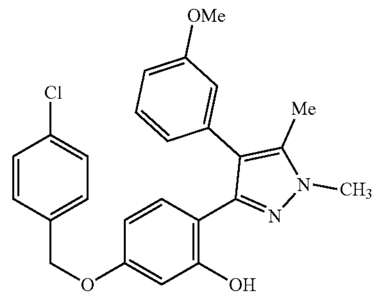 [SMILES: COc1cccc(-c2c(-c3ccc(OCc4ccc(Cl)cc4)cc3O)nn(C)c2C)c1] | F |
| NUCC-0198315 | 434.9 | 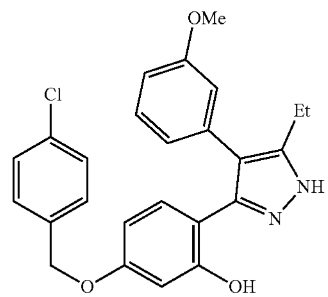 [SMILES: CCc1[nH]nc(-c2ccc(OCc3ccc(Cl)cc3)cc2O)c1-c1cccc(OC)c1] | F |
| NUCC-0198316 | 449.0 | 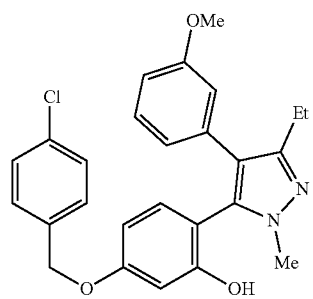 [SMILES: CCc1nn(C)c(-c2ccc(OCc3ccc(Cl)cc3)cc2O)c1-c1cccc(OC)c1] | F |
| NUCC-0198317 | 449.0 | 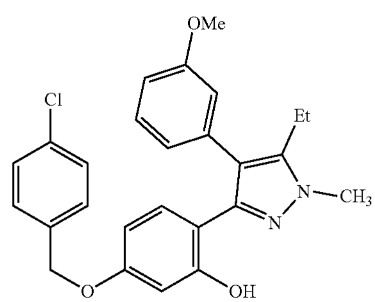 [SMILES: CCc1c(-c2cccc(OC)c2)c(-c2ccc(OCc3ccc(Cl)cc3)cc2O)nn1C] | F |
| NUCC-0198318 | 512.8 | 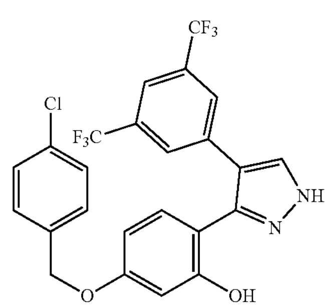 [SMILES: Oc1cc(OCc2ccc(Cl)cc2)ccc1-c1n[nH]cc1-c1cc(C(F)(F)F)cc(C(F)(F)F)c1] | E |

TABLE 1-continued

Representative Compounds

| Molecule Name | Molecular weight (g/mol) | Structure | Synthesis Method |
|---|---|---|---|
| NUCC-0198319 | 526.9 | 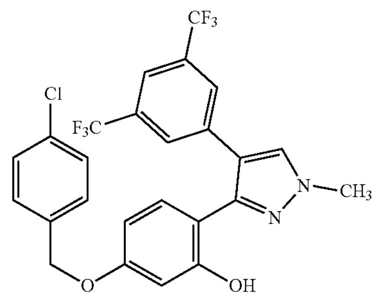 [SMILES: Cn1cc(-c2cc(C(F)(F)F)cc(C(F)(F)F)c2)c(-c2ccc(OCc3ccc(Cl)cc3)cc2O)n1] | E |
| NUCC-0198320 | 377.8 | 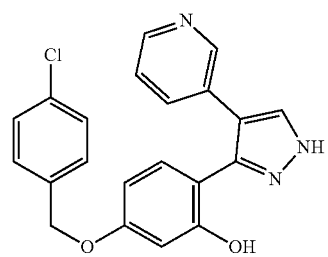 [SMILES: Oc1cc(OCc2ccc(Cl)cc2)ccc1-c1n[nH]cc1-c1cccnc1] | E |
| NUCC-0198321 | 391.9 | 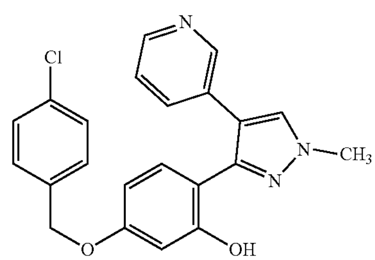 [SMILES: Cn1cc(-c2cccnc2)c(-c2ccc(OCc3ccc(Cl)cc3)cc2O)n1] | E |
| NUCC-0198322 | 366.8 | 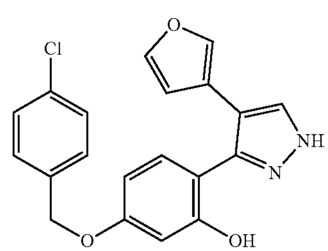 [SMILES: Oc1cc(OCc2ccc(Cl)cc2)ccc1-c1n[nH]cc1-c1ccoc1] | F |
| NUCC-0198323 | 380.8 | 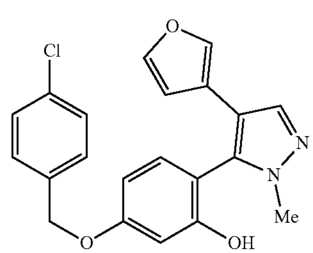 [SMILES: Cn1ncc(-c2ccoc2)c1-c1ccc(OCc2ccc(Cl)cc2)cc1O] | E |

TABLE 1-continued

Representative Compounds

| Molecule Name | Molecular weight (g/mol) | Structure | Synthesis Method |
|---|---|---|---|
| NUCC-0198324 | 380.8 | 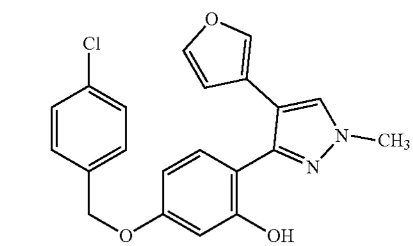 [SMILES: Cn1cc(-c2ccoc2)c(-c2ccc(OCc3ccc(Cl)cc3)cc2O)n1] | E |
| NUCC-0198325 | 434.8 | 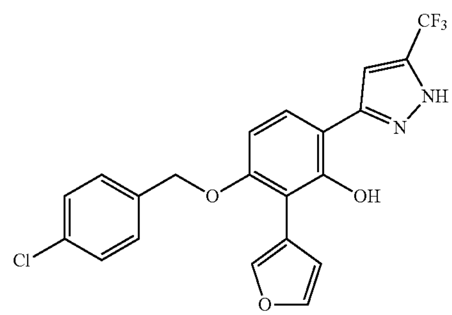 [SMILES: Oc1c(-c2cc(C(F)(F)F)[nH]n2)ccc(OCc2ccc(Cl)cc2)c1-c1ccoc1] | B |
| NUCC-0198326 | 420.9 | 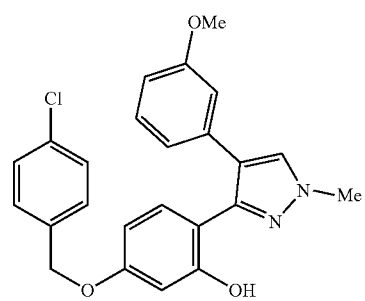 [SMILES: COc1cccc(-c2cn(C)nc2-c2ccc(OCc3ccc(Cl)cc3)cc2O)c1] | E |
| NUCC-0198352 | 404.9 | 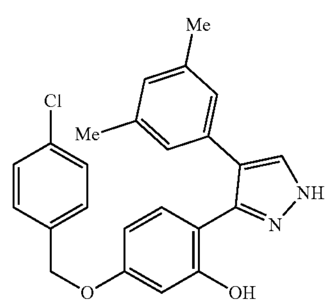 [SMILES: Cc1cc(C)cc(-c2c[nH]nc2-c2ccc(OCc3ccc(Cl)cc3)cc2O)c1] | E |
| NUCC-0198353 | 418.9 | 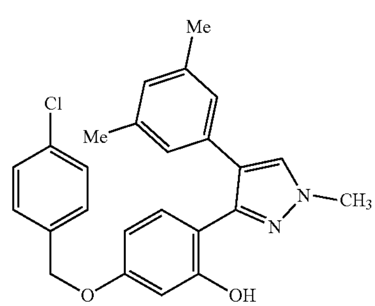 [SMILES: Cc1cc(C)cc(-c2cn(C)nc2-c2ccc(OCc3ccc(Cl)cc3)cc2O)c1] | E |

TABLE 1-continued

Representative Compounds

| Molecule Name | Molecular weight (g/mol) | Structure | Synthesis Method |
|---|---|---|---|
| NUCC-0198354 | 418.9 | 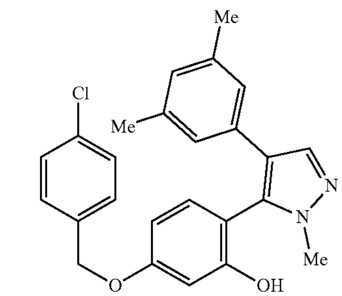 [SMILES: Cc1cc(C)cc(-c2cnn(C)c2-c2ccc(OCc3ccc(Cl)cc3)cc2O)c1] | E |
| NUCC-0198355 | 390.9 | 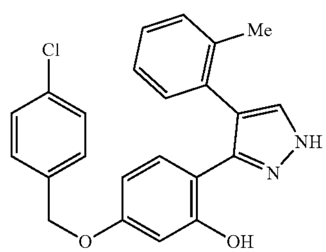 [SMILES: Cc1ccccc1-c1c[nH]nc1-c1ccc(OCc2ccc(Cl)cc2)cc1O] | E |
| NUCC-0198356 | 404.9 | 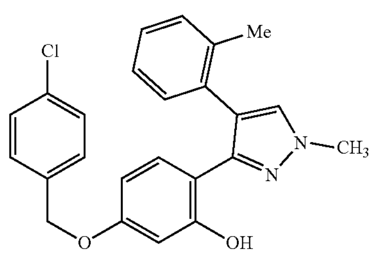 [SMILES: Cc1ccccc1-c1cn(C)nc1-c1ccc(OCc2ccc(Cl)cc2)cc1O] | E |
| NUCC-0198357 | 406.9 | 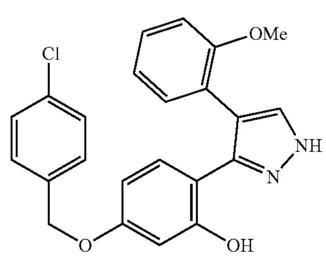 [SMILES: COc1ccccc1-c1c[nH]nc1-c1ccc(OCc2ccc(Cl)cc2)cc1O] | E |
| NUCC-0198358 | 420.9 | 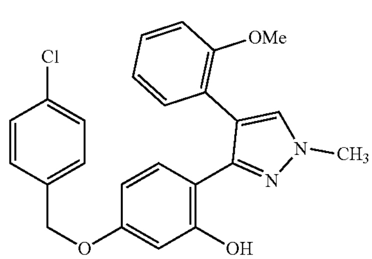 [SMILES: COc1ccccc1-c1cn(C)nc1-c1ccc(OCc2ccc(Cl)cc2)cc1O] | E |

TABLE 1-continued
Representative Compounds
| Molecule Name | Molecular weight (g/mol) | Structure | Synthesis Method |
|---|---|---|---|
| NUCC-0198359 | 418.9 | 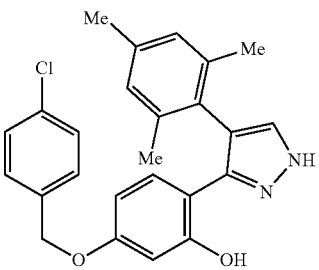 [SMILES: Cc1cc(C)c(-c2c[nH]nc2-c2ccc(OCc3ccc(Cl)cc3)cc2O)c(C)c1] | E |
| NUCC-0198360 | 433.0 | 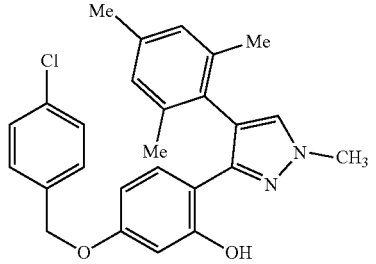 [SMILES: Cc1cc(C)c(-c2cn(C)nc2-c2ccc(OCc3ccc(Cl)cc3)cc2O)c(C)c1] | E |
| NUCC-0198361 | 380.8 | 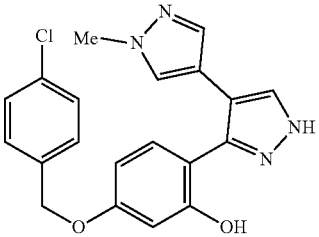 [SMILES: Cn1cc(-c2c[nH]nc2-c2ccc(OCc3ccc(Cl)cc3)cc2O)cn1] | E |
| NUCC-0198362 | 394.9 | 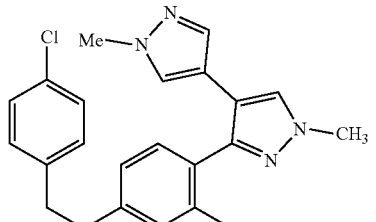 | E |
| NUCC-0198391 | 469.9 | 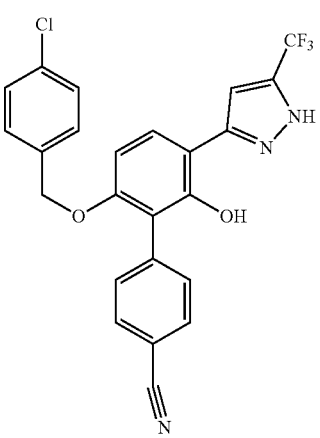 [SMILES: N#Cc1ccc(-c2c(OCc3ccc(Cl)cc3)ccc(-c3cc(C(F)(F)F)[nH]n3)c2O)cc1] | B |

TABLE 1-continued

Representative Compounds

| Molecule Name | Molecular weight (g/mol) | Structure | Synthesis Method |
|---|---|---|---|
| NUCC-0198392 | 483.9 | 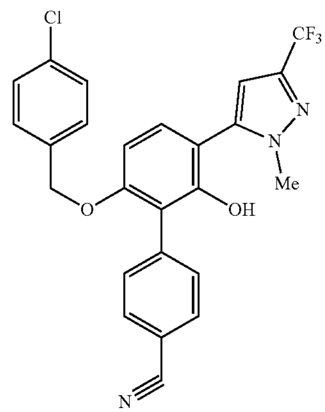 [SMILES: Cn1nc(C(F)(F)F)cc1-c1ccc(OCc2ccc(Cl)cc2)c(-c2ccc(C#N)cc2)c1O] | B |
| NUCC-0198393 | 483.9 | 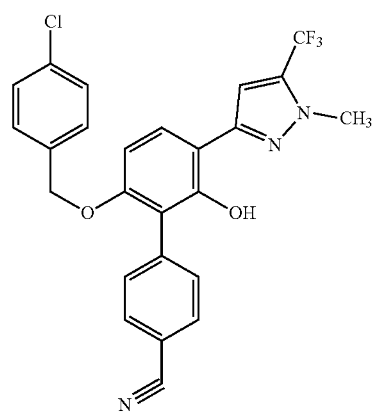 [SMILES: Cn1nc(-c2ccc(OCc3ccc(Cl)cc3)c(-c3ccc(C#N)cc3)c2O)cc1C(F)(F)F] | B |
| NUCC-0198394 | 487.9 | 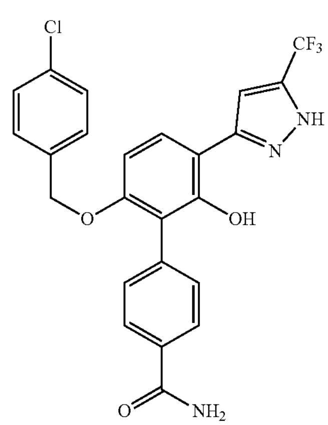 [SMILES: NC(=O)c1ccc(-c2c(OCc3ccc(Cl)cc3)ccc(-c3cc(C(F)(F)F)[nH]n3)c2O)cc1] | B |

TABLE 1-continued

Representative Compounds

| Molecule Name | Molecular weight (g/mol) | Structure | Synthesis Method |
|---|---|---|---|
| NUCC-0198395 | 514.9 | 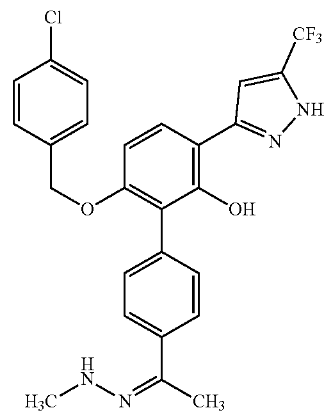 [SMILES: CN/N=C(/C)c1ccc(-c2c(OCc3ccc(Cl)cc3)ccc(-c3cc(C(F)(F)F)[nH]n3)c2O)cc1] | B |
| NUCC-0198396 | 529.0 | 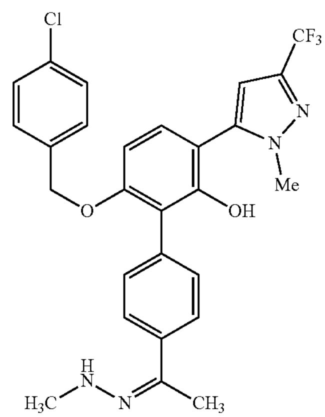 [SMILES: CN/N=C(/C)c1ccc(-c2c(OCc3ccc(Cl)cc3)ccc(-c3cc(C(F)(F)F)nn3C)c2O)cc1] | B |
| NUCC-0198397 | 529.0 | 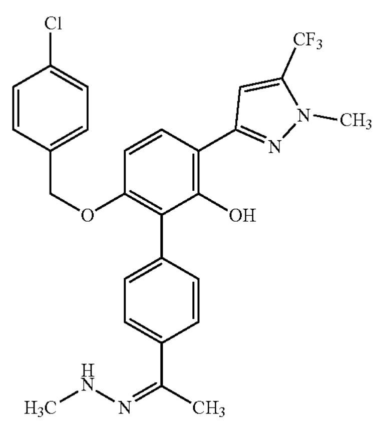 [SMILES: CN/N=C(/C)c1ccc(-c2c(OCc3ccc(Cl)cc3)ccc(-c3cc(C(F)(F)F)n(C)n3)c2O)cc1] | B |

TABLE 1-continued

Representative Compounds

| Molecule Name | Molecular weight (g/mol) | Structure | Synthesis Method |
|---|---|---|---|
| NUCC-0198398 | 469.9 | 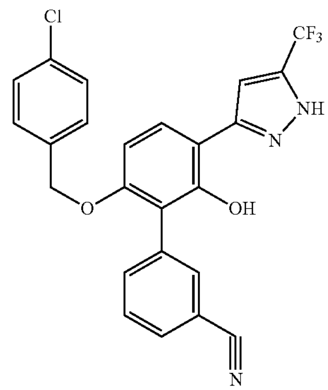 [SMILES: N#Cc1cccc(-c2c(OCc3ccc(Cl)cc3)ccc(-c3cc(C(F)(F)F)[nH]n3)c2O)c1] | B |
| NUCC-0198399 | 483.9 | 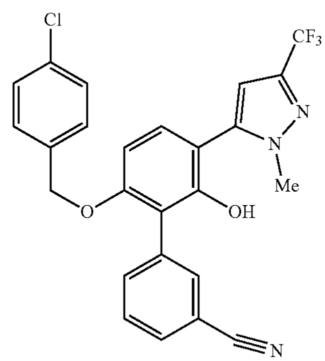 [SMILES: Cn1nc(C(F)(F)F)cc1-c1ccc(OCc2ccc(Cl)cc2)c(-c2cccc(C#N)c2)c1O] | B |
| NUCC-0198400 | 483.9 | 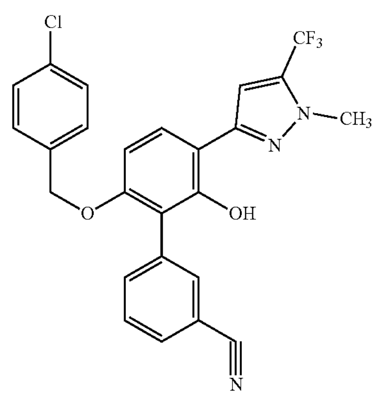 [SMILES: Cn1nc(-c2ccc(OCc3ccc(Cl)cc3)c(-c3cccc(C#N)c3)c2O)cc1C(F)(F)F] | B |
| NUCC-0198401 | 487.9 | 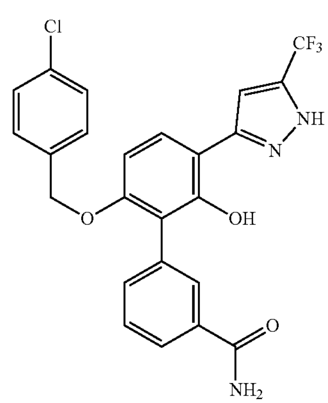 [SMILES: NC(=O)c1cccc(-c2c(OCc3ccc(Cl)cc3)ccc(-c3cc(C(F)(F)F)[nH]n3)c2O)c1] | B |

TABLE 1-continued

Representative Compounds

| Molecule Name | Molecular weight (g/mol) | Structure | Synthesis Method |
|---|---|---|---|
| NUCC-0198402 | 501.9 | 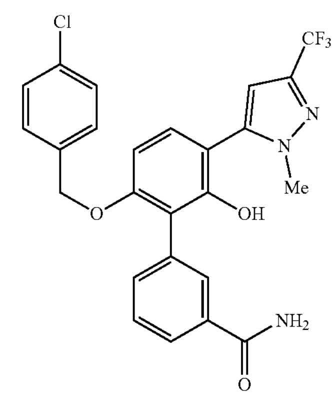 [SMILES: Cn1nc(C(F)(F)F)cc1-c1ccc(OCc2ccc(Cl)cc2)c(-c2cccc(C(N)=O)c2)c1O] | B |
| NUCC-0198403 | 514.9 | 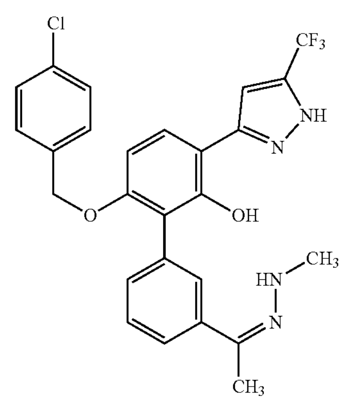 [SMILES: CN/N=C(/C)c1cccc(-c2c(OCc3ccc(Cl)cc3)ccc(-c3cc(C(F)(F)F)[nH]n3)c2O)c1] | B |
| NUCC-0198404 | 529.0 | 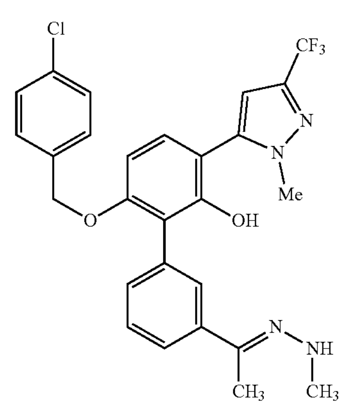 [SMILES: CN/N=C(\C)c1cccc(-c2c(OCc3ccc(Cl)cc3)ccc(-c3cc(C(F)(F)F)nn3C)c2O)c1] | B |

TABLE 1-continued
Representative Compounds
| Molecule Name | Molecular weight (g/mol) | Structure | Synthesis Method |
|---|---|---|---|
| NUCC-0198405 | 529.0 | 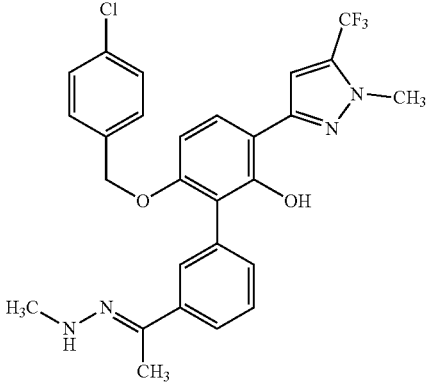 | B |
| NUCC-0198406 | 364.3 | 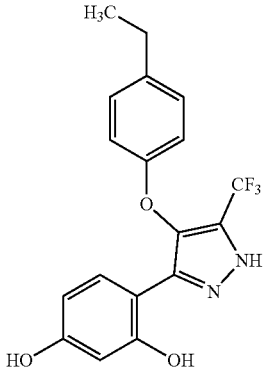 [SMILES: CCc1ccc(Oc2c(-c3ccc(O)cc3O)n[nH]c2C(F)(F)F)cc1] | A |
| NUCC-0198407 | 461.7 | 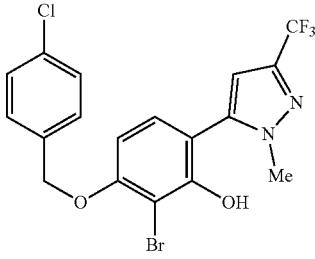 [SMILES: Cn1nc(C(F)(F)F)cc1-c1ccc(OCc2ccc(Cl)cc2)c(Br)c1O] | B |
| NUCC-0198408 | 461.7 | 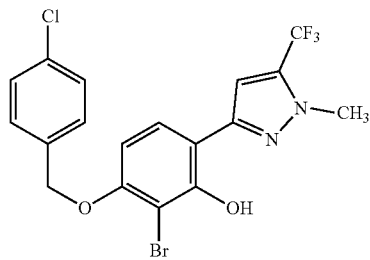 [SMILES: Cn1nc(-c2ccc(OCc3ccc(Cl)cc3)c(Br)c2O)cc1C(F)(F)F] | B |

TABLE 1-continued
Representative Compounds
| Molecule Name | Molecular weight (g/mol) | Structure | Synthesis Method |
|---|---|---|---|
| NUCC-0198409 | 501.9 | 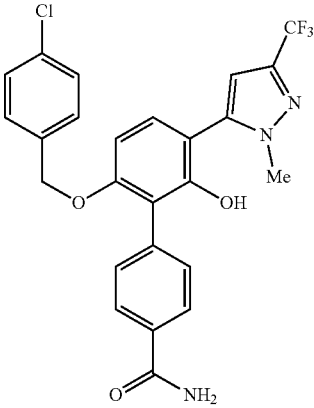 [SMILES: Cn1nc(C(F)(F)F)cc1-c1ccc(OCc2ccc(Cl)cc2)c(-c2ccc(C(N)=O)cc2)c1O] | B |
| NUCC-0198410 | 542.9 | 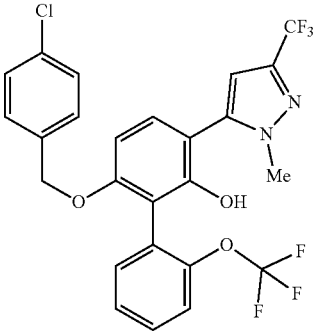 [SMILES: Cn1nc(C(F)(F)F)cc1-c1ccc(OCc2ccc(Cl)cc2)c(-c2ccccc2OC(F)(F)F)c1O] | B |
| NUCC-0198411 | 378.4 | 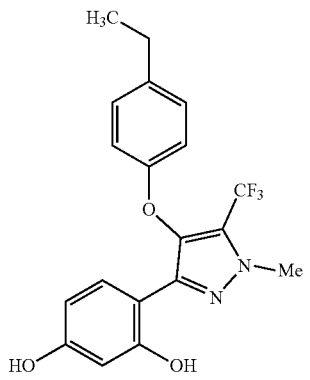 [SMILES: CCc1ccc(Oc2c(-c3ccc(O)cc3O)nn(C)c2C(F)(F)F)cc1] | A |
| NUCC-0198412 | 382.8 | 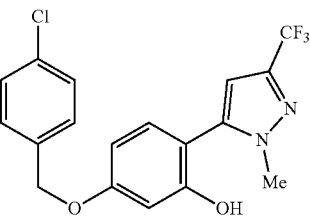 | H |

TABLE 1-continued

Representative Compounds

| Molecule Name | Molecular weight (g/mol) | Structure | Synthesis Method |
|---|---|---|---|
| NUCC-0200489 | 473.9 | 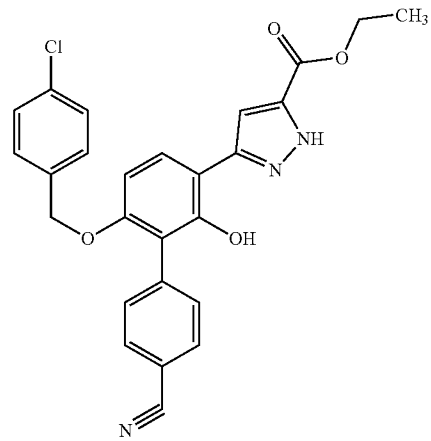 [SMILES: CCOC(=O)c1cc(-c2ccc(OCc3ccc(Cl)cc3)c(-c3ccc(C#N)cc3)c2O)n[nH]1] | C |
| NUCC-0200490 | 493.3 | 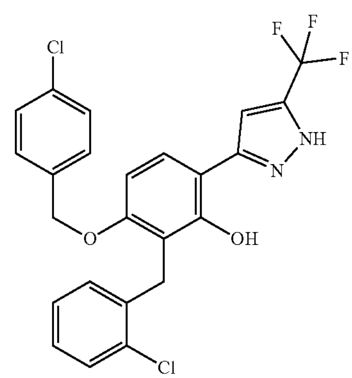 [SMILES: Oc1c(-c2cc(C(F)(F)F)[nH]n2)ccc(OCc2ccc(Cl)cc2)c1Cc1ccccc1Cl] | — |
| NUCC-0200491 | 353.7 | 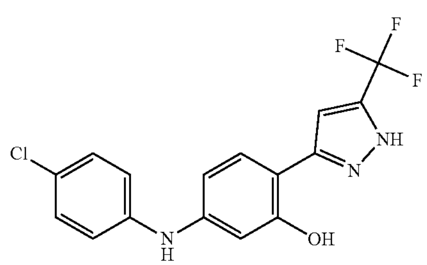 [SMILES: Oc1cc(Nc2ccc(Cl)cc2)ccc1-c1cc(C(F)(F)F)[nH]n1] | G |
| NUCC-0200492 | 367.8 | 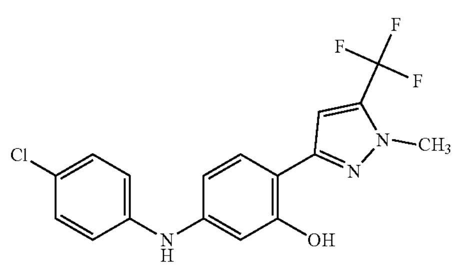 [SMILES: Cn1nc(-c2ccc(Nc3ccc(Cl)cc3)cc2O)cc1C(F)(F)F] | G |

TABLE 1-continued
Representative Compounds
| Molecule Name | Molecular weight (g/mol) | Structure | Synthesis Method |
|---|---|---|---|
| NUCC-0200493 | 367.8 | 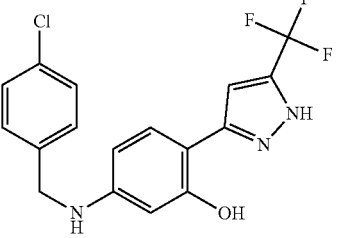 | G |
| NUCC-0200494 | 381.8 | 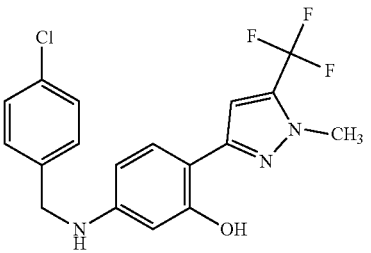 [SMILES: Cn1nc(-c2ccc(NCc3ccc(Cl)cc3)cc2O)cc1C(F)(F)F] | G |
| NUCC-0200495 | 456.3 | 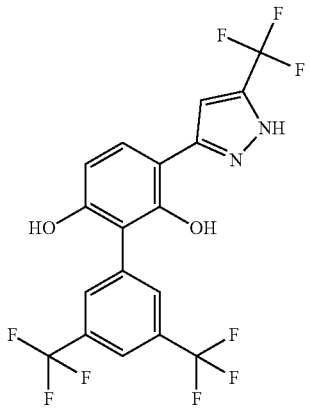 [SMILES: Oc1ccc(-c2cc(C(F)(F)F)[nH]n2)c(O)c1-c1cc(C(F)(F)F)cc(C(F)(F)F)c1] | B |
| NUCC-0200496 | 380.3 | 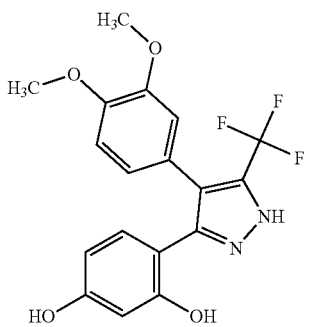 [SMILES: COc1ccc(-c2c(-c3ccc(O)cc3O)n[nH]c2C(F)(F)F)cc1OC] | F |
| NUCC-0200497 | 243.2 | 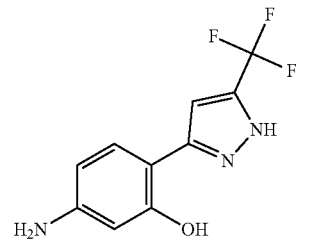 [SMILES: Nc1ccc(-c2cc(C(F)(F)F)[nH]n2)c(O)c1] | G |

TABLE 1-continued
Representative Compounds
| Molecule Name | Molecular weight (g/mol) | Structure | Synthesis Method |
|---|---|---|---|
| NUCC-0200498 | 257.2 | 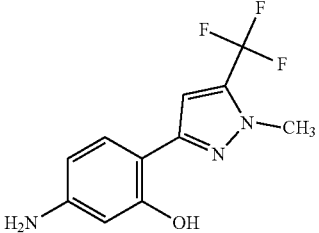 [SMILES: Cn1nc(-c2ccc(N)cc2O)cc1C(F)(F)F] | G |
| NUCC-0200499 | 458.9 | 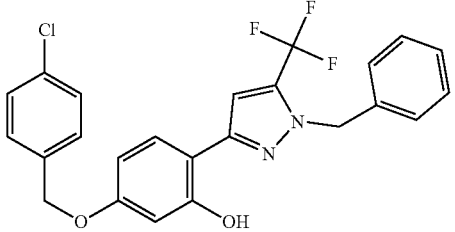 [SMILES: Oc1cc(OCc2ccc(Cl)cc2)ccc1-c1cc(C(F)(F)F)n(Cc2ccccc2)n1] | H |
| NUCC-0200500 | 524.9 | 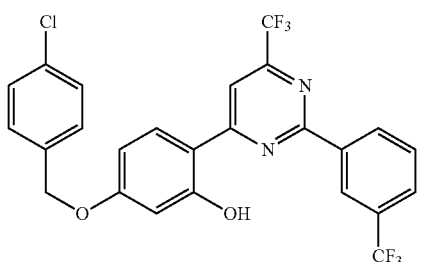 | H |
| NUCC-0200501 | 592.9 | 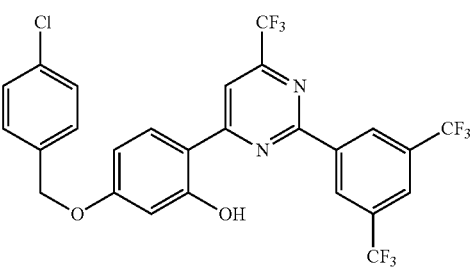 [SMILES: Oc1cc(OCc2ccc(Cl)cc2)ccc1-c1cc(C(F)(F)F)nc(-c2cc(C(F)(F)F)cc(C(F)(F)F)c2)n1] | H |
| NUCC-0200502 | 395.8 | 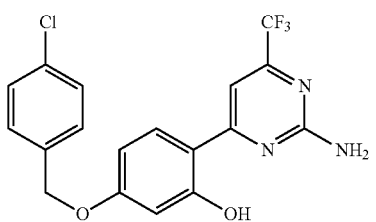 [SMILES: Nc1nc(-c2ccc(OCc3ccc(Cl)cc3)cc2O)cc(C(F)(F)F)n1] | H |
| NUCC-0200503 | 474.8 | 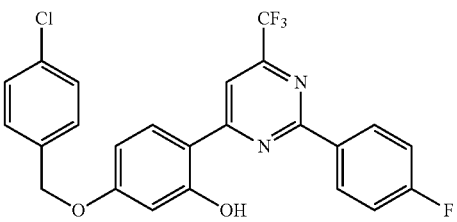 [SMILES: Oc1cc(OCc2ccc(Cl)cc2)ccc1-c1cc(C(F)(F)F)nc(-c2ccc(F)cc2)n1] | H |

TABLE 1-continued

Representative Compounds

| Molecule Name | Molecular weight (g/mol) | Structure | Synthesis Method |
|---|---|---|---|
| NUCC-0200557 | 444.9 | 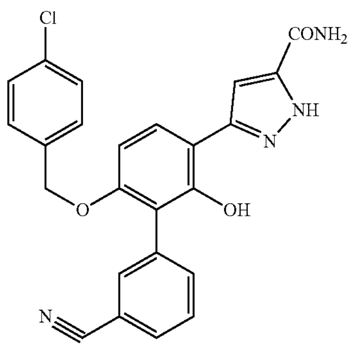 [SMILES: N#Cc1cccc(-c2c(OCc3ccc(Cl)cc3)ccc(-c3cc(C(N)=O)[nH]n3)c2O)c1] | B |
| NUCC-0200558 | 458.9 | 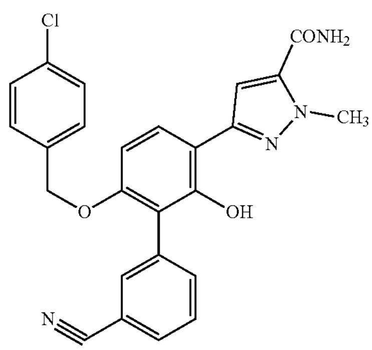 [SMILES: Cn1nc(-c2ccc(OCc3ccc(Cl)cc3)c(-c3cccc(C#N)c3)c2O)cc1C(N)=O] | B |
| NUCC-0200559 | 355.3 | 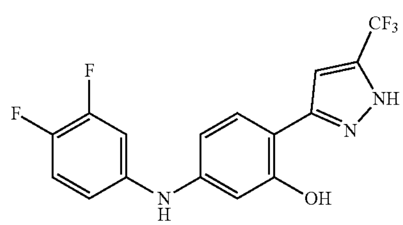 [SMILES: Oc1cc(Nc2ccc(F)c(F)c2)ccc1-c1cc(C(F)(F)F)[nH]n1] | G |
| NUCC-0200560 | 369.3 | 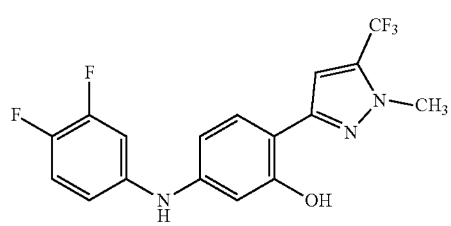 [SMILES: Cn1nc(-c2ccc(Nc3ccc(F)c(F)c3)cc2O)cc1C(F)(F)F] | G |
| NUCC-0200561 | 363.3 | 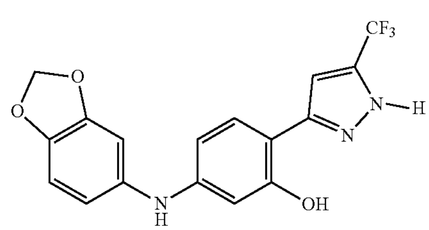 [SMILES: Oc1cc(Nc2ccc3c(c2)OCO3)ccc1-c1cc(C(F)(F)F)[nH]n1] | G |

TABLE 1-continued

Representative Compounds

| Molecule Name | Molecular weight (g/mol) | Structure | Synthesis Method |
|---|---|---|---|
| NUCC-0200562 | 377.3 | 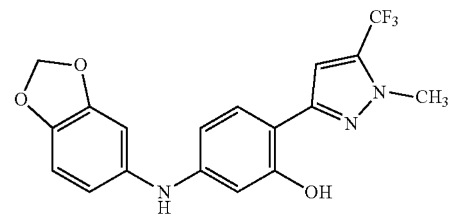 [SMILES: Cn1nc(-c2ccc(Nc3ccc4c(c3)OCO4)cc2O)cc1C(F)(F)F] | G |
| NUCC-0200563 | 362.3 | 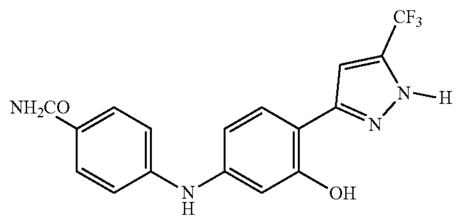 | G |
| NUCC-0200564 | 376.3 | 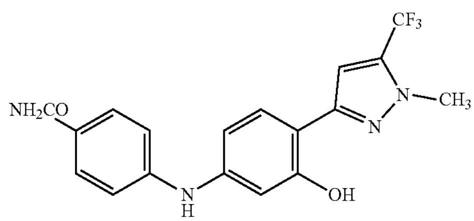 | G |
| NUCC-0200565 | 320.3 | 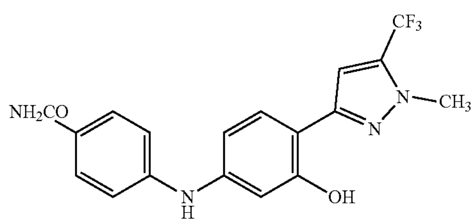 | G |
| NUCC-0200566 | 334.3 | 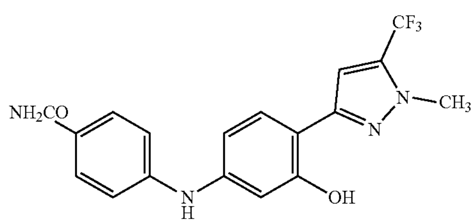 | G |
| NUCC-0200567 | 326.3 | 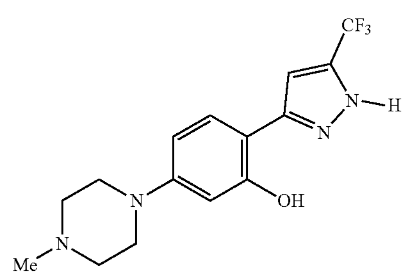 [SMILES: CN1CCN(c2ccc(-c3cc(C(F)(F)F)[nH]n3)c(O)c2)CC1] | G |

TABLE 1-continued

Representative Compounds

| Molecule Name | Molecular weight (g/mol) | Structure | Synthesis Method |
|---|---|---|---|
| NUCC-0200568 | 340.4 | 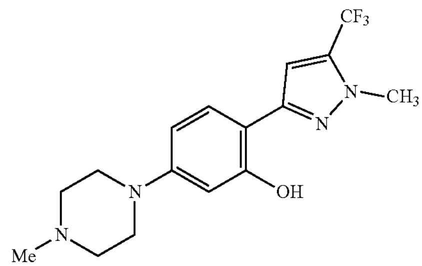 [SMILES: CN1CCN(c2ccc(-c3cc(C(F)(F)F)n(C)n3)c(O)c2)CC1] | G |
| NUCC-0200569 | 385.4 | 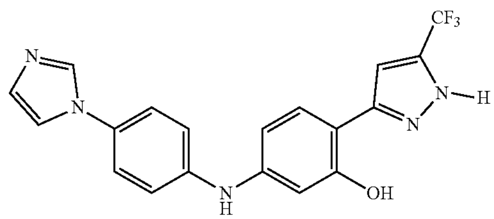 [SMILES: Oc1cc(Nc2ccc(-n3ccnc3)cc2)ccc1-c1cc(C(F)(F)F)[nH]n1] | G |
| NUCC-0200570 | 368.7 | 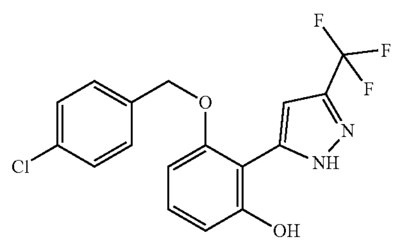 [SMILES: Oc1cccc(OCc2ccc(Cl)cc2)c1-c1cc(C(F)(F)F)n[nH]1] | D |
| NUCC-0200571 | 469.9 | 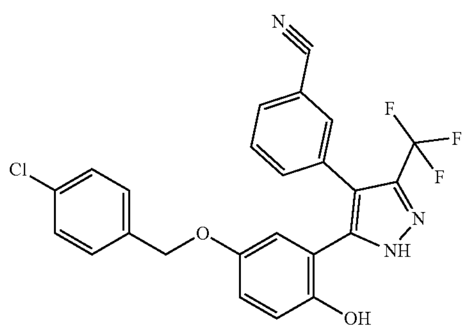 [SMILES: N#Cc1cccc(-c2c(C(F)(F)F)n[nH]c2-c2cc(OCc3ccc(Cl)cc3)ccc2O)c1] | D |
| NUCC-0200572 | 458.9 | 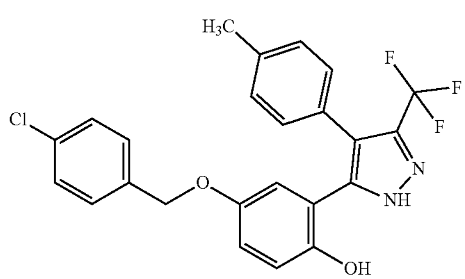 [SMILES: Cc1ccc(-c2c(C(F)(F)F)n[nH]c2-c2cc(OCc3ccc(Cl)cc3)ccc2O)cc1] | D |

TABLE 1-continued

Representative Compounds

| Molecule Name | Molecular weight (g/mol) | Structure | Synthesis Method |
|---|---|---|---|
| NUCC-0200573 | 368.7 | 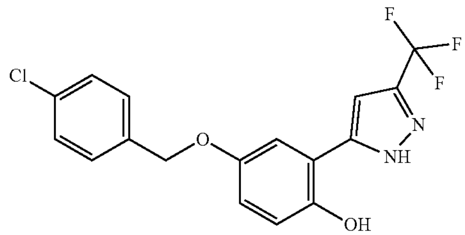 [SMILES: Oc1ccc(OCc2ccc(Cl)cc2)cc1-c1cc(C(F)(F)F)n[nH]1] | D |
| NUCC-0200574 | 228.2 | 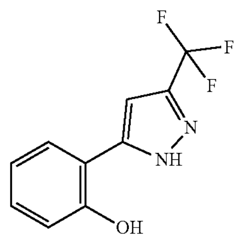 [SMILES: Oc1ccccc1-c1cc(C(F)(F)F)n[nH]1] | H |
| NUCC-0200575 | 462.8 | 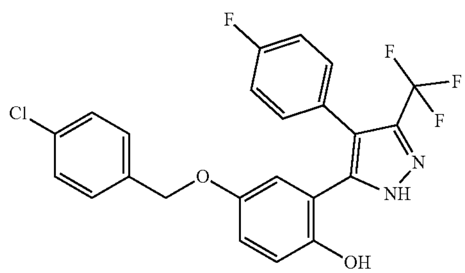 [SMILES: Oc1ccc(OCc2ccc(Cl)cc2)cc1-c1[nH]nc(C(F)(F)F)c1-c1ccc(F)cc1] | D |
| NUCC-0200576 | 479.3 | 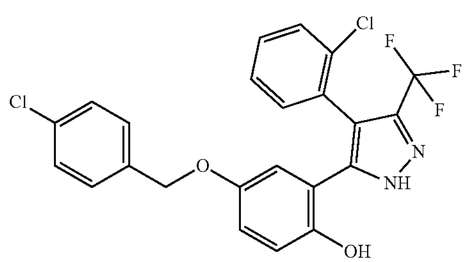 [SMILES: Oc1ccc(OCc2ccc(Cl)cc2)cc1-c1[nH]nc(C(F)(F)F)c1-c1ccccc1Cl] | D |
| NUCC-0200577 | 442.8 | 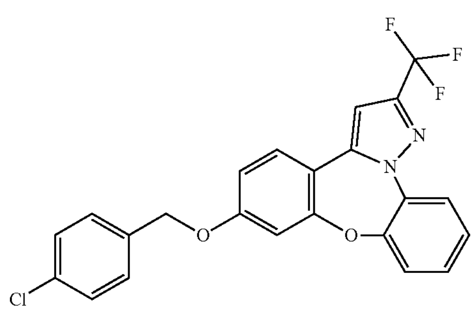 [SMILES: FC(F)(F)c1cc2n(n1)-c1ccccc1Oc1cc(OCc3ccc(Cl)cc3)ccc1-2] | |

TABLE 1-continued

Representative Compounds

| Molecule Name | Molecular weight (g/mol) | Structure | Synthesis Method |
|---|---|---|---|
| NUCC-0200677 | 328.8 | 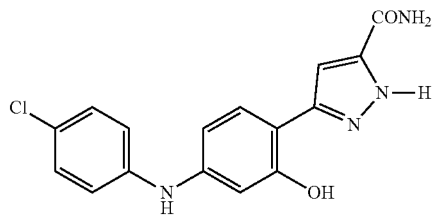 [SMILES: NC(=O)c1cc(-c2ccc(Nc3ccc(Cl)cc3)cc2O)n[nH]1] | G |
| NUCC-0200678 | 310.7 | 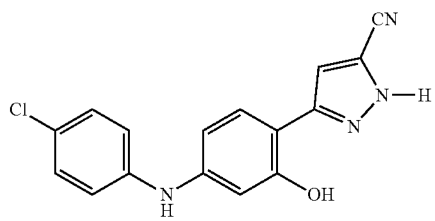 [SMILES: N#Cc1cc(-c2ccc(Nc3ccc(Cl)cc3)cc2O)n[nH]1] | G |
| NUCC-0200679 | 354.7 | 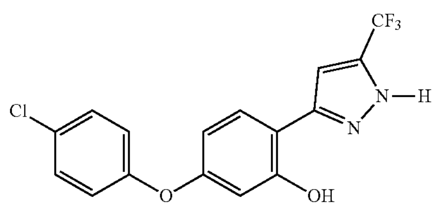 [SMILES: Oc1cc(Oc2ccc(Cl)cc2)ccc1-c1cc(C(F)(F)F)[nH]n1] | G |
| NUCC-0200680 | 473.9 | 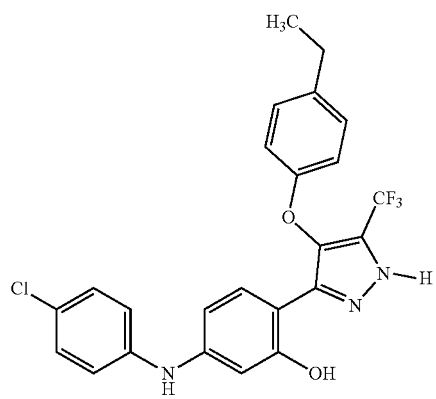 [SMILES: CCc1ccc(Oc2c(-c3ccc(Nc4ccc(Cl)cc4)cc3O)n[nH]c2C(F)(F)F)cc1] | G |
| NUCC-0200681 | 474.9 | 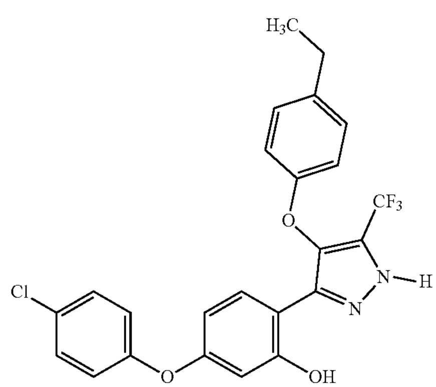 [SMILES: CCc1ccc(Oc2c(-c3ccc(Oc4ccc(Cl)cc4)cc3O)n[nH]c2C(F)(F)F)cc1] | G |

TABLE 1-continued
Representative Compounds
| Molecule Name | Molecular weight (g/mol) | Structure | Synthesis Method |
|---|---|---|---|
| NUCC-0200682 | 377.4 | 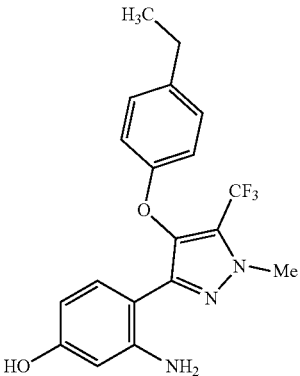 [SMILES: CCc1ccc(Oc2c(-c3ccc(O)cc3N)nn(C)c2C(F)(F)F)cc1] | A |
| NUCC-0200683 | 348.3 | 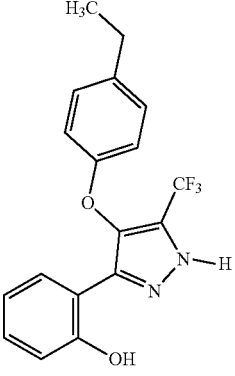 [SMILES: CCc1ccc(Oc2c(-c3ccccc3O)n[nH]c2C(F)(F)F)cc1] | A |
| NUCC-0200684 | 362.4 | 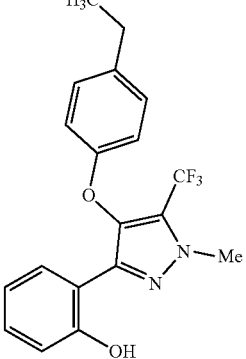 | A |
| NUCC-0200685 | 238.3 | 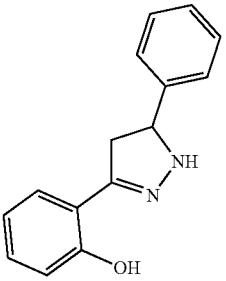 [SMILES: Oc1ccccc1C1=NNC(c2ccccc2)C1] | — |

TABLE 1-continued

Representative Compounds

| Molecule Name | Molecular weight (g/mol) | Structure | Synthesis Method |
|---|---|---|---|
| NUCC-0200686 | 502.9 | 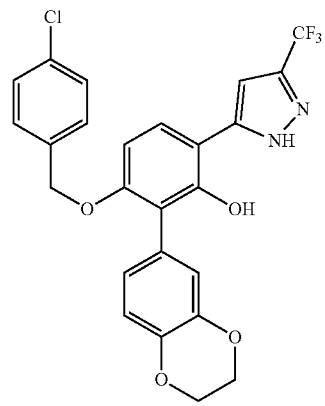 [SMILES: Oc1c(-c2cc(C(F)(F)F)n[nH]2)ccc(OCc2ccc(Cl)cc2)c1-c1ccc2c(c1)OCCO2] | B |
| NUCC-0200687 | 243.2 | 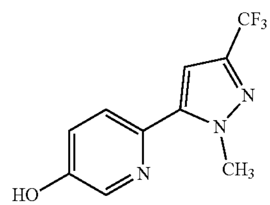 [SMILES: Cn1nc(C(F)(F)F)cc1-c1ccc(O)cn1] | D |
| NUCC-0200688 | 242.2 | 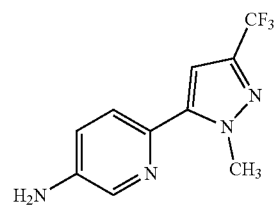 [SMILES: Cn1nc(C(F)(F)F)cc1-c1ccc(N)cn1] | D |
| NUCC-0200689 | 244.2 | 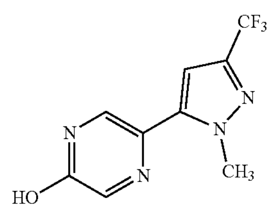 [SMILES: Cn1nc(C(F)(F)F)cc1-c1cnc(O)cn1] | D |
| NUCC-0200690 | 367.8 | 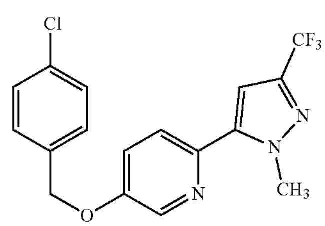 [SMILES: Cn1nc(C(F)(F)F)cc1-c1ccc(OCc2ccc(Cl)cc2)cn1] | D |
| NUCC-0200691 | 366.8 | 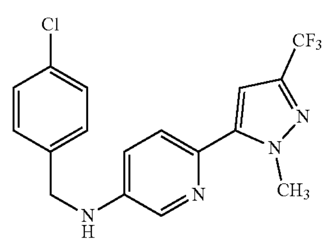 [SMILES: Cn1nc(C(F)(F)F)cc1-c1ccc(NCc2ccc(Cl)cc2)cn1] | D |

TABLE 1-continued

Representative Compounds

| Molecule Name | Molecular weight (g/mol) | Structure | Synthesis Method |
|---|---|---|---|
| NUCC-0200692 | 368.7 | 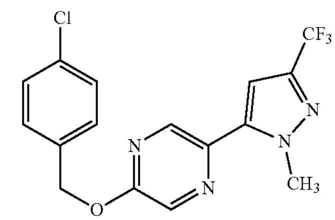 [SMILES: Cn1nc(C(F)(F)F)cc1-c1cnc(OCc2ccc(Cl)cc2)cn1] | D |
| NUCC-0200721 | 388.2 | 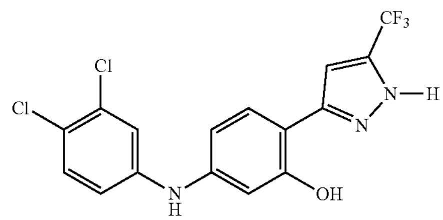 [SMILES: Oc1cc(Nc2ccc(Cl)c(Cl)c2)ccc1-c1cc(C(F)(F)F)[nH]n1] | G |
| NUCC-0200722 | 327.4 | 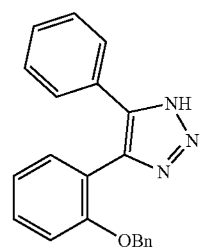 [SMILES: c1ccc(COc2ccccc2-c2nn[nH]c2-c2ccccc2)cc1] | — |
| NUCC-0200723 | 470.3 | 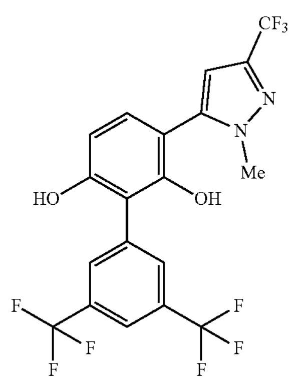 [SMILES: Cn1nc(C(F)(F)F)cc1-c1ccc(O)c(-c2cc(C(F)(F)F)cc(C(F)(F)F)c2)c1O] | B |
| NUCC-0200724 | 470.3 | 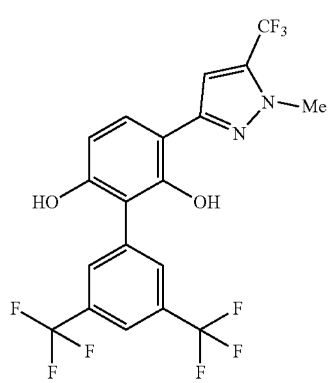 [SMILES: Cn1nc(-c2ccc(O)c(-c3cc(C(F)(F)F)cc(C(F)(F)F)c3)c2O)cc1C(F)(F)F] | B |

TABLE 1-continued
Representative Compounds
| Molecule Name | Molecular weight (g/mol) | Structure | Synthesis Method |
|---|---|---|---|
| NUCC-0200725 | 512.8 | 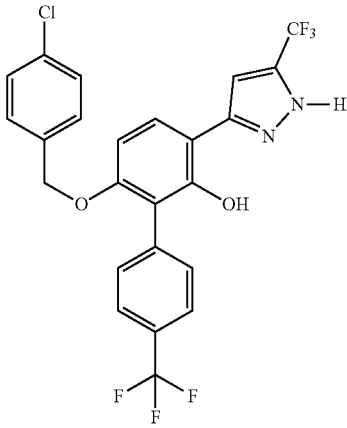 [SMILES: Oc1c(-c2cc(C(F)(F)F)[nH]n2)ccc(OCc2ccc(Cl)cc2)c1-c1ccc(C(F)(F)F)cc1] | B |
| NUCC-0200726 | 526.9 | 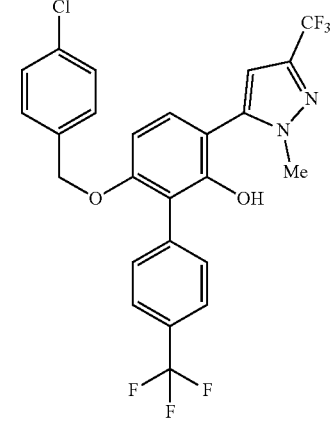 [SMILES: Cn1nc(C(F)(F)F)cc1-c1ccc(OCc2ccc(Cl)cc2)c(-c2ccc(C(F)(F)F)cc2)c1O] | B |
| NUCC-0200727 | 526.9 | 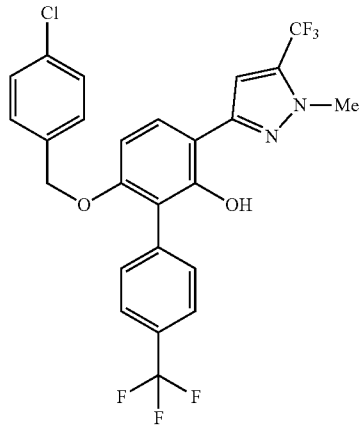 [SMILES: Cn1nc(-c2ccc(OCc3ccc(Cl)cc3)c(-c3ccc(C(F)(F)F)cc3)c2O)cc1C(F)(F)F] | B |

TABLE 1-continued

Representative Compounds

| Molecule Name | Molecular weight (g/mol) | Structure | Synthesis Method |
|---|---|---|---|
| NUCC-0200728 | 547.3 | 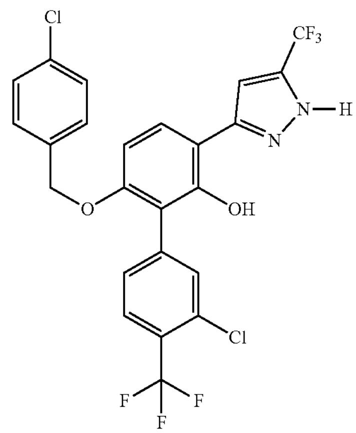 [SMILES: Oc1c(-c2cc(C(F)(F)F)[nH]n2)ccc(OCc2ccc(Cl)cc2)c1-c1ccc(C(F)(F)F)c(Cl)c1] | B |
| NUCC-0200729 | 561.3 | 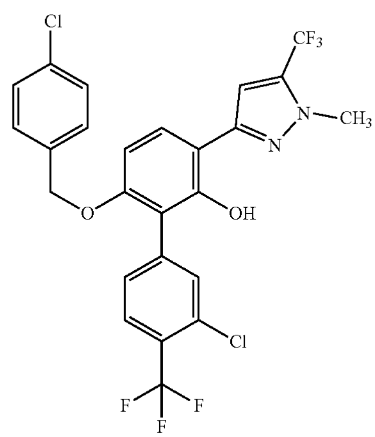 [SMILES: Cn1nc(-c2ccc(OCc3ccc(Cl)cc3)c(-c3ccc(C(F)(F)F)c(Cl)c3)c2O)cc1C(F)(F)F] | B |
| NUCC-0200730 | 512.8 | 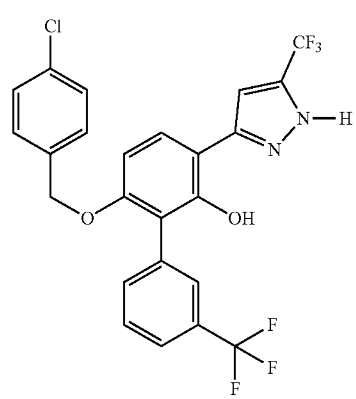 [SMILES: Oc1c(-c2cc(C(F)(F)F)[nH]n2)ccc(OCc2ccc(Cl)cc2)c1-c1cccc(C(F)(F)F)c1] | B |

TABLE 1-continued

Representative Compounds

| Molecule Name | Molecular weight (g/mol) | Structure | Synthesis Method |
|---|---|---|---|
| NUCC-0200731 | 526.9 | 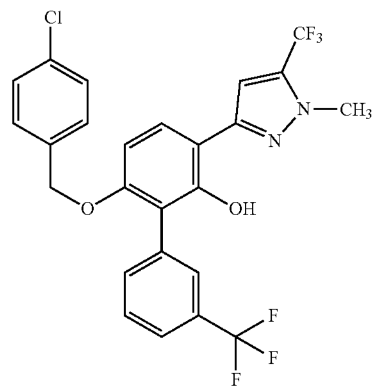 [SMILES: Cn1nc(-c2ccc(OCc3ccc(Cl)cc3)c(-c3cccc(C(F)(F)F)c3)c2O)cc1C(F)(F)F] | B |
| NUCC-0200732 | 547.3 | 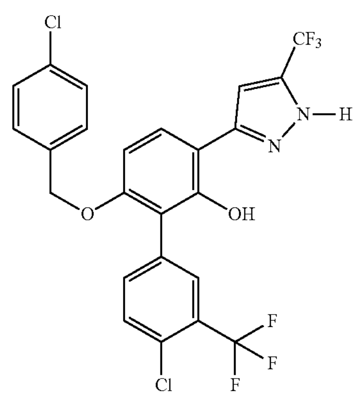 [SMILES: Oc1c(-c2cc(C(F)(F)F)[nH]n2)ccc(OCc2ccc(Cl)cc2)c1-c1ccc(Cl)c(C(F)(F)F)c1] | B |
| NUCC-0200733 | 561.3 | 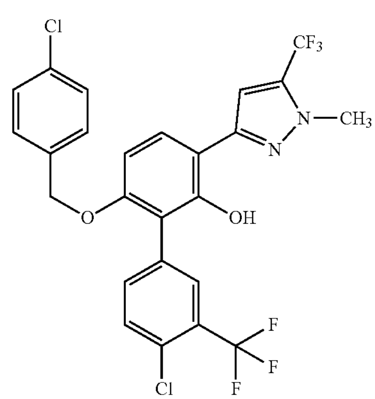 [SMILES: Cn1nc(-c2ccc(OCc3ccc(Cl)cc3)c(-c3ccc(Cl)c(C(F)(F)F)c3)c2O)cc1C(F)(F)F] | B |

TABLE 1-continued
Representative Compounds
| Molecule Name | Molecular weight (g/mol) | Structure | Synthesis Method |
|---|---|---|---|
| NUCC-0200734 | 530.8 | 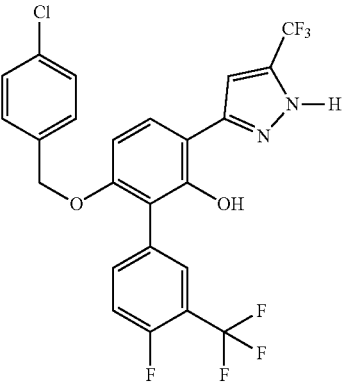 [SMILES: Oc1c(-c2cc(C(F)(F)F)[nH]n2)ccc(OCc2ccc(Cl)cc2)c1-c1ccc(F)c(C(F)(F)F)c1] | B |
| NUCC-0200735 | 544.9 | 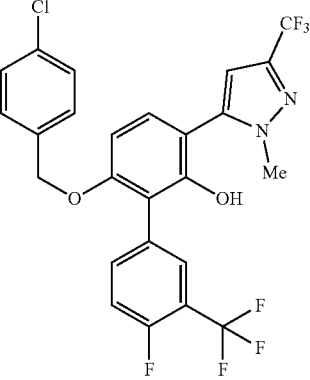 [SMILES: Cn1nc(C(F)(F)F)cc1-c1ccc(OCc2ccc(Cl)cc2)c(-c2ccc(F)c(C(F)(F)F)c2)c1O] | B |
| NUCC-0200736 | 544.9 | 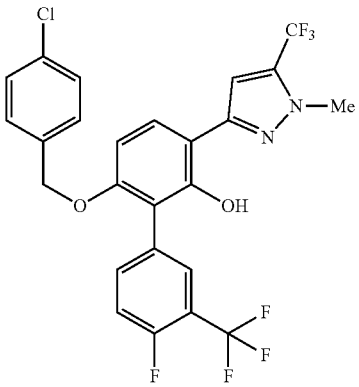 [SMILES: Cn1nc(-c2ccc(OCc3ccc(Cl)cc3)c(-c3ccc(F)c(C(F)(F)F)c3)c2O)cc1C(F)(F)F] | B |

TABLE 1-continued
Representative Compounds
| Molecule Name | Molecular weight (g/mol) | Structure | Synthesis Method |
|---|---|---|---|
| NUCC-0200737 | 547.3 | 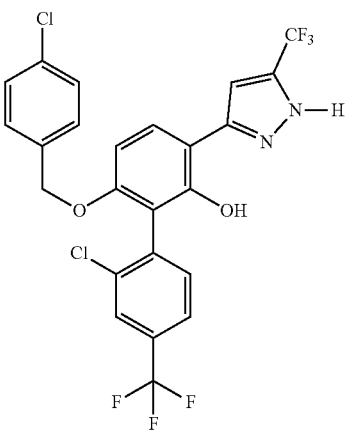 [SMILES: Oc1c(-c2cc(C(F)(F)F)[nH]n2)ccc(OCc2ccc(Cl)cc2)c1-c1ccc(C(F)(F)F)cc1Cl] | B |
| NUCC-0200738 | 561.3 | 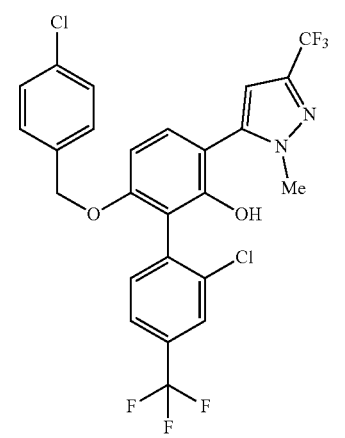 [SMILES: Cn1nc(C(F)(F)F)cc1-c1ccc(OCc2ccc(Cl)cc2)c(-c2ccc(C(F)(F)F)cc2Cl)c1O] | B |
| NUCC-0200739 | 396.8 | 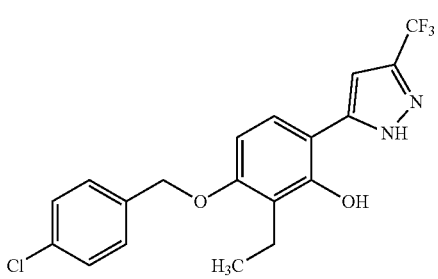 [SMILES: CCc1c(OCc2ccc(Cl)cc2)ccc(-c2cc(C(F)(F)F)n[nH]2)c1O] | D |
| NUCC-0200740 | 410.8 | 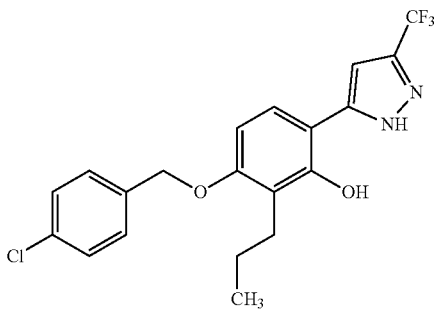 [SMILES: CCCc1c(OCc2ccc(Cl)cc2)ccc(-c2cc(C(F)(F)F)n[nH]2)c1O] | D |

TABLE 1-continued
Representative Compounds
| Molecule Name | Molecular weight (g/mol) | Structure | Synthesis Method |
|---|---|---|---|
| NUCC-0200741 | 367.8 | 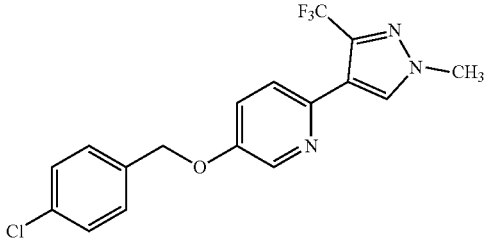 [SMILES: Cn1cc(-c2ccc(OCc3ccc(Cl)cc3)cn2)c(C(F)(F)F)n1] | D |
| NUCC-0200742 | 366.8 | 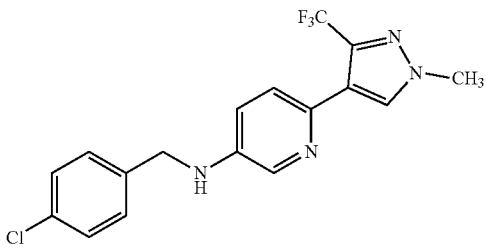 [SMILES: Cn1cc(-c2ccc(NCc3ccc(Cl)cc3)cn2)c(C(F)(F)F)n1] | D |
| NUCC-0200743 | 384.8 | 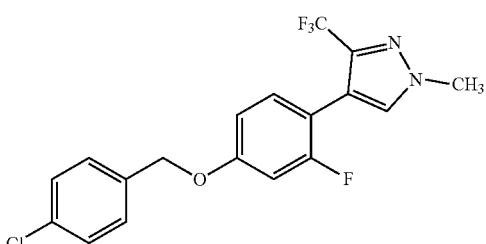 | D |
| NUCC-0200744 | 401.2 | 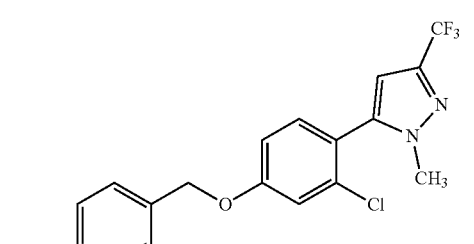 | D |
| NUCC-0200745 | 381.8 | 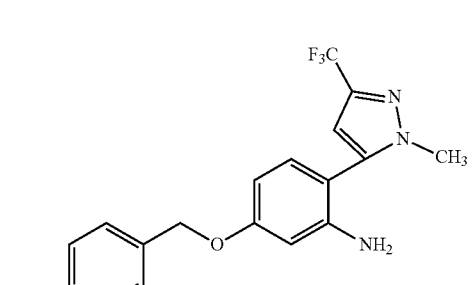 | D |

TABLE 1-continued

Representative Compounds

| Molecule Name | Molecular weight (g/mol) | Structure | Synthesis Method |
|---|---|---|---|
| NUCC-0200746 | 381.8 | 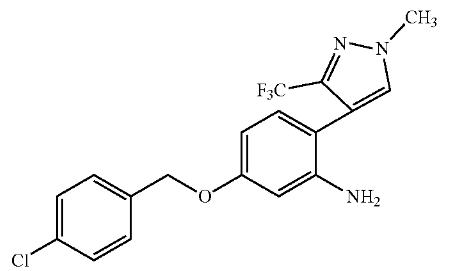 [SMILES: Cn1cc(-c2ccc(OCc3ccc(Cl)cc3)cc2N)c(C(F)(F)F)n1] | D |
| NUCC-0200747 | 368.7 | 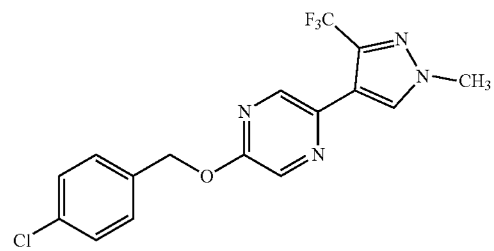 | D |
| NUCC-0196314.2 | 382.8 | 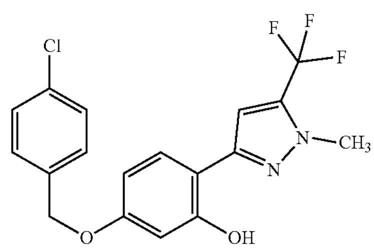 [SMILES: Cn1nc(-c2ccc(OCc3ccc(Cl)cc3)cc2O)cc1C(F)(F)F] | H |
| NUCC-0198412.2 | 382.8 | 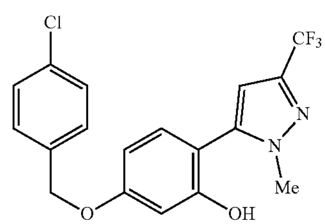 [SMILES: Cn1nc(C(F)(F)F)cc1-c1ccc(OCc2ccc(Cl)cc2)cc1O] | H |
| NUCC-0200812 | 391.8 | 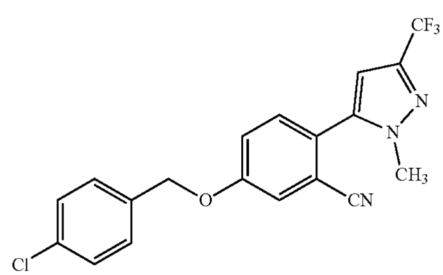 [SMILES: Cn1nc(C(F)(F)F)cc1-c1ccc(OCc2ccc(Cl)cc2)cc1C#N] | D |
| NUCC-0200813 | 396.8 | 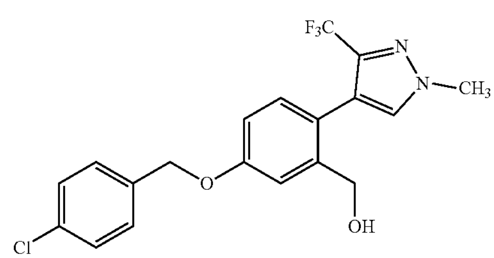 [SMILES: Cn1cc(-c2ccc(OCc3ccc(Cl)cc3)cc2CO)c(C(F)(F)F)n1] | D |

TABLE 1-continued

Representative Compounds

| Molecule Name | Molecular weight (g/mol) | Structure | Synthesis Method |
|---|---|---|---|
| NUCC-0200814 | 401.2 | 4-[4-(4-chlorobenzyloxy)-2-chlorophenyl]-1-methyl-3-(trifluoromethyl)-1H-pyrazole | D |
| NUCC-0200815 | 394.8 | 2-[4-(4-chlorobenzyloxy)-2-formylphenyl]-1-methyl-3-(trifluoromethyl)-1H-pyrazole | D |
| NUCC-0200816 | 409.8 | 2-[5-(4-chlorobenzyloxy)-2-(1-methyl-3-(trifluoromethyl)-1H-pyrazol-5-yl)phenyl]carboxamide | D |
| NUCC-0200817 | 395.8 | 4-chloro-N-[4-(1-methyl-3-(trifluoromethyl)-1H-pyrazol-5-yl)-3-hydroxyphenyl]benzamide | D |
| NUCC-0200970 | 584.9 | methyl 3-[6-(4-chlorobenzyloxy)-3'-[3,5-bis(trifluoromethyl)phenyl]-2'-hydroxybiphenyl-3-yl]-1-methyl-1H-pyrazole-5-carboxylate | C |

TABLE 1-continued
Representative Compounds
| Molecule Name | Molecular weight (g/mol) | Structure | Synthesis Method |
|---|---|---|---|
| NUCC-0200971 | 570.9 | 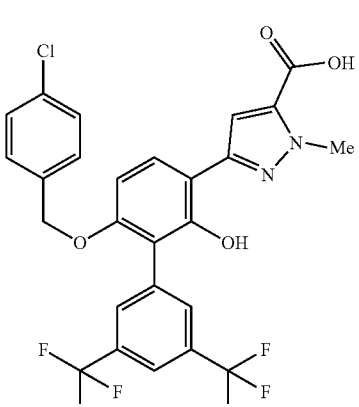 | C |
| NUCC-0200972 | 584.9 | 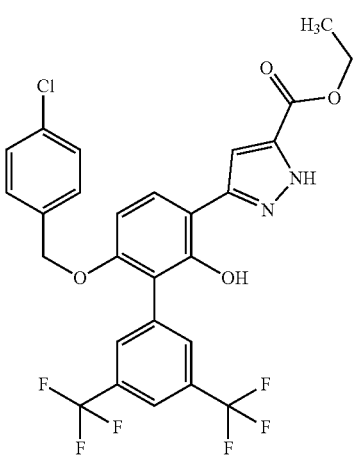 [SMILES: CCOC(=O)c1cc(-c2ccc(OCc3ccc(Cl)cc3)c(-c3cc(C(F)(F)F)cc(C(F)(F)F)c3)c2O)n[nH]1] | C |
| NUCC-0200973 | 556.9 | 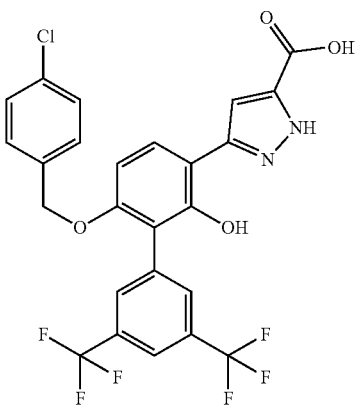 [SMILES: O=C(O)c1cc(-c2ccc(OCc3ccc(Cl)cc3)c(-c3cc(C(F)(F)F)cc(C(F)(F)F)c3)c2O)n[nH]1] | C |

TABLE 1-continued

Representative Compounds

| Molecule Name | Molecular weight (g/mol) | Structure | Synthesis Method |
|---|---|---|---|
| NUCC-0200974 | 526.9 | 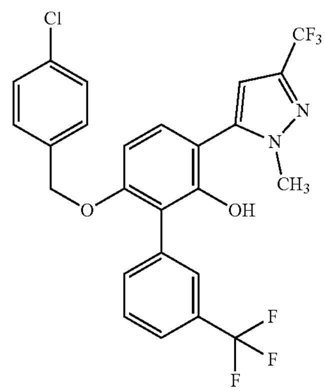 [SMILES: Cn1nc(C(F)(F)F)cc1-c1ccc(OCc2ccc(Cl)cc2)c(-c2cccc(C(F)(F)F)c2)c1O] | B |
| NUCC-0200975 | 561.3 | 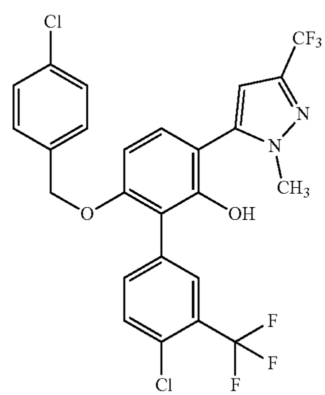 [SMILES: Cn1nc(C(F)(F)F)cc1-c1ccc(OCc2ccc(Cl)cc2)c(-c2ccc(Cl)c(C(F)(F)F)c2)c1O] | B |
| NUCC-0200976 | 394.8 | 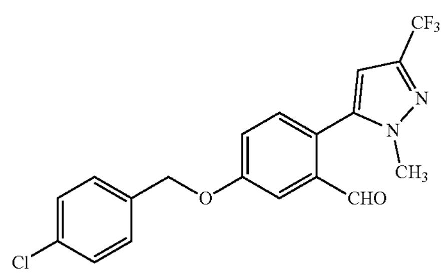 [SMILES: Cn1nc(C(F)(F)F)cc1-c1ccc(OCc2ccc(Cl)cc2)cc1C=O] | D |
| NUCC-0200977 | 384.8 | 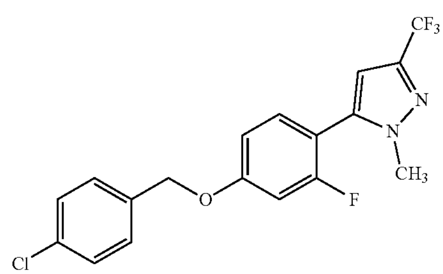 [SMILES: Cn1nc(C(F)(F)F)cc1-c1ccc(OCc2ccc(Cl)cc2)cc1F] | D |

TABLE 1-continued

Representative Compounds

| Molecule Name | Molecular weight (g/mol) | Structure | Synthesis Method |
|---|---|---|---|
| NUCC-0200978 | 396.8 | 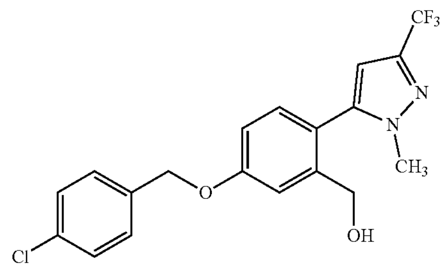 [SMILES: Cn1nc(C(F)(F)F)cc1-c1ccc(OCc2ccc(Cl)cc2)cc1CO] | D |
| NUCC-0200979 | 470.7 | 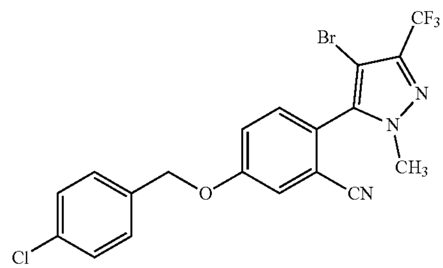 [SMILES: Cn1nc(C(F)(F)F)c(Br)c1-c1ccc(OCc2ccc(Cl)cc2)cc1C#N] | — |
| NUCC-0201023 | 561.4 | 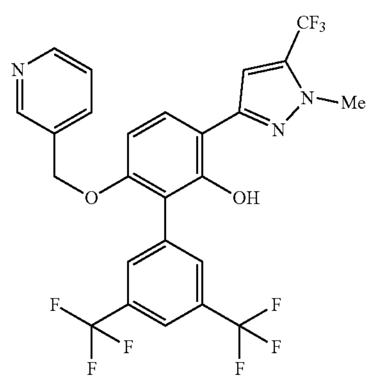 [SMILES: Cn1nc(-c2ccc(OCc3cccnc3)c(-c3cc(C(F)(F)F)cc(C(F)(F)F)c3)c2O)cc1C(F)(F)F] | B |
| NUCC-0201024 | 594.9 | 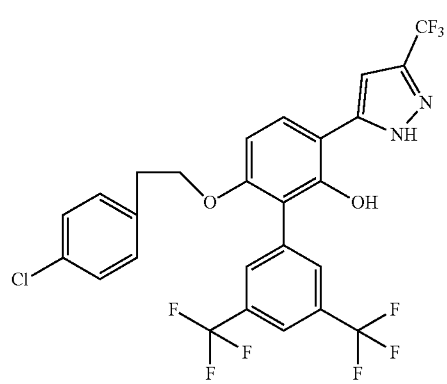 [SMILES: Oc1c(-c2cc(C(F)(F)F)n[nH]2)ccc(OCCc2ccc(Cl)cc2)c1-c1cc(C(F)(F)F)cc(C(F)(F)F)c1] | B |

TABLE 1-continued
Representative Compounds
| Molecule Name | Molecular weight (g/mol) | Structure | Synthesis Method |
|---|---|---|---|
| NUCC-0201025 | 608.9 | 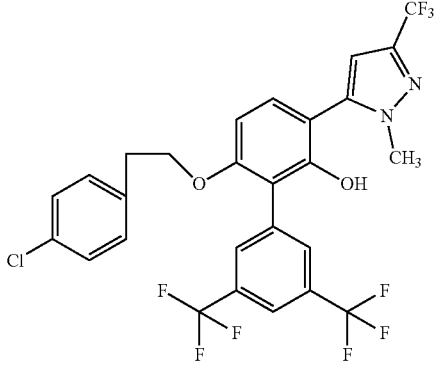 [SMILES: Cn1nc(C(F)(F)F)cc1-c1ccc(OCCc2ccc(Cl)cc2)c(-c2cc(C(F)(F)F)cc(C(F)(F)F)c2)c1O] | B |
| NUCC-0201026 | 608.9 | 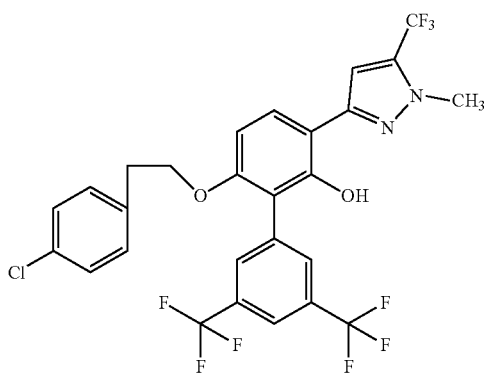 | B |
| NUCC-0201027 | 590.4 | 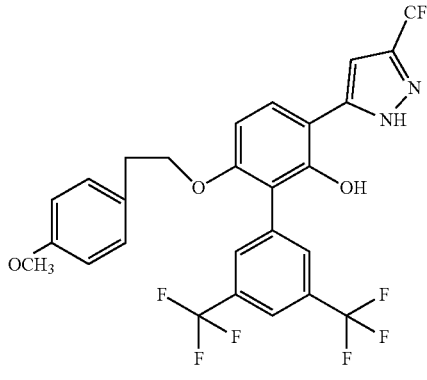 | B |
| NUCC-0201028 | 604.5 | 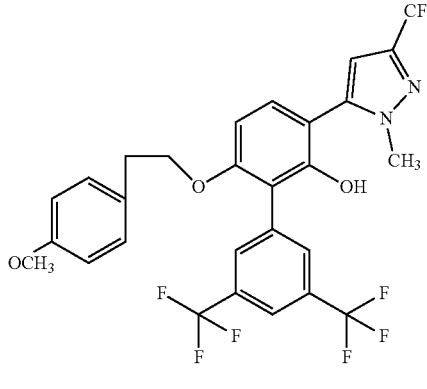 | B |

TABLE 1-continued

Representative Compounds

| Molecule Name | Molecular weight (g/mol) | Structure | Synthesis Method |
|---|---|---|---|
| NUCC-0201029 | 604.5 | 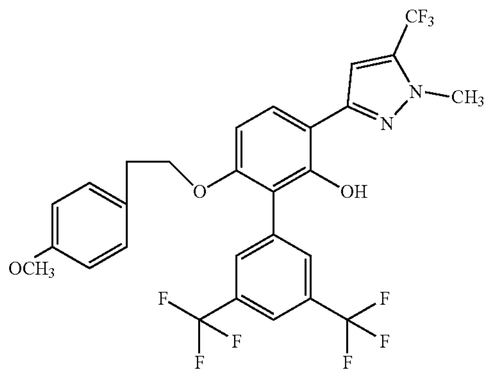 [SMILES: COc1ccc(CCOc2ccc(-c3cc(C(F)(F)F)n(C)n3)c(O)c2-c2cc(C(F)(F)F)cc(C(F)(F)F)c2)cc1] | B |
| NUCC-0201030 | 508.4 | 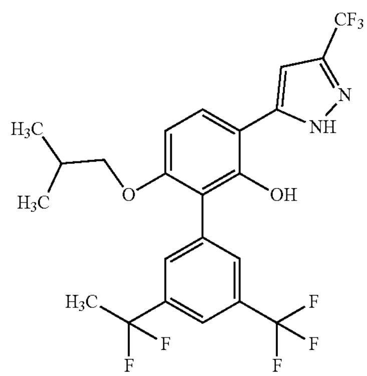 [SMILES: CC(C)COc1ccc(-c2cc(C(F)(F)F)n[nH]2)c(O)c1-c1cc(C(C)(F)F)cc(C(F)(F)F)c1] | B |
| NUCC-0201031 | 512.4 | 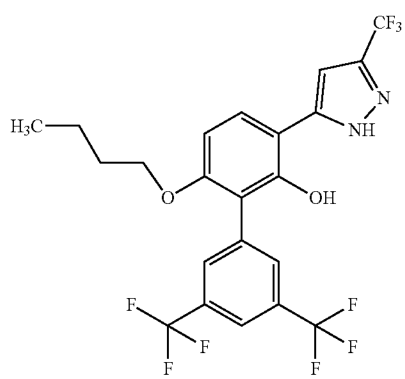 [SMILES: CCCCOc1ccc(-c2cc(C(F)(F)F)n[nH]2)c(O)c1-c1cc(C(F)(F)F)cc(C(F)(F)F)c1] | B |
| NUCC-0201032 | 553.4 | 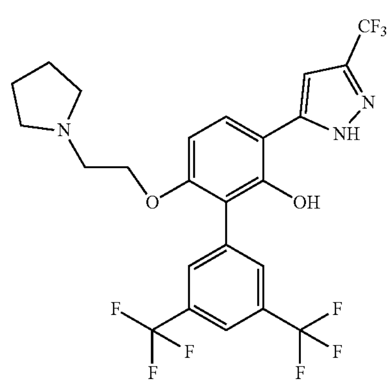 [SMILES: Oc1c(-c2cc(C(F)(F)F)n[nH]2)ccc(OCCN2CCCC2)c1-c1cc(C(F)(F)F)cc(C(F)(F)F)c1] | B |

TABLE 1-continued
Representative Compounds
| Molecule Name | Molecular weight (g/mol) | Structure | Synthesis Method |
|---|---|---|---|
| NUCC-0201033 | 564.4 | 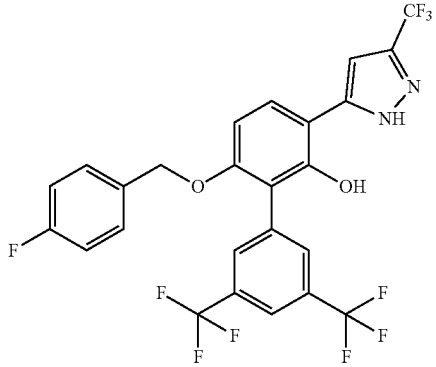 [SMILES: Oc1c(-c2cc(C(F)(F)F)n[nH]2)ccc(OCc2ccc(F)cc2)c1-c1cc(C(F)(F)F)cc(C(F)(F)F)c1] | B |
| NUCC-0201034 | 578.4 | 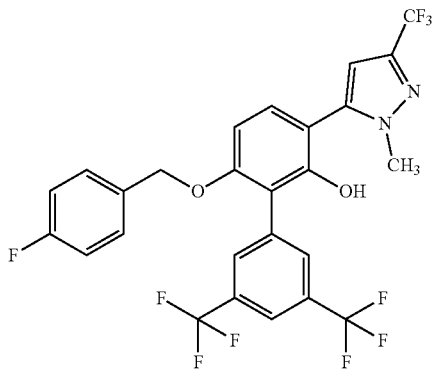 [SMILES: Cn1nc(C(F)(F)F)cc1-c1ccc(OCc2ccc(F)cc2)c(-c2cc(C(F)(F)F)cc(C(F)(F)F)c2)c1O] | B |
| NUCC-0201035 | 578.4 | 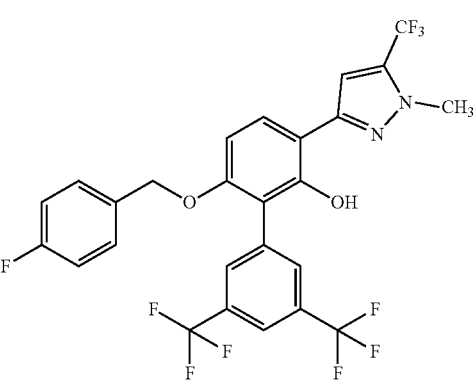 [SMILES: Cn1nc(-c2ccc(OCc3ccc(F)cc3)c(-c3cc(C(F)(F)F)cc(C(F)(F)F)c3)c2O)cc1C(F)(F)F] | B |
| NUCC-0201036 | 522.9 | 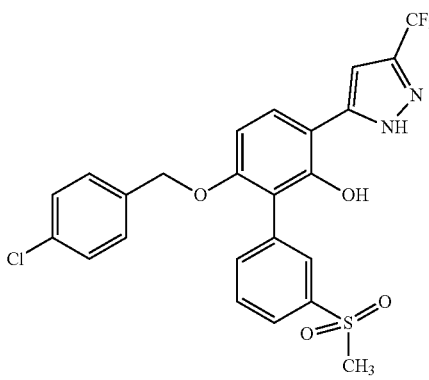 | B |

TABLE 1-continued
Representative Compounds
| Molecule Name | Molecular weight (g/mol) | Structure | Synthesis Method |
|---|---|---|---|
| NUCC-0201037 | 513.8 | 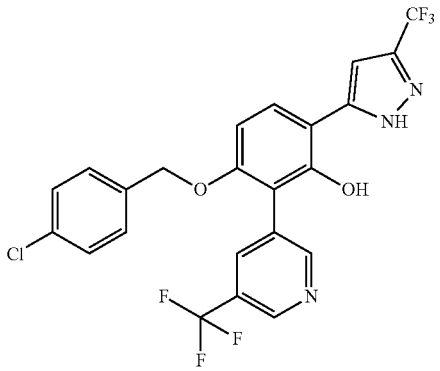 [SMILES: Oc1c(-c2cc(C(F)(F)F)n[nH]2)ccc(OCc2ccc(Cl)cc2)c1-c1cncc(C(F)(F)F)c1] | B |
| NUCC-0201038 | 470.8 | 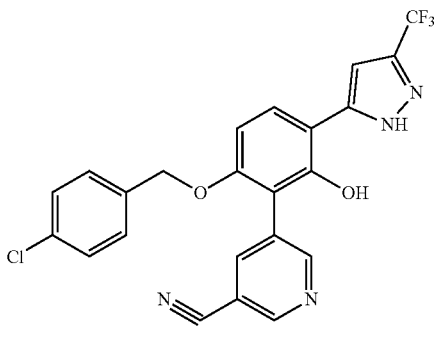 [SMILES: N#Cc1cncc(-c2c(OCc3ccc(Cl)cc3)ccc(-c3cc(C(F)(F)F)n[nH]3)c2O)c1] | B |
| NUCC-0201039 | 557.9 | 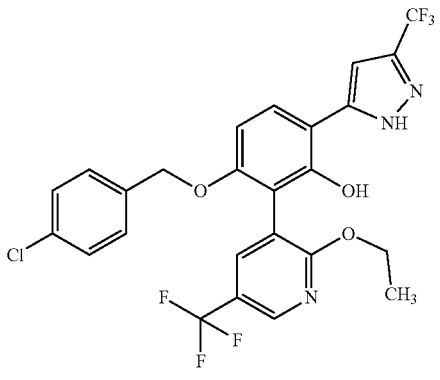 [SMILES: CCOc1ncc(C(F)(F)F)cc1-c1c(OCc2ccc(Cl)cc2)ccc(-c2cc(C(F)(F)F)n[nH]2)c1O] | B |
| NUCC-0201040 | 463.8 | 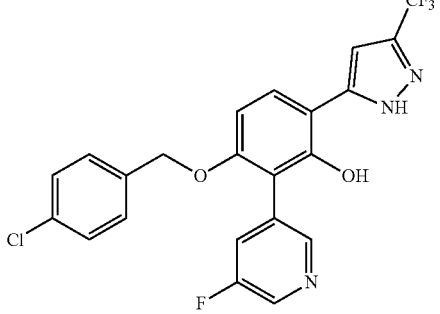 | B |

TABLE 1-continued

Representative Compounds

| Molecule Name | Molecular weight (g/mol) | Structure | Synthesis Method |
|---|---|---|---|
| NUCC-0201041 | 576.4 | 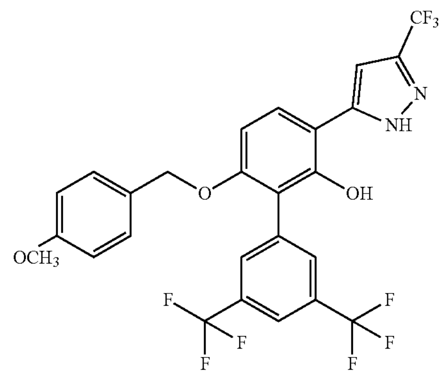 [SMILES: COc1ccc(COc2ccc(-c3cc(C(F)(F)F)n[nH]3)c(O)c2-c2cc(C(F)(F)F)cc(C(F)(F)F)c2)cc1] | B |
| NUCC-0201042 | 590.4 | 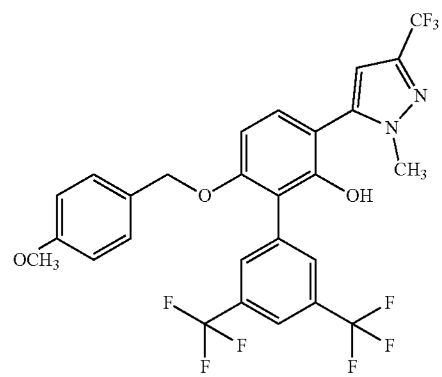 [SMILES: COc1ccc(COc2ccc(-c3cc(C(F)(F)F)nn3C)c(O)c2-c2cc(C(F)(F)F)cc(C(F)(F)F)c2)cc1] | B |
| NUCC-0201043 | 590.4 | 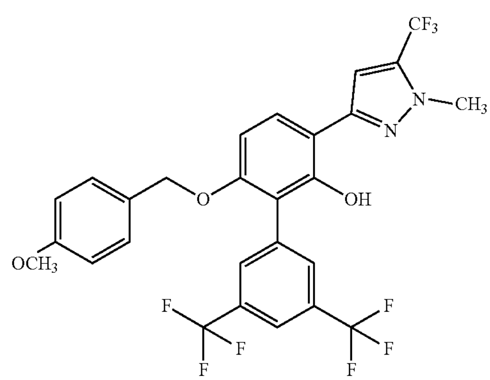 [SMILES: COc1ccc(COc2ccc(-c3cc(C(F)(F)F)n(C)n3)c(O)c2-c2cc(C(F)(F)F)cc(C(F)(F)F)c2)cc1] | B |
| NUCC-0201192 | 473.4 | 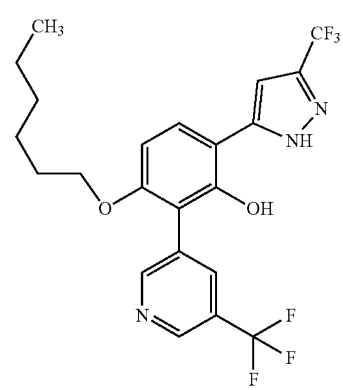 [SMILES: CCCCCCOc1ccc(-c2cc(C(F)(F)F)n[nH]2)c(O)c1-c1cncc(C(F)(F)F)c1] | B |

TABLE 1-continued

Representative Compounds

| Molecule Name | Molecular weight (g/mol) | Structure | Synthesis Method |
|---|---|---|---|
| NUCC-0201193 | 402.4 | 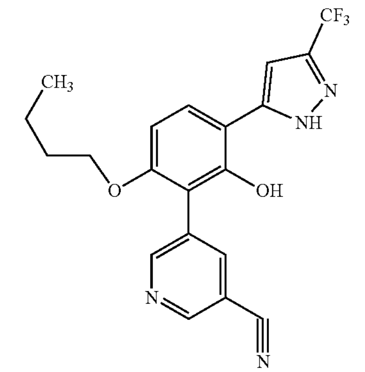 [SMILES: CCCCOc1ccc(-c2cc(C(F)(F)F)n[nH]2)c(O)c1-c1cncc(C#N)c1] | B |
| NUCC-0201194 | 430.4 | 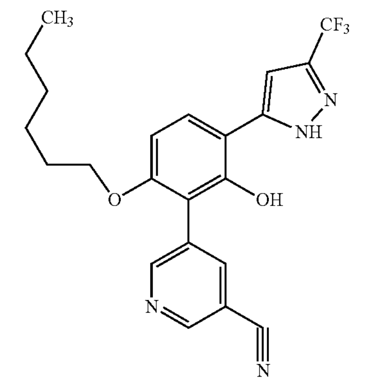 [SMILES: CCCCCCOc1ccc(-c2cc(C(F)(F)F)n[nH]2)c(O)c1-c1cncc(C#N)c1] | B |
| NUCC-0201195 | 416.4 | 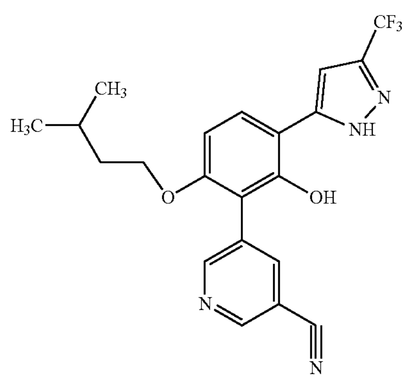 [SMILES: CC(C)CCOc1ccc(-c2cc(C(F)(F)F)n[nH]2)c(O)c1-c1cncc(C#N)c1] | B |
| NUCC-0201196 | 540.4 | 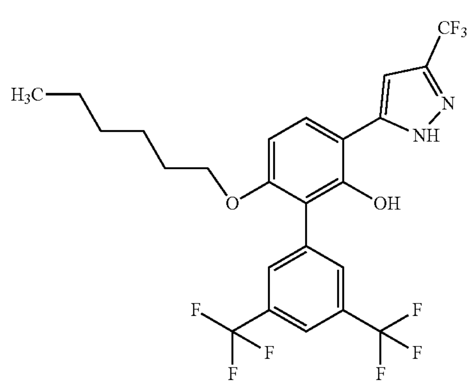 [SMILES: CCCCCCOc1ccc(-c2cc(C(F)(F)F)n[nH]2)c(O)c1-c1cc(C(F)(F)F)cc(C(F)(F)F)c1] | B |

TABLE 1-continued

Representative Compounds

| Molecule Name | Molecular weight (g/mol) | Structure | Synthesis Method |
|---|---|---|---|
| NUCC-0201197 | 498.3 | 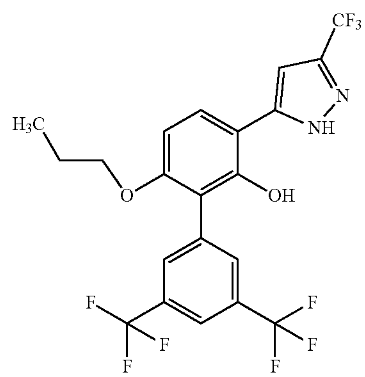 [SMILES: CCCOc1ccc(-c2cc(C(F)(F)F)n[nH]2)c(O)c1-c1cc(C(F)(F)F)cc(C(F)(F)F)c1] | B |
| NUCC-0201198 | 526.4 | 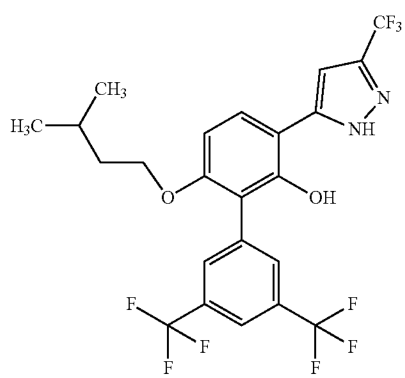 [SMILES: CC(C)CCOc1ccc(-c2cc(C(F)(F)F)n[nH]2)c(O)c1-c1cc(C(F)(F)F)cc(C(F)(F)F)c1] | B |
| NUCC-0201199 | 776.6 | 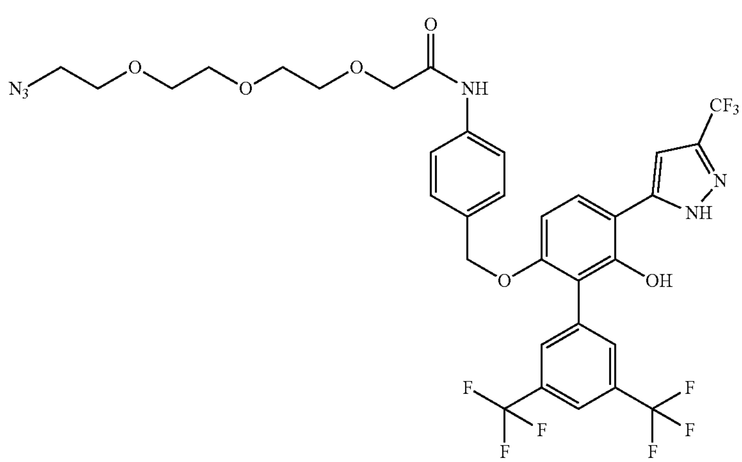 [SMILES: [N-]=[N+]=NCCOCCOCCOCC(=O)Nc1ccc(COc2ccc(-c3cc(C(F)(F)F)n[nH]3)c(O)c2-c2cc(C(F)(F)F)cc(C(F)(F)F)c2)cc1] | J |

TABLE 1-continued

Representative Compounds

| Molecule Name | Molecular weight (g/mol) | Structure | Synthesis Method |
|---|---|---|---|
| NUCC-0201200 | 820.7 | 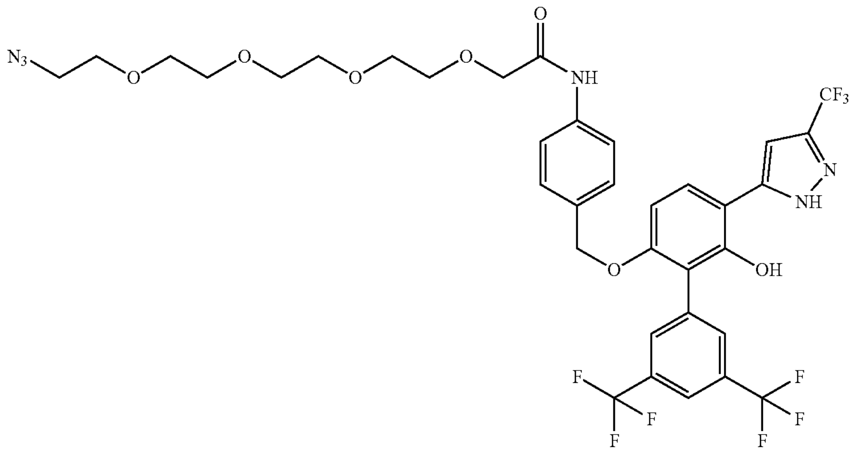 [SMILES: [N-]=[N+]=NCCOCCOCCOCCOCC(=O)Nc1ccc(COc2ccc(-c3cc(C(F)(F)F)n[nH]3)c(O)c2-c2cc(C(F)(F)F)cc(C(F)(F)F)c2)cc1] | J |
| NUCC-0201201 | 561.4 | 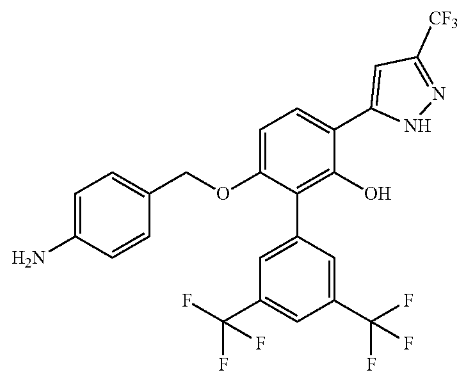 [SMILES: Nc1ccc(COc2ccc(-c3cc(C(F)(F)F)n[nH]3)c(O)c2-c2cc(C(F)(F)F)cc(C(F)(F)F)c2)cc1] | B |
| NUCC-0201202 | 1088.9 | 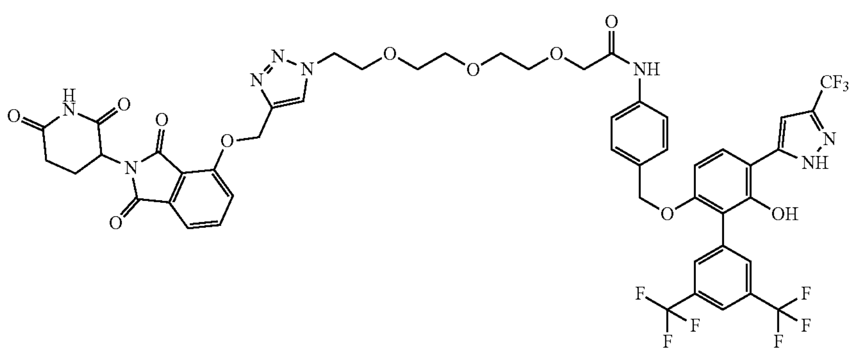 [SMILES: O=C1CCC(N2C(=O)c3cccc(OCc4cn(CCOCCOCCOCC(=O)Nc5ccc(COc6ccc(-c7cc(C(F)(F)F)n[nH]7)c(O)c6-c6cc(C(F)(F)F)cc(C(F)(F)F)c6)cc5)nn4)c3C2=O)C(=O)N1] | J |
| NUCC-0201203 | 1133.0 | 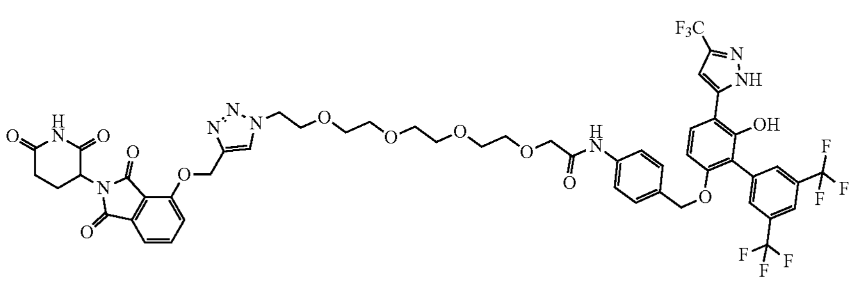 [SMILES: O=C1CCC(N2C(=O)c3cccc(OCc4cn(CCOCCOCCOCCOCC(=O)Nc5ccc(COc6ccc(-c7cc(C(F)(F)F)n[nH]7)c(O)c6-c6cc(C(F)(F)F)cc(C(F)(F)F)c6)cc5)nn4)c3C2=O)C(=O)N1] | J |

TABLE 1-continued

Representative Compounds

| Molecule Name | Molecular weight (g/mol) | Structure | Synthesis Method |
|---|---|---|---|
| NUCC-0201204 | 459.4 | 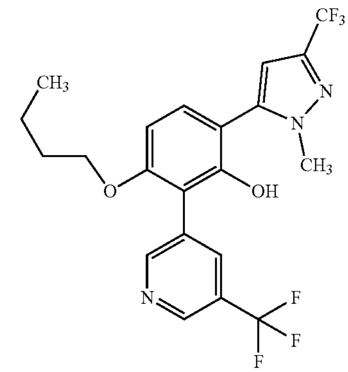 [SMILES: CCCCOc1ccc(-c2cc(C(F)(F)F)nn2C)c(O)c1-c1cncc(C(F)(F)F)c1] | B |
| NUCC-0201205 | 487.4 | 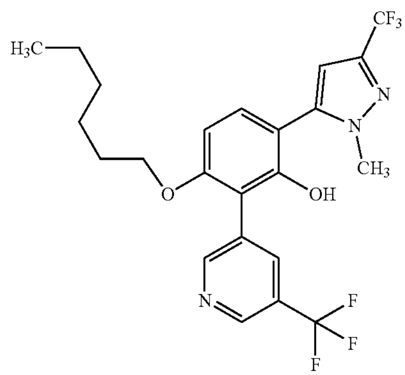 [SMILES: CCCCCCOc1ccc(-c2cc(C(F)(F)F)nn2C)c(O)c1-c1cncc(C(F)(F)F)c1] | B |
| NUCC-0201206 | 473.4 | 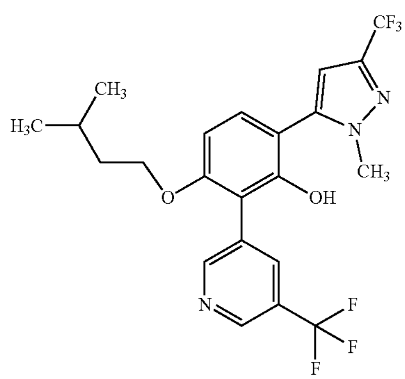 [SMILES: CC(C)CCOc1ccc(-c2cc(C(F)(F)F)nn2C)c(O)c1-c1cncc(C(F)(F)F)c1] | B |
| NUCC-0201207 | 444.5 | 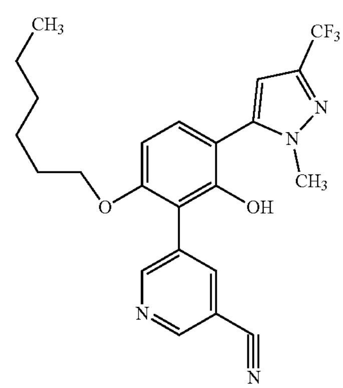 [SMILES: CCCCCCOc1ccc(-c2cc(C(F)(F)F)nn2C)c(O)c1-c1cncc(C#N)c1] | B |

TABLE 1-continued
Representative Compounds
| Molecule Name | Molecular weight (g/mol) | Structure | Synthesis Method |
|---|---|---|---|
| NUCC-0201208 | 430.4 | 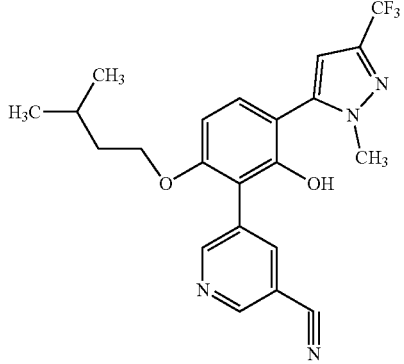 [SMILES: CC(C)CCOc1ccc(-c2cc(C(F)(F)F)nn2C)c(O)c1-c1cncc(C#N)c1] | B |
| NUCC-0201209 | 459.4 | 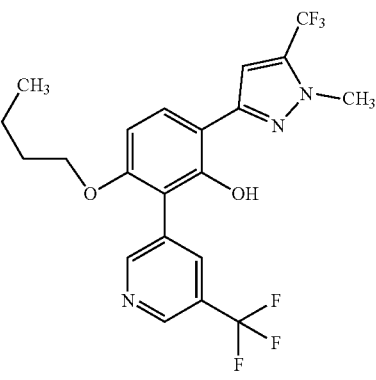 [SMILES: CCCCOc1ccc(-c2cc(C(F)(F)F)n(C)n2)c(O)c1-c1cncc(C(F)(F)F)c1] | B |
| NUCC-0201210 | 487.4 | 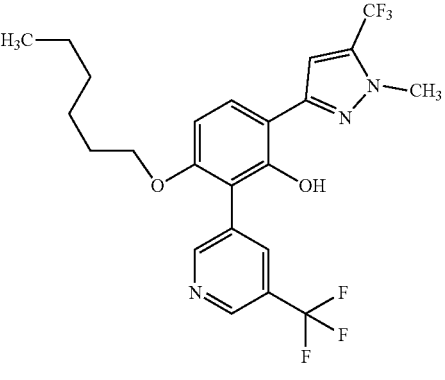 [SMILES: CCCCCCOc1ccc(-c2cc(C(F)(F)F)n(C)n2)c(O)c1-c1cncc(C(F)(F)F)c1] | B |
| NUCC-0201211 | 473.4 | 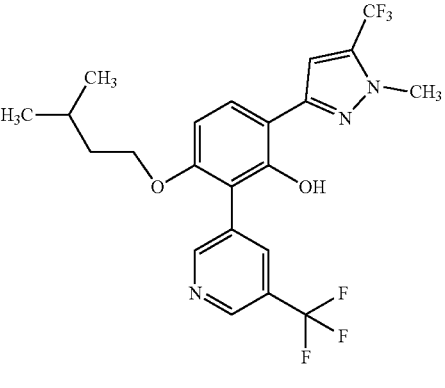 [SMILES: CC(C)CCOc1ccc(-c2cc(C(F)(F)F)n(C)n2)c(O)c1-c1cncc(C(F)(F)F)c1] | B |

TABLE 1-continued

Representative Compounds

| Molecule Name | Molecular weight (g/mol) | Structure | Synthesis Method |
|---|---|---|---|
| NUCC-0201212 | 444.5 | 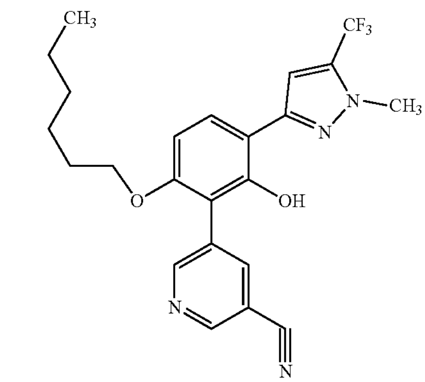 [SMILES: CCCCCCOc1ccc(-c2cc(C(F)(F)F)n(C)n2)c(O)c1-c1cncc(C#N)c1] | B |
| NUCC-0201213 | 430.4 | 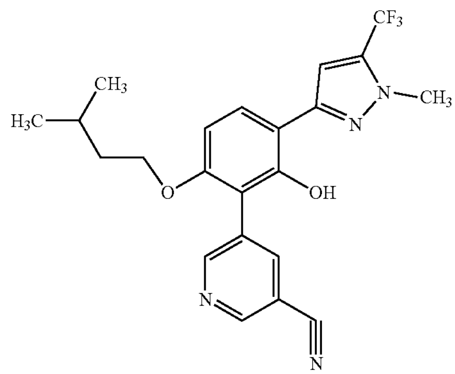 [SMILES: CC(C)CCOc1ccc(-c2cc(C(F)(F)F)n(C)n2)c(O)c1-c1cncc(C#N)c1] | B |
| NUCC-0201219 | 600.4 | 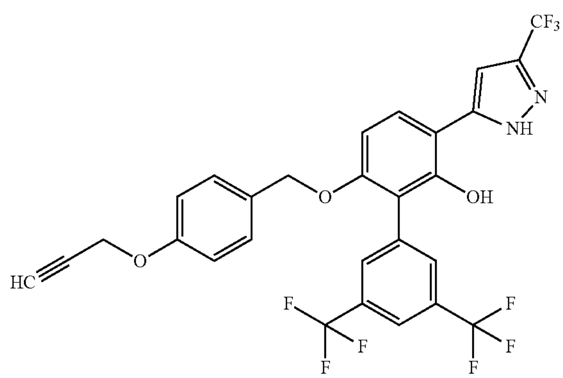 [SMILES: C#CCOc1ccc(COc2ccc(-c3cc(C(F)(F)F)n[nH]3)c(O)c2-c2cc(C(F)(F)F)cc(C(F)(F)F)c2)cc1] | B |
| NUCC-0201220 | 470.3 | 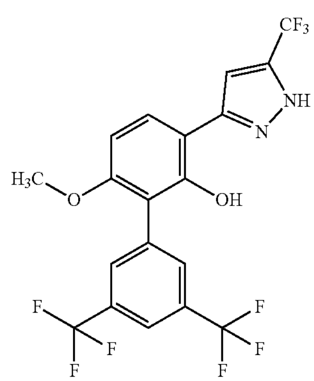 [SMILES: COc1ccc(-c2cc(C(F)(F)F)[nH]n2)c(O)c1-c1cc(C(F)(F)F)cc(C(F)(F)F)c1] | B |

TABLE 1-continued

Representative Compounds

| Molecule Name | Molecular weight (g/mol) | Structure | Synthesis Method |
|---|---|---|---|
| NUCC-0201221 | 484.3 | 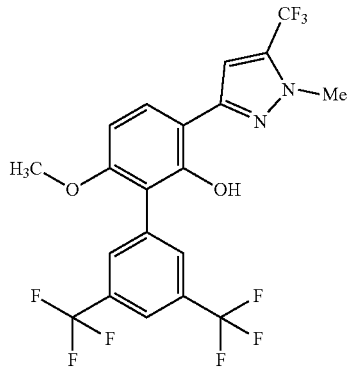 [SMILES: COc1ccc(-c2cc(C(F)(F)F)n(C)n2)c(O)c1-c1cc(C(F)(F)F)cc(C(F)(F)F)c1] | B |
| NUCC-0201222 | 484.3 | 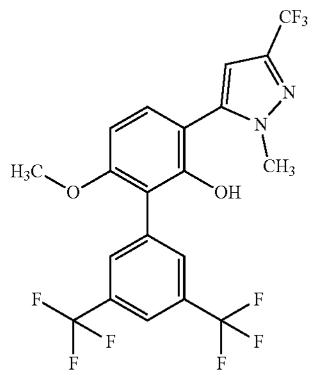 [SMILES: COc1ccc(-c2cc(C(F)(F)F)nn2C)c(O)c1-c1cc(C(F)(F)F)cc(C(F)(F)F)c1] | B |
| NUCC-0201223 | 566.8 | 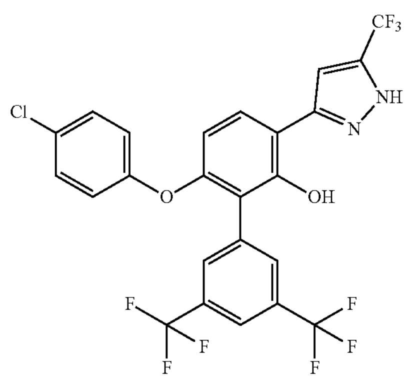 [SMILES: Oc1c(-c2cc(C(F)(F)F)[nH]n2)ccc(Oc2ccc(Cl)cc2)c1-c1cc(C(F)(F)F)cc(C(F)(F)F)c1] | G |
| NUCC-0201224 | 583.9 | 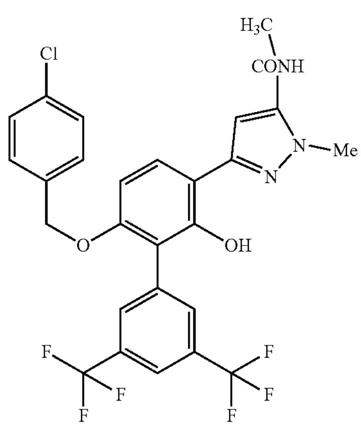 | C |

TABLE 1-continued

Representative Compounds

| Molecule Name | Molecular weight (g/mol) | Structure | Synthesis Method |
|---|---|---|---|
| NUCC-0201225 | 478.8 | 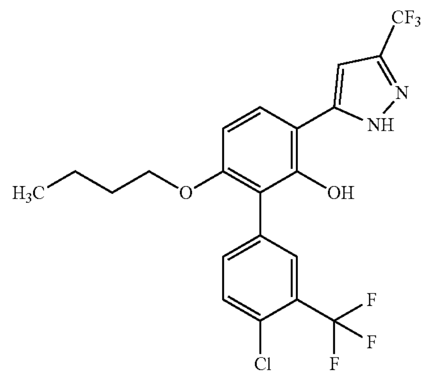 [SMILES: CCCCOc1ccc(-c2cc(C(F)(F)F)n[nH]2)c(O)c1-c1ccc(Cl)c(C(F)(F)F)c1] | B |
| NUCC-0201226 | 484.9 | 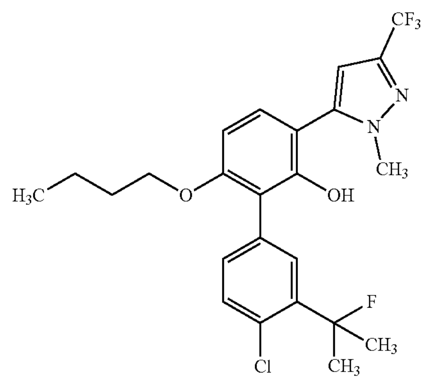 [SMILES: CCCCOc1ccc(-c2cc(C(F)(F)F)nn2C)c(O)c1-c1ccc(Cl)c(C(C)(C)F)c1] | B |
| NUCC-0201227 | 492.9 | 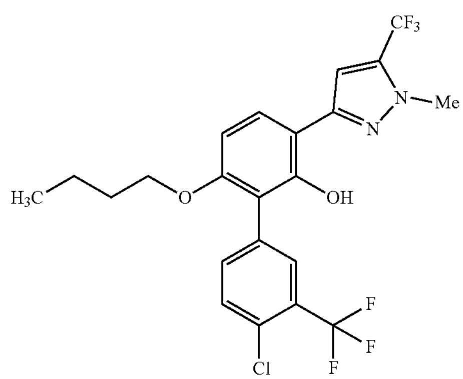 [SMILES: CCCCOc1ccc(-c2cc(C(F)(F)F)n(C)n2)c(O)c1-c1ccc(Cl)c(C(F)(F)F)c1] | B |
| NUCC-0201630 | 527.9 | 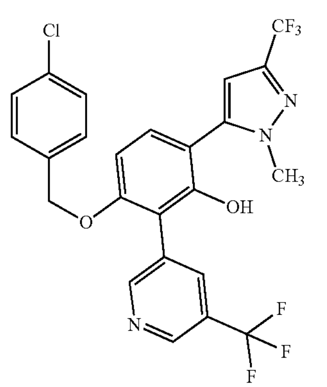 [SMILES: Cn1nc(C(F)(F)F)cc1-c1ccc(OCc2ccc(Cl)cc2)c(-c2cncc(C(F)(F)F)c2)c1O] | B |

TABLE 1-continued
Representative Compounds
| Molecule Name | Molecular weight (g/mol) | Structure | Synthesis Method |
|---|---|---|---|
| NUCC-0201631 | 527.9 | 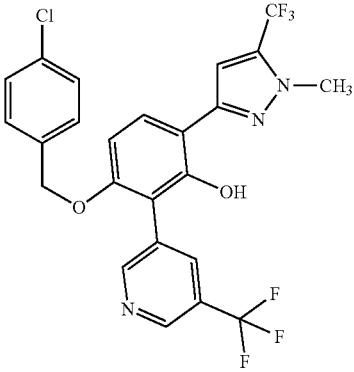 [SMILES: Cn1nc(-c2ccc(OCc3ccc(Cl)cc3)c(-c3cncc(C(F)(F)F)c3)c2O)cc1C(F)(F)F] | B |
| NUCC-0201632 | 484.9 | 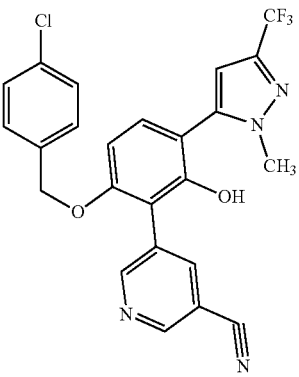 [SMILES: Cn1nc(C(F)(F)F)cc1-c1ccc(OCc2ccc(Cl)cc2)c(-c2cncc(C#N)c2)c1O] | B |
| NUCC-0201633 | 484.9 | 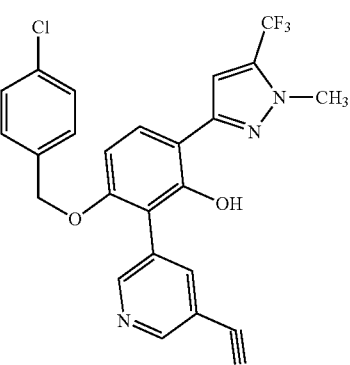 | B |
| NUCC-0201634 | 492.9 | 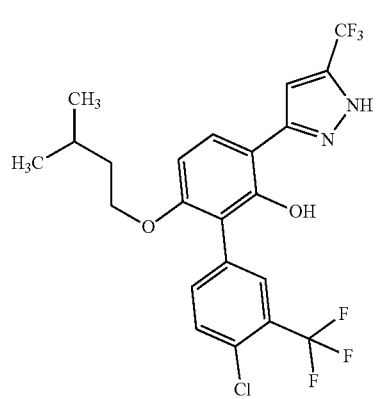 [SMILES: CC(C)CCOc1ccc(-c2cc(C(F)(F)F)[nH]n2)c(O)c1-c1ccc(Cl)c(C(F)(F)F)c1] | B |

TABLE 1-continued

Representative Compounds

| Molecule Name | Molecular weight (g/mol) | Structure | Synthesis Method |
|---|---|---|---|
| NUCC-0201635 | 506.9 | 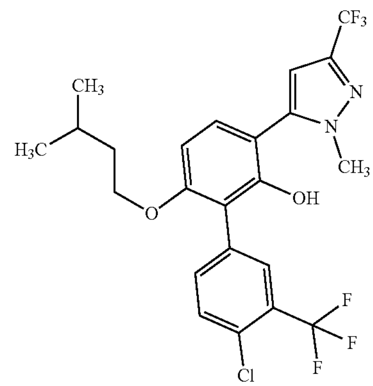 [SMILES: CC(C)CCOc1ccc(-c2cc(C(F)(F)F)nn2C)c(O)c1-c1ccc(Cl)c(C(F)(F)F)c1] | B |
| NUCC-0201636 | 459.4 | 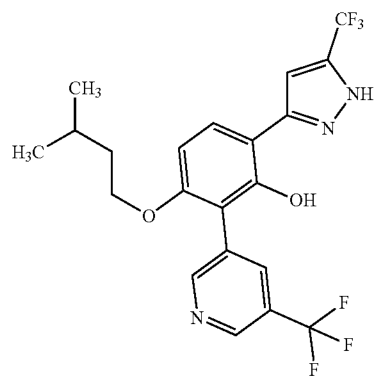 [SMILES: CC(C)CCOc1ccc(-c2cc(C(F)(F)F)[nH]n2)c(O)c1-c1cncc(C(F)(F)F)c1] | B |
| NUCC-0201637 | 445.4 | 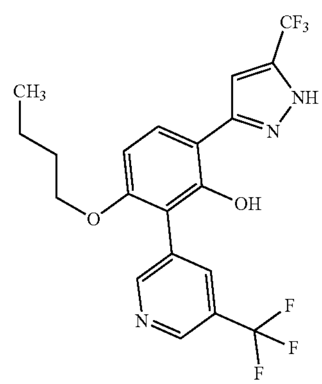 [SMILES: CCCCOc1ccc(-c2cc(C(F)(F)F)[nH]n2)c(O)c1-c1cncc(C(F)(F)F)c1] | B |
| NUCC-0201638 | 416.4 | 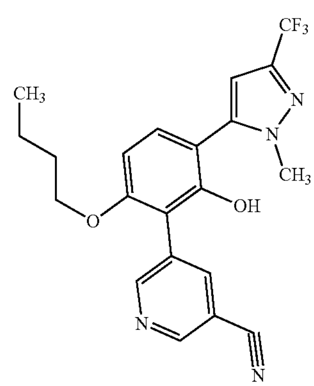 [SMILES: CCCCOc1ccc(-c2cc(C(F)(F)F)nn2C)c(O)c1-c1cncc(C#N)c1] | B |

TABLE 1-continued
Representative Compounds
| Molecule Name | Molecular weight (g/mol) | Structure | Synthesis Method |
|---|---|---|---|
| NUCC-0201639 | 416.4 | 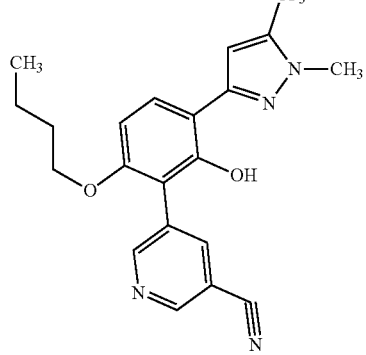 | B |
| NUCC-0201640 | 479.8 | 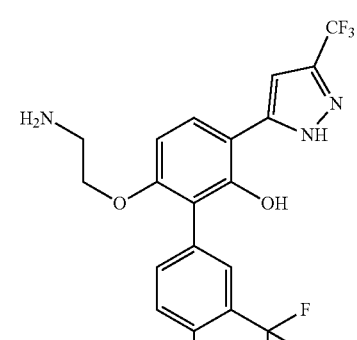 | B |
| NUCC-0201641 | 479.8 | 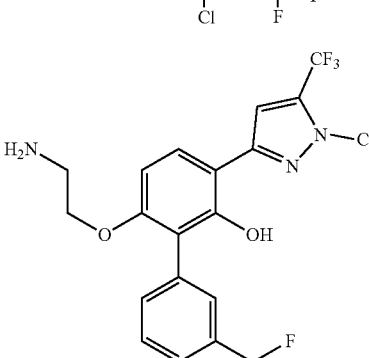 | B |
| NUCC-0201642 | 493.8 | 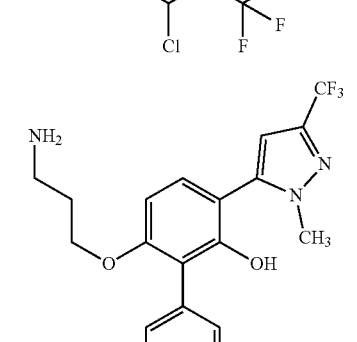 | B |

TABLE 1-continued
Representative Compounds
| Molecule Name | Molecular weight (g/mol) | Structure | Synthesis Method |
|---|---|---|---|
| NUCC-0201643 | 493.8 | 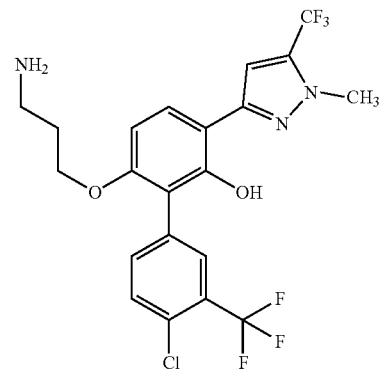 [SMILES: Cn1nc(-c2ccc(OCCCN)c(-c3ccc(Cl)c(C(F)(F)F)c3)c2O)cc1C(F)(F)F] | B |
| NUCC-0201644 | 532.4 | 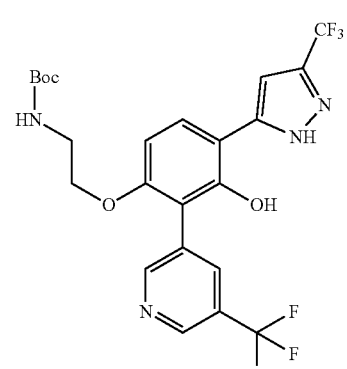 | B |
| NUCC-0201645 | 432.3 | 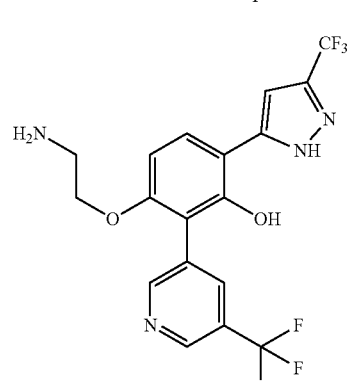 | B |
| NUCC-0201646 | 479.8 | 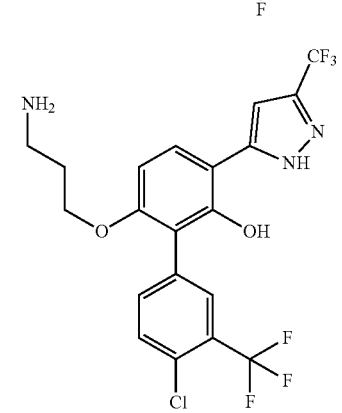 | B |

TABLE 1-continued

Representative Compounds

| Molecule Name | Molecular weight (g/mol) | Structure | Synthesis Method |
|---|---|---|---|
| NUCC-0201647 | 465.8 | 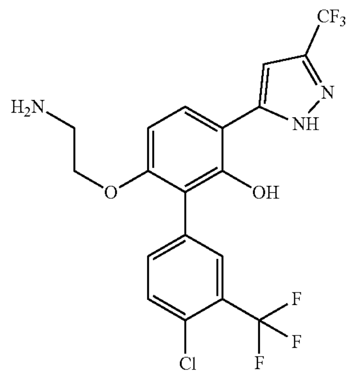 [SMILES: NCCOc1ccc(-c2cc(C(F)(F)F)n[nH]2)c(O)c1-c1ccc(Cl)c(C(F)(F)F)c1] | B |
| NUCC-0201648 | 605.4 | 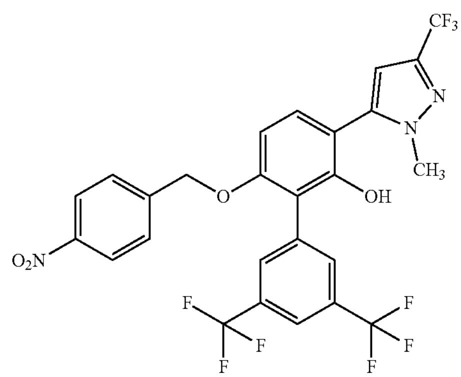 [SMILES: Cn1nc(C(F)(F)F)cc1-c1ccc(OCc2ccc([N+](=O)[O-])cc2)c(-c2cc(C(F)(F)F)cc(C(F)(F)F)c2)c1O] | B |
| NUCC-0201649 | 605.4 | 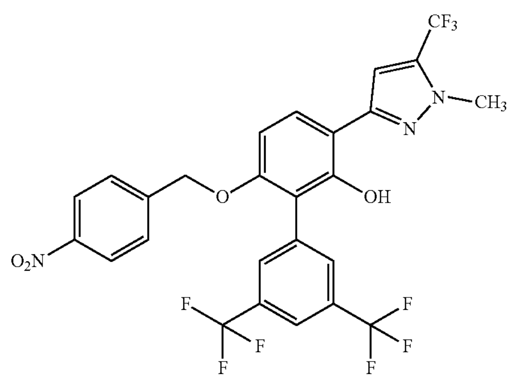 [SMILES: Cn1nc(-c2ccc(OCc3ccc([N+](=O)[O-])cc3)c(-c3cc(C(F)(F)F)cc(C(F)(F)F)c3)c2O)cc1C(F)(F)F] | B |
| NUCC-0201650 | 600.9 | 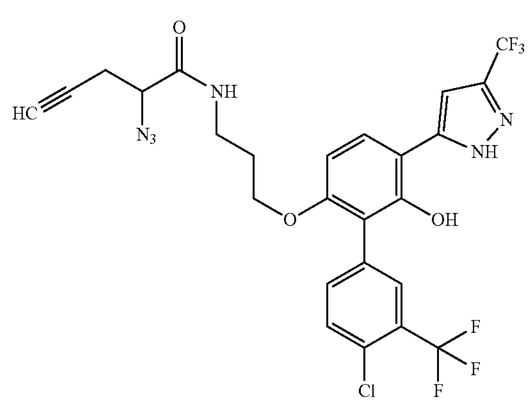 [SMILES: C#CCC(N=[N+]=[N-])C(=O)NCCCOc1ccc(-c2cc(C(F)(F)F)n[nH]2)c(O)c1-c1ccc(Cl)c(C(F)(F)F)c1] | B |

TABLE 1-continued
Representative Compounds
| Molecule Name | Molecular weight (g/mol) | Structure | Synthesis Method |
|---|---|---|---|
| NUCC-0201651 | 526.4 | 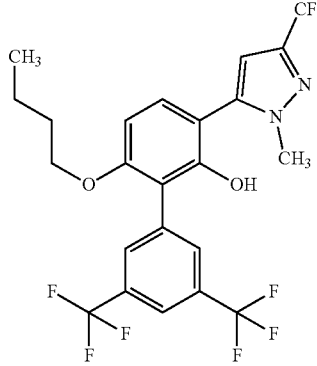 | B |
| NUCC-0201652 | 526.4 | 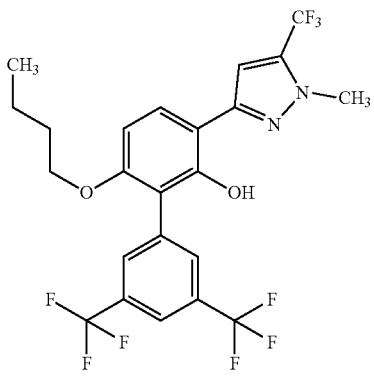 [SMILES: CCCCOc1ccc(-c2cc(C(F)(F)F)n(C)n2)c(O)c1-c1cc(C(F)(F)F)cc(C(F)(F)F)c1] | B |
| NUCC-0201653 | 538.4 | 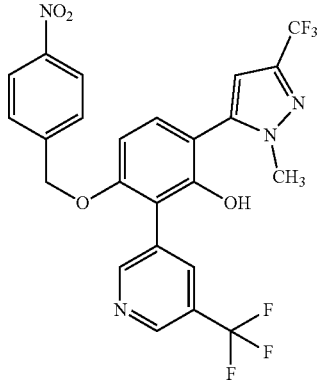 [SMILES: Cn1nc(C(F)(F)F)cc1-c1ccc(OCc2ccc([N+](=O)[O-])cc2)c(-c2cncc(C(F)(F)F)c2)c1O] | B |
| NUCC-0201654 | 538.4 | 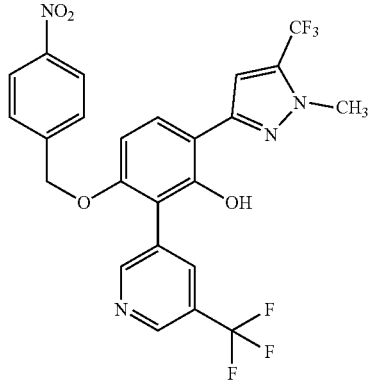 [SMILES: Cn1nc(-c2ccc(OCc3ccc([N+](=O)[O-])cc3)c(-c3cncc(C(F)(F)F)c3)c2O)cc1C(F)(F)F] | B |

TABLE 1-continued

Representative Compounds

| Molecule Name | Molecular weight (g/mol) | Structure | Synthesis Method |
|---|---|---|---|
| NUCC-0201655 | 560.5 | 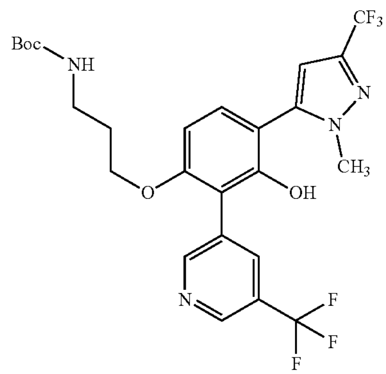 [SMILES: Cn1nc(C(F)(F)F)cc1-c1ccc(OCCCNC(=O)OC(C)(C)C)c(-c2cncc(C(F)(F)F)c2)c1O] | B |
| NUCC-0201656 | 560.5 | 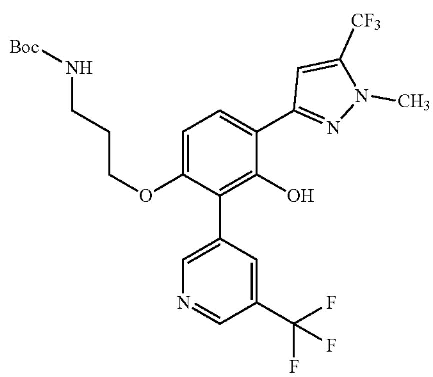 [SMILES: Cn1nc(-c2ccc(OCCCNC(=O)OC(C)(C)C)c(-c3cncc(C(F)(F)F)c3)c2O)cc1C(F)(F)F] | B |
| NUCC-0201657 | 594.0 | 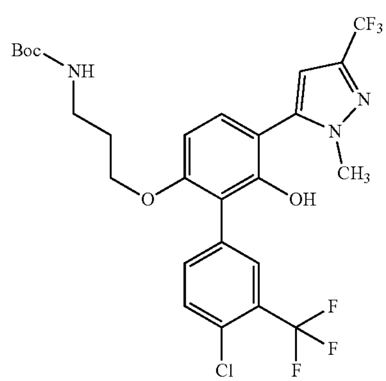 [SMILES: Cn1nc(C(F)(F)F)cc1-c1ccc(OCCCNC(=O)OC(C)(C)C)c(-c2ccc(Cl)c(C(F)(F)F)c2)c1O] | B |
| NUCC-0201658 | 594.0 | 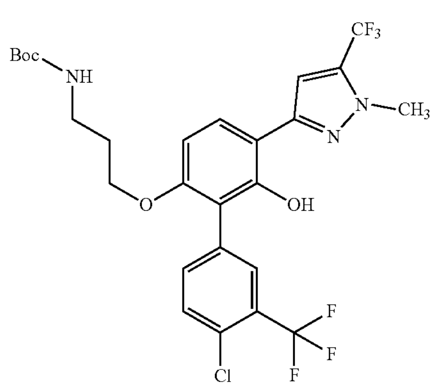 [SMILES: Cn1nc(-c2ccc(OCCCNC(=O)OC(C)(C)C)c(-c3ccc(Cl)c(C(F)(F)F)c3)c2O)cc1C(F)(F)F] | B |

TABLE 1-continued

Representative Compounds

| Molecule Name | Molecular weight (g/mol) | Structure | Synthesis Method |
|---|---|---|---|
| NUCC-0201659 | 559.9 | 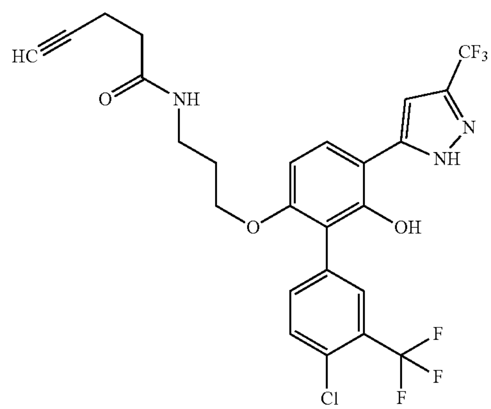 [SMILES: C#CCCC(=O)NCCCOc1ccc(-c2cc(C(F)(F)F)n[nH]2)c(O)c1-c1ccc(Cl)c(C(F)(F)F)c1] | I |
| NUCC-0201660 | 1000.9 | 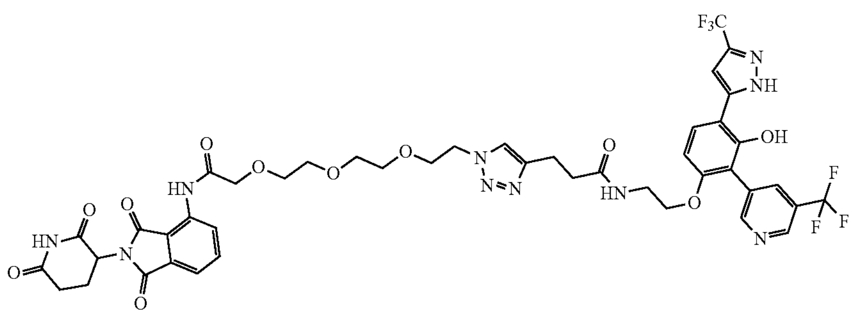 [SMILES: O=C(CCc1cn(CCOCCOCCOCC(=O)Nc2cccc3c2C(=O)N(C2CCC(=O)NC2=O)C3=O)nn1)NCCOc1ccc(-c2cc(C(F)(F)F)n[nH]2)c(O)c1-c1cncc(C(F)(F)F)c1] | J |
| NUCC-0201661 | 434 | 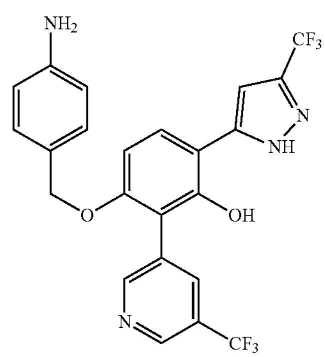 [SMILES: Nc1ccc(COc2ccc(-c3cc(C(F)(F)F)n[nH]3)c(O)c2-c2cncc(C(F)(F)F)c2)cc1] | B |
| NUCC-0201694 | 581.5 | 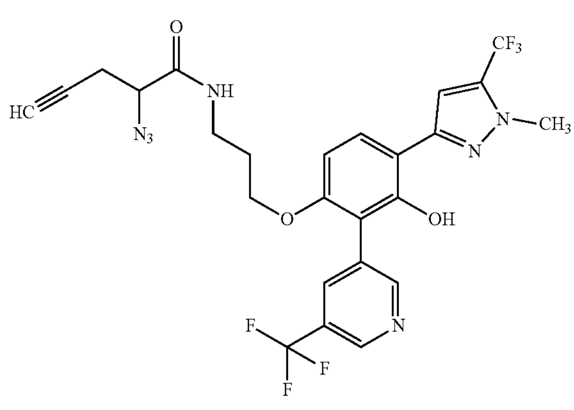 [SMILES: C#CCC(N=[N+]=[N-])C(=O)NCCCOc1ccc(-c2cc(C(F)(F)F)n(C)n2)c(O)c1-c1cncc(C(F)(F)F)c1] | I |

TABLE 1-continued

Representative Compounds

| Molecule Name | Molecular weight (g/mol) | Structure | Synthesis Method |
|---|---|---|---|
| NUCC-0201695 | 614.9 | 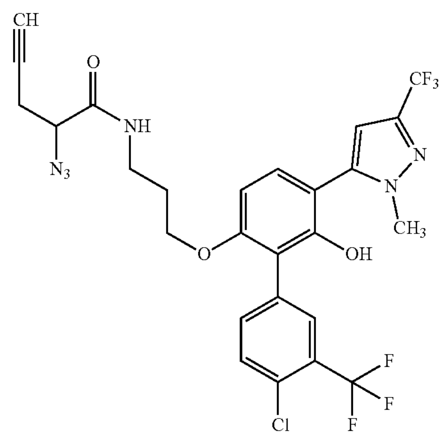 [SMILES: C#CCC(N=[N+]=[N-])C(=O)NCCCOc1ccc(-c2cc(C(F)(F)F)nn2C)c(O)c1-c1ccc(Cl)c(C(F)(F)F)c1] | I |
| NUCC-0201696 | 581.5 | 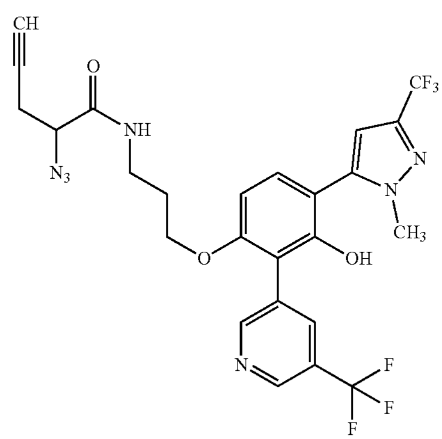 [SMILES: C#CCC(N=[N+]=[N-])C(=O)NCCCOc1ccc(-c2cc(C(F)(F)F)nn2C)c(O)c1-c1cncc(C(F)(F)F)c1] | I |
| NUCC-0201697 | 553.4 | 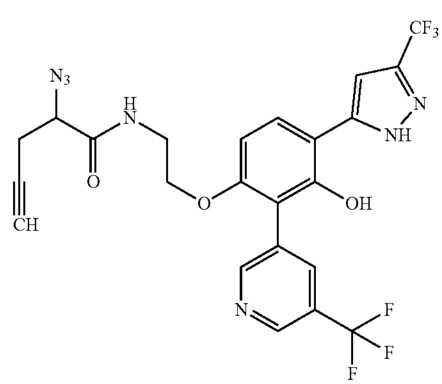 [SMILES: C#CCC(N=[N+]=[N-])C(=O)NCCOc1ccc(-c2cc(C(F)(F)F)n[nH]2)c(O)c1-c1cncc(C(F)(F)F)c1] | I |

TABLE 1-continued

Representative Compounds

| Molecule Name | Molecular weight (g/mol) | Structure | Synthesis Method |
|---|---|---|---|
| NUCC-0201698 | 629.5 | 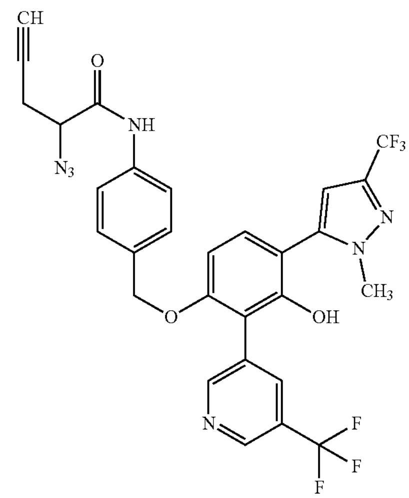 [SMILES: C#CCC(N=[N+]=[N-])C(=O)Nc1ccc(COc2ccc(-c3cc(C(F)(F)F)nn3C)c(O)c2-c2cncc(C(F)(F)F)c2)cc1] | I |
| NUCC-0201699 | 629.5 | 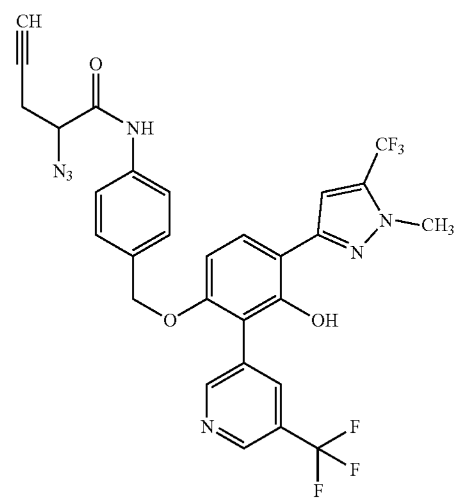 [SMILES: C#CCC(N=[N+]=[N-])C(=O)Nc1ccc(COc2ccc(-c3cc(C(F)(F)F)n(C)n3)c(O)c2-c2cncc(C(F)(F)F)c2)cc1] | I |
| NUCC-0201702 | 1021.3 | 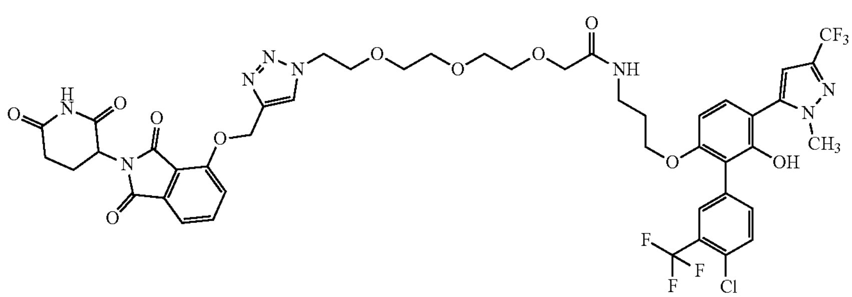 [SMILES: Cn1nc(C(F)(F)F)cc1-c1ccc(OCCCNC(=O)COCCOCCOCCn2cc(COc3cccc4c3C(=O)N(C3CCC(=O)NC3=O)C4=O)nn2)c(-c2ccc(Cl)c(C(F)(F)F)c2)c1O] | J |

TABLE 1-continued

Representative Compounds

| Molecule Name | Molecular weight (g/mol) | Structure | Synthesis Method |
|---|---|---|---|
| NUCC-0201703 | 987.9 | 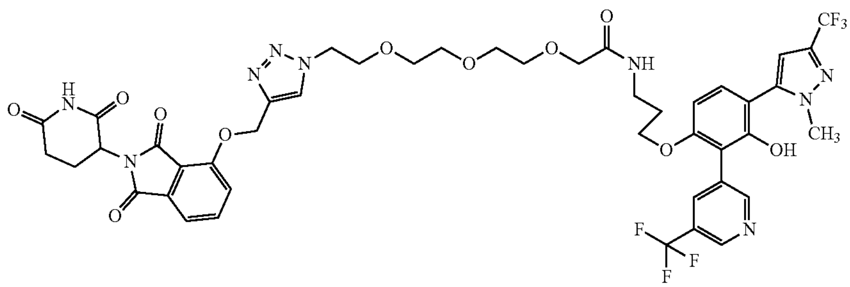 [SMILES: Cn1nc(C(F)(F)F)cc1-c1ccc(OCCCNC(=O)COCCOCCOCCn2cc(COc3cccc4c3C(=O)N(C3CCC(=O)NC3=O)C4=O)nn2)c(-c2cncc(C(F)(F)F)c2)c1O] | J |
| NUCC-0201704 | 959.8 | 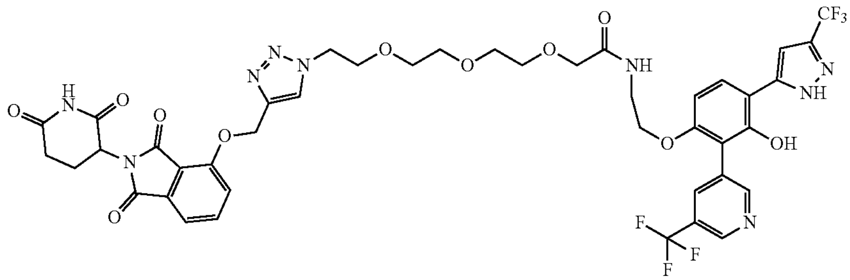 [SMILES: O=C(COCCOCCOCCn1cc(COc2cccc3c2C(=O)N(C2CCC(=O)NC2=O)C3=O)nn1)NCCOc1ccc(-c2cc(C(F)(F)F)n[nH]2)c(O)c1-c1cncc(C(F)(F)F)c1] | J |
| NUCC-0201705 | 312.3 | 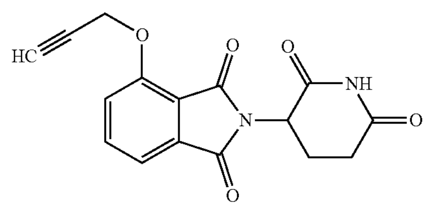 [SMILES: C#CCOc1cccc2c1C(=O)N(C1CCC(=O)NC1=O)C2=O] | J |
| NUCC-0201909 | 450.9 | 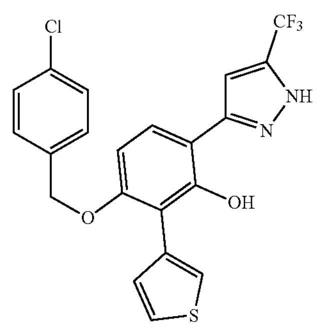 [SMILES: Oc1c(-c2cc(C(F)(F)F)[nH]n2)ccc(OCc2ccc(Cl)cc2)c1-c1ccsc1] | B |
| NUCC-0201910 | 408.8 | 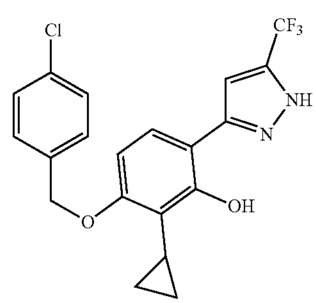 [SMILES: Oc1c(-c2cc(C(F)(F)F)[nH]n2)ccc(OCc2ccc(Cl)cc2)c1C1CC1] | B |

TABLE 1-continued
Representative Compounds
| Molecule Name | Molecular weight (g/mol) | Structure | Synthesis Method |
|---|---|---|---|
| NUCC-0201911 | 537.9 | 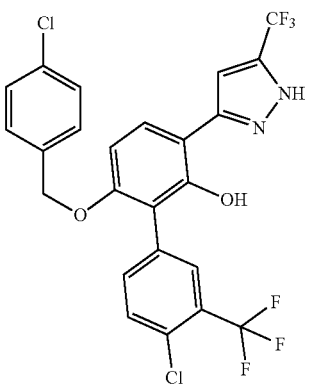 [SMILES: Oc1c(-c2cc(C(F)(F)F)[nH]n2)ccc(OCc2ccc(Cl)cc2)c1-c1ccc(Cl)c(C(F)(F)F)c1] | B |
| NUCC-0201912 | 551.9 | 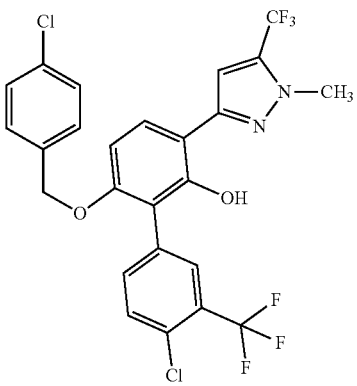 [SMILES: Cn1nc(-c2ccc(OCc3ccc(Cl)cc3)c(-c3ccc(Cl)c(C(F)(F)F)c3)c2O)cc1C(F)(F)F] | B |
| NUCC-0201913 | 551.9 | 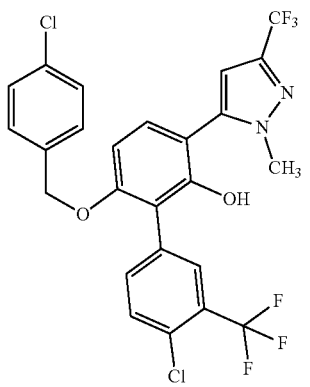 [SMILES: Cn1nc(C(F)(F)F)cc1-c1ccc(OCc2ccc(Cl)cc2)c(-c2ccc(Cl)c(C(F)(F)F)c2)c1O] | B |
TABLE 2
Biological Activity of Representative Compounds
| Molecule Name | Potency code <10 ++++ 10-30 +++ 30-40 ++ >40 + | EMSA IC50(uM) |
|---|---|---|
| NUCC-0176234 | + | 123.1 |
| NUCC-0176242 | ++ | 89 |
| NUCC-0176243 | + | |
| NUCC-0176244 | + | |

TABLE 2-continued

Biological Activity of Representative Compounds

| Molecule Name | Potency code <10 ++++ 10-30 +++ 30-40 ++ >40 + | EMSA IC50(uM) |
|---|---|---|
| NUCC-0176245 | ++ | 95 |
| NUCC-0176246 | + | |
| NUCC-0176247 | + | |
| NUCC-0176248 | + | 96 |
| NUCC-0176249 | + | |
| NUCC-0176250 | + | |
| NUCC-0176251 | + | |
| NUCC-0176252 | + | |
| NUCC-0176253 | + | |
| NUCC-0176254 | + | |
| NUCC-0176255 | + | |
| NUCC-0176256 | + | |
| NUCC-0176257 | + | |
| NUCC-0176258 | + | |
| NUCC-0176259 | + | |
| NUCC-0176260 | + | |
| NUCC-0176261 | + | |
| NUCC-0176262 | + | |
| NUCC-0196282 | + | |
| NUCC-0196283 | ++++ | 49 |
| NUCC-0196284 | + | |
| NUCC-0196285 | + | |
| NUCC-0196286 | + | |
| NUCC-0196287 | + | |
| NUCC-0196288 | + | |
| NUCC-0196289 | + | |
| NUCC-0196290 | + | |
| NUCC-0196291 | + | |
| NUCC-0196294 | + | |
| NUCC-0196295 | +++ | 66.8 |
| NUCC-0196296 | + | |
| NUCC-0196297 | + | |
| NUCC-0196298 | ++ | |
| NUCC-0196299 | + | |
| NUCC-0196301 | + | |
| NUCC-0196302 | + | |
| NUCC-0196303 | + | |
| NUCC-0196304 | +++ | |
| NUCC-0196305 | ++++ | |
| NUCC-0196306 | + | |
| NUCC-0196311 | + | |
| NUCC-0196312 | + | |
| NUCC-0196313 | ++++ | |
| NUCC-0196314 | + | |
| NUCC-0196340 | ++ | |
| NUCC-0196341 | + | |
| NUCC-0196342 | ++++ | 64.4 |
| NUCC-0196343 | + | |
| NUCC-0196344 | +++ | |
| NUCC-0196345 | + | |
| NUCC-0196346 | + | |
| NUCC-0196347 | + | |
| NUCC-0196348 | +++ | |
| NUCC-0196349 | + | |
| NUCC-0196350 | +++ | |
| NUCC-0196351 | + | |
| NUCC-0196352 | + | |
| NUCC-0196353 | + | |
| NUCC-0196354 | + | |
| NUCC-0196355 | +++ | |
| NUCC-0196356 | + | |
| NUCC-0196357 | +++ | |
| NUCC-0196358 | + | |
| NUCC-0196359 | + | |
| NUCC-0196360 | + | |
| NUCC-0196361 | ++++ | 63 |
| NUCC-0196362 | ++ | 102.2 |
| NUCC-0196363 | ++++ | 61.8 |
| NUCC-0196364 | + | |
| NUCC-0196365 | + | |
| NUCC-0196366 | + | |
| NUCC-0198293 | + | |
| NUCC-0198294 | + | |
| NUCC-0198295 | ++++ | 53.3 |
| NUCC-0198296 | + | |
| NUCC-0198297 | + | |
| NUCC-0198298 | + | |
| NUCC-0198299 | + | |
| NUCC-0198300 | + | |
| NUCC-0198301 | + | |
| NUCC-0198302 | + | |
| NUCC-0198303 | + | |
| NUCC-0198304 | + | |
| NUCC-0198305 | + | |
| NUCC-0198306 | + | |
| NUCC-0198307 | + | |
| NUCC-0198308 | + | |
| NUCC-0198309 | ++++ | 61.2 |
| NUCC-0198310 | + | |
| NUCC-0198311 | + | |
| NUCC-0198312 | + | |
| NUCC-0198313 | + | |
| NUCC-0198314 | + | |
| NUCC-0198315 | + | |
| NUCC-0198316 | + | |
| NUCC-0198317 | + | |
| NUCC-0198318 | ++ | |
| NUCC-0198319 | + | |
| NUCC-0198320 | + | |
| NUCC-0198321 | + | |
| NUCC-0198322 | ++ | |
| NUCC-0198323 | + | |
| NUCC-0198324 | + | |
| NUCC-0198325 | + | |
| NUCC-0198326 | + | |
| NUCC-0198352 | + | |
| NUCC-0198353 | + | |
| NUCC-0198354 | + | |
| NUCC-0198355 | + | |
| NUCC-0198356 | + | |
| NUCC-0198357 | + | |
| NUCC-0198358 | + | |
| NUCC-0198359 | ++ | |
| NUCC-0198360 | + | |
| NUCC-0198361 | + | |
| NUCC-0198362 | + | |
| NUCC-0198391 | ++++ | |
| NUCC-0198392 | + | |
| NUCC-0198393 | + | |
| NUCC-0198394 | ++ | |
| NUCC-0198395 | + | |
| NUCC-0198396 | + | |
| NUCC-0198397 | + | |
| NUCC-0198398 | ++++ | |
| NUCC-0198399 | ++++ | |
| NUCC-0198400 | + | |
| NUCC-0198401 | + | |
| NUCC-0198402 | + | |
| NUCC-0198403 | + | |
| NUCC-0198404 | + | |
| NUCC-0198405 | + | |
| NUCC-0198406 | ++++ | |
| NUCC-0198407 | +++ | |
| NUCC-0198408 | + | |
| NUCC-0198409 | + | |
| NUCC-0198410 | + | |
| NUCC-0198411 | +++ | |
| NUCC-0198412 | + | |
| NUCC-0200489 | + | |
| NUCC-0200490 | + | |
| NUCC-0200491 | ++++ | |
| NUCC-0200492 | +++ | |
| NUCC-0200493 | + | |

TABLE 2-continued

Biological Activity of Representative Compounds

| Molecule Name | Potency code <10 ++++ 10-30 +++ 30-40 ++ >40 + | EMSA IC50(uM) |
|---|---|---|
| NUCC-0200494 | + | |
| NUCC-0200495 | ++++ | |
| NUCC-0200496 | + | |
| NUCC-0200497 | + | |
| NUCC-0200498 | + | |
| NUCC-0200499 | + | |
| NUCC-0200500 | + | |
| NUCC-0200501 | + | |
| NUCC-0200502 | + | |
| NUCC-0200503 | + | |
| NUCC-0200557 | + | |
| NUCC-0200558 | ++++ | |
| NUCC-0200559 | ++ | |
| NUCC-0200560 | + | |
| NUCC-0200561 | + | |
| NUCC-0200562 | + | |
| NUCC-0200563 | + | |
| NUCC-0200564 | + | |
| NUCC-0200565 | + | |
| NUCC-0200566 | + | |
| NUCC-0200567 | + | |
| NUCC-0200568 | + | |
| NUCC-0200569 | + | |
| NUCC-0200570 | + | |
| NUCC-0200571 | + | |
| NUCC-0200572 | + | |
| NUCC-0200573 | + | |
| NUCC-0200574 | + | |
| NUCC-0200575 | ++++ | |
| NUCC-0200576 | ++++ | |
| NUCC-0200677 | + | |
| NUCC-0200678 | + | |
| NUCC-0200679 | ++ | |
| NUCC-0200680 | + | |
| NUCC-0200681 | ++++ | |
| NUCC-0200682 | + | |
| NUCC-0200683 | +++ | |
| NUCC-0200684 | + | |
| NUCC-0200685 | + | |
| NUCC-0200686 | + | |
| NUCC-0200687 | + | |
| NUCC-0200688 | + | |
| NUCC-0200689 | + | |
| NUCC-0200690 | + | |
| NUCC-0200691 | + | |
| NUCC-0200692 | + | |
| NUCC-0200721 | ++++ | |
| NUCC-0200722 | + | |
| NUCC-0200723 | ++ | |
| NUCC-0200724 | + | |
| NUCC-0200725 | + | |
| NUCC-0200726 | + | |
| NUCC-0200727 | + | |
| NUCC-0200728 | + | |
| NUCC-0200729 | + | |
| NUCC-0200730 | + | |
| NUCC-0200731 | + | |
| NUCC-0200732 | + | |
| NUCC-0200733 | + | |
| NUCC-0200734 | + | |
| NUCC-0200735 | + | |
| NUCC-0200736 | + | |
| NUCC-0200737 | + | |
| NUCC-0200738 | +++ | |
| NUCC-0200739 | + | |
| NUCC-0200740 | + | |
| NUCC-0200741 | + | |
| NUCC-0200742 | + | |
| NUCC-0200743 | + | |
| NUCC-0200744 | + | |
| NUCC-0200745 | + | |
| NUCC-0200746 | + | |
| NUCC-0200747 | + | |
| NUCC-0196314.2 | + | |
| NUCC-0198412.2 | + | |
| NUCC-0200812 | + | |
| NUCC-0200813 | + | |
| NUCC-0200814 | + | |
| NUCC-0200815 | + | |
| NUCC-0200816 | + | |
| NUCC-0200817 | + | |
| NUCC-0200970 | + | |
| NUCC-0200971 | ++++ | |
| NUCC-0200972 | + | |
| NUCC-0200973 | ++++ | |
| NUCC-0200974 | + | |
| NUCC-0200975 | + | |
| NUCC-0200976 | + | |
| NUCC-0200977 | + | |
| NUCC-0200978 | + | |
| NUCC-0200979 | + | |
| NUCC-0201023 | + | |
| NUCC-0201024 | ++++ | |
| NUCC-0201025 | ++ | |
| NUCC-0201026 | + | |
| NUCC-0201027 | +++ | |
| NUCC-0201028 | + | |
| NUCC-0201029 | + | |
| NUCC-0201030 | + | |
| NUCC-0201031 | + | |
| NUCC-0201032 | + | |
| NUCC-0201033 | + | |
| NUCC-0201034 | + | |
| NUCC-0201035 | + | |
| NUCC-0201036 | ++ | |
| NUCC-0201037 | +++ | |
| NUCC-0201038 | ++++ | |
| NUCC-0201039 | +++ | |
| NUCC-0201040 | +++ | |
| NUCC-0201041 | + | |
| NUCC-0201042 | + | |
| NUCC-0201043 | + | |
| NUCC-0201192 | +++ | |
| NUCC-0201193 | ++++ | |
| NUCC-0201194 | + | |
| NUCC-0201195 | ++++ | |
| NUCC-0201196 | +++ | |
| NUCC-0201197 | +++ | |
| NUCC-0201198 | +++ | |
| NUCC-0201199 | +++ | |
| NUCC-0201200 | + | |
| NUCC-0201201 | ++++ | |
| NUCC-0201202 | +++ | |
| NUCC-0201203 | ++ | |
| NUCC-0201204 | +++ | |
| NUCC-0201205 | ++++ | |
| NUCC-0201206 | ++++ | |
| NUCC-0201207 | +++ | |
| NUCC-0201208 | ++++ | |
| NUCC-0201209 | + | |
| NUCC-0201210 | + | |
| NUCC-0201211 | + | |
| NUCC-0201212 | + | |
| NUCC-0201213 | ++++ | |
| NUCC-0201219 | ++++ | |
| NUCC-0201220 | ++++ | |
| NUCC-0201221 | + | |
| NUCC-0201222 | +++ | |
| NUCC-0201223 | ++++ | |
| NUCC-0201224 | ++++ | |
| NUCC-0201225 | + | |
| NUCC-0201226 | +++ | |
| NUCC-0201227 | ++++ | |
| NUCC-0201630 | + | |

TABLE 2-continued

Biological Activity of Representative Compounds

| Molecule Name | Potency code <10 ++++ 10-30 +++ 30-40 ++ >40 + | EMSA IC50(uM) |
|---|---|---|
| NUCC-0201631 | + | |
| NUCC-0201632 | +++ | |
| NUCC-0201633 | + | |
| NUCC-0201634 | ++ | |
| NUCC-0201635 | + | |
| NUCC-0201636 | + | |
| NUCC-0201637 | + | |
| NUCC-0201638 | + | |
| NUCC-0201639 | + | |
| NUCC-0201640 | + | |
| NUCC-0201641 | + | |
| NUCC-0201642 | + | |
| NUCC-0201643 | + | |
| NUCC-0201644 | + | |
| NUCC-0201646 | + | |
| NUCC-0201647 | + | |
| NUCC-0201648 | + | |
| NUCC-0201649 | + | |
| NUCC-0201651 | + | |
| NUCC-0201652 | + | |
| NUCC-0201653 | +++ | |
| NUCC-0201654 | + | |
| NUCC-0201655 | + | |
| NUCC-0201656 | + | |
| NUCC-0201657 | + | |
| NUCC-0201658 | ++ | |
| NUCC-0201659 | + | |
| NUCC-0201660 | + | |
| NUCC-0201661 | + | |
| NUCC-0201694 | + | |
| NUCC-0201695 | + | |
| NUCC-0201696 | ++ | |
| NUCC-0201697 | + | |
| NUCC-0201698 | + | |
| NUCC-0201699 | + | |
| NUCC-0201702 | + | |
| NUCC-0201703 | + | |
| NUCC-0201704 | + | |
| NUCC-0201705 | + | |
| NUCC-0201909 | + | |
| NUCC-0201910 | + | |
| NUCC-0201911 | + | |
| NUCC-0201912 | + | |
| NUCC-0201913 | + | |

TABLE 3

Biological Activity of Representative Compounds

| Molecule Name | MYCCAP IC50(uM)[a] | PC12 IC50 [b] | MLM % at 60 min[c] | Plasma Protein Binding (mouse) |
|---|---|---|---|---|
| NUCC-0176242 | 3.1 | 9.8 | | |
| NUCC-0176245 | 4.1 | | | |
| NUCC-0176248 | 3.4 | 7.8 | | |
| NUCC-0196283 | 2.3 | | | |
| NUCC-0196295 | 12.2 | | | |
| NUCC-0196312 | 4.8 | | | |
| NUCC-0196313 | 4.2 | | | |
| NUCC-0196342 | 3.5 | | 87.4 | |
| NUCC-0196344 | 6.6 | | | |
| NUCC-0196348 | 110.0 | | | |
| NUCC-0196350 | 4.3 | | | |
| NUCC-0196355 | 11.8 | | | |
| NUCC-0196357 | 6.9 | | | |
| NUCC-0196360 | 39.6 | | | |
| NUCC-0196361 | 3.8 | 30.7 | 72.9 | >99.9% |
| NUCC-0196362 | 4.0 | | | |
| NUCC-0196363 | 4.0 | | 88.6 | |
| NUCC-0198295 | 4.6 | | | |
| NUCC-0198309 | 4.0 | | 74 | |
| NUCC-0198318 | 4.3 | | | |
| NUCC-0198322 | 6.5 | | | |
| NUCC-0198359 | 7.6 | | | |
| NUCC-0198391 | 3.4 | | | |
| NUCC-0198394 | 7.3 | | | |
| NUCC-0198398 | 4.3 | | | |
| NUCC-0198399 | 2.5 | | 80.3 | |
| NUCC-0198406 | 17.5 | | | |
| NUCC-0198407 | 7.8 | | | |
| NUCC-0200558 | 49.3 | 31.0 | | |
| NUCC-0200739 | 2.2 | 19.4 | 46.4 | |
| NUCC-0200972 | 5.1 | 81.0 | 60.3 | >99.9% |
| NUCC-0200973 | 68.3 | 29.6 | | |
| NUCC-0200974 | 10.2 | | | |
| NUCC-0200975 | 6.1 | 38.4 | | |
| NUCC-0200976 | 3.9 | 63.3 | 21.8 | >99.9% |
| NUCC-0201032 | 1.0 | 11.0 | 30.5 | >99.9% |
| NUCC-0201038 | 6.8 | 18.3 | | |
| NUCC-0201039 | 13.6 | | | |
| NUCC-0201041 | 12.6 | 127.7 | | |
| NUCC-0201194 | 4.2 | 59.8 | | |
| NUCC-0201195 | 14.9 | 70.3 | | |
| NUCC-0201196 | 4.5 | | 66.6 | |
| NUCC-0201197 | 3.4 | 18.6 | | |
| NUCC-0201198 | 2.6 | 8.2 | | |
| NUCC-0201199 | 3.0 | 12.7 | | |
| NUCC-0201202 | 4.0 | 23.1 | | |
| NUCC-0201203 | 32.4 | | | |
| NUCC-0201204 | 23.0 | | | |
| NUCC-0201205 | 9.5 | 36.3 | | |
| NUCC-0201206 | 5.0 | | | |
| NUCC-0201207 | 5.7 | | 52.7 | |
| NUCC-0201209 | 4.4 | | 10.3 | |
| NUCC-0201212 | 23.7 | 30.8 | | |
| NUCC-0201219 | 9.5 | | | |
| NUCC-0201220 | 4.9 | 91.6 | | |
| NUCC-0201221 | 1.2 | | | |
| NUCC-0201223 | 5.1 | 40.6 | 75.8 | |
| NUCC-0201224 | 1.1 | 11.6 | | |
| NUCC-0201225 | 19.0 | 82.6 | | |
| NUCC-0201227 | 4.5 | 1.0 | | |
| NUCC-0201630 | 15.4 | 42.3 | | |
| NUCC-0201633 | 4.6 | 27.3 | | |
| NUCC-0201656 | 5.5 | 18.0 | | |
| NUCC-0201699 | 24.3 | | | |

[a] Cell viability of MycCap cells
[b] Cell viability of PC12 cells
[c] % remaining of compound after 60 min treatment with mouse liver microsomes

REFERENCES

[1] Huang M, Weiss W A. 2013. Neuroblastoma and MYNC. Cold Spring Harb Perspect Med 3: a014415.

[2] Roussel M F, Robinson G W. 2013. Role of MYC in medulloblastoma. Cold Spring Harb Perspect Med 3: a014308.

[3] Gabay M, Li Y, Felsher D W. 2014. MYC activation is a hall mark of cancer initiation and maintenance. Cold Spring Harb Perspect Med doi: 10.1101/cshperspect.a014241.

[4] Schmitz R, Ceribelli M, et. al. 2014. Oncogenic mechanisms in Burkitt lymphoma. Cold Spring Harb Perspect Med 4: a014282.

[5] Michael R. McKeown and James E. Bradner, Cold Spring Harb Perspect Med 2014; 4:a014266
[6] Soucek L, Whitfield J R, et. al. 2013. Inhibition of MYC family proteins eradicates KRas-driven lung cancer in mice. Genes Dev 27: 504-513.
[7] S. Fletcher, E. V. Prochownik, Small-molecule inhibitors of the MYC oncoprotein, Biochim. Biophys. Acta (2014).

Example 2—Biological Assays

Figure 11:
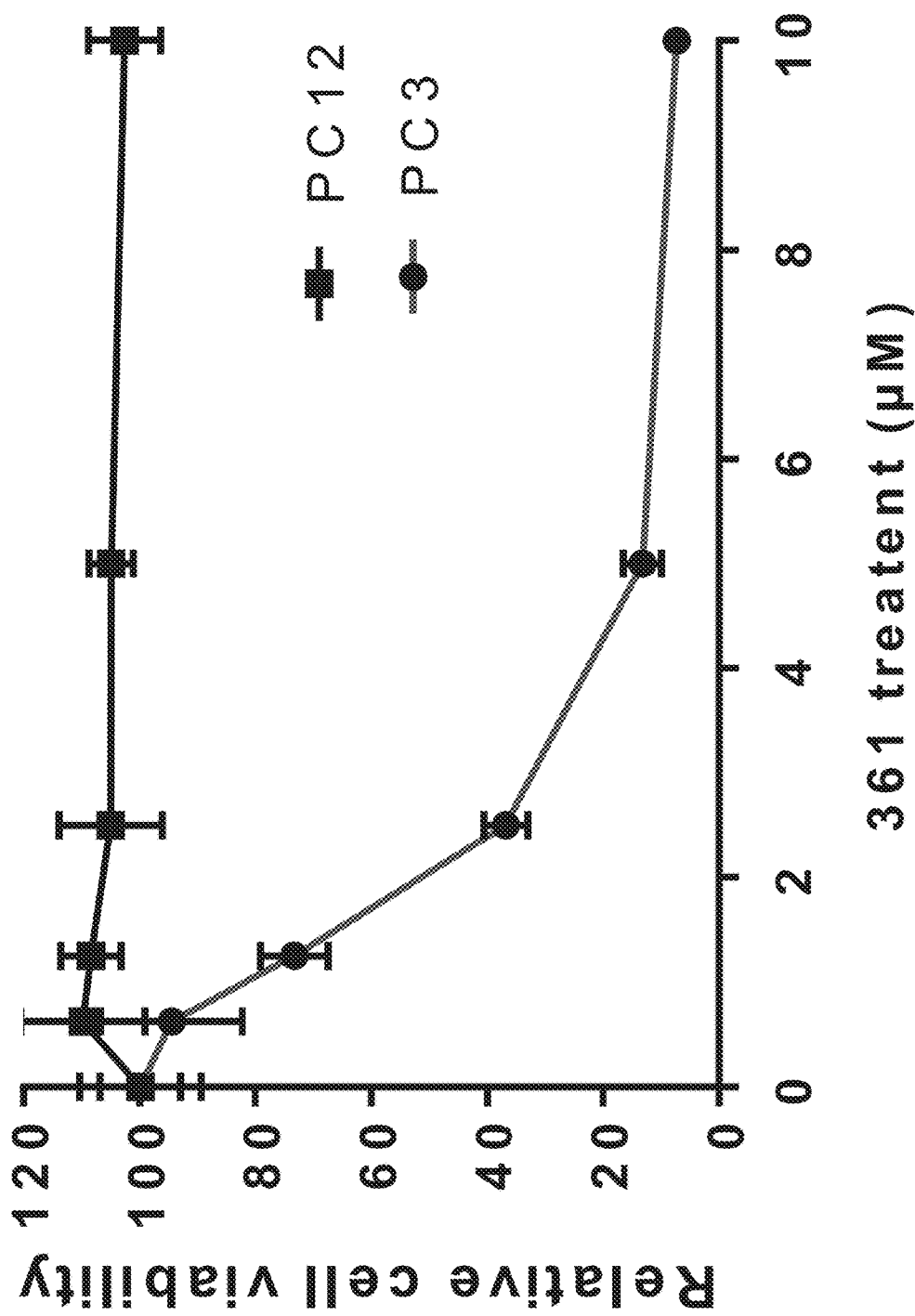
FIG. 11. Myc inhibitor 361 specifically inhibits proliferation of Myc dependent cell line PC3, but not Myc independent cell line PC12.

Proliferation Assay (FIG. 11).

PC3 prostate cancer cell line with high Myc level and PC12 pheochromocytoma tumor cell line with non functional Max protein, which is not dependent on Myc-Max complex, were phased from ATCC. Cells were plated in 96 well plate at 1000 cells per well, and Myc inhibitor 361 at various concentrations was added to the cells next day. After 3 days of treatment, fresh medium with 361 were added again, and cell viability was measured by MTS assay at day 5 after the treatment. (See FIG. 11).

Figure 12:
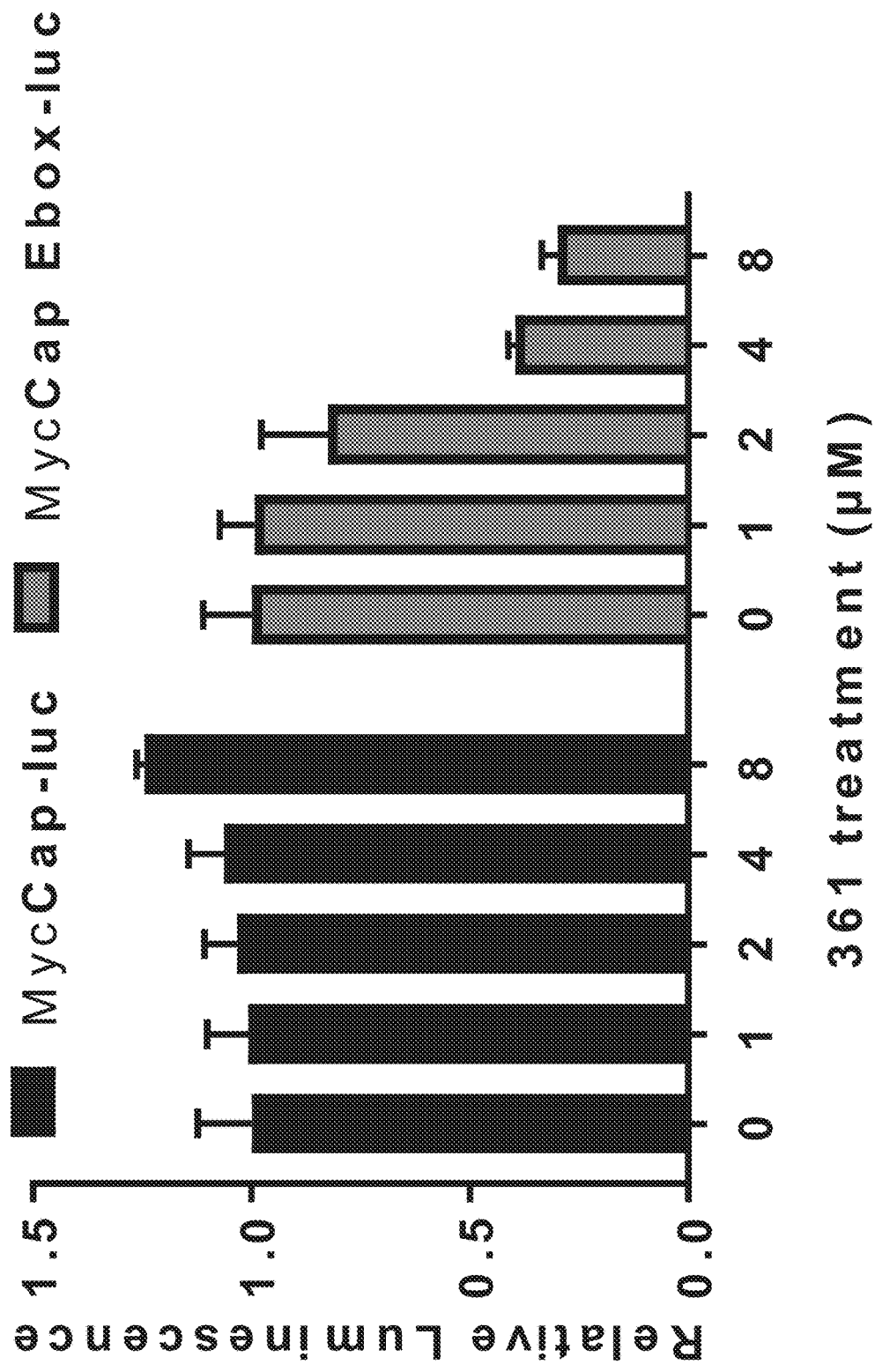
FIG. 12. Myc inhibitor 361 inhibits c-Myc transcription activity as an early event before affecting cell viability.

Myc Ebox Luciferase Reporter Assay (FIG. 12).

MycCap cells stably expressing luciferase with CMV promoter (MycCap-luc) or c-Myc E-box-luciferase reporter (MycCap Ebox-luc) were plated at 10000 cells per well in 96 well white-wall plate. Serial dilutions of 361 were treated next day. At 4 hours of treatment, luminescence signal was determined immediately after adding 150 µg/ml of Luciferin to the well. (See FIG. 12).

Figure 13:
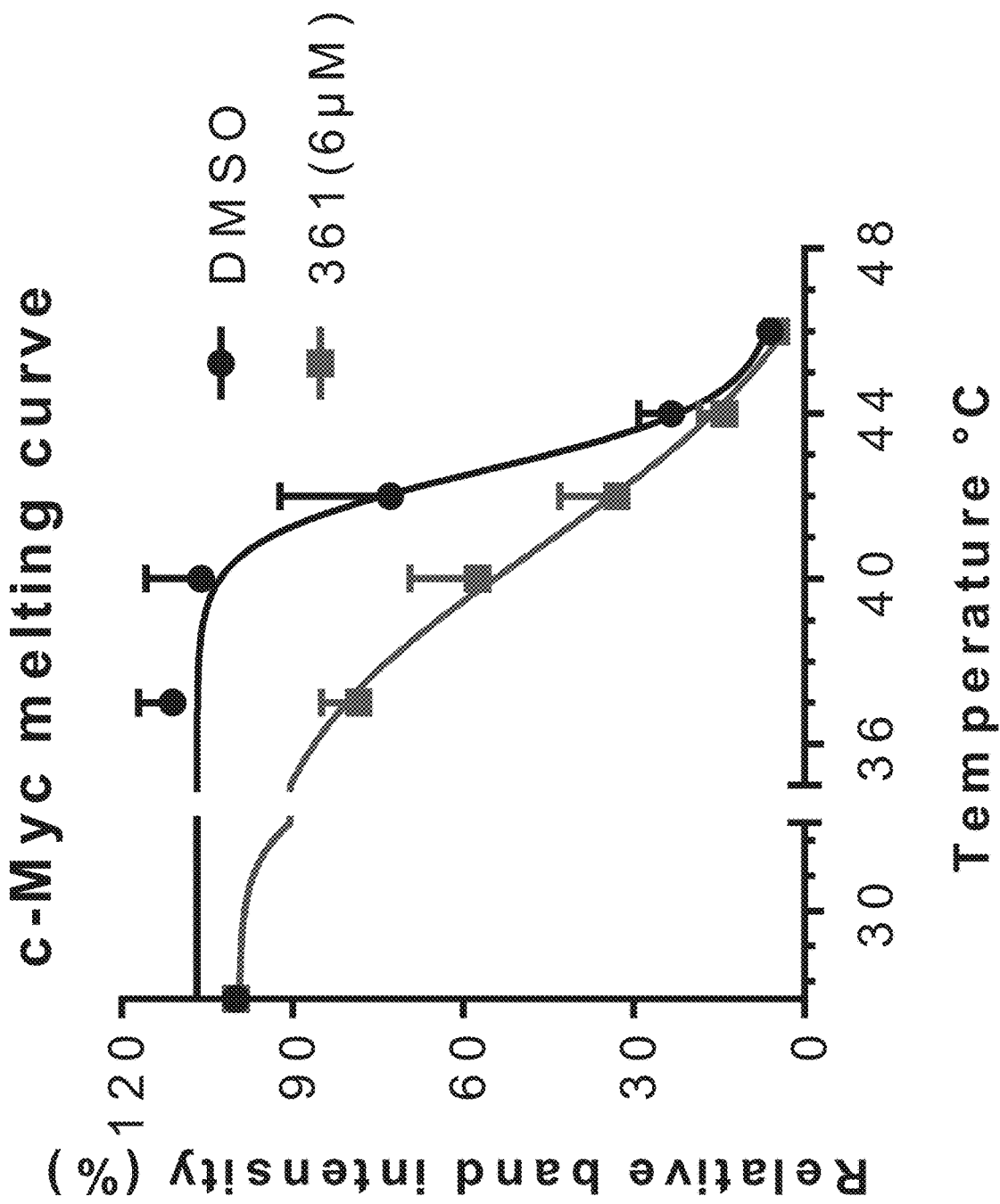
FIG. 13. Myc inhibitor 361 inhibits c-Myc transcription activity as an early event before affecting cell viability.

Cellular Thermal Shift Assay (CETSA) (FIG. 13).

PC3 cells with 70 to 80% confluence in 15 cm culture dish were treated with 6 µM of 361 or vehicle (DMSO) for 30 min. Cells were harvested and washed once with PBS, then suspended in 1 mL of PBS supplemented with proteinase and phosphatase inhibitors. The PBS contained 6 µM of 361 or vehicle (DMSO) accordingly at this step. The cell suspension was distributed into seven to ten 0.2-ml PCR tubes with 1000 volume (about 1 million cells) and each tube was designated a temperature point. Samples were heated at their designated temperatures for 2 min in AB 96-well thermal cycler. Immediately after heating, remove and incubate the tubes at room temperature for 3 min. After this 3 min incubation, immediately snap-freeze in liquid nitrogen, and stored at −80 C°. To lysis cells, three freeze and thaw cycles in LN was performed. The tubes are vortexed briefly after each thawing. Cell lysis was collected and cell debris together with precipitated and aggregated proteins were removed by centrifuging samples at 20,000 g for 20 min at 4° C. Cell lysis samples were boiled for 5 min at 90° C. after adding loading buffer, and ready for Western Blot analysis. c-Myc antibody is from Abcam (Ab32072). Data was generated from three independent experiments, and c-Myc protein intensity was quantified through Image1. (See FIG. 13).

Figure 14:
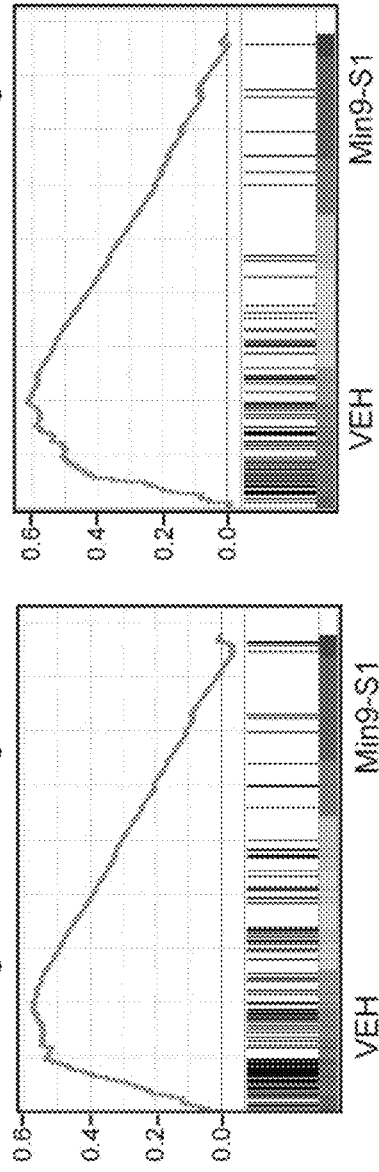
FIG. 14. MYC inhibitor Min9-S1 impairs MYC transcriptional program.
Figure 14:
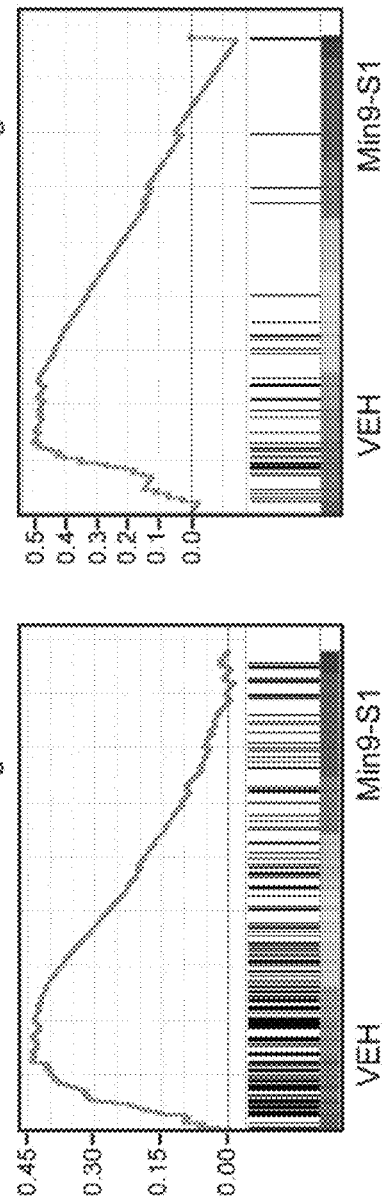
Figure 14:
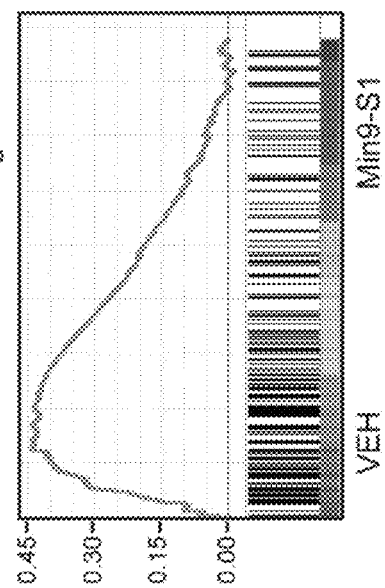

Gene Expression Profiling Analysis (FIG. 14).

PC3 cells were treated with 10 µM of Min9-S1 for 24 hours. mRNA was extracted using RNAeasy Plus mini kit(Qiagen, Cat. 74134). The gene expression profiling was analyzed using HTA 2.0 from Affymetrix. GSEA of four Myc-dependent gene signature sets (Zeller et al., 2003; Schuhmacher et al., 2001; Kim et al., 2006; Schlosser et al., 2005) in transcriptional profiles of PC3 treated with Min9-S1 or vehicle (VEH) shows strong correlation with down-regulation of expression by Min9-S1 treatment. Gene sets suppressed in Min9-S1 treated PC3 cells including the number of genes in each set (n), the normalized enrichment score (NES), and test of statistical significance (FDR q value) were listed in the table. (See FIG. 14).

Figure 15:
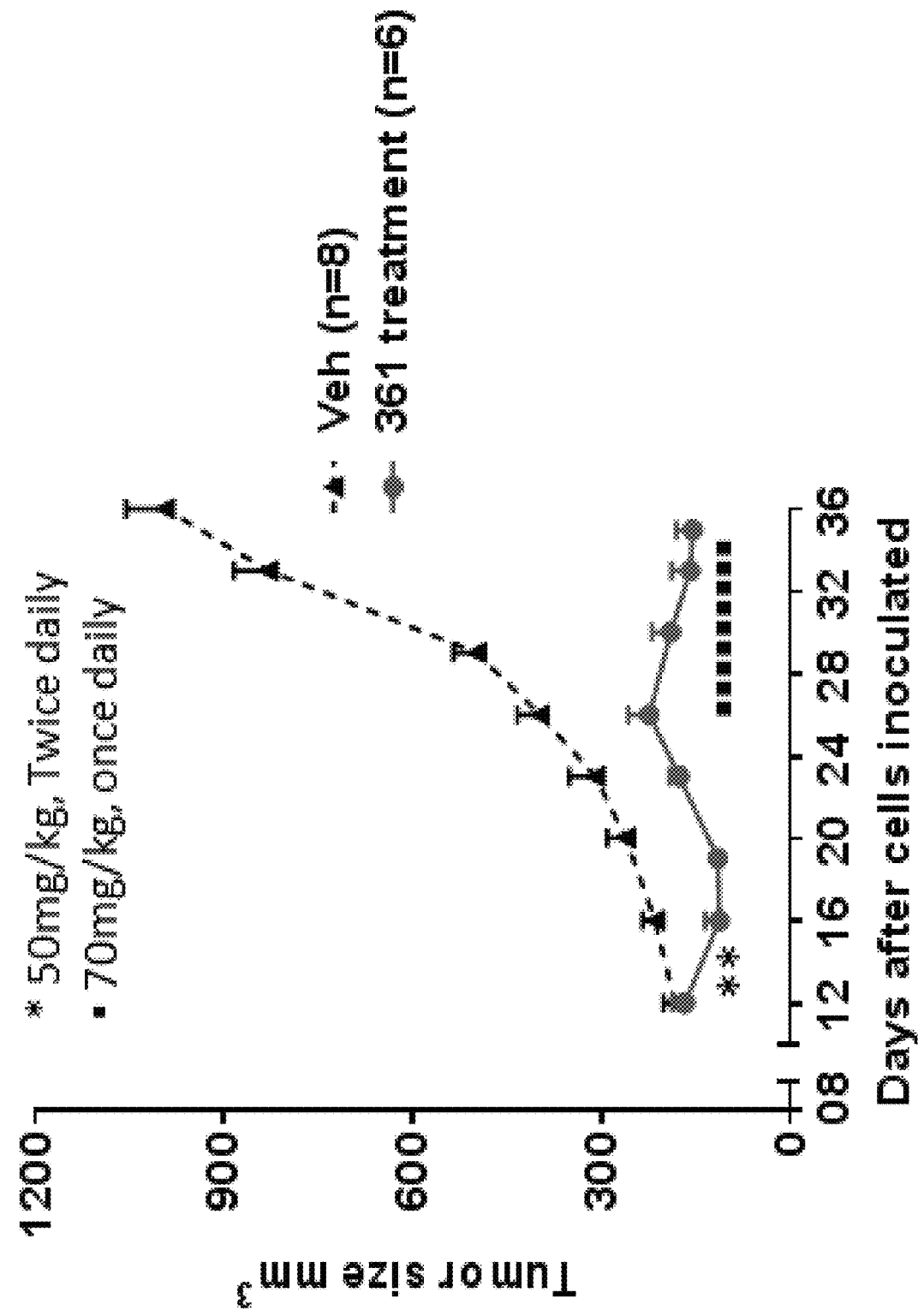
FIG. 15. Myc inhibitor 361 reduces tumor volume in a mouse prostate cancer allograft model.

MycCap FVB Allograft Model (FIG. 15).

FVB mice were inoculated with $1\times10^6$ of MycCap cells in 100 ul of matrigel subcutaneously on both flanks of the mice. When tumor size reached average size of 150 mm$^3$, mice were randomized based on tumor volume to 2 groups. Mice were administered with 50 mg/kg of 361 or vehicle (Veh) twice daily intra-peritoneally for two days. The treatment was suspended for 10 day, and initiated the treatment with a lower dose 70 mg/kg daily for another 9 days. Tumor size was measured twice a week during the experiment. (See FIG. 15).

Figure 16:
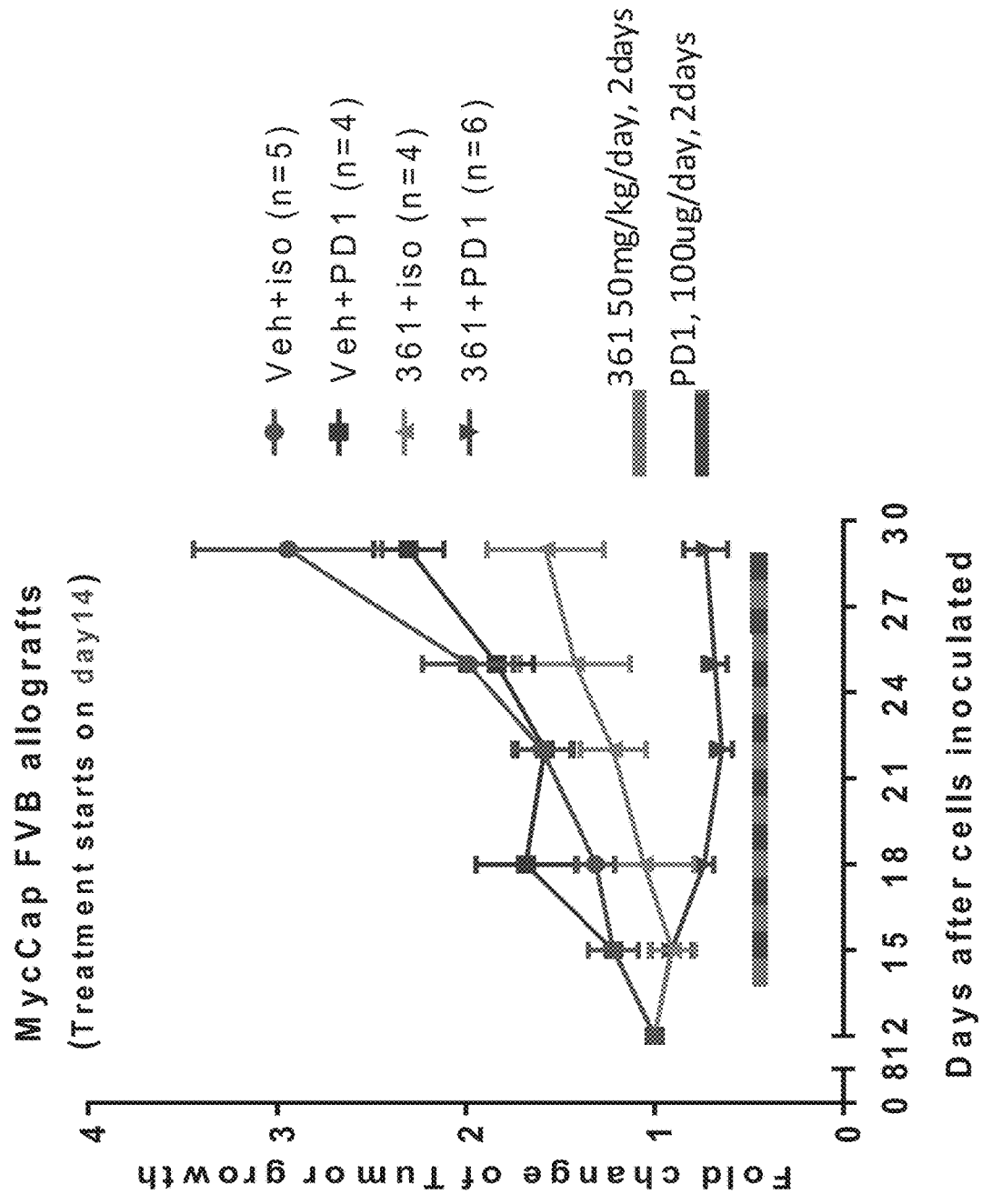
FIG. 16. Myc inhibitor 361 combination with Immunotherapy significantly blocks tumor progression.

Myc Inhibitor 361 Combination with Immunotherapy (FIG. 16).

MycCap FVB allograft model was treated with 361 (50 mg/kg) for two days, following by two days of anti-PD-1 antibody (100 ug/day), and kept this 4-day treatment cycle for 4 cycles. (See FIG. 16).

Figure 17:
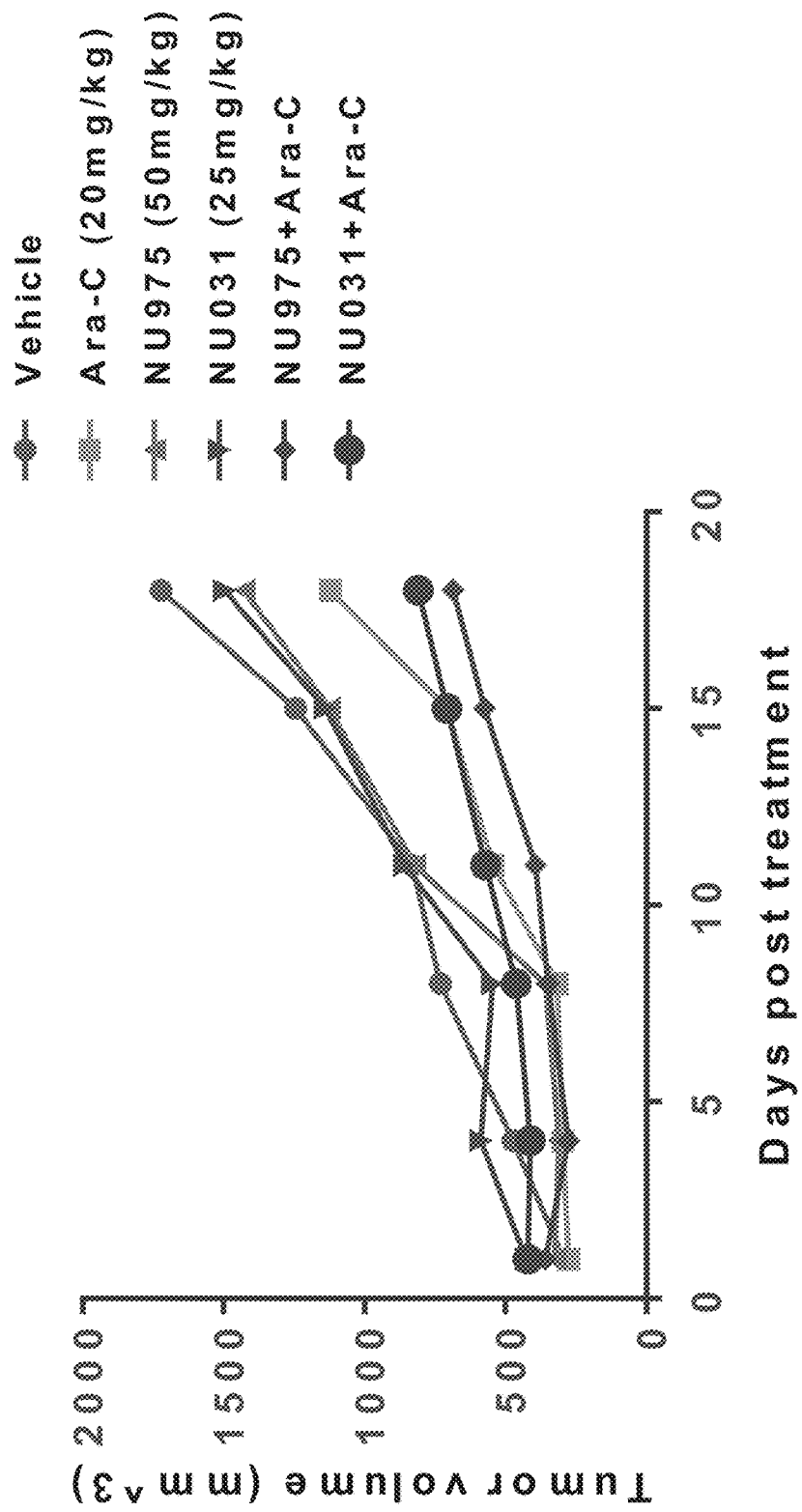
FIG. 17. Myc inhibitor 975 and 031 shows significant synergic anti-tumor effect with Ara-C in a AML mice xenograft model.

Myc Inhibitor Combination Treatment with Ara-C in AML Xenograft Model (FIG. 17).

CB17 SCID mice were inoculated with MV411 cells at the density of $5\times10^6$ suspended in PBS and matrigel (1:1). The mice were randomized based on tumor volume into 6 different groups after the tumor reached ~200 to 500 mm$^3$. The mice were treated either with vehicle, NU031, NU975 alone or in combination with cytarabine (Ara-C). The combination treatment shows significant difference compared to control group. (See FIG. 17).

NCI60 Profiling—NCI 60 Cell One-Dose Screen

General Description.

As of early 2007 all compounds submitted to the NCI 60 Cell screen are tested initially at a single high dose (10-5 M) in the full NCI 60 cell panel. Only compounds which satisfy pre-determined threshold inhibition criteria in a minimum number of cell lines will progress to the full 5-dose assay. The threshold inhibition criteria for progression to the 5-dose screen was selected to efficiently capture compounds with anti-proliferative activity based on careful analysis of historical DTP screening data. The threshold criteria may be updated as additional data becomes available.

Interpretation of One-Dose Data.

The One-dose data will be reported as a mean graph of the percent growth of treated cells and will be similar in appearance to mean graphs from the 5-dose assay. The number reported for the One-dose assay is growth relative to the no-drug control, and relative to the time zero number of cells. This allows detection of both growth inhibition (values between 0 and 100) and lethality (values less than 0). This is the same as for the 5-dose assay, described below. For example, a value of 100 means no growth inhibition. A value of 40 would mean 60% growth inhibition. A value of 0 means no net growth over the course of the experiment. A value of −40 would mean 40% lethality. A value of −100 means all cells are dead. Information from the One-dose mean graph is available for COMPARE analysis.

Figure 18:
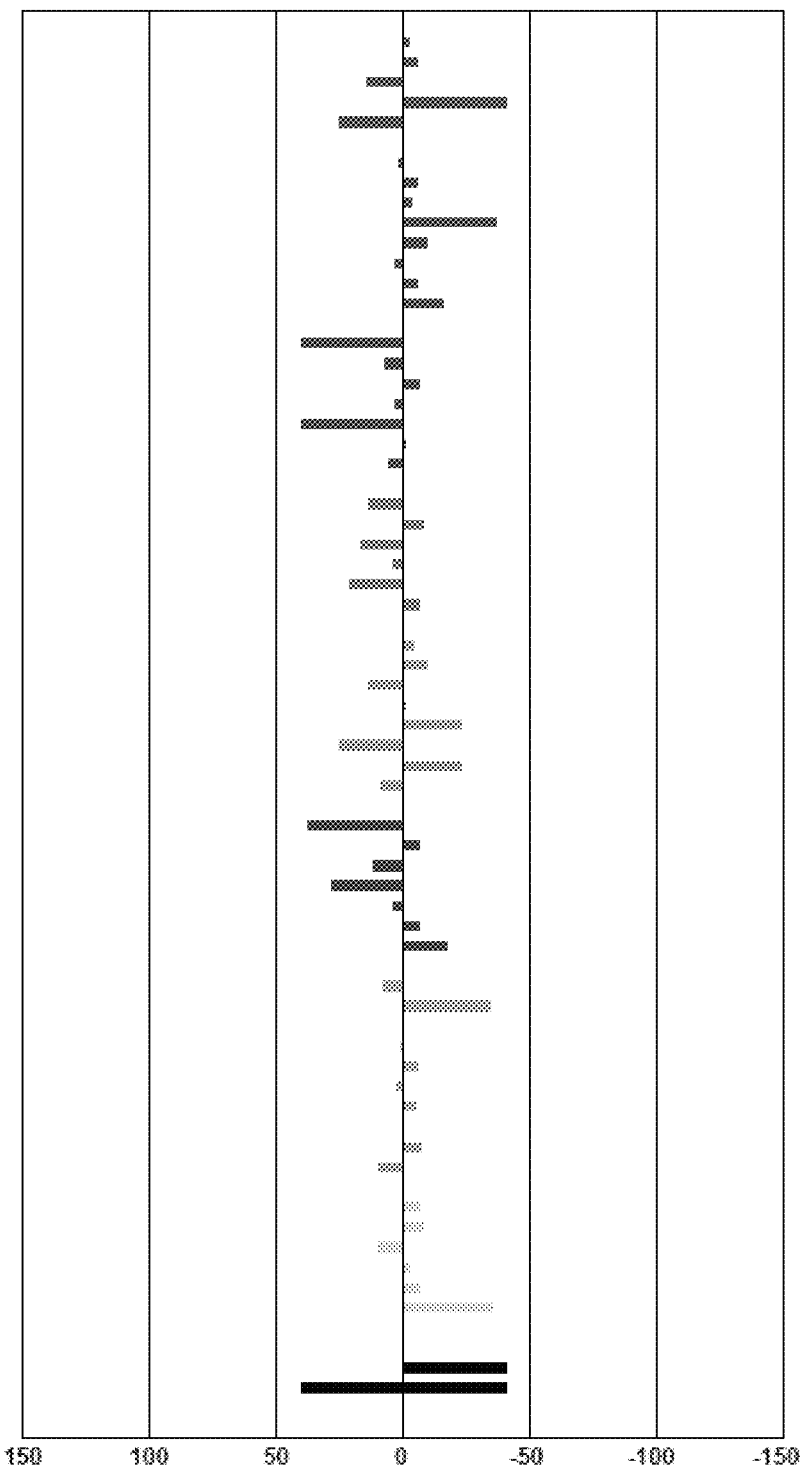
FIG. 18. NCI60 profiling of compound 201195 at a single concentration of 10 uM. The panel/cell line, in order from top to bottom, includes: leukemia (CCRF-CEM, HL-60 (TB), MOLT-4, RPMI-8226, SR), non-small cell lung cancer (A549/ATCC, EKVX. HOP-62, HOP-92, NCI-H23, NCI-H322M, NCI-H460, NCI-H522), colon cancer (COLO 205, HCC-2998, HCT-116, HCT-15, HT29, KM12, SW-620), CNS cancer (SF-268, SF-295, SF-539, SNB-19, SNB-75, U251), melanoma (LOX IMVI, MALME-3M, M14, MDA-MB-435, SK-MEL-2, SK-MEL-28, UACC-257, UACC-62), ovarian cancer (IGROV1, OVCAR-3, OVCAR-4, OVCAR-5, OVCAR-8, NCI/ADR-RES, SK-OV-3), renal cancer (786-0, A498, ACHN, CAKI-1, SN12C, TK-10, UO-31), prostate cancer (PC-3, DU-145), breast cancer (MCF7, MDA-MB-231/ATCC, HS 578T, BT-549, T-47D, MDA-MB-468). The bottom bars additionally correspond to mean, delta, and range. The growth percent values can be found in Table 4.
Figure 19:
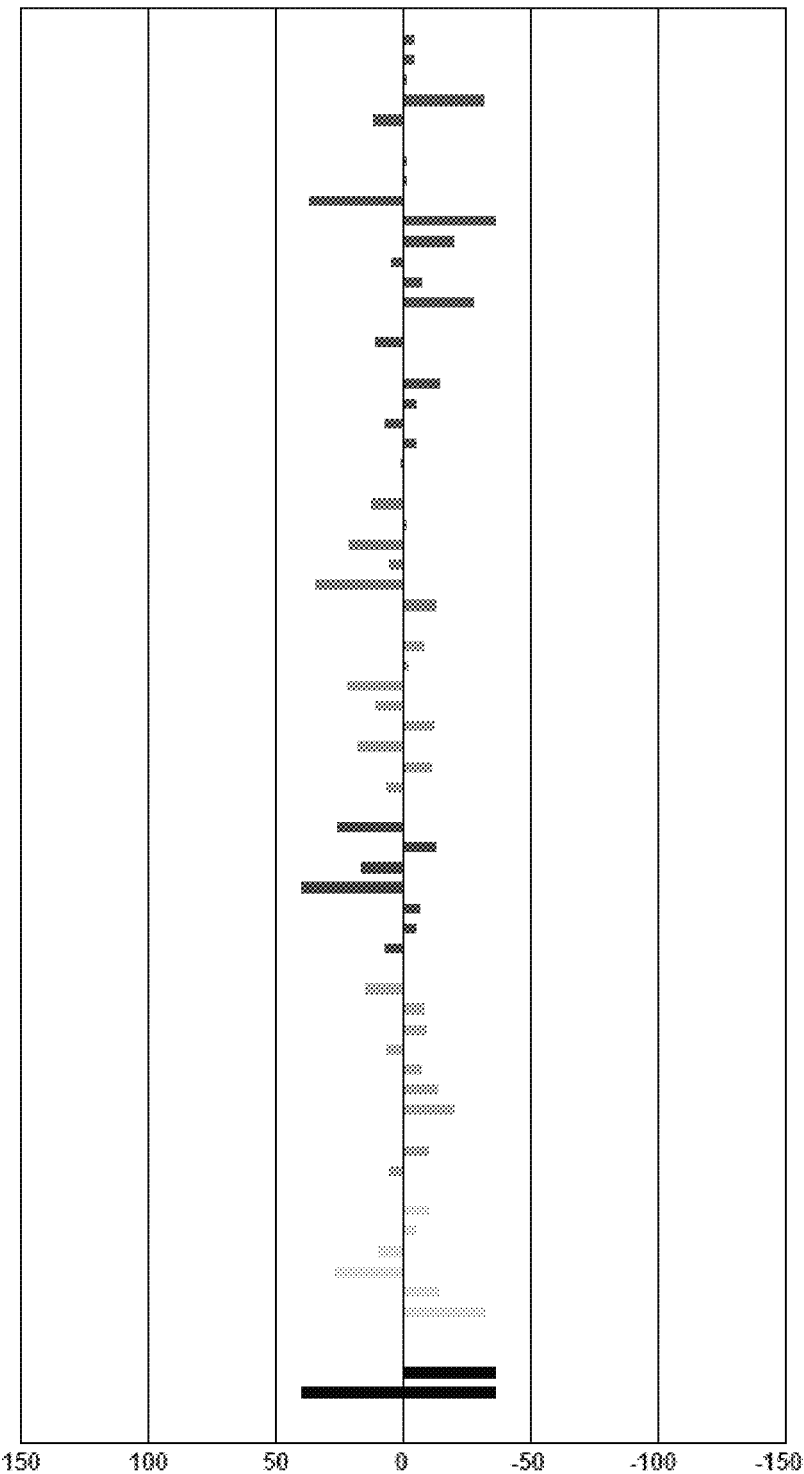
FIG. 19. NCI60 profiling of compound 200975 at a single concentration of 10 uM. The panel/cell line, in order from top to bottom, includes: leukemia (CCRF-CEM, HL-60 (TB), MOLT-4, RPMI-8226, SR), non-small cell lung cancer (A549/ATCC, EKVX, HOP-62, HOP-92, NCI-H23, NCI-H322M, NCI-H460, NCI-H522), colon cancer (COLO 205, HCC-2998, HCT-116, HCT-15, HT29, KM12, SW-620), CNS cancer (SF-268, SF-295,SF-539, SNB-19, SNB-75, U251), melanoma (LOX IMVI, MALME-3M, M14, MDA-MB-435, SK-MEL-2, SK-MEL-28, UACC-257, UACC-62), ovarian cancer (IGROV1, OVCAR-3, OVCAR-4, OVCAR-5, OVCAR-8, NCI/ADR-RES, SK-OV-3), renal cancer (786-0,A498, ACHN, CAKI-1, SN12C, TK-10, UO-31), prostate cancer (PC-3, DU-145), breast cancer (MCF7, MDA-MB-231/ATCC, HS 578T, BT-549, T-47D, MDA-MB-468). The bottom bars additionally correspond to mean, delta, and range. The growth percent values can be found in Table 5.
Figure 20:
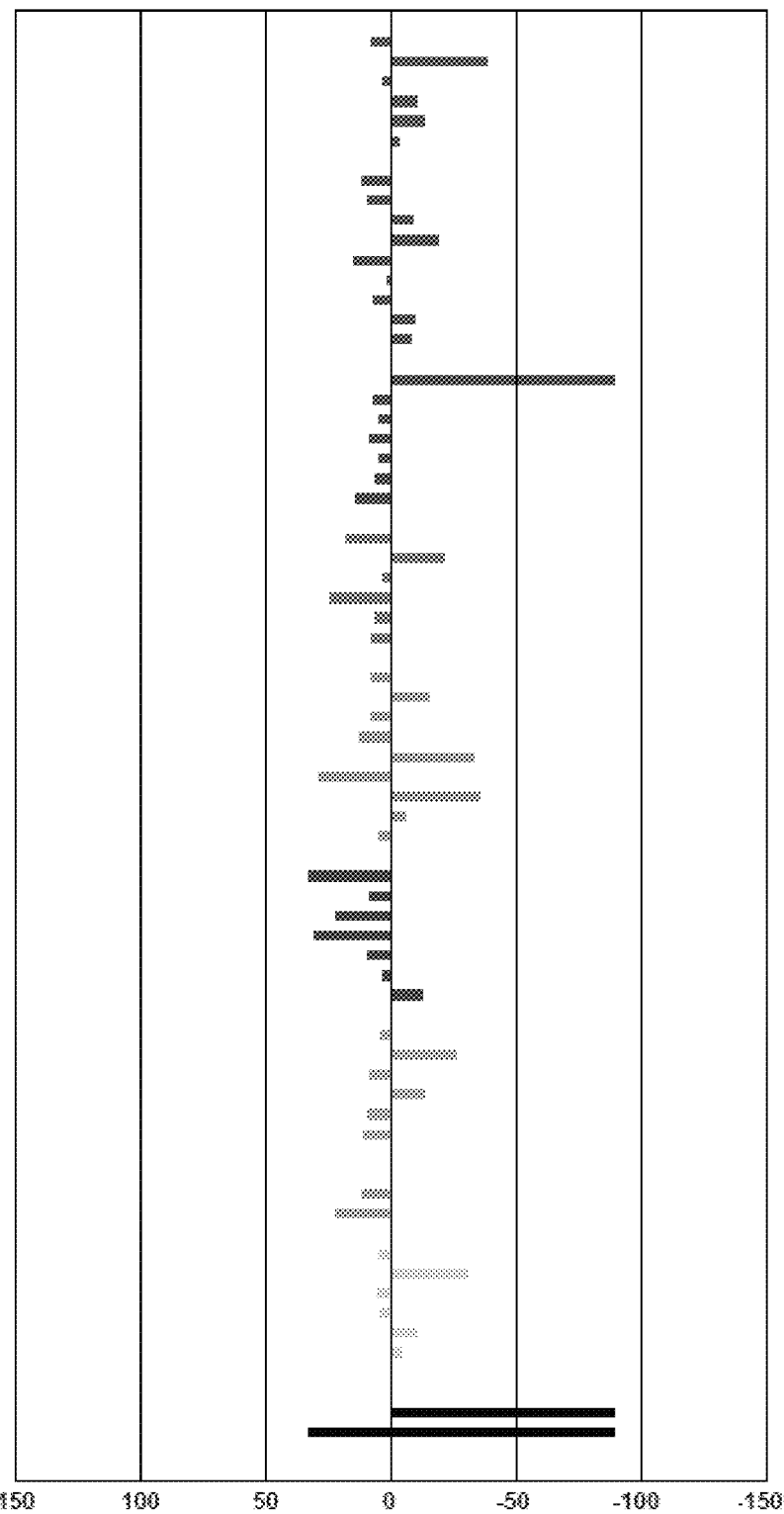
FIG. 20. NCI60 profiling of compound 196361 at a single concentration of 10 uM. The panel/cell line, in order from top to bottom, includes: leukemia (CCRF-CEM, HL-60 (TB), MOLT-4, RPMI-8226, SR), non-small cell lung cancer (A549/ATCC, EKVX. HOP-62, HOP-92, NCI-H23, NCI-H322M, NCI-H460, NCI-H522), colon cancer (COLO 205, HCC-2998, HCT-116, HCT-15, HT29, KM12, SW-620), CNS cancer (SF-268, SF-295,SF-539, SNB-19, SNB-75, U251), melanoma (LOX IMVI, MALME-3M, M14, MDA-MB-435, SK-MEL-2, SK-MEL-28, UACC-257, UACC-62), ovarian cancer (IGROV1, OVCAR-3, OVCAR-4, OVCAR-5, OVCAR-8, NCI/ADR-RES, SK-OV-3), renal cancer (786-0,A498, ACHN, CAKI-1, SN12C, TK-10, UO-31), prostate cancer (PC-3, DU-145), breast cancer (MCF7, MDA-MB-231/ATCC, HS 578T, BT-549, T-47D, MDA-MB-468). The bottom bars additionally correspond to mean, delta, and range. The growth percent values can be found in Table 6.

NCI 60 Cell Five-Dose Screen (FIG. 18, FIG. 19, and FIG. 20; and Tables 4-6).

Compounds which exhibit significant growth inhibition in the One-Dose Screen are evaluated against the 60 cell panel at five concentration levels.

TABLE 4

Developmental Therapeutics Program
One Dose Mean Graph (See FIG. 18)

NSC: D-804956/1  
Conc: 1.00E-5 Molar  
Experiment ID: 18OS064  
Test Date: May 21, 2018  
Report Date: Aug. 22, 2018

| Panel/Cell Line | Growth Percent |
|---|---|
| Leukemia | |
| CCRF-CEM | 6.67 |
| HL-60(TB) | 3.64 |
| MOLT-4 | 22.96 |
| RPMI-8226 | −31.83 |
| SR | 33.69 |
| Non-Small Cell Lung Cancer | |
| A549/ATCC | 10.39 |
| EKVX | 3.52 |
| HOP-62 | 5.79 |
| HOP-92 | −27.95 |
| NCI-H23 | −0.16 |
| NCI-H322M | 12.44 |
| NCI-H460 | 3.48 |
| NCI-H522 | −6.89 |
| Colon Cancer | |
| COLO 205 | 49.05 |
| HCC-2998 | 16.23 |
| HCT-116 | 2.41 |
| HCT-15 | 11.96 |
| HT29 | 48.91 |
| KM12 | 7.94 |
| SW-620 | 14.25 |
| CNS Cancer | |
| SF-268 | 21.93 |
| SF-295 | 0.83 |
| SF-539 | 25.17 |
| SNB-19 | 13.09 |
| SNB-75 | 30.14 |
| U251 | 2.85 |
| Melanoma | |
| LOX IMVI | 5.15 |
| MALME-3M | −0.80 |
| M14 | 22.46 |
| MDA-MB-435 | 7.91 |
| SK-MEL-2 | −13.82 |
| SK-MEL-28 | 33.67 |
| UACC-257 | −14.05 |
| UACC-62 | 17.46 |
| Ovarian Cancer | |
| IGROV1 | 46.89 |
| OVCAR-3 | 2.95 |
| OVCAR-4 | 20.48 |
| OVCAR-5 | 36.89 |
| OVCAR-8 | 12.48 |
| NCI/ADR-RES | 2.45 |
| SK-OV-3 | −7.94 |
| Renal Cancer | |
| 786-0 | 17.07 |
| A498 | −25.54 |
| ACHN | 8.84 |
| CAKI-1 | 9.47 |
| SN12C | 3.81 |
| TK-10 | 11.38 |
| UO-31 | 3.89 |
| Prostate Cancer | |
| PC-3 | 1.74 |
| DU-145 | 17.95 |
| Breast Cancer | |
| MCF7 | 2.95 |
| MDA-MB-231/ATCC | 1.43 |
| HS 578T | 17.96 |
| BT-549 | 6.56 |
| T-47D | 2.83 |
| MDA-MB-468 | −26.3 |
| Mean | 9.05 |
| Delta | 40.88 |
| Range | 80.88 |

TABLE 5

Developmental Therapeutics Program
One Dose Mean Graph (See FIG. 19)

NSC: D-804955/1  
Conc: 1.00E-5 Molar  
Experiment ID: 18050S64  
Test Date: May 21, 2018  
Report Date: Aug. 22, 2018

| Panel/Cell Line | Growth Percent |
|---|---|
| Leukemia | |
| CCRF-CEM | 9.89 |
| HL-60(TB) | 9.30 |
| MOLT-4 | 12.26 |
| RPMI-B226 | −17.88 |
| SR | 25.07 |
| Non-Small Cell Lung Cancer | |
| A549/ATCC | 12.83 |
| EKVX | 12.77 |
| HOP-62 | 50.48 |
| HOP-92 | −22.43 |
| NCI-H23 | −6.46 |
| NCI-H322M | 18.15 |
| NCI-H460 | 6.25 |
| NCI-H522 | −13.66 |
| Colon Cancer | |
| COLO 205 | 24.55 |
| HCC-2998 | 13.50 |
| HCT-116 | −0.40 |
| HCT-15 | 8.53 |
| HT29 | 20.44 |
| KM12 | 8.83 |
| SW-620 | 13.94 |
| CNS Cancer | |
| SF-268 | 26.01 |
| SF-295 | 12.82 |
| SF-539 | 34.37 |
| SNB-19 | 19.21 |
| SNB-75 | 47.69 |
| U251 | 0.82 |
| Melanoma | |
| LOX IMVI | 5.24 |
| MALME-3M | 12.24 |
| M14 | 35.38 |
| MDA-MB-435 | 24.66 |
| SK-MEL-2 | 1.95 |
| SK-MEL-28 | 31.16 |
| UACC-257 | 2.35 |
| UACC-62 | 19.68 |
| Ovarian Cancer | |
| IGROV1 | 38.95 |
| OVCAR-3 | 1.24 |

TABLE 5-continued

Developmental Therapeutics Program
One Dose Mean Graph (See FIG. 19)

NSC: D-804955/1　　Conc: 1.00E-5 Molar　　Test Date: May 21, 2018
Experiment ID: 18050S64　　Report Date: Aug. 22, 2018

| Panel/Cell Line | Growth Percent |
|---|---|
| OVGAR-4 | 30.19 |
| OVCAR-5 | 53.43 |
| OVCAR-8 | 7.41 |
| NCI/ADR-RES | 8.38 |
| SK-OV-3 | 20.62 |
| Renal Cancer | |
| 786-0 | 28.42 |
| A498 | 5.29 |
| ACHN | 5.21 |
| CAKI-1 | 19.80 |
| SN12C | 6.24 |
| TK-10 | 0.36 |
| UO-31 | −6.34 |
| Prostate Cancer | |
| PC-3 | 3.78 |
| DU-145 | 19.03 |
| Breast Cancer | |
| MCF7 | 4.01 |
| MDA-MB-231/ATCC | 8.70 |
| HS 578T | 22.83 |
| BT-549 | 39.82 |
| T-47D | −0.38 |
| MDA-MB-468 | −18.75 |
| Mean | 13.53 |
| Delta | 35.96 |
| Range | 75.86 |

TABLE 6

Developmental Therapeutics Program
One Dose Mean Graph (See FIG. 20)

NSC: D-795899/1　　Conc: 1.00E-5 Molar　　Test Date: Feb. 21, 2017
Experiment ID: 1702OS60　　Report Date: Aug. 22, 2018

| Panel/Cell Line | Growth Percent |
|---|---|
| Leukemia | |
| CCRF-CEM | 6.82 |
| HL-60(TB | −39.89 |
| K-562 | 1.63 |
| MOLT-4 | −11.7 |
| RPMI-8226 | −14.54 |
| SR | −4.24 |
| Non-Small Cell Lung Cancer | |
| A549/ATCC | 10.52 |
| EKVX | 7.70 |
| HOP-62 | −9.87 |
| HOP-92 | −20.08 |
| NCI-H226 | 13.90 |
| NCI-H23 | 0.56 |
| NCI-H322M | 5.67 |
| NCI-460 | −10.44 |
| NCI-H522 | −9.19 |
| Colon Cancer | |
| COLO 205 | −90.71 |
| HCC-2998 | 5.78 |
| HCT-116 | 3.65 |
| HCT-15 | 7.50 |
| HT29 | 3.77 |
| KM12 | 5.04 |
| SW-620 | 13.14 |
| CNS Cancer | |
| SF-268 | 16.59 |
| SF-295 | −22.60 |
| SF-539 | 2.13 |
| SNB-19 | 22.58 |
| SNB-75 | 4.92 |
| U251 | 6.17 |
| Melanoma | |
| LOX IMVI | 6.23 |
| MALME-3M | −15.91 |
| M14 | 6.30 |
| MDA-MB-435 | 11.38 |
| SK-MEL-2 | −33.97 |
| SK-MEL-28 | 28.00 |
| SK-MIEL-5 | −36.59 |
| UACC-257 | −7.16 |
| UACC-62 | 3.02 |
| Ovarian Cancer | |
| IGROV1 | 31.40 |
| OVCAR-3 | 7.02 |
| OVCAR-4 | 20.71 |
| OVCAR-5 | 29.10 |
| OVCAR-8 | 8.36 |
| NCI/ADR-RES | 1.98 |
| SK-OV-3 | −13.54 |
| Renal Cancer | |
| 786-0 | 2.41 |
| A498 | −26.88 |
| ACHN | 7.22 |
| RXF 393 | −14.51 |
| 5N12C | 7.93 |
| TK-10 | 9.29 |
| UO-31 | −1.27 |
| Prostate Cancer | |
| PC-3 | 10.73 |
| DU-145 | 20.58 |
| Breast Cancer | |
| MCF7 | 3.01 |
| MDA-MB-231/ATCC | −31.51 |
| HS 578T | 4.39 |
| BT-549 | 2.72 |
| T-47D | −11.64 |
| MDA-MB-468 | −5.00 |
| Mean | −1.21 |
| Delta | 89.50 |
| Range | 122.11 |

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Additional four, 10-fold or ½ log serial dilutions are made to provide a total of five drug concentrations plus control. Aliquots of 100 μl of these different drug dilutions are added to the appropriate microtiter wells already containing 100 μl of medium, resulting in the required final drug concentrations.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

[(Ti−Tz)/(C−Tz)]×100 for concentrations for which Ti>/=Tz

[(Ti−Tz)/Tz]×100 for concentrations for which Ti<Tz.

Three dose response parameters are calculated for each experimental agent. Growth inhibition of 50% (GI50) is calculated from [(Ti−Tz)/(C−Tz)]×100=50, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from [(Ti−Tz)/Tz]×100=−50. Values are calculated for each of these three parameters if the level of activity is reached; however, if the effect is not reached or is exceeded, the value for that parameter is expressed as greater or less than the maximum or minimum concentration tested. Results are shown in FIG. 18, FIG. 19, and FIG. 20.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. A compound having a formula I:

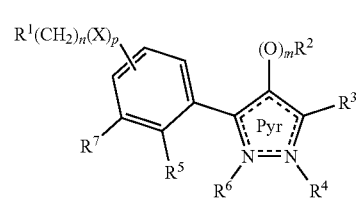

wherein
R$^1$ is hydrogen or R$^1$ is an alkyl group, an aryl group, a benzyl group, a heteroaryl group, a cycloalkyl group, a benzoyl group, or a cycloheteroalkyl group, optionally R$^1$ is substituted at one or more positions with one or more of alkyl, alkoxy, haloalkyl, haloalkoxy, aryl, heteroaryl, hydroxyl, halo, cyano, amido, hydrazonyl, carbonyl, carboxyl, —NH—C(O)—CH$_2$—(OCH$_2$)$_y$—N$_3$, —NH—C(O)-alkylene-alkynyl optionally substituted with azido, —O-alkylene-alkynyl,

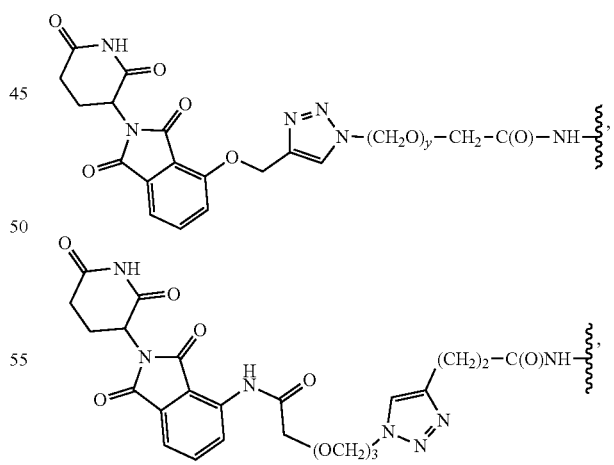

amino, nitro, and alkoxycarbonyl;
n is 0, 1, or 2;
p is 0 or 1;
X is O or NH, or R$^1$(CH$_2$)$_n$(X)$_p$— is N-piperazinyl optionally N-substituted with alkyl;
m is 0 or 1;
y is 3 or 4;

R² is hydrogen or halo, or R² is an alkyl group, an aryl group, a benzyl group, a heteroaryl group, a cycloalkyl group, or a cycloheteroalkyl group, optionally R² is substituted at one or more positions with one or more of alkyl, alkoxy, haloalkyl, haloalkoxy, hydroxyl, halo, cyano, amido, hydrazonyl, carbonyl, and carboxyl;

R³ is hydrogen, alkyl, alkoxy, haloalkyl, haloalkoxy, aryl, benzyl, hydroxyl, halo, amido, hydrazonyl, carbonyl, carboxyl, cyano, and alkoxycarbonyl;

R⁴ is not present, or R⁴ is hydrogen, amino, alkyl, or R⁴ is aryl or benzyl; R⁴ optionally is substituted at one or more positions with one or more of alkyl, alkoxy, haloalkyl, haloalkoxy, aryl (e.g., phenyl), hydroxyl, halo, cyano, amido, hydrazonyl, carbonyl, carboxyl, alkoxycarbonyl, aryloxy, and alkylaryloxy;

R⁵ is hydrogen, alkyl, alkoxy, haloalkyl, haloalkoxy, hydroxyl, cyano, amino, amido, —C(O)H, hydroxyalkyl, or halo;

R⁶ is not present, or R⁶ is hydrogen, amino, alkyl, or R⁶ is aryl or benzyl; R⁶ optionally is substituted at one or more positions with one or more of alkyl, alkoxy, haloalkyl, haloalkoxy, aryl, hydroxyl, halo, cyano, amido, hydrazonyl, carbonyl, carboxyl, alkoxycarbonyl, aryloxy, and alkylaryloxy, or R⁶ and R⁵ together form a ring structure having a formula

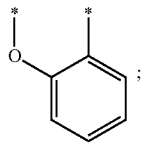

R⁷ is hydrogen or halo, or R⁷ is an alkyl group, an aryl group, a benzyl group, a 5-membered heteroaryl group containing one oxygen or sulfur, a 6-membered heteroaryl group containing one nitrogen, a cycloalkyl group, or a cycloheteroalkyl group, optionally R⁷ is substituted at one or more positions with one or more of alkyl, alkoxy, haloalkyl, haloalkoxy, hydroxyl, halo, cyano, amido, hydrazonyl, carbonyl, carboxyl, sulfonyl-alkyl, and alkoxycarbonyl;

with the proviso that at least one of R⁴ and R⁶ is present;

with the proviso that if R⁵ is hydrogen, then p is 1 and m is 1;

with the proviso that if R¹(CH₂)ₙ(X)ₚ— is hydrogen, hydroxyl, or alkyl, and R⁵ is hydroxyl, then m is 1, or at least one of R² and R³ is not hydrogen; and with the proviso that if (i) R¹(CH₂)ₙ(X)ₚ— and R⁵ are hydroxyl, (ii) R³, R⁴, and R⁷ are hydrogen, and (iii) m is 1, then R² is a substituted aryl.

2. The compound of claim 1, wherein at least one of R² and R⁷ is an aryl group, a benzyl group, a heteroaryl group, a cycloalkyl group, or a cycloheteroalkyl group, and R² optionally is substituted at one or more positions with one or more of alkyl, alkoxy, haloalkyl, haloalkoxy, hydroxyl, halo, cyano, amido, hydrazonyl, carbonyl, and carboxyl, and R⁷ optionally is substituted at one or more positions with one or more of alkyl, alkoxy, haloalkyl, haloalkoxy, hydroxyl, halo, cyano, amido, hydrazonyl, carbonyl, carboxyl, and alkoxycarbonyl.

3. The compound of claim 1, wherein m is 0 and R² is hydrogen; or wherein R⁷ is hydrogen.

4. The compound of claim 1, wherein R² is an aryl group, a benzyl group, a heteroaryl group, a cycloalkyl group, or a cycloheteroalkyl group, and R² optionally is substituted at one or more positions with one or more of alkyl, alkoxy, haloalkyl, haloalkoxy, hydroxyl, halo, cyano, amido, hydrazonyl, carbonyl, carboxyl; and wherein R⁷ is hydrogen.

5. The compound of claim 1, wherein m is 0 and R² is hydrogen; and wherein R⁷ is an aryl group, a benzyl group, a heteroaryl group, a cycloalkyl group, or a cycloheteroalkyl group, and R⁷ optionally is substituted at one or more positions with one or more of alkyl, alkoxy, haloalkyl, haloalkoxy, hydroxyl, halo, cyano, amido, hydrazonyl, carbonyl, carboxyl, and alkoxycarbonyl.

6. The compound of claim 1 having a formula I(i) or I(ii):

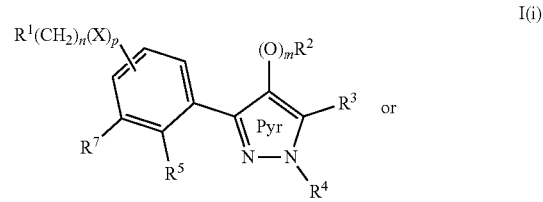

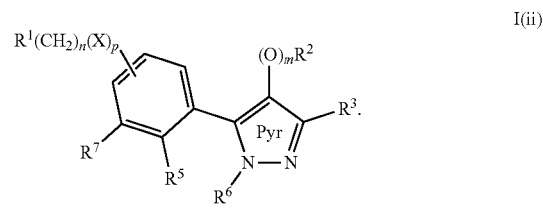

7. The compound of claim 1 having a formula selected from Ia(i), Ia(ii), Ib(i), Ib(ii), Ic(i), and Ic(ii):

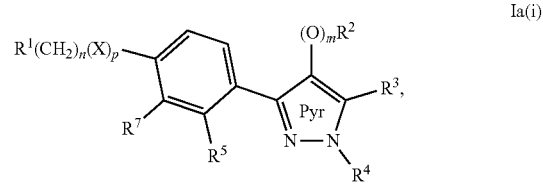

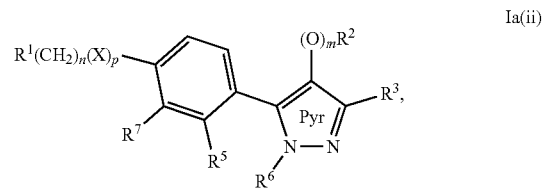

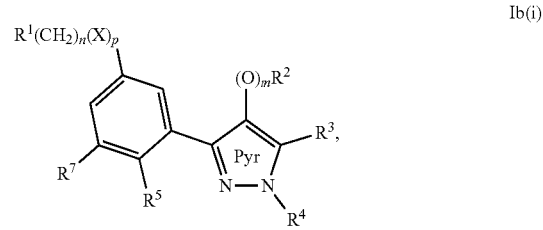

-continued

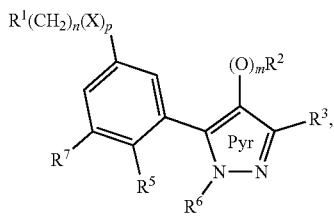

Ib(ii)

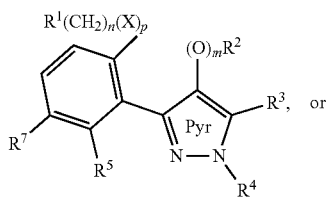

Ic(i)

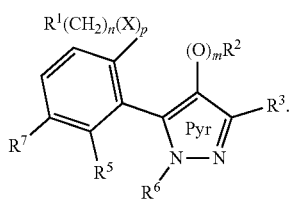

Ic(ii)

8. A pharmaceutical composition comprising a compound of claim 1 and a suitable pharmaceutical carrier, excipient, or diluent.

9. A method of treating cancer comprising administering the composition of claim 8 to a patient having cancer.

10. The compound of claim 1, wherein
R$^1$ is hydrogen or R$^1$ is an alkyl group, an aryl group, a benzyl group, a heteroaryl group, a cycloalkyl group, a benzoyl group, or a cycloheteroalkyl group, optionally R$^1$ is substituted at one or more positions with one or more of alkyl, alkoxy, haloalkyl, haloalkoxy, aryl, heteroaryl, hydroxyl, halo, cyano, amido, hydrazonyl, carbonyl, carboxyl, —NH—C(O)—CH$_2$—(OCH$_2$)$_y$—N$_3$, —NH—C(O)-alkylene-alkynyl optionally substituted with azido, —O-alkylene-alkynyl, amino, nitro, and alkoxycarbonyl.

11. The compound of claim 1, wherein R$^1$ is

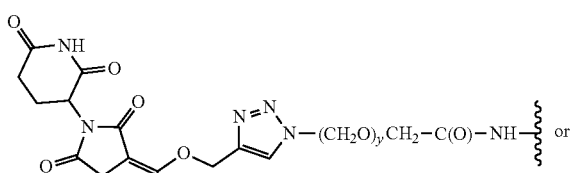 or

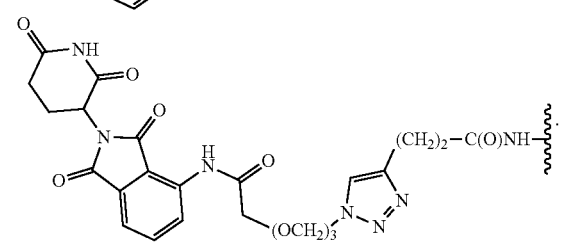

12. The method of claim 9, wherein at least one of R$^2$ and R$^7$ is an aryl group, a benzyl group, a heteroaryl group, a cycloalkyl group, or a cycloheteroalkyl group, and R$^2$ optionally is substituted at one or more positions with one or more of alkyl, alkoxy, haloalkyl, haloalkoxy, hydroxyl, halo, cyano, amido, hydrazonyl, carbonyl, and carboxyl, and R$^7$ optionally is substituted at one or more positions with one or more of alkyl, alkoxy, haloalkyl, haloalkoxy, hydroxyl, halo, cyano, amido, hydrazonyl, carbonyl, carboxyl, and alkoxycarbonyl.

13. The method of claim 9, wherein m is 0 and R$^2$ is hydrogen; or wherein R$^7$ is hydrogen.

14. The method of claim 9, wherein R$^2$ is an aryl group, a benzyl group, a heteroaryl group, a cycloalkyl group, or a cycloheteroalkyl group, and R$^2$ optionally is substituted at one or more positions with one or more of alkyl, alkoxy, haloalkyl, haloalkoxy, hydroxyl, halo, cyano, amido, hydrazonyl, carbonyl, carboxyl; and wherein R$^7$ is hydrogen.

15. The method of claim 9, wherein m is 0 and R$^2$ is hydrogen; and wherein R$^7$ is an aryl group, a benzyl group, a heteroaryl group, a cycloalkyl group, or a cycloheteroalkyl group, and R$^7$ optionally is substituted at one or more positions with one or more of alkyl, alkoxy, haloalkyl, haloalkoxy, hydroxyl, halo, cyano, amido, hydrazonyl, carbonyl, carboxyl, and alkoxycarbonyl.

16. The method of claim 9, wherein the compound has a formula I(i) or I(ii):

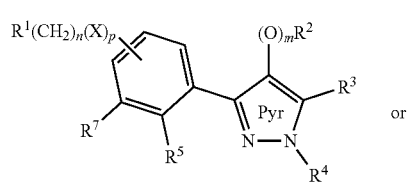

I(i)

or

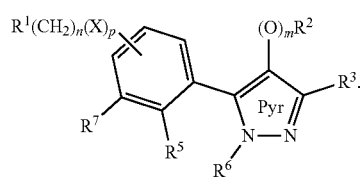

I(ii)

17. The method of claim 9, wherein the compound has a formula selected from Ia(i), Ia(ii), Ib(i), Ib(ii), Ic(i), and Ic(ii):

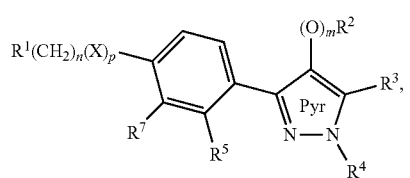

Ia(i)

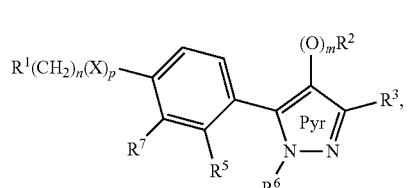

Ia(ii)

-continued

Ib(i) 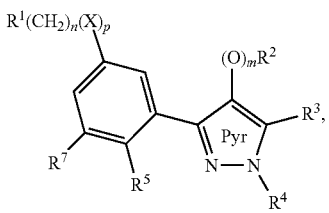

Ib(ii) 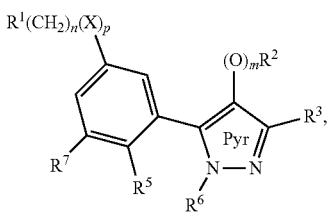

Ic(i) 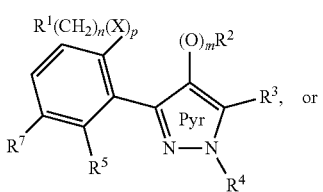

or

Ic(ii) 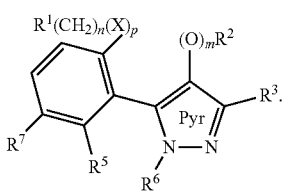

18. The method of claim 9, wherein
R¹ is hydrogen or R¹ is an alkyl group, an aryl group, a benzyl group, a heteroaryl group, a cycloalkyl group, a benzoyl group, or a cycloheteroalkyl group, optionally R¹ is substituted at one or more positions with one or more of alkyl, alkoxy, haloalkyl, haloalkoxy, aryl, heteroaryl, hydroxyl, halo, cyano, amido, hydrazonyl, carbonyl, carboxyl, —NH—C(O)—CH$_2$-(OCH$_2$)$_y$—N$_3$, —NH—C(O)-alkylene-alkynyl optionally substituted with azido,—O-alkylene-alkynyl, amino, nitro, and alkoxycarbonyl.

19. The method of claim 9, wherein R¹ is

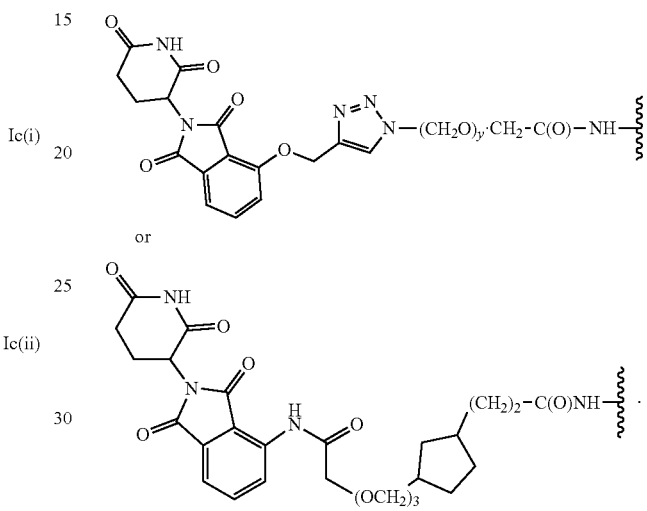

* * * * *